(12) United States Patent
Wang et al.

(10) Patent No.: US 10,206,997 B2
(45) Date of Patent: Feb. 19, 2019

(54) FACILITATOR-DNA COMBINATION VACCINE

(76) Inventors: Bin Wang, Beijing (CN); Shuang Geng, Shanghai (CN)

( * ) Notice: Subject to any disclaimer, the term of this patent is extended or adjusted under 35 U.S.C. 154(b) by 0 days.

(21) Appl. No.: 14/356,414

(22) PCT Filed: Nov. 10, 2011

(86) PCT No.: PCT/CN2011/001662
§ 371 (c)(1),
(2), (4) Date: Sep. 16, 2014

(87) PCT Pub. No.: WO2013/067652
PCT Pub. Date: May 16, 2013

(65) Prior Publication Data
US 2015/0004194 A1    Jan. 1, 2015

(51) Int. Cl.
| | | |
|---|---|---|
| *A61K 31/195* | (2006.01) | |
| *A61K 31/20* | (2006.01) | |
| *A61K 31/30* | (2006.01) | |
| *A61K 31/7004* | (2006.01) | |
| *A61K 36/05* | (2006.01) | |
| *A61K 39/29* | (2006.01) | |
| *A61K 9/00* | (2006.01) | |
| *A61K 39/39* | (2006.01) | |
| *C12N 7/00* | (2006.01) | |
| *A61K 39/12* | (2006.01) | |
| *A61K 39/00* | (2006.01) | |

(52) U.S. Cl.
CPC .......... *A61K 39/292* (2013.01); *A61K 9/0009* (2013.01); *A61K 39/12* (2013.01); *A61K 39/39* (2013.01); *C12N 7/00* (2013.01); *A61K 2039/53* (2013.01); *A61K 2039/54* (2013.01); *A61K 2039/55505* (2013.01); *A61K 2039/55511* (2013.01); *A61K 2039/57* (2013.01); *A61K 2039/572* (2013.01); *C12N 2710/00034* (2013.01); *C12N 2730/10134* (2013.01)

(58) Field of Classification Search
CPC ................ A61K 2039/53; A61K 39/39; A61K 2039/54; A61K 2039/55505
See application file for complete search history.

(56) References Cited

U.S. PATENT DOCUMENTS

| | | |
|---|---|---|
| 3,805,783 A | 4/1974 | Ismach |
| 4,342,310 A | 8/1982 | Lindmayer et al. |
| 4,447,223 A | 5/1984 | Kaye et al. |
| 4,554,101 A | 11/1985 | Hopp |
| 5,505,697 A | 4/1996 | McKinnon, Jr. et al. |
| 5,702,359 A | 12/1997 | Hofmann et al. |
| 5,739,118 A | 4/1998 | Carrano et al. |
| 6,009,347 A | 12/1999 | Hofmann |
| 6,120,493 A | 9/2000 | Hofmann |
| 6,208,893 B1 | 3/2001 | Hofmann |
| 6,520,950 B1 | 2/2003 | Hofmann et al. |
| 6,763,264 B2 | 7/2004 | Hofmann |
| 7,171,264 B1 | 1/2007 | Hofmann et al. |
| 7,245,963 B2 | 7/2007 | Draghia-Akli et al. |
| 7,328,064 B2 | 2/2008 | Mathiesen et al. |
| 2008/0234655 A1 | 9/2008 | Mathiesen et al. |
| 2010/0009970 A1* | 1/2010 | Johansen ............ A61K 31/136 514/218 |
| 2010/0143401 A1 | 6/2010 | Wang et al. |

FOREIGN PATENT DOCUMENTS

| | | |
|---|---|---|
| CN | 103998055 A | 8/2014 |
| WO | WO2009000891 | * 12/2008 |
| WO | WO2009023270 | * 2/2009 |
| WO | WO2009136979 | * 11/2011 |

OTHER PUBLICATIONS

Kaufmann et al., "Challenges and responses in human vaccine development", 2014, Current Opinion in Immunology, 28:18-26.*
Nakanishi et al., "Effect of partial Na pump and Na—H exchange inhibition on Ca during acidosis in cardiac cells", Am J Physiol. 1991, 261:C758-66.*
Sandgren et al. "Differential Role for Macropinocytosis in Mediating Entry of the two forms of Vaccinia Virus into Dendritic Cells", PLoS Pathogens, 2010, 6(4):1-16.*
International Search Report & Written Opinion, issued in corresponding International Application No. PCT/CN2011/001662, dated Aug. 23, 2012, 15 pages.
First Office Action issued in corresponding Chinese Patent Application No. CN201180074728.3, dated Apr. 28, 2015, 14 pages.
Beignon, A. S. et al., Endocytosis of HIV-1 activates plsmacytoid dendritic cells via Toll-like receptor-viral RNA interactions. The Journal of Clinical Investigation. Nov. 2005, vol. 115, No. 11, pp. 3265-3275.
Davies, J. C., New therapeutic approaches for cystic fibrosis lung disease. Journal of the royal society of medicine, 2002, vol. 95, suppl. No. 41, pp. 58-67.
Devasahayam, M., Factors affecting the presentation of exofenous Hepatitis B virus core antigen. Indian Journal of Experimental Biology., Aug. 2007, vol. 45, pp. 689-695.
Guan, P. et al., MHCPred: a server for quantitative prediction of peptide—MHC binding, Nucleic Acids Res. 2003 31:3621-3624.
Guan, P. et al., MHCPred: bringing a quantitative dimention to the online prediction of MHC binding, Appl Bioinformatics. 2003 2:63-66.
Hattotuwagama, CK et al., Quantitative online prediction of peptide beinding to the major histocompatibility complex, J. Mol Graph Model. 2004 22:195-207.
Kyte et al. J. Mol. Biol. 157:105-132 (1982).

* cited by examiner

*Primary Examiner* — Barry A Chestnut

(57) ABSTRACT

Provided herein is a vaccine that combines a vaccine facilitator and a DNA construct encoding an antigen to elicit antigen-specific antibody responses, wherein the vaccine facilitator is a Na/K pump inhibitor. Cellular entry of the DNA is accelerated as compared to other vaccines that do not contain the vaccine facilitator.

17 Claims, 12 Drawing Sheets

Specification includes a Sequence Listing.

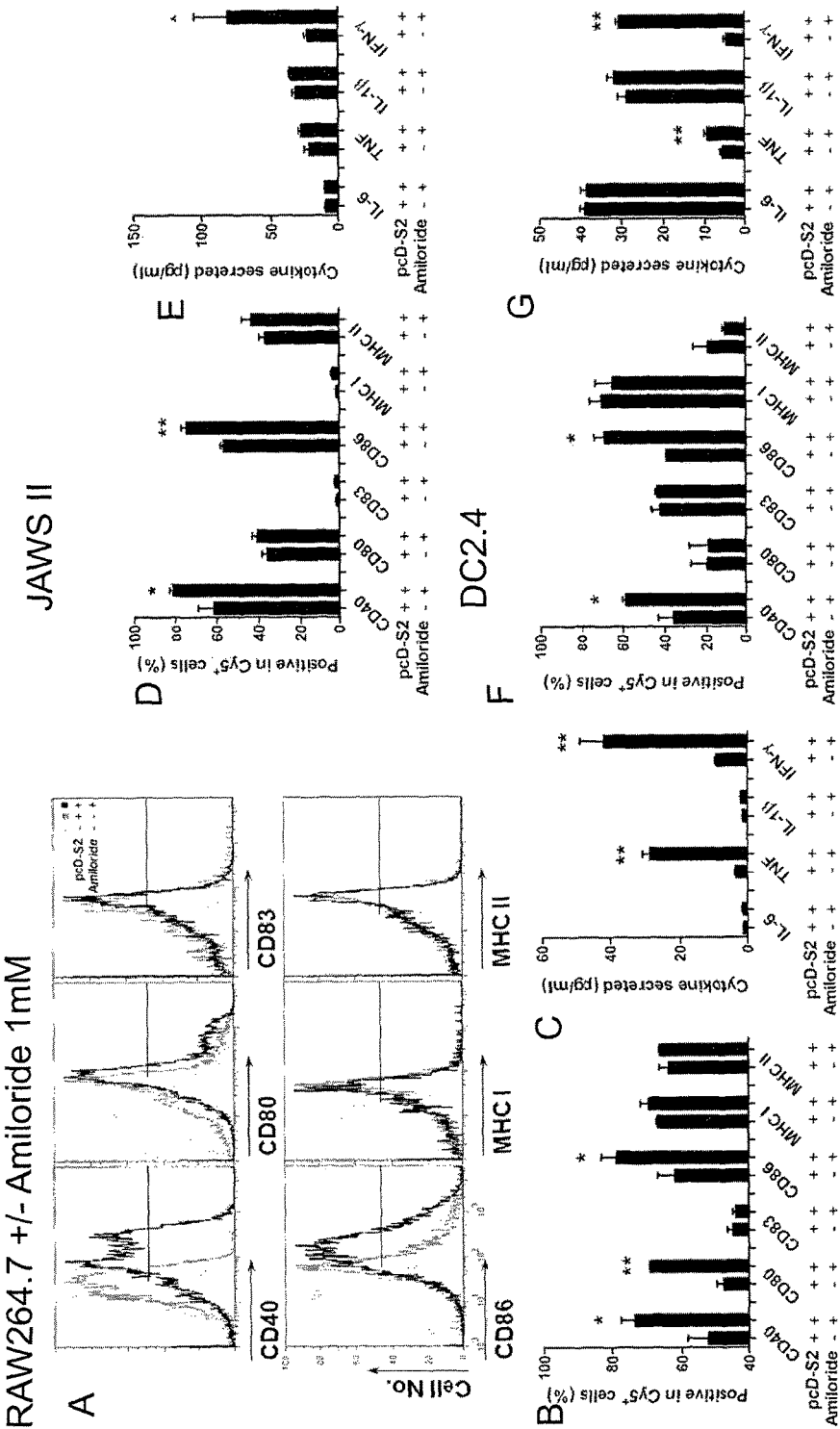

Amiloride on immune response

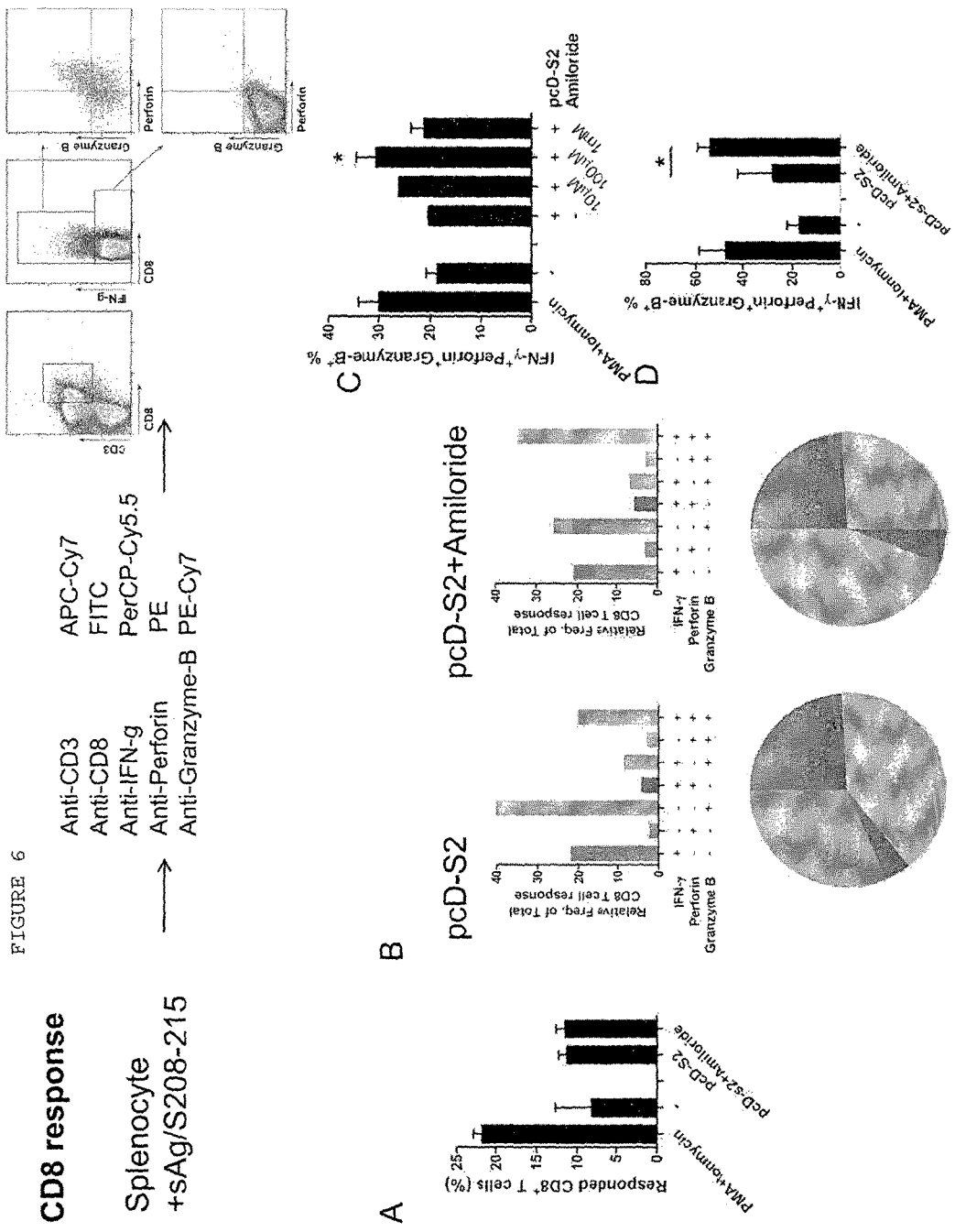

SEQUENCE LISTING

<160> NUMBER OF SEQ ID NOS: 105

<210> SEQ ID NO 1
<211> LENGTH: 9
<212> TYPE: PRT
<213> ORGANISM: Influenza virus

<400> SEQUENCE: 1

Thr Tyr Gln Arg Thr Arg Ala Leu Val
1               5

<210> SEQ ID NO 2
<211> LENGTH: 23
<212> TYPE: PRT
<213> ORGANISM: Influenza virus

<400> SEQUENCE: 2

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 3
<211> LENGTH: 1695
<212> TYPE: DNA
<213> ORGANISM: Influenza virus

<400> SEQUENCE: 3

```
atgaaggcta tcctcgtcgt gctgctgtac accttcgcca ccgccaacgc cgatacctg      60
tgcatcggct accacgccaa caacagcacc gacaccgtgg ataccgtgct ggaaaagaac    120
gtgaccgtga cccacagcgt gaacctgctg aagataagc acaacggcaa gctgtgcaag    180
ctgagaggcg tggcccctct gcacctgggc aagtgcaata tcgccggctg gattctgggc    240
aaccccgagt gcgagagcct gtctaccgct agctcctggt cctacatcgt ggagacaagc    300
agcagcgaca acggcacctg ttaccccggc gacttcatcg actacgagga actgcgggag    360
cagctgagca gcgtgtccag cttcgagcgg ttcgagatct cccccaagac cagctcctgg    420
cccaaccacg acagcaacaa gggcgtgacc gccgcctgtc ctcacgctgg cgccaagagc    480
ttctacaaga acctgatctg gctggtcaag aagggcaaca gctaccccaa gctgagcaag    540
agctacatca acgacaaggg caaagaggtc ctcgtcctct ggggcatcca ccaccctagc    600
accagcgccg accagcagag cctgtaccag aacgccgacg cctacgtgtt cgtgggctca    660
tctcggtaca gcaagaagtt caagcccgag atcgccatca gacccaaagt gcgggaccag    720
gaaggccgga tgaactacta ctggaccctg gtggagcccg cgacaagat caccttcgag    780
gccaccggca atctggtggt gcccagatac gccttcgcca tggaaagaaa cgccggcagc    840
ggcatcatca tcagcgacac ccccgtgcac gactgcaaca ccacctgtca gacccccaag    900
ggcgccatca caccagcct gcccttccag aacatccacc ccatcaccat cggcaagtgc    960
cctaagtacg tgaagtccac taagctcaga ctggccaccg gcctgagaaa cgtgcccagc   1020
atccagagca gaggcctgtt tggcgccatt gccggcttta tcgagggcgg ctggaccgga   1080
atggtggacg ggtggtacgg ctaccaccac cagaatgagc agggcagcgg ctacgccgcc   1140
gacctgaagt ccacacagaa cgccatcgac gagatcacca caaagtgaa cagcgtgatc   1200
gagaagatga acacccagtt caccgccgtg ggcaaagagt caaccacct ggaaaagcgg   1260
atcgagaacc tgaacaagaa ggtggacgac ggcttcctgg acatctggac ctacaacgcc   1320
gagctgctgt tgctgctgga aaacgagcgg accctggact accacgactc caacgtgaag   1380
aatctgtacg agaaagtgcg gagccagctg aagaacaacg ccaaagagat cggcaacggc   1440
tgcttcgagt tctaccacaa gtgcgacaac acctgtatgg aaagcgtgaa gaacggcacc   1500
tacgactacc ccaagtacag cgaggaagcc aagctgaacc gggaagagat cgacggcgtg   1560
```

```
aagctggaaa gcacccggat ctaccagatc ctggccatct actctactgt ggccagctca    1620
ctggtgctgg tggtgtccct gggcgccatc tccttttgga tgtgctccaa cggcagcctg    1680
cagtgccgga tctgc                                                    1695
```

<210> SEQ ID NO 4
<211> LENGTH: 566
<212> TYPE: PRT
<213> ORGANISM: Influenza virus

<400> SEQUENCE: 4

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350
```

```
Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 5
<211> LENGTH: 1719
<212> TYPE: DNA
<213> ORGANISM: Influenza virus

<400> SEQUENCE: 5
ggtaccaagc ttgccaccat ggccatcatc tacctgatcc tgctgttcac cgccgtgcgg      60
ggcgaccaga tctgcatcgg ctaccacgcc aacaacagca ccgagaaggt ggacaccatc     120
ctggaacgga cgtgaccgt gacccacgcc aaggacatcc tggaaaagac cacaacggc      180 aagctgtgca agctgaacgg catcccccc ctggaactgg cgactgcag cattgccggc      240 tggctgctgg caaccccga gtgcgaccgg ctgctgtccg tgcccgagtg gagctacatc     300
atggaaaaag agaaccccg ggacggcctg tgctaccccg cagcttcaa cgactacgag      360 gaactgaagc acctgctgtc cagcgtgaag cacttcgaga aggtgaaaat cctgcccaag     420
gaccggtgga cccagcacac caccaccggc ggcagcagag cctgtgccgt gagcggcaac     480
cccagcttct tccggaacat ggtgtggctg accaagaagg gcagcaacta ccccgtggcc     540
aagggcagct acaacaacac ctccggagaa cagatgctga tcatctgggg cgtgcaccac     600
cccaacgacg agacagagca gcggaccctg taccagaacg tgggcaccta cgtgagcgtg     660
ggcaccagca ccctgaacaa gcggagcacc cccgagatcg ccacccggcc aaggtgaac      720 ggcctgggca gccggatgga attcagctgg accctgctgg acatgtggga caccatcaac     780
ttcgagagca ccggcaacct gatcgccccc gagtacggct tcaagatcag caagcgggc      840
```

```
agcagcggca tcatgaaaac cgagggcacc ctggaaaact gcgagacaaa gtgccagacc    900
cccctgggcg ccatcaacac caccctgccc ttccacaacg tgcacccct gaccatcggc     960
gagtgcccca agtacgtgaa gagcgagaag ctggtgctgg ccaccggcct gcggaacgtg   1020
ccccagatcg agagcagggg cctgttcggc gccattgccg gattcatcga gggcggctgg   1080
cagggcatgg tggacgggtg gtacggctac caccacagca acgaccaggg cagcggctac   1140
gccgccgaca agagagcac ccagaaggcc ttcgacggca tcaccaacaa ggtgaacagc    1200
gtgatcgaga gatgaacac ccagttcgag gccgtgggca agagttcag caacctggaa     1260
cggcggctgg aaaacctgaa caagaaaatg gaagatggct tcctggacgt gtggacctac   1320
aacgccgagc tgctggtgct gatggaaaac gagaggaccc tggacttcca cgacagcaac   1380
gtgaagaacc tgtacgacaa agtgcggatg cagctgcggg acaacgtgaa agagctgggc   1440
aacggctgct tcgagttcta ccacaagtgc gacgacgagt gcatgaactc cgtgaagaac   1500
ggcacctacg actaccctaa gtacgaggaa gagtccaagc tgaaccggaa cgagatcaag   1560
ggcgtgaagc tgtccagcat gggcgtgtac cagatcctgg ccatctacgc caccgtggcc   1620
ggcagcctga gcctggctat tatgatggct ggcatcagct tttggatgtg cagcaacggc   1680
agcctgcagt gccggatctg catctgatga ctcgagctc                           1719
```

<210> SEQ ID NO 6
<211> LENGTH: 562
<212> TYPE: PRT
<213> ORGANISM: Influenza virus

<400> SEQUENCE: 6

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220
```

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
            245                 250                 255

Ser Thr Gly Asn Leu Ile Ala Pro Glu Tyr Gly Phe Lys Ile Ser Lys
        260                 265                 270

Arg Gly Ser Ser Gly Ile Met Lys Thr Glu Gly Thr Leu Glu Asn Cys
    275                 280                 285

Glu Thr Lys Cys Gln Thr Pro Leu Gly Ala Ile Asn Thr Thr Leu Pro
290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
            325                 330                 335

Ile Glu Ser Arg Gly Leu Phe Gly Ala Ile Ala Gly Phe Ile Glu Gly
        340                 345                 350

Gly Trp Gln Gly Met Val Asp Gly Trp Tyr Gly Tyr His His Ser Asn
    355                 360                 365

Asp Gln Gly Ser Gly Tyr Ala Ala Asp Lys Glu Ser Thr Gln Lys Ala
370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
            405                 410                 415

Leu Glu Asn Leu Asn Lys Lys Met Glu Asp Gly Phe Leu Asp Val Trp
        420                 425                 430

Thr Tyr Asn Ala Glu Leu Leu Val Leu Met Glu Asn Glu Arg Thr Leu
    435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
            485                 490                 495

Tyr Asp Tyr Pro Lys Tyr Glu Glu Ser Lys Leu Asn Arg Asn Glu
        500                 505                 510

Ile Lys Gly Val Lys Leu Ser Ser Met Gly Val Tyr Gln Ile Leu Ala
    515                 520                 525

Ile Tyr Ala Thr Val Ala Gly Ser Leu Ser Leu Ala Ile Met Met Ala
530                 535                 540

Gly Ile Ser Phe Trp Met Cys Ser Asn Gly Ser Leu Gln Cys Arg Ile
545                 550                 555                 560

Cys Ile

<210> SEQ ID NO 7
<211> LENGTH: 1695
<212> TYPE: DNA
<213> ORGANISM: Influenza virus

<400> SEQUENCE: 7
aaggccaagc tgctggtgct gctgtgcacc ttcgccgcca ccaacgccga caccatctgc    60
atcggctacc acgccaacaa cagcaccgac accgtggata ccgtgctgga aaagaacgtg   120
accgtgaccc acagcgtgaa cctgctggaa gataagcaca acggcaagct gtgcaagctg   180

```
aagggaatcg ccccccctgca gctgggcaag tgcaatatcg ccggctggat tctgggcaac      240
cccgagtgcg agagcctgag cagcaagagc agctggtcct acatcgtgga aaccccccaac     300 agcgagaacg gcacctgtta ccccggcgac ttcgccgact acgaggaact gcgcgagcag      360
ctgagcagcg tgtccagctt cgagagattc gagatcttcc ccaagaccag cagctggccc      420
aaccacgacg tgaccaaggg cgtgaccgct agctgtagcc acgcaggcgc cagcagcttc      480
tacaagaacc tgctgtggct gaccaagaag aacggcagct accccaagct gagcaagagc      540
tacatcaaca acaaagaaaa agaggtgctg gtcctctggg gcgtccacca ccccagcaca      600
atcgccgacc agcagagcct gtaccagaac gagaacgccc acgtgtccgt gggcagcagc      660
cactacagcc ggaagttcac ccccgagatc gccaagcggc ccaaagtgcg ggaccaggaa      720
ggccggatca actactactg gaccctgctg aacccggcg acaccatcat cttcgaggcc       780
aacggcaacc tgatcgcccc cagatacgcc ttcgccctga gcagaggctt cggcagcggc      840
atcatcatca gcaacgcccc catgcacgac tgcgacacca gtgccagac ccctcagggc       900 gccatcaaca gcagcctgcc cttccagaac atccaccccg tgaccatcgg cgagtgcccc     960
aaatacgtgc ggagcaccaa gctgcggatg gccaccggcc tgcggaacat ccccagcatc    1020
cagagcagag gcctgttcgg cgccattgcc ggcttcatcg agggcggctg gaccggaatg    1080
gtggacgggt ggtacggcta ccaccaccag aatgagcagg gcagcggcta cgccgccgac    1140
cagaagtcca cccagaacgc catcgacggc atcaccaaca agtgaacag cgtgatcgag     1200 aagatgaaca cccagttcac cgccgtgggc aaagagttca acaagctgga aaagcggatg    1260
gaaaacctga caagaaggt ggacgacggc ttcctggaca tctggaccta caacgccgaa     1320
ctgctcgtgc tgctggaaaa cgagcggacc ctggacttcc acgacagcaa cgtgaagaac    1380
ctgtacgaga aagtgaagtc ccagctgaag aacaacgcca agagatcgg caacggctgc    1440 ttcgagttct accacaagtg caacaacgag tgcatggaaa gcgtgaagaa cggaacctac     1500
gactacccca gtacagcga ggaaagcaag ctgaaccggg aagagatcga cggcgtgaag     1560
ctggaatcca tgggcgtgta ccagatcctg gccatctaca gcaccgtggc tagcagcctg    1620
gtgctgctgg tgtccctggg cgccatctcc ttttggatgt gctccaacgg cagcctgcag    1680
tgccggatct gcatc                                                     1695
```

<210> SEQ ID NO 8
<211> LENGTH: 565
<212> TYPE: PRT
<213> ORGANISM: Influenza virus

<400> SEQUENCE: 8

```
Lys Ala Lys Leu Leu Val Leu Leu Cys Thr Phe Ala Ala Thr Asn Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Lys His Asn Gly Lys Leu Cys Lys Leu Lys Gly Ile Ala
    50                  55                  60

Pro Leu Gln Leu Gly Lys Cys Asn Ile Ala Gly Trp Ile Leu Gly Asn
65                  70                  75                  80

Pro Glu Cys Glu Ser Leu Ser Ser Lys Ser Trp Ser Tyr Ile Val
                85                  90                  95
```

-continued

Glu Thr Pro Asn Ser Glu Asn Gly Thr Cys Tyr Pro Gly Asp Phe Ala
                100                 105                 110

Asp Tyr Glu Glu Leu Arg Glu Gln Leu Ser Ser Val Ser Ser Phe Glu
            115                 120                 125

Arg Phe Glu Ile Phe Pro Lys Thr Ser Ser Trp Pro Asn His Asp Val
        130                 135                 140

Thr Lys Gly Val Thr Ala Ser Cys Ser His Ala Gly Ala Ser Ser Phe
145                 150                 155                 160

Tyr Lys Asn Leu Leu Trp Leu Thr Lys Lys Asn Gly Ser Tyr Pro Lys
                165                 170                 175

Leu Ser Lys Ser Tyr Ile Asn Asn Lys Glu Lys Glu Val Leu Val Leu
            180                 185                 190

Trp Gly Val His His Pro Ser Thr Ile Ala Asp Gln Gln Ser Leu Tyr
        195                 200                 205

Gln Asn Glu Asn Ala Tyr Val Ser Val Gly Ser Ser His Tyr Ser Arg
210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Ile Ser Asn Ala Pro Met
        275                 280                 285

His Asp Cys Asp Thr Lys Cys Gln Thr Pro Gln Gly Ala Ile Asn Ser
290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln

```
                515                 520                 525
Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 9
<211> LENGTH: 1749
<212> TYPE: DNA
<213> ORGANISM: Influenza virus

<400> SEQUENCE: 9
aaggccatca tcgtgctgct gatggtggtc acaagcaacg ccgaccggat ctgcaccggc      60
atcaccagca gcaacagccc ccacgtggtc aaaaccgcca cccagggcga agtgaacgtg     120
accggcgtga tccccctgac caccaccccc accaagagcc acttcgccaa cctgaagggc     180
accaagaccc ggggaaagct gtgccccaag tgcctgaact gcaccgacct ggacgtggcc     240
ctgggcagac ctatgtgcgt gggcaccacc cctagcgcca aggccagcat cctgcacgaa     300
gtgcggcccg tgaccagcgg ctgcttcccc atcatgcacg accggaccaa gatccggcag     360
ctccccaacc tgctgcgggg ctacgagaac atccggctga gcaccagaa cgtgatcaac      420 gccgagaagg ccctggcgg cccttacaga ctgggcacaa gcggctcttg ccccaacgcc     480
accagcaaga gcggcttttt cgccacaatg gcctgggccg tgcccaagga caacaacaag     540
accgccacca ccccctgac cgtggaagtg ccctacatct gcaccgaggg cgaggaccag      600
atcaccgtgt ggggcttcca cagcgataac aagacccaga tgaagaacct gtacggcgac     660 agcaacccc agaagttcac cagctccgcc aacggcgtga ccacccacta cgtgtcccag      720
atcggcggct ccccgacca gacagaggat ggcggcctgc cccagagcgg cagaatcgtg      780
gtggactaca tggtgcagaa gcccggcaag accggcacca tcgtgtacca gcggggcatc     840
ctgctgcccc agaaagtgtg gtgcgccagc ggccggtcca agtgatcaa gggcagcctg      900 cctctgatcg gcgaggccga ttgcctgcac gagaagtacg gcggcctgaa caagagcaag     960
ccctactaca ccggcgagca cgccaaagcc atcggcaact gccccatctg ggtcaaaacc    1020
cccctgaagc tggccaacgg caccaagtac cggcctcccg ccaagctgct gaagagcgg     1080 ggcttcttcg cgctatcgc cggctttctg gaaggcggct gggagggcat gatcgccggc    1140
tggcacggct acacatctca cggcgctcat ggcgtggccg tggccgctga tctgaagtcc    1200
acccaggaag ccatcaacaa gatcaccaag aacctgaaca gcctgagcga gctggaagtg    1260
aagaatctgc agcggctgag cggcgccatg acgagctgc acaacgagat cctgaactg      1320 gacgagaagg tggacgacct gcgggccgac accatctcca gccagatcga gctggccgtg    1380
ctgctgtcca acgagggcat catcaacagc gaggacgagc atctgctggc cctgaacgg     1440 aagctgaaga agatgctggg ccctagcgcc gtggacatcg caacggctg cttcgagaca    1500 aagcacaagt gcaaccagac ctgcctggac cggatcgctg ccggcacctt caacgccggc    1560
gagttcagcc tgcccacctt cgacagcctg aacatcaccg ccgccagcct gaacgacgac    1620
ggcctggaca ccacaccat cctgctgtac tacagcaccg cagcctccag cctggccgtg    1680
accctgatga tcgccatctt catcgtgtac atggtgtctc gggacaacgt gtcctgcagc    1740
atctgcctg                                                            1749
```

<210> SEQ ID NO 10
<211> LENGTH: 583
<212> TYPE: PRT
<213> ORGANISM: Influenza virus

<400> SEQUENCE: 10

```
Lys Ala Ile Ile Val Leu Leu Met Val Val Thr Ser Asn Ala Asp Arg
1               5                   10                  15

Ile Cys Thr Gly Ile Thr Ser Ser Asn Ser Pro His Val Val Lys Thr
            20                  25                  30

Ala Thr Gln Gly Glu Val Asn Val Thr Gly Val Ile Pro Leu Thr Thr
        35                  40                  45

Thr Pro Thr Lys Ser His Phe Ala Asn Leu Lys Gly Thr Lys Thr Arg
    50                  55                  60

Gly Lys Leu Cys Pro Lys Cys Leu Asn Cys Thr Asp Leu Asp Val Ala
65                  70                  75                  80

Leu Gly Arg Pro Met Cys Val Gly Thr Thr Pro Ser Ala Lys Ala Ser
                85                  90                  95

Ile Leu His Glu Val Arg Pro Val Thr Ser Gly Cys Phe Pro Ile Met
            100                 105                 110

His Asp Arg Thr Lys Ile Arg Gln Leu Pro Asn Leu Leu Arg Gly Tyr
        115                 120                 125

Glu Asn Ile Arg Leu Ser Thr Gln Asn Val Ile Asn Ala Glu Lys Ala
    130                 135                 140

Pro Gly Gly Pro Tyr Arg Leu Gly Thr Ser Gly Ser Cys Pro Asn Ala
145                 150                 155                 160

Thr Ser Lys Ser Gly Phe Phe Ala Thr Met Ala Trp Ala Val Pro Lys
                165                 170                 175

Asp Asn Asn Lys Thr Ala Thr Asn Pro Leu Thr Val Glu Val Pro Tyr
            180                 185                 190

Ile Cys Thr Glu Gly Glu Asp Gln Ile Thr Val Trp Gly Phe His Ser
        195                 200                 205

Asp Asn Lys Thr Gln Met Lys Asn Leu Tyr Gly Asp Ser Asn Pro Gln
    210                 215                 220

Lys Phe Thr Ser Ser Ala Asn Gly Val Thr Thr His Tyr Val Ser Gln
225                 230                 235                 240

Ile Gly Gly Phe Pro Asp Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Ile Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380
```

```
Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580

<210> SEQ ID NO 11
<211> LENGTH: 2142
<212> TYPE: DNA
<213> ORGANISM: Influenza virus

<400> SEQUENCE: 11
ggatccatgg actggacctg gattctgttc ctggtggccg ccgccaccag agtgcacagc    60
agagtgatgg gcatccagcg gaattgccag cacctgtgga gatggggcac catgatcctg    120
ggcatgatca tcatctgctc tgccgccgag aacctgtggg tgaccgtgta ctacggcgtg    180
cctgtgtgga aggacgccga gaccaccctg ttctgcgcca gcgacgccaa ggcctacgat    240
accgaagtgc acaatgtgtg gccaccacac gcctgcgtgc ctaccgatcc caacccccag    300
gagatcaacc tggagaacgt gaccgaggag ttcaacatgt ggaagaacaa catggtggag    360
cagatgcaca ccgacatcat cagcctgtgg gaccagagcc tgaagccttg cgtgaagctg    420
acccctctgt gcgtgaccct gaactgcagc aacgtgaacg tgaccaccaa catcatgaag    480
ggcgagatca gaactgcag cttcaacatg accaccgagc tgcgggacaa gaagcagaaa    540
gtgtacagcc tgttctacaa gctggacgtg gtgcagatca caagagcaa cagcagcagc    600 cagtaccggc tgatcaactg caacaccagc gccatcaccc aggcctgccc caaagtgagc    660
ttcgagccca tccccatcca ctactgcgcc cctgccggct cgccatcct gaagtgcaag    720 gacaaggagt ttaacggcac cggccctgc aagaatgtga gcaccgtgca gtgcacccac    780
ggcatcaagc ccgtggtgtc cacccagctg ctgctgaacg gcagcctggc cgaggaggaa    840
gtgatgatcc ggagcgagaa catcaccaac aacgccaaga acatcatcgt gcagctgacc    900
aagcccgtga agatcaattg cacccggccc aacaacaaca cccggaagag catcagaatc    960
```

```
ggccctggcc aggccttcta cgccaccggc gacatcatcg gcgatatcag gcaggcccac   1020
tgcaatgtga gccggaccga gtggaacgag accctgcaga agtggccaa gcagctgcgg    1080 aagtacttca acaacaagac catcatcttc accaacagca gcggcggcag actgagaatc   1140
accacccaca gcttcaattg tggcggcgag ttcttctact gcaataccct cggcctgttc   1200
aacagcacct ggaacggcaa cggcaccaag aagaagaaca gcaccgagag caacgacacc   1260
atcaccctgc cctgccggat caagcagatc atcaatatgt ggcagagggt gggccaggcc   1320
atgtacgccc ctcccatcca gggcgtgatc agatgcgaga gcaacatcac cggcctgctg   1380
ctgaccagag atggcggcga caacaacagc aagaacgaga ccttcagacc tggcggcgga   1440
gacatgaggg acaactggcg gagcgagctg tacaagtaca agtggtgaa gatcgagccc    1500 ctgggcgtgg ccccccaccaa ggccaagaga gagtggtgg agcgggagaa gagagctgtg    1560
ggcatcggcg ccgtgttcct gggcttcctg ggagccgccg aagcaccat gggagccgcc    1620 agcatcaccc tgaccgtgca ggccagacag ctgctgagcg gcattgtgca gcagcagagc   1680
aacctgctga gagccatcga ggcccagcag cacctgctga agctgacagt gtggggcatc   1740
aaacagctgc aggcccgcgt gctggccgtg gagagatacc tgaaggacca gcagctgctg   1800
ggcatctggg gctgcagcgg caagctgatc tgcaccacca acgtgccctg gaatagcagc   1860
tggagcaaca gagccagag cgagatctgg gacaacatga cctggctgca gtgggacaag   1920
gagatcagca actacaccga tatcatctac aacctgatcg aggagagcca gaaccagcag   1980
gagaagaacg agcaggatct gctggcccctg gacaagtggg ccaacctgtg gaactggttc   2040
gacatcagca actggctgtg gtacatcaag atcttcatca tgattgtggg cggcctgatc   2100
ggcctgagaa tcgtgttcgc cgtgctgtct gtgtgactcg ag                      2142
```

<210> SEQ ID NO 12
<211> LENGTH: 709
<212> TYPE: PRT
<213> ORGANISM: Influenza virus

<400> SEQUENCE: 12

```
Met Asp Trp Thr Trp Ile Leu Phe Leu Val Ala Ala Thr Arg Val
1               5                   10                  15

His Ser Arg Val Met Gly Ile Gln Arg Asn Cys Gln His Leu Trp Arg
            20                  25                  30

Trp Gly Thr Met Ile Leu Gly Met Ile Ile Cys Ser Ala Ala Glu
            35                  40                  45

Asn Leu Trp Val Thr Val Tyr Tyr Gly Val Pro Val Trp Lys Asp Ala
    50                  55                  60

Glu Thr Thr Leu Phe Cys Ala Ser Asp Ala Lys Ala Tyr Asp Thr Glu
65                  70                  75                  80

Val His Asn Val Trp Ala Thr His Ala Cys Val Pro Thr Asp Pro Asn
                85                  90                  95

Pro Gln Glu Ile Asn Leu Glu Asn Val Thr Glu Glu Phe Asn Met Trp
            100                 105                 110

Lys Asn Asn Met Val Glu Gln Met His Thr Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Ser Asn Val Asn Val Thr Thr Asn Ile Met Lys Gly Glu
145                 150                 155                 160
```

-continued

```
Ile Lys Asn Cys Ser Phe Asn Met Thr Thr Glu Leu Arg Asp Lys Lys
            165                 170                 175
Gln Lys Val Tyr Ser Leu Phe Tyr Lys Leu Asp Val Val Gln Ile Asn
        180                 185                 190
Lys Ser Asn Ser Ser Ser Gln Tyr Arg Leu Ile Asn Cys Asn Thr Ser
    195                 200                 205
Ala Ile Thr Gln Ala Cys Pro Lys Val Ser Phe Glu Pro Ile Pro Ile
210                 215                 220
His Tyr Cys Ala Pro Ala Gly Phe Ala Ile Leu Lys Cys Lys Asp Lys
225                 230                 235                 240
Glu Phe Asn Gly Thr Gly Pro Cys Lys Asn Val Ser Thr Val Gln Cys
                245                 250                 255
Thr His Gly Ile Lys Pro Val Val Ser Thr Gln Leu Leu Asn Gly
            260                 265                 270
Ser Leu Ala Glu Glu Val Met Ile Arg Ser Glu Asn Ile Thr Asn
        275                 280                 285
Asn Ala Lys Asn Ile Ile Val Gln Leu Thr Lys Pro Val Lys Ile Asn
    290                 295                 300
Cys Thr Arg Pro Asn Asn Asn Thr Arg Lys Ser Ile Arg Ile Gly Pro
305                 310                 315                 320
Gly Gln Ala Phe Tyr Ala Thr Gly Asp Ile Ile Gly Asp Ile Arg Gln
                325                 330                 335
Ala His Cys Asn Val Ser Arg Thr Glu Trp Asn Glu Thr Leu Gln Lys
            340                 345                 350
Val Ala Lys Gln Leu Arg Lys Tyr Phe Asn Asn Lys Thr Ile Ile Phe
        355                 360                 365
Thr Asn Ser Ser Gly Gly Arg Leu Arg Ile Thr Thr His Ser Phe Asn
    370                 375                 380
Cys Gly Gly Glu Phe Phe Tyr Cys Asn Thr Ser Gly Leu Phe Asn Ser
385                 390                 395                 400
Thr Trp Asn Gly Asn Gly Thr Lys Lys Asn Ser Thr Glu Ser Asn
                405                 410                 415
Asp Thr Ile Thr Leu Pro Cys Arg Ile Lys Gln Ile Ile Asn Met Trp
            420                 425                 430
Gln Arg Val Gly Gln Ala Met Tyr Ala Pro Pro Ile Gln Gly Val Ile
        435                 440                 445
Arg Cys Glu Ser Asn Ile Thr Gly Leu Leu Leu Thr Arg Asp Gly Gly
    450                 455                 460
Asp Asn Asn Ser Lys Asn Glu Thr Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Arg Arg Val Val Glu
            500                 505                 510
Arg Glu Lys Arg Ala Val Gly Ile Gly Ala Val Phe Leu Gly Phe Leu
        515                 520                 525
Gly Ala Ala Gly Ser Thr Met Gly Ala Ala Ser Ile Thr Leu Thr Val
    530                 535                 540
Gln Ala Arg Gln Leu Leu Ser Gly Ile Val Gln Gln Ser Asn Leu
545                 550                 555                 560
Leu Arg Ala Ile Glu Ala Gln Gln His Leu Leu Lys Leu Thr Val Trp
                565                 570                 575
Gly Ile Lys Gln Leu Gln Ala Arg Val Leu Ala Val Glu Arg Tyr Leu
```

-continued

```
            580                 585                 590
Lys Asp Gln Gln Leu Leu Gly Ile Trp Gly Cys Ser Gly Lys Leu Ile
                595                 600                 605

Cys Thr Thr Asn Val Pro Trp Asn Ser Ser Trp Ser Asn Lys Ser Gln
            610                 615                 620

Ser Glu Ile Trp Asp Asn Met Thr Trp Leu Gln Trp Asp Lys Glu Ile
625                 630                 635                 640

Ser Asn Tyr Thr Asp Ile Ile Tyr Asn Leu Ile Glu Glu Ser Gln Asn
                645                 650                 655

Gln Gln Glu Lys Asn Glu Gln Asp Leu Leu Ala Leu Asp Lys Trp Ala
            660                 665                 670

Asn Leu Trp Asn Trp Phe Asp Ile Ser Asn Trp Leu Trp Tyr Ile Lys
                675                 680                 685

Ile Phe Ile Met Ile Val Gly Gly Leu Ile Gly Leu Arg Ile Val Phe
            690                 695                 700

Ala Val Leu Ser Val
705
```

<210> SEQ ID NO 13
<211> LENGTH: 2734
<212> TYPE: DNA
<213> ORGANISM: Influenza virus

<400> SEQUENCE: 13

```
ggatccgcca ccatggactg gacctggatt ctgttcctgg tggccgccgc caccagagtg    60
cacagcagag tgaagggcat ccggaagaac taccagcacc tgtggagatg ggcaccatg   120
ctgctgggca tgctgatgat ctgttctgcc gccgagaagc tgtgggtgac cgtgtactac   180
ggcgtgcctg tgtggaagga ggccaccacc accctgttct cgccagcga cgccaaggcc   240
tacgataccg aagtgcacaa tgtgtgggcc acccacgcct gcgtgcctac cgatcccaac   300
cctcaggaag tggtgctgga aacgtgacc gagaacttca acatgtggaa gaacaacatg   360
gtggagcaga tgcacgagga catcatcagc ctgtgggacc agagcctgaa gccttgcgtg   420
aagctgaccc ctctgtgcgt gaccctgaac tgcaccgacc tgagcggcga aagatggag   480
aagggcgaga tcaagaactg cagcttcaac atcaccacct ccatccggga caaagtgcag   540
aaggagtacg ccctgttcta caagctggac gtggtgccca tcgacaacga caacaccagc   600
taccggctga tcagctgcaa caccagcgtg atcacccagg cctgccccaa agtgagcttc   660
gagcccatcc ccatccacta ctgcgcccct gccggcttcg ccatcctgaa gtgcaacgac   720
aagaagttca cggcaccgg ccccttgcacc aatgtgagca ccgtgcagtg cacccacggc   780
atcagacccg tggtgtccac ccagctgctg ctgaacggca gcctggccga ggaagaagtg   840
gtgatccgga gcgagaattt caccaacaac gccaagacca tcatcgtgca gctgaacgag   900
agcgtggaga tcaactgcac ccggcccaac aacaatatccc ggaagagcat ccacatcggc   960
cctggccagg ccttctacac caccggcgag atcatcggcg atatcaggca ggcccactgc  1020
aatatcagcc gggccaagtg gaacaacacc ctgaagcaga tcgtgaagaa gctgcgggag  1080
cagttccggca acaagaccat cgtgttcaac cagagcagcg gcggcagacc tagaatcgtg  1140
atgcacagct tcaactgtgg cggcgagttc ttctactgca cacaacccca gctgttcaac  1200
agcacctgga cgtgaacgg acctggaac aacaaccg agggcaacga ccatcatcacc  1260
ctgccctgcc ggatcaagca gatcatcaat atgtggcagg aggtgggcaa ggccatgtac  1320
gcccctccca tcagaggcca gatccggtgc agcagcaata tcaccggcct gctgctgacc  1380
```

```
agagatggcg gcaacaataa caccaacgag accgagatct ttagacctgg cggcggagac    1440
atgagggaca actggcggag cgagctgtac aagtacaaag tggtgaagat cgagcccctg    1500
ggcgtggccc ccaccaaggc caagagaaga gtggtgcagc gggagaagag agctgtgggc    1560
atcggcgcca tgtttctggg ctttctggga gccgccggaa gcaccatggg agccgccagc    1620
atgaccctga ccgtgcaggc cagacagctg ctgagcggca tcgtgcagca gcagaacaac    1680
ctgctgagag ccatcgaggc ccagcagcac ctgctgcagc tgacagtgtg gggcatcaag    1740
cagctgcagg cccgcgtgct ggccgtggag agatacctga aggaccagca gctgctggga    1800
atctggggct gcagcggcaa gctgatctgc accaccaccg tgccctggaa cgccagctgg    1860
agcaacaaga gcctggacga gatctgggac aacatgacct ggatggagtg ggagcgggag    1920
atcgacaact acaccagcct gatctacacc ctgatcgagg agagccagaa ccagcaggag    1980
aagaacgagc aggagctgct ggagctggac aagtgggcca gcctgtggaa ctggttcgac    2040
atcaccaact ggctgtggta catcaagatc ttcatcatga ttgtgggcgg cctgatcggc    2100
ctgagaatcg tgttcgccgt gctgagcatc taccccctacg acgtgcccga ttacgcctga    2160
gaattcgtaa gtaagtgtca tatgggagag ctcgactaga ctggacagcc aatgacgggt    2220
aagagagtga catttctcac taacctaaga caggagggcc gtcaaagcta ctgcctaatc    2280
caatgacggg taatagtgac aagaaatgta tcactccaac ctaagacagg cgcagcctcc    2340
gagggatgtg tcttttgttt tttataatta aaaagggtga catgtccgga gccgtgctgc    2400
ccggatgatg tcttggcctc tgtttgctac cggtatcgat gttaacgtcg accccgggct    2460
cgaggtaagt aagtgtcata tgggagagct cgactagact ggacagccaa tgacgggtaa    2520
gagagtgaca tttctcacta acctaagaca ggagggccgt caaagctact gcctaatcca    2580
atgacgggta atagtgacaa gaaatgtatc actccaacct aagacaggcg cagcctccga    2640
gggatgtgtc ttttgttttt tataattaaa aagggtgaca tgtccggagc cgtgctgccc    2700
ggatgatgtc ttggcctctg tttgctgcgg ccgc                                 2734
```

<210> SEQ ID NO 14
<211> LENGTH: 715
<212> TYPE: PRT
<213> ORGANISM: Influenza virus

<400> SEQUENCE: 14

```
Met Asp Trp Thr Trp Ile Leu Phe Leu Val Ala Ala Thr Arg Val
1               5                   10                  15

His Ser Arg Val L

```
Asp Gln Ser Leu Lys Pro Cys Val Lys Leu Thr Pro Leu Cys Val Thr
130                 135                 140

Leu Asn Cys Thr Asp Leu Ser Gly Glu Lys Met Glu Lys Gly Glu Ile
145                 150                 155                 160

Lys Asn Cys Ser Phe Asn Ile Thr Thr Ser Ile Arg Asp Lys Val Gln
                165                 170                 175

Lys Glu Tyr Ala Leu Phe Tyr Lys Leu Asp Val Val Pro Ile Asp Asn
                180                 185                 190

Asp Asn Thr Ser Tyr Arg Leu Ile Ser Cys Asn Thr Ser Val Ile Thr
            195                 200                 205

Gln Ala Cys Pro Lys Val Ser Phe Glu Pro Ile Pro Ile His Tyr Cys
210                 215                 220

Ala Pro Ala Gly Phe Ala Ile Leu Lys Cys Asn Asp Lys Lys Phe Asn
225                 230                 235                 240

Gly Thr Gly Pro Cys Thr Asn Val Ser Thr Val Gln Cys Thr His Gly
                245                 250                 255

Ile Arg Pro Val Val Ser Thr Gln Leu Leu Leu Asn Gly Ser Leu Ala
                260                 265                 270

Glu Glu Glu Val Val Ile Arg Ser Glu Asn Phe Thr Asn Asn Ala Lys
                275                 280                 285

Thr Ile Ile Val Gln Leu Asn Glu Ser Val Glu Ile Asn Cys Thr Arg
290                 295                 300

Pro Asn Asn Asn Thr Arg Lys Ser Ile His Ile Gly Pro Gly Gln Ala
305                 310                 315                 320

Phe Tyr Thr Thr Gly Glu Ile Ile Gly Asp Ile Arg Gln Ala His Cys
                325                 330                 335

Asn Ile Ser Arg Ala Lys Trp Asn Asn Thr Leu Lys Gln Ile Val Lys
            340                 345                 350

Lys Leu Arg Glu Gln Phe Gly Asn Lys Thr Ile Val Phe Asn Gln Ser
            355                 360                 365

Ser Gly Gly Arg Pro Arg Ile Val Met His Ser Phe Asn Cys Gly Gly
        370                 375                 380

Glu Phe Phe Tyr Cys Asn Thr Thr Gln Leu Phe Asn Ser Thr Trp Asn
385                 390                 395                 400

Val Asn Gly Thr Trp Asn Asn Asn Thr Glu Gly Asn Asp Thr Ile Thr
                405                 410                 415

Leu Pro Cys Arg Ile Lys Gln Ile Ile Asn Met Trp Gln Glu Val Gly
                420                 425                 430

Lys Ala Met Tyr Ala Pro Pro Ile Arg Gly Gln Ile Arg Cys Ser Ser
            435                 440                 445

Asn Ile Thr Gly Leu Leu Leu Thr Arg Asp Gly Gly Asn Asn Asn Thr
450                 455                 460

Asn Glu Thr Glu Ile Phe Arg Pro Gly Gly Gly Asp Met Arg Asp Asn
465                 470                 475                 480

Trp Arg Ser Glu Leu Tyr Lys Tyr Lys Val Val Lys Ile Glu Pro Leu
                485                 490                 495

Gly Val Ala Pro Thr Lys Ala Lys Arg Arg Val Val Gln Arg Glu Lys
                500                 505                 510

Arg Ala Val Gly Ile Gly Ala Met Phe Leu Gly Phe Leu Gly Ala Ala
            515                 520                 525

Gly Ser Thr Met Gly Ala Ala Ser Met Thr Leu Thr Val Gln Ala Arg
530                 535                 540

Gln Leu Leu Ser Gly Ile Val Gln Gln Gln Asn Asn Leu Leu Arg Ala
```

| | | | | | | | | | | | | |
|---|---|---|---|---|---|---|---|---|---|---|---|---|
| 545 | | | | 550 | | | | 555 | | | | 560 |

Ile Glu Ala Gln Gln His Leu Leu Gln Leu Thr Val Trp Gly Ile Lys
                       565                           570                        575

Gln Leu Gln Ala Arg Val Leu Ala Val Glu Arg Tyr Leu Lys Asp Gln
             580                            585                           590

Gln Leu Leu Gly Ile Trp Gly Cys Ser Gly Lys Leu Ile Cys Thr Thr
               595                            600                        605

Thr Val Pro Trp Asn Ala Ser Trp Ser Asn Lys Ser Leu Asp Glu Ile
            610                            615                          620

Trp Asp Asn Met Thr Trp Met Glu Trp Glu Arg Glu Ile Asp Asn Tyr
625                             630                           635                     640

Thr Ser Leu Ile Tyr Thr Leu Ile Glu Glu Ser Gln Asn Gln Gln Glu
                       645                           650                        655

Lys Asn Glu Gln Glu Leu Leu Glu Leu Asp Lys Trp Ala Ser Leu Trp
               660                            665                        670

Asn Trp Phe Asp Ile Thr Asn Trp Leu Trp Tyr Ile Lys Ile Phe Ile
                  675                            680                        685

Met Ile Val Gly Gly Leu Ile Gly Leu Arg Ile Val Phe Ala Val Leu
            690                            695                          700

Ser Ile Tyr Pro Tyr Asp Val Pro Asp Tyr Ala
705                           710                           715

<210> SEQ ID NO 15
<211> LENGTH: 2140
<212> TYPE: DNA
<213> ORGANISM: Influenza virus

<400> SEQUENCE: 15

| | | |
|---|---|---|
| ggatccgcca ccatggattg gacctggatt ctgttcctgg tggccgccgc cacaagagtg | 60 |
| cacagcagag tgcggggcat cctgagaaat tgccagcagt ggtggatctg gggcattctg | 120 |
| gggttctgga tgctgatgat ctgcaacgtg atgggcaacc tgtgggtgac cgtgtactac | 180 |
| ggcgtgcctg tgtggaagga ggccaagacc accctgttct gtgccagcga tgccaaggcc | 240 |
| tacgagaccg aggtgcacaa tgtgtgggcc acccacgcct gtgtgcccac cgatcccaac | 300 |
| cctcaggaga tggtgctgga aacgtgacc gagaacttca acatgtggaa gaacgacatg | 360 |
| gtggaccaga tgcacgagga catcatcagc ctgtgggacc agagcctgaa gccttgcgtg | 420 |
| aagctgaccc ctctgtgcgt gaccctgaac tgccggaaca acgtgaacaa caacaacacc | 480 |
| atgaaggagg agatcaagaa ctgcagcttc aacatcacca ccgagctgcg ggacaagaag | 540 |
| cagaaggtgt acgccctgtt ctaccggctg gacatcgtgc cctgaacga agaacaac | 600 |
| agcaacgact accggctgat caactgcaac accagcgcca tcacccaggc ctgtcccaag | 660 |
| gtgtccttcg accccatccc catccactat tgtgccctg ccggctacgc catcctgaag | 720 |
| tgcaacaaca agaccttcaa cggcaccggc ccctgcaata atgtgagcac cgtgcagtgt | 780 |
| acccacggca tcaagcctgt ggtgtccacc cagctgctgc tgaatggcag cctggccgag | 840 |
| gaggagatta tcatccggag cgagaacctg accaacaacg ccaagaccat cattgtgcac | 900 |
| ctgaatgaga gcgtggagat cgtgtgtacc cggcccaaca caataccccg gaagagcatc | 960 |
| agaatcggcc ctggccagac cttttacgcc accggcgaca tcatcggcga tatcaggcag | 1020 |
| gcccactgca atatcagcga ggagaagtgg aacaagaccc tgcagcgggt gtccgagaag | 1080 |
| ctgaaggagc acttcccca taagaccatc aagttcgccc ctagcagcgg cggcagactg | 1140 |
| gagatcacca cccacagctt caactgcagg ggcgagttct tctactgcaa taccagcaag | 1200 |

```
ctgttcaaca gcacctacat gcccaacagc accaacaata ccaacaccac catcaccctg    1260
ccctgccgga tcaagcagat catcaatatg tggcaggaag tgggcagagc catgtacgcc    1320
cctcccatcg agggcaacat cacctgcaag tccaacatca ccggcctgct gctgacaaga    1380
gatggcggca gaacgacac caatgacacc gagaccttca gacctggcgg cggagacatg    1440
agggacaact ggcggagcga gctgtacaag tacaaggtgg tggagatcaa gcctctgggc    1500 gtggcccta ccaaggccaa gaggagagtg gtggagaggg agaagagagc cgtgggcatc    1560
ggcgccgtgt ttctgggctt tctgggagcc gccggatcta caatgggagc cgccagcatc    1620
acactgaccg tgcaggccag acagctgctg agcggcatcg tgcagcagca gagcaatctg    1680
ctgagagcca tcgaggccca gcagcacatg ctgcagctga cagtgtgggg catcaagcag    1740
ctgcagacca gagtgctggc catcgagcgc tacctgaagg atcagcagct gctgggcatc    1800
tggggctgta gcggcaagct gatctgtacc accgccgtgc cttggaatag cagctggagc    1860
aacaagagcc aggaggacat ctgggacaac atgacctgga tgcagtggga ccgggagatc    1920
agcaactaca ccgacaccat ctacaggctg ctggaggaca gccagaacca gcaggagaag    1980
aacgagaagg acctgctggc cctggacagc tggaagaacc tgtggaactg gttcgacatc    2040
accaactggc tgtggtacat caagatcttc atcatgattg tgggcggcct gatcggcctg    2100
agaatcatct tcgccgtgct gagcatctga tagcggccgc                          2140
```

<210> SEQ ID NO 16
<211> LENGTH: 705
<212> TYPE: PRT
<213> ORGANISM: Influenza virus

<400> SEQUENCE: 16

```
Met Asp Trp Thr Trp Ile Leu Phe Leu Val Ala Ala Thr Arg Val
1               5                  10                  15

His Ser Arg Val Arg Gly Ile Leu Arg Asn Cys Gln Gln Trp Trp Ile
            20                  25                  30

Trp Gly Ile Leu Gly Phe Trp Met Leu Met Ile Cys Asn Val Met Gly
        35                  40                  45

Asn Leu Trp Val Thr Val Tyr Tyr Gly Val Pro Val Trp Lys Glu Ala
    50                  55                  60

Lys Thr Thr Leu Phe Cys Ala Ser Asp Ala Lys Ala Tyr Glu Thr Glu
65                  70                  75                  80

Val His Asn Val Trp Ala Thr His Ala Cys Val Pro Thr Asp Pro Asn
                85                  90                  95

Pro Gln Glu Met Val Leu Glu Asn Val Thr Glu Asn Phe Asn Met Trp
            100                 105                 110

Lys Asn Asp Met Val Asp Gln Met His Glu Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Arg Asn Asn Val Asn Asn Asn Thr Met Lys Glu Glu
145                 150                 155                 160

Ile Lys Asn Cys Ser Phe Asn Ile Thr Thr Glu Leu Arg Asp Lys Lys
                165                 170                 175

Gln Lys Val Tyr Ala Leu Phe Tyr Arg Leu Asp Ile Val Pro Leu Asn
            180                 185                 190

Glu Lys Asn Asn Ser Asn Asp Tyr Arg Leu Ile Asn Cys Asn Thr Ser
        195                 200                 205
```

```
Ala Ile Thr Gln Ala Cys Pro Lys Val Ser Phe Asp Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Asn Gly
                260                 265                 270

Ser Leu Ala Glu Glu Ile Ile Arg Ser Glu Asn Leu Thr Asn
        275                 280                 285

Asn Ala Lys Thr Ile Ile Val His Leu Asn Glu Ser Val Glu Ile Val
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Ile Ser Glu Glu Lys Trp Asn Lys Thr Leu Gln Arg
                340                 345                 350

Val Ser Glu Lys Leu Lys Glu His Phe Pro Asn Lys Thr Ile Lys Phe
        355                 360                 365

Ala Pro Ser Ser Gly Gly Arg Leu Glu Ile Thr Thr His Ser Phe Asn
370                 375                 380

Cys Arg Gly Glu Phe Phe Tyr Cys Asn Thr Ser Lys Leu Phe Asn Ser
385                 390                 395                 400

Thr Tyr Met Pro Asn Ser Thr Asn Asn Thr Asn Thr Thr Ile Thr Leu
                405                 410                 415

Pro Cys Arg Ile Lys Gln Ile Ile Asn Met Trp Gln Glu Val Gly Arg
                420                 425                 430

Ala Met Tyr Ala Pro Pro Ile Glu Gly Asn Ile Thr Cys Lys Ser Asn
                435                 440                 445

Ile Thr Gly Leu Leu Leu Thr Arg Asp Gly Gly Lys Asn Asp Thr Asn
450                 455                 460

Asp Thr Glu Thr Phe Arg Pro Gly Gly Gly Asp Met Arg Asp Asn Trp
465                 470                 475                 480

Arg Ser Glu Leu Tyr Lys Tyr Lys Val Val Glu Ile Lys Pro Leu Gly
                485                 490                 495

Val Ala Pro Thr Lys Ala Lys Arg Arg Val Val Glu Arg Glu Lys Arg
                500                 505                 510

Ala Val Gly Ile Gly Ala Val Phe Leu Gly Phe Leu Gly Ala Ala Gly
        515                 520                 525

Ser Thr Met Gly Ala Ala Ser Ile Thr Leu Thr Val Gln Ala Arg Gln
        530                 535                 540

Leu Leu Ser Gly Ile Val Gln Gln Ser Asn Leu Leu Arg Ala Ile
545                 550                 555                 560

Glu Ala Gln Gln His Met Leu Gln Leu Thr Val Trp Gly Ile Lys Gln
                565                 570                 575

Leu Gln Thr Arg Val Leu Ala Ile Glu Arg Tyr Leu Lys Asp Gln Gln
                580                 585                 590

Leu Leu Gly Ile Trp Gly Cys Ser Gly Lys Leu Ile Cys Thr Thr Ala
                595                 600                 605

Val Pro Trp Asn Ser Ser Trp Ser Asn Lys Ser Gln Glu Asp Ile Trp
610                 615                 620
```

| | | | | | | | | | | | | |
|---|---|---|---|---|---|---|---|---|---|---|---|---|
|Asp|Asn|Met|Thr|Trp|Met|Gln|Trp|Asp|Arg|Glu|Ile|Ser|Asn|Tyr|Thr|
|625| | | |630| | | |635| | | |640|

| | | | | | | | | | | | |
|---|---|---|---|---|---|---|---|---|---|---|---|
|Asp|Thr|Ile|Tyr|Arg|Leu|Leu|Glu|Asp|Ser|Gln|Asn|Gln|Gln|Glu|Lys|
| | | |645| | | |650| | | |655|

Asn Glu Lys Asp Leu Leu Ala Leu Asp Ser Trp Lys Asn Leu Trp Asn
            660             665             670

Trp Phe Asp Ile Thr Asn Trp Leu Trp Tyr Ile Lys Ile Phe Ile Met
        675             680             685

Ile Val Gly Gly Leu Ile Gly Leu Arg Ile Ile Phe Ala Val Leu Ser
        690             695             700

Ile
705

<210> SEQ ID NO 17
<211> LENGTH: 2089
<212> TYPE: DNA
<213> ORGANISM: Influenza virus

<400> SEQUENCE: 17

```
gggcatcaag cggaattacc agcacctgtg gaagtggggc accatgctgc tgggcatgct      60
gatgacctgc agcgtggccg agaacctgtg ggtgaccgtg tactacggcg tgcctgtgtg     120
gaaggaagcc accaccaccc tgttctgcgc cagcgatgcc aagagctaca gaccgaggc     180
ccacaatatc tgggccaccc acgcctgcgt gcctaccgat cccaaccctc aggagatcga     240
gctggagaac gtgaccgaga acttcaacat gtggaagaac aacatggtgg agcagatgca     300
cgaggacatc atcagcctgt gggaccagag cctgaagcct gcgtgaagc tgacccctct     360
gtgcgtgacc ctgaactgca ccgacggcat gaggaacgac accaacgata ccaacgtgac     420
catggaggag ggcgagatga agaactgcag cttcaacatc accaccgaag tgcgggacaa     480
gaagaagcag gtgcacgccc tgttctacaa gctggacgtg gtgcccatcg acgacaacaa     540
caccaacaac agcaactacc ggctgatcaa ctgcaacacc agcgccatca cccaggcctg     600
ccccaaagtg accttcgagc ccatccccat ccactactgc gcccctgccg gcttcgccat     660
cctgaagtgc aaggataaga agttcaacgg caccggcccc tgcaagaatg tgagcaccgt     720
gcagtgcacc cacggcatca gacccgtggt gtccacccag ctgctgctga acggcagcct     780
ggccgaggag gagatcatca tccggagcga gaacctgacc aacaacgcca agatcatcat     840
tgtgcagctg aacgagagcg tgaccatcaa ttgcacccgg ccctacaaca tacccggaa     900
gcgcatcccc atcggcctgg ccaggcctt ctacaccacc agaggcatca tcggcgacat     960
cagacaggcc cactgcaata tcagcggagc cgagtggaat aagaccctgc agcaggtggc    1020
caagaagctg ggcgacctgc tgaacaagac caccatcatc ttcaagccta gcagcggcgg    1080
cagacctaga atcaccaccc acagcttcaa ttgtggcggc gagttcttct actgcaatac    1140
cagccggctg ttcaacagca cctggagcaa gaacagcacc agcaactcca ccaaggagaa    1200
caacaccatc accctgccct gccggatcaa gcagatcatc aatatgtggc agggagtggg    1260
caaggccatg tacgcccctc ccatcgaggg cctgatcaag tgcagcagca acatcaccgg    1320
cctgctgctg accagagatg gcggagccaa caactcccac aacgagacct tcagacctgg    1380
cggcggagac atgagggaca actggcggag cgagctgtac aagtacaaag tggtgaagat    1440
cgagcccctg ggcgtggccc ccaccagagc caagagaaga gtggtggagc gggagaagag    1500
agccatcgga ctgggcgcca tgttcctggg cttcctggga gccgcggaa gcaccatggg    1560
agccgccagc ctgaccctga ccgtgcaggc cagacagctg ctgagcggca tcgtgcagca    1620
```

```
gcagaacaac ctgctgagag ccattgaggc ccagcagcac ctgctgcagc tgacagtgtg   1680
gggcattaag cagctgcagg ccaggattct ggccgtggag cgctacctga aggatcagca   1740
gctgctggga atctggggct gcagcggcaa gcacatctgc accaccaccg tgccttggaa   1800
tagcagctgg agcaacaaga gcctggacga gatctggaac aacatgacct ggatggagtg   1860
ggagagggag atcgacaact acaccggcct gatctacagc ctgatcgagg agagccagac   1920
ccagcaggag aagaacgagc aggagctgct ggagctggac aagtgggcca gcctgtggaa   1980
ctggttcagc atcacccagt ggctgtggta catcaagatc ttcatcatga ttgtgggcgg   2040
cctgatcggc ctgagaatcg tgttcgccgt gctgagcctg tgactcgag             2089
```

<210> SEQ ID NO 18
<211> LENGTH: 714
<212> TYPE: PRT
<213> ORGANISM: Influenza virus

<400> SEQUENCE: 18

```
Met Asp Trp Thr Trp Ile Leu Phe Leu Val Ala Ala Thr Arg Val
1               5                   10                  15

His Ser Arg Val Arg Gly Ile Lys Arg Asn Tyr Gln His Leu Trp Lys
            20                  25                  30

Trp Gly Thr Met Leu Leu Gly Met Leu Met Thr Cys Ser Val Ala Glu
        35                  40                  45

Asn Leu Trp Val Thr Val Tyr Tyr Gly Val Pro Val Trp Lys Glu Ala
    50                  55                  60

Thr Thr Thr Leu Phe Cys Ala Ser Asp Ala Lys Ser Tyr Lys Thr Glu
65                  70                  75                  80

Ala His Asn Ile Trp Ala Thr His Ala Cys Val Pro Thr Asp Pro Asn
                85                  90                  95

Pro Gln Glu Ile Glu Leu Glu Asn Val Thr Glu Asn Phe Asn Met Trp
            100                 105                 110

Lys Asn Asn Met Val Glu Gln Met His Glu Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Thr Asp Gly Met Arg Asn Asp Thr Asn Asp Thr Asn Val
145                 150                 155                 160

Thr Met Glu Glu Gly Glu Met Lys Asn Cys Ser Phe Asn Ile Thr Thr
                165                 170                 175

Glu Val Arg Asp Lys Lys Lys Gln Val His Ala Leu Phe Tyr Lys Leu
            180                 185                 190

Asp Val Val Pro Ile Asp Asp Asn Asn Thr Asn Asn Ser Asn Tyr Arg
        195                 200                 205

Leu Ile Asn Cys Asn Thr Ser Ala Ile Thr Gln Ala Cys Pro Lys Val
    210                 215                 220

Thr Phe Glu Pro Ile Pro Ile His Tyr Cys Ala Pro Ala Gly Phe Ala
225                 230                 235                 240

Ile Leu Lys Cys Lys Asp Lys Lys Phe Asn Gly Thr Gly Pro Cys Lys
                245                 250                 255

Asn Val Ser Thr Val Gln Cys Thr His Gly Ile Arg Pro Val Val Ser
            260                 265                 270

Thr Gln Leu Leu Leu Asn Gly Ser Leu Ala Glu Glu Ile Ile Ile
        275                 280                 285
```

-continued

Arg Ser Glu Asn Leu Thr Asn Asn Ala Lys Ile Ile Ile Val Gln Leu
290                 295                 300

Asn Glu Ser Val Thr Ile Asn Cys Thr Arg Pro Tyr Asn Asn Thr Arg
305                 310                 315                 320

Lys Arg Ile Pro Ile Gly Leu Gly Gln Ala Phe Tyr Thr Thr Arg Gly
                325                 330                 335

Ile Ile Gly Asp Ile Arg Gln Ala His Cys Asn Ile Ser Gly Ala Glu
                340                 345                 350

Trp Asn Lys Thr Leu Gln Gln Val Ala Lys Lys Leu Gly Asp Leu Leu
            355                 360                 365

Asn Lys Thr Thr Ile Ile Phe Lys Pro Ser Ser Gly Gly Arg Pro Arg
370                 375                 380

Ile Thr Thr His Ser Phe Asn Cys Gly Gly Glu Phe Phe Tyr Cys Asn
385                 390                 395                 400

Thr Ser Arg Leu Phe Asn Ser Thr Trp Ser Lys Asn Ser Thr Ser Asn
                405                 410                 415

Ser Thr Lys Glu Asn Asn Thr Ile Thr Leu Pro Cys Arg Ile Lys Gln
            420                 425                 430

Ile Ile Asn Met Trp Gln Gly Val Gly Lys Ala Met Tyr Ala Pro Pro
                435                 440                 445

Ile Glu Gly Leu Ile Lys Cys Ser Ser Asn Ile Thr Gly Leu Leu Leu
450                 455                 460

Thr Arg Asp Gly Gly Ala Asn Asn Ser His Asn Glu Thr Phe Arg Pro
465                 470                 475                 480

Gly Gly Gly Asp Met Arg Asp Asn Trp Arg Ser Glu Leu Tyr Lys Tyr
                485                 490                 495

Lys Val Val Lys Ile Glu Pro Leu Gly Val Ala Pro Thr Arg Ala Lys
            500                 505                 510

Arg Arg Val Val Glu Arg Glu Lys Arg Ala Ile Gly Leu Gly Ala Met
                515                 520                 525

Phe Leu Gly Phe Leu Gly Ala Ala Gly Ser Thr Met Gly Ala Ala Ser
530                 535                 540

Leu Thr Leu Thr Val Gln Ala Arg Gln Leu Leu Ser Gly Ile Val Gln
545                 550                 555                 560

Gln Gln Asn Asn Leu Leu Arg Ala Ile Glu Ala Gln Gln His Leu Leu
                565                 570                 575

Gln Leu Thr Val Trp Gly Ile Lys Gln Leu Gln Ala Arg Ile Leu Ala
            580                 585                 590

Val Glu Arg Tyr Leu Lys Asp Gln Gln Leu Leu Gly Ile Trp Gly Cys
                595                 600                 605

Ser Gly Lys His Ile Cys Thr Thr Thr Val Pro Trp Asn Ser Ser Trp
610                 615                 620

Ser Asn Lys Ser Leu Asp Glu Ile Trp Asn Asn Met Thr Trp Met Glu
625                 630                 635                 640

Trp Glu Arg Glu Ile Asp Asn Tyr Thr Gly Leu Ile Tyr Ser Leu Ile
                645                 650                 655

Glu Glu Ser Gln Thr Gln Gln Glu Lys Asn Glu Gln Glu Leu Leu Glu
            660                 665                 670

Leu Asp Lys Trp Ala Ser Leu Trp Asn Trp Phe Ser Ile Thr Gln Trp
                675                 680                 685

Leu Trp Tyr Ile Lys Ile Phe Ile Met Ile Val Gly Gly Leu Ile Gly
690                 695                 700

Leu Arg Ile Val Phe Ala Val Leu Ser Leu

<210> SEQ ID NO 19
<211> LENGTH: 1049
<212> TYPE: DNA
<213> ORGANISM: Influenza virus

<400> SEQUENCE: 19

```
ggatccgcca ccatggactg gacctggatt ctgttcctgg tggccgctgc caccagagtg      60
cacagcagca agagaagcgt ggtgggttgg cctacagtgc gggagaggat gagaagagcc     120
gagcctgccg ccgatggagt gggcgccgtg tctagagatc tggagaagca cggcgccatc     180
accagcagca ataccgccgc caacaatgcc gactgcgcct ggctggaggc ccaggaggag     240
gaggaagtgg gcttccctgt gagagcccag gtggccctga gccatgac ctacaaggcc      300
gccgtggatc tgagccactt cctgaaggag aagggcggcc tggagggcct gatctacagc     360
cagaagcggc aggacatcct ggatctgtgg gtgtaccaca cccagggcta cttccccgac     420
tggcagaatt acacccctgg ccctggcatc agatacccct tgaccttcgg ctggtgcttc     480
aagctggtgc ctgtggagcc tgagaaagtg gaggaggcca acgagggcga gaacaattct     540
gccgcccacc ctatgagcct gcacggcatg acgatcccg agagggaagt gctggtgtgg      600
aagttcgaca gcaggctggc cttccaccac atggccagag agctgcaccc cgagtactac     660
aaggactgcc ggggcaggaa gagaagaagc gccggcagaa gcggcgacag cgacgaggag     720
ctgctgaaaa cagtgcggct gatcaagttc ctgtaccaga gcaaccctcc tcccagcccc     780
gagggcacca gacaggcccg agaaaccgg aggaggcgt ggagagagag cagcggcag      840
atcagaagca tcagcgagtg gattctgagc acctacctgg gcagacccgc cgagcccgtg     900
ccccctgcagc tgccccccct ggagagactg accctggact gcaacgagga ctgcggcacc     960
agcggcaccc agggagtggg cagcccccag atcctggtgg agagccctgc cgtgctggag    1020
agcggcacca aggagtgatg agcggccgc                                     1049
```

<210> SEQ ID NO 20
<211> LENGTH: 341
<212> TYPE: PRT
<213> ORGANISM: Influenza virus

<400> SEQUENCE: 20

```
Met Asp Trp Thr Trp Ile Leu Phe Leu Val Ala Ala Thr Arg Val
1               5                   10                  15

His Ser Ser Lys Arg Ser Val Val Gly Trp Pro Thr Val Arg Glu Arg
            20                  25                  30

Met Arg Arg Ala Glu Pro Ala Ala Asp Gly Val Gly Ala Val Ser Arg
        35                  40                  45

Asp Leu Glu Lys His Gly Ala Ile Thr Ser Ser Asn Thr Ala Ala Asn
    50                  55                  60

Asn Ala Asp Cys Ala Trp Leu Glu Ala Gln Glu Glu Glu Val Gly
65                  70                  75                  80

Phe Pro Val Arg Ala Gln Val Ala Leu Arg Ala Met Thr Tyr Lys Ala
                85                  90                  95

Ala Val Asp Leu Ser His Phe Leu Lys Glu Lys Gly Gly Leu Glu Gly
            100                 105                 110

Leu Ile Tyr Ser Gln Lys Arg Gln Asp Ile Leu Asp Leu Trp Val Tyr
        115                 120                 125

His Thr Gln Gly Tyr Phe Pro Asp Trp Gln Asn Tyr Thr Pro Gly Pro
```

```
                    130                 135                 140
Gly Ile Arg Tyr Pro Leu Thr Phe Gly Trp Cys Phe Lys Leu Val Pro
145                 150                 155                 160

Val Glu Pro Glu Lys Val Glu Glu Ala Asn Glu Gly Glu Asn Asn Ser
                165                 170                 175

Ala Ala His Pro Met Ser Leu His Gly Met Asp Asp Pro Glu Arg Glu
                180                 185                 190

Val Leu Val Trp Lys Phe Asp Ser Arg Leu Ala Phe His His Met Ala
            195                 200                 205

Arg Glu Leu His Pro Glu Tyr Tyr Lys Asp Cys Arg Gly Arg Lys Arg
        210                 215                 220

Arg Ser Ala Gly Arg Ser Gly Asp Ser Asp Glu Glu Leu Leu Lys Thr
225                 230                 235                 240

Val Arg Leu Ile Lys Phe Leu Tyr Gln Ser Asn Pro Pro Pro Ser Pro
                245                 250                 255

Glu Gly Thr Arg Gln Ala Arg Arg Asn Arg Arg Arg Trp Arg Glu
            260                 265                 270

Arg Gln Arg Gln Ile Arg Ser Ile Ser Glu Trp Ile Leu Ser Thr Tyr
        275                 280                 285

Leu Gly Arg Pro Ala Glu Pro Val Pro Leu Gln Leu Pro Pro Leu Glu
    290                 295                 300

Arg Leu Thr Leu Asp Cys Asn Glu Asp Cys Gly Thr Ser Gly Thr Gln
305                 310                 315                 320

Gly Val Gly Ser Pro Gln Ile Leu Val Glu Ser Pro Ala Val Leu Glu
                325                 330                 335

Ser Gly Thr Lys Glu
            340

<210> SEQ ID NO 21
<211> LENGTH: 1863
<212> TYPE: DNA
<213> ORGANISM: Influenza virus

<400> SEQUENCE: 21
ggatccgcca ccatggactg gacctggatt ctgtttctgg tcgccgccgc cacaagagtg    60
cacagcggcg ccagagccag cgtgctgtcc ggcggcaagc tggacgccct ggagaagatc   120
agactgaggc ctggcggcaa gaagaagtac cggctgaagc accttgtgtg ggccagcaga   180
gagctggaga gattcgccct gaatcctggc ctgctggaga ccagcgaggg ctgtaagcag   240
atcatcggcc agctgcagcc cgccctgcag accggcagcg aggagctgag aagcctgtac   300
aacaccgtgg ccaccctgta ctgcgtgcac gagaagatcg aggtgaagga caccaaggag   360
gccctggaca gatcgagga ggagcagaac aagagcaagc agaaggccca gcaggccgcc   420
gccgacaccg gcaacagcag ccaggtgtcc cagaactacc ccatcgtgca gaatctgcag   480
ggccagatgt gcaccaggc catcagcccc agaaccctga tgcctgggt gaaggtgatc   540 gaggagaagg ccttcagccc tgaggtgatc cctatgttca gcgccctgag cgagggcgcc   600
acacctcagg acctgaacac catgctgaac acagtggggg gccaccaggc cgccatgcag   660
atgctgaagg ataccatcaa cgaggaggcc gccgagtggg acagactgca ccccgtgcac   720
gccggaccta tcgccctgg ccagatgaga gagcccagag cagcgacat cgccggcacc   780 acctccaccc tgcaagagca gatcggctgg atgaccagca cccccccat ccctgtgggc   840 gacatctaca gcggtggat catcctgggc ctgaacaaga ttgtgaggat gtacagcccc   900
```

-continued

```
gtgtccatcc tggatatcag gcagggcccc aaggagccct tcagagacta cgtggaccgg    960
ttcttcaaga ccctgagagc cgagcaggcc agccaggacg tgaagaactg gatgaccgag   1020
accctgctgg tgcagaacgc caaccccgac tgtaagacca tcctgagagc cctgggccct   1080
ggcgccaccc tggaggagat gatgaccgcc tgccagggag tgggcggacc cggccacaag   1140
gccagagtgc tggccgaggc catgagccag gccaccaaca gcaacatcat gatgcagcgg   1200
ggcaacttca gaggcccag gaggatcgtg aagtgcttca actgtggcaa ggagggccac   1260
atcgccagaa actgtagggc ccccaggaag aagggctgct ggaagtgtgg caaagagggg   1320
caccagatga aggactgtac cgagcggcag gccaatttcc tggggaagat ctggcccagc   1380
cacaagggca gacccggcaa tttcctgcag agcagacctg agcccaccgc ccctcccgcc   1440
gagagcttcg gcttcggcga ggagatcacc cccagcccca gcaggagcc aaggacaga    1500
gagctgtacc ctctggccag cctgaagagc ctgttcggca cgatcccct gagccagtac   1560
ccctacgacg tgcccgatta cgcctgagaa ttcgtaagta agtgtcatat gggagagctc   1620
gactagactg gacagccaat gacgggtaag agagtgacat ttctcactaa cctaagacag   1680
gagggccgtc aaagctactg cctaatccaa tgacgggtaa tagtgacaag aaatgtatca   1740
ctccaaccta agacaggcgc agcctccgag ggatgtgtct tttgttttt ataattaaaa   1800
agggtgacat gtccggagcc gtgctgcccg atgatgtct tggcctctgt ttgctgcggc    1860
cgc                                                                 1863
```

<210> SEQ ID NO 22
<211> LENGTH: 524
<212> TYPE: PRT
<213> ORGANISM: Influenza virus

<400> SEQUENCE: 22

```
Met Asp Trp Thr Trp Ile Leu Phe Leu Val Ala Ala Thr Arg Val
1               5                   10                  15

His Ser Gly Ala Arg Ala Ser Val Leu Ser Gly Gly Lys Leu Asp Ala
            20                  25                  30

Trp Glu Lys Ile Arg Leu Arg Pro Gly Gly Lys Lys Lys Tyr Arg Leu
        35                  40                  45

Lys His Leu Val Trp Ala Ser Arg Glu Leu Glu Arg Phe Ala Leu Asn
    50                  55                  60

Pro Gly Leu Leu Glu Thr Ser Glu Gly Cys Lys Gln Ile Ile Gly Gln
65                  70                  75                  80

Leu Gln Pro Ala Leu Gln Thr Gly Ser Glu Glu Leu Arg Ser Leu Tyr
                85                  90                  95

Asn Thr Val Ala Thr Leu Tyr Cys Val His Glu Lys Ile Glu Val Lys
            100                 105                 110

Asp Thr Lys Glu Ala Leu Asp Lys Ile Glu Glu Glu Gln Asn Lys Ser
        115                 120                 125

Lys Gln Lys Ala Gln Gln Ala Ala Ala Asp Thr Gly Asn Ser Ser Gln
    130                 135                 140

Val Ser Gln Asn Tyr Pro Ile Val Gln Asn Leu Gln Gly Gln Met Val
145                 150                 155                 160

His Gln Ala Ile Ser Pro Arg Thr Leu Asn Ala Trp Val Lys Val Ile
                165                 170                 175

Glu Glu Lys Ala Phe Ser Pro Glu Val Ile Pro Met Phe Ser Ala Leu
            180                 185                 190

Ser Glu Gly Ala Thr Pro Gln Asp Leu Asn Thr Met Leu Asn Thr Val
```

```
                    195                 200                 205
Gly Gly His Gln Ala Ala Met Gln Met Leu Lys Asp Thr Ile Asn Glu
            210                 215                 220
Glu Ala Ala Glu Trp Asp Arg Leu His Pro Val His Ala Gly Pro Ile
225                 230                 235                 240
Ala Pro Gly Gln Met Arg Glu Pro Arg Gly Ser Asp Ile Ala Gly Thr
                245                 250                 255
Thr Ser Thr Leu Gln Glu Gln Ile Gly Trp Met Thr Ser Asn Pro Pro
            260                 265                 270
Ile Pro Val Gly Asp Ile Tyr Lys Arg Trp Ile Ile Leu Gly Leu Asn
                275                 280                 285
Lys Ile Val Arg Met Tyr Ser Pro Val Ser Ile Leu Asp Ile Arg Gln
290                 295                 300
Gly Pro Lys Glu Pro Phe Arg Asp Tyr Val Asp Arg Phe Phe Lys Thr
305                 310                 315                 320
Leu Arg Ala Glu Gln Ala Ser Gln Asp Val Lys Asn Trp Met Thr Glu
                325                 330                 335
Thr Leu Leu Val Gln Asn Ala Asn Pro Asp Cys Lys Thr Ile Leu Arg
            340                 345                 350
Ala Leu Gly Pro Gly Ala Thr Leu Glu Glu Met Met Thr Ala Cys Gln
                355                 360                 365
Gly Val Gly Gly Pro Gly His Lys Ala Arg Val Leu Ala Glu Ala Met
370                 375                 380
Ser Gln Ala Thr Asn Ser Asn Ile Met Met Gln Arg Gly Asn Phe Arg
385                 390                 395                 400
Gly Pro Arg Arg Ile Val Lys Cys Phe Asn Cys Gly Lys Glu Gly His
                405                 410                 415
Ile Ala Arg Asn Cys Arg Ala Pro Arg Lys Lys Gly Cys Trp Lys Cys
            420                 425                 430
Gly Lys Glu Gly His Gln Met Lys Asp Cys Thr Glu Arg Gln Ala Asn
            435                 440                 445
Phe Leu Gly Lys Ile Trp Pro Ser His Lys Gly Arg Pro Gly Asn Phe
450                 455                 460
Leu Gln Ser Arg Pro Glu Pro Thr Ala Pro Pro Ala Glu Ser Phe Gly
465                 470                 475                 480
Phe Gly Glu Glu Ile Thr Pro Ser Pro Lys Gln Glu Pro Lys Asp Arg
                485                 490                 495
Glu Leu Tyr Pro Leu Ala Ser Leu Lys Ser Leu Phe Gly Asn Asp Pro
            500                 505                 510
Leu Ser Gln Tyr Pro Tyr Asp Val Pro Asp Tyr Ala
            515                 520

<210> SEQ ID NO 23
<211> LENGTH: 692
<212> TYPE: PRT
<213> ORGANISM: Influenza virus

<400> SEQUENCE: 23

Ser Arg Val Met Gly Ile Gln Arg Asn Cys Gln His Leu Trp Arg Trp
1               5                   10                  15
Gly Thr Met Ile Leu Gly Met Ile Ile Ile Cys Ser Ala Ala Glu Asn
            20                  25                  30
Leu Trp Val Thr Val Tyr Tyr Gly Val Pro Val Trp Lys Asp Ala Glu
        35                  40                  45
```

-continued

```
Thr Thr Leu Phe Cys Ala Ser Asp Ala Lys Ala Tyr Asp Thr Glu Val
     50                  55                  60
His Asn Val Trp Ala Thr His Ala Cys Val Pro Thr Asp Pro Asn Pro
 65                  70                  75                  80
Gln Glu Ile Asn Leu Glu Asn Val Thr Glu Glu Phe Asn Met Trp Lys
                 85                  90                  95
Asn Asn Met Val Glu Gln Met His Thr Asp Ile Ile Ser Leu Trp Asp
             100                 105                 110
Gln Ser Leu Lys Pro Cys Val Lys Leu Thr Pro Leu Cys Val Thr Leu
         115                 120                 125
Asn Cys Ser Asn Val Asn Val Thr Thr Asn Ile Met Lys Gly Glu Ile
130                 135                 140
Lys Asn Cys Ser Phe Asn Met Thr Thr Glu Leu Arg Asp Lys Lys Gln
145                 150                 155                 160
Lys Val Tyr Ser Leu Phe Tyr Lys Leu Asp Val Val Gln Ile Asn Lys
                 165                 170                 175
Ser Asn Ser Ser Ser Gln Tyr Arg Leu Ile Asn Cys Asn Thr Ser Ala
             180                 185                 190
Ile Thr Gln Ala Cys Pro Lys Val Ser Phe Glu Pro Ile Pro Ile His
         195                 200                 205
Tyr Cys Ala Pro Ala Gly Phe Ala Ile Leu Lys Cys Lys Asp Lys Glu
210                 215                 220
Phe Asn Gly Thr Gly Pro Cys Lys Asn Val Ser Thr Val Gln Cys Thr
225                 230                 235                 240
His Gly Ile Lys Pro Val Val Ser Thr Gln Leu Leu Leu Asn Gly Ser
                 245                 250                 255
Leu Ala Glu Glu Glu Val Met Ile Arg Ser Glu Asn Ile Thr Asn Asn
             260                 265                 270
Ala Lys Asn Ile Ile Val Gln Leu Thr Lys Pro Val Lys Ile Asn Cys
         275                 280                 285
Thr Arg Pro Asn Asn Asn Thr Arg Lys Ser Ile Arg Ile Gly Pro Gly
290                 295                 300
Gln Ala Phe Tyr Ala Thr Gly Asp Ile Ile Gly Asp Ile Arg Gln Ala
305                 310                 315                 320
His Cys Asn Val Ser Arg Thr Glu Trp Asn Glu Thr Leu Gln Lys Val
                 325                 330                 335
Ala Lys Gln Leu Arg Lys Tyr Phe Asn Asn Lys Thr Ile Ile Phe Thr
             340                 345                 350
Asn Ser Ser Gly Gly Arg Leu Arg Ile Thr Thr His Ser Phe Asn Cys
         355                 360                 365
Gly Gly Glu Phe Phe Tyr Cys Asn Thr Ser Gly Leu Phe Asn Ser Thr
370                 375                 380
Trp Asn Gly Asn Gly Thr Lys Lys Asn Ser Thr Glu Ser Asn Asp
385                 390                 395                 400
Thr Ile Thr Leu Pro Cys Arg Ile Lys Gln Ile Ile Asn Met Trp Gln
                 405                 410                 415
Arg Val Gly Gln Ala Met Tyr Ala Pro Pro Ile Gln Gly Val Ile Arg
             420                 425                 430
Cys Glu Ser Asn Ile Thr Gly Leu Leu Leu Thr Arg Asp Gly Gly Asp
         435                 440                 445
Asn Asn Ser Lys Asn Glu Thr Phe Arg Pro Gly Gly Gly Asp Met Arg
450                 455                 460
Asp Asn Trp Arg Ser Glu Leu Tyr Lys Tyr Lys Val Val Lys Ile Glu
```

```
                465                 470                 475                 480
    Pro Leu Gly Val Ala Pro Thr Lys Ala Lys Arg Arg Val Val Glu Arg
                    485                 490                 495

Glu Lys Arg Ala Val Gly Ile Gly Ala Val Phe Leu Gly Phe Leu Gly
                500                 505                 510

Ala Ala Gly Ser Thr Met Gly Ala Ser Ile Thr Leu Thr Val Gln
                515                 520                 525

Ala Arg Gln Leu Leu Ser Gly Ile Val Gln Gln Ser Asn Leu Leu
                530                 535                 540

Arg Ala Ile Glu Ala Gln Gln His Leu Leu Lys Leu Thr Val Trp Gly
    545                 550                 555                 560

Ile Lys Gln Leu Gln Ala Arg Val Leu Ala Val Glu Arg Tyr Leu Lys
                    565                 570                 575

Asp Gln Gln Leu Leu Gly Ile Trp Gly Cys Ser Gly Lys Leu Ile Cys
                    580                 585                 590

Thr Thr Asn Val Pro Trp Asn Ser Ser Trp Ser Asn Lys Ser Gln Ser
                    595                 600                 605

Glu Ile Trp Asp Asn Met Thr Trp Leu Gln Trp Asp Lys Glu Ile Ser
                    610                 615                 620

Asn Tyr Thr Asp Ile Ile Tyr Asn Leu Ile Glu Ser Gln Asn Gln
    625                 630                 635                 640

Gln Glu Lys Asn Glu Gln Asp Leu Leu Ala Leu Asp Lys Trp Ala Asn
                    645                 650                 655

Leu Trp Asn Trp Phe Asp Ile Ser Asn Trp Leu Trp Tyr Ile Lys Ile
                    660                 665                 670

Phe Ile Met Ile Val Gly Gly Leu Ile Gly Leu Arg Ile Val Phe Ala
                675                 680                 685

Val Leu Ser Val
                690

<210> SEQ ID NO 24
<211> LENGTH: 697
<212> TYPE: PRT
<213> ORGANISM: Influenza virus

<400> SEQUENCE: 24

Arg Val Lys Gly Ile Arg Lys Asn Tyr Gln His Leu Trp Arg Trp Gly
    1               5                   10                  15

Thr Met Leu Leu Gly Met Leu Met Ile Cys Ser Ala Ala Glu Lys Leu
                    20                  25                  30

Trp Val Thr Val Tyr Tyr Gly Val Pro Val Trp Lys Glu Ala Thr Thr
                35                  40                  45

Thr Leu Phe Cys Ala Ser Asp Ala Lys Ala Tyr Asp Thr Glu Val His
            50                  55                  60

Asn Val Trp Ala Thr His Ala Cys Val Pro Thr Asp Pro Asn Pro Gln
    65                  70                  75                  80

Glu Val Val Leu Glu Asn Val Thr Glu Asn Phe Asn Met Trp Lys Asn
                    85                  90                  95

Asn Met Val Glu Gln Met His Glu Asp Ile Ile Ser Leu Trp Asp Gln
                    100                 105                 110

Ser Leu Lys Pro Cys Val Lys Leu Thr Pro Leu Cys Val Thr Leu Asn
                115                 120                 125

Cys Thr Asp Leu Ser Gly Glu Lys Met Glu Lys Gly Glu Ile Lys Asn
            130                 135                 140
```

-continued

```
Cys Ser Phe Asn Ile Thr Thr Ser Ile Arg Asp Lys Val Gln Lys Glu
145                 150                 155                 160

Tyr Ala Leu Phe Tyr Lys Leu Asp Val Val Pro Ile Asp Asn Asp Asn
                165                 170                 175

Thr Ser Tyr Arg Leu Ile Ser Cys Asn Thr Ser Val Ile Thr Gln Ala
            180                 185                 190

Cys Pro Lys Val Ser Phe Glu Pro Ile Pro Ile His Tyr Cys Ala Pro
        195                 200                 205

Ala Gly Phe Ala Ile Leu Lys Cys Asn Asp Lys Lys Phe Asn Gly Thr
    210                 215                 220

Gly Pro Cys Thr Asn Val Ser Thr Val Gln Cys Thr His Gly Ile Arg
225                 230                 235                 240

Pro Val Val Ser Thr Gln Leu Leu Leu Asn Gly Ser Leu Ala Glu Glu
                245                 250                 255

Glu Val Val Ile Arg Ser Glu Asn Phe Thr Asn Asn Ala Lys Thr Ile
                260                 265                 270

Ile Val Gln Leu Asn Glu Ser Val Glu Ile Asn Cys Thr Arg Pro Asn
            275                 280                 285

Asn Asn Thr Arg Lys Ser Ile His Ile Gly Pro Gly Gln Ala Phe Tyr
        290                 295                 300

Thr Thr Gly Glu Ile Ile Gly Asp Ile Arg Gln Ala His Cys Asn Ile
305                 310                 315                 320

Ser Arg Ala Lys Trp Asn Asn Thr Leu Lys Gln Ile Val Lys Lys Leu
                325                 330                 335

Arg Glu Gln Phe Gly Asn Lys Thr Ile Val Phe Asn Gln Ser Ser Gly
                340                 345                 350

Gly Arg Pro Arg Ile Val Met His Ser Phe Asn Cys Gly Gly Glu Phe
            355                 360                 365

Phe Tyr Cys Asn Thr Thr Gln Leu Phe Asn Ser Thr Trp Asn Val Asn
        370                 375                 380

Gly Thr Trp Asn Asn Thr Glu Gly Asn Asp Thr Ile Thr Leu Pro
385                 390                 395                 400

Cys Arg Ile Lys Gln Ile Ile Asn Met Trp Gln Glu Val Gly Lys Ala
                405                 410                 415

Met Tyr Ala Pro Pro Ile Arg Gly Gln Ile Arg Cys Ser Ser Asn Ile
                420                 425                 430

Thr Gly Leu Leu Leu Thr Arg Asp Gly Gly Asn Asn Thr Asn Glu
            435                 440                 445

Thr Glu Ile Phe Arg Pro Gly Gly Gly Asp Met Arg Asp Asn Trp Arg
        450                 455                 460

Ser Glu Leu Tyr Lys Tyr Lys Val Val Lys Ile Glu Pro Leu Gly Val
465                 470                 475                 480

Ala Pro Thr Lys Ala Lys Arg Arg Val Gln Arg Glu Lys Arg Ala
                485                 490                 495

Val Gly Ile Gly Ala Met Phe Leu Gly Phe Leu Gly Ala Ala Gly Ser
            500                 505                 510

Thr Met Gly Ala Ala Ser Met Thr Leu Thr Val Gln Ala Arg Gln Leu
        515                 520                 525

Leu Ser Gly Ile Val Gln Gln Asn Asn Leu Leu Arg Ala Ile Glu
    530                 535                 540

Ala Gln Gln His Leu Leu Gln Leu Thr Val Trp Gly Ile Lys Gln Leu
545                 550                 555                 560

Gln Ala Arg Val Leu Ala Val Glu Arg Tyr Leu Lys Asp Gln Gln Leu
```

```
              565                 570                 575
Leu Gly Ile Trp Gly Cys Ser Gly Lys Leu Ile Cys Thr Thr Thr Val
            580                 585                 590

Pro Trp Asn Ala Ser Trp Ser Asn Lys Ser Leu Asp Glu Ile Trp Asp
            595                 600                 605

Asn Met Thr Trp Met Glu Trp Glu Arg Glu Ile Asp Asn Tyr Thr Ser
610                 615                 620

Leu Ile Tyr Thr Leu Ile Glu Glu Ser Gln Asn Gln Gln Glu Lys Asn
625                 630                 635                 640

Glu Gln Glu Leu Leu Glu Leu Asp Lys Trp Ala Ser Leu Trp Asn Trp
                645                 650                 655

Phe Asp Ile Thr Asn Trp Leu Trp Tyr Ile Lys Ile Phe Ile Met Ile
                660                 665                 670

Val Gly Gly Leu Ile Gly Leu Arg Ile Val Phe Ala Val Leu Ser Ile
            675                 680                 685

Tyr Pro Tyr Asp Val Pro Asp Tyr Ala
            690                 695

<210> SEQ ID NO 25
<211> LENGTH: 687
<212> TYPE: PRT
<213> ORGANISM: Influenza virus

<400> SEQUENCE: 25

Arg Val Arg Gly Ile Leu Arg Asn Cys Gln Gln Trp Trp Ile Trp Gly
1               5                   10                  15

Ile Leu Gly Phe Trp Met Leu Met Ile Cys Asn Val Met Gly Asn Leu
                20                  25                  30

Trp Val Thr Val Tyr Tyr Gly Val Pro Val Trp Lys Glu Ala Lys Thr
            35                  40                  45

Thr Leu Phe Cys Ala Ser Asp Ala Lys Ala Tyr Glu Thr Glu Val His
        50                  55                  60

Asn Val Trp Ala Thr His Ala Cys Val Pro Thr Asp Pro Asn Pro Gln
65                  70                  75                  80

Glu Met Val Leu Glu Asn Val Thr Glu Asn Phe Asn Met Trp Lys Asn
                85                  90                  95

Asp Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Arg Asn Asn Val Asn Asn Asn Thr Met Lys Glu Glu Ile Lys
    130                 135                 140

Asn Cys Ser Phe Asn Ile Thr Thr Glu Leu Arg Asp Lys Lys Gln Lys
145                 150                 155                 160

Val Tyr Ala Leu Phe Tyr Arg Leu Asp Ile Val Pro Leu Asn Glu Lys
                165                 170                 175

Asn Asn Ser Asn Asp Tyr Arg Leu Ile Asn Cys Asn Thr Ser Ala Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Asn Gly Thr Gly Pro Cys Asn Asn Val Ser Thr Val Gln Cys Thr His
225                 230                 235                 240
```

```
Gly Ile Lys Pro Val Val Ser Thr Gln Leu Leu Asn Gly Ser Leu
            245                 250                 255

Ala Glu Glu Ile Ile Ile Arg Ser Glu Asn Leu Thr Asn Asn Ala
        260                 265                 270

Lys Thr Ile Ile Val His Leu Asn Glu Ser Val Glu Ile Val Cys Thr
        275                 280                 285

Arg Pro Asn Asn Asn Thr Arg Lys Ser Ile Arg Ile Gly Pro Gly Gln
290                 295                 300

Thr Phe Tyr Ala Thr Gly Asp Ile Ile Gly Asp Ile Arg Gln Ala His
305                 310                 315                 320

Cys Asn Ile Ser Glu Glu Lys Trp Asn Lys Thr Leu Gln Arg Val Ser
            325                 330                 335

Glu Lys Leu Lys Glu His Phe Pro Asn Lys Thr Ile Lys Phe Ala Pro
        340                 345                 350

Ser Ser Gly Gly Arg Leu Glu Ile Thr Thr His Ser Phe Asn Cys Arg
        355                 360                 365

Gly Glu Phe Phe Tyr Cys Asn Thr Ser Lys Leu Phe Asn Ser Thr Tyr
        370                 375                 380

Met Pro Asn Ser Thr Asn Asn Thr Asn Thr Thr Ile Thr Leu Pro Cys
385                 390                 395                 400

Arg Ile Lys Gln Ile Ile Asn Met Trp Gln Glu Val Gly Arg Ala Met
            405                 410                 415

Tyr Ala Pro Pro Ile Glu Gly Asn Ile Thr Cys Lys Ser Asn Ile Thr
        420                 425                 430

Gly Leu Leu Leu Thr Arg Asp Gly Gly Lys Asn Asp Thr Asn Asp Thr
        435                 440                 445

Glu Thr Phe Arg Pro Gly Gly Gly Asp Met Arg Asp Asn Trp Arg Ser
450                 455                 460

Glu Leu Tyr Lys Tyr Lys Val Val Glu Ile Lys Pro Leu Gly Val Ala
465                 470                 475                 480

Pro Thr Lys Ala Lys Arg Arg Val Val Glu Arg Glu Lys Arg Ala Val
            485                 490                 495

Gly Ile Gly Ala Val Phe Leu Gly Phe Leu Gly Ala Ala Gly Ser Thr
        500                 505                 510

Met Gly Ala Ala Ser Ile Thr Leu Thr Val Gln Ala Arg Gln Leu Leu
        515                 520                 525

Ser Gly Ile Val Gln Gln Gln Ser Asn Leu Leu Arg Ala Ile Glu Ala
        530                 535                 540

Gln Gln His Met Leu Gln Leu Thr Val Trp Gly Ile Lys Gln Leu Gln
545                 550                 555                 560

Thr Arg Val Leu Ala Ile Glu Arg Tyr Leu Lys Asp Gln Gln Leu Leu
            565                 570                 575

Gly Ile Trp Gly Cys Ser Gly Lys Leu Ile Cys Thr Thr Ala Val Pro
        580                 585                 590

Trp Asn Ser Ser Trp Ser Asn Lys Ser Gln Glu Asp Ile Trp Asp Asn
        595                 600                 605

Met Thr Trp Met Gln Trp Asp Arg Glu Ile Ser Asn Tyr Thr Asp Thr
610                 615                 620

Ile Tyr Arg Leu Leu Glu Asp Ser Gln Asn Gln Glu Lys Asn Glu
625                 630                 635                 640

Lys Asp Leu Leu Ala Leu Asp Ser Trp Lys Asn Leu Trp Asn Trp Phe
            645                 650                 655

Asp Ile Thr Asn Trp Leu Trp Tyr Ile Lys Ile Phe Ile Met Ile Val
```

```
                660                 665                 670
Gly Gly Leu Ile Gly Leu Arg Ile Ile Phe Ala Val Leu Ser Ile
            675                 680                 685

<210> SEQ ID NO 26
<211> LENGTH: 696
<212> TYPE: PRT
<213> ORGANISM: Influenza virus

<400> SEQUENCE: 26

Arg Val Arg Gly Ile Lys Arg Asn Tyr Gln His Leu Trp Lys Trp Gly
1               5                   10                  15

Thr Met Leu Leu Gly Met Leu Met Thr Cys Ser Val Ala Glu Asn Leu
            20                  25                  30

Trp Val Thr Val Tyr Tyr Gly Val Pro Val Trp Lys Glu Ala Thr Thr
        35                  40                  45

Thr Leu Phe Cys Ala Ser Asp Ala Lys Ser Tyr Lys Thr Glu Ala His
    50                  55                  60

Asn Ile Trp Ala Thr His Ala Cys Val Pro Thr Asp Pro Asn Pro Gln
65                  70                  75                  80

Glu Ile Glu Leu Glu Asn Val Thr Glu Asn Phe Asn Met Trp Lys Asn
                85                  90                  95

Asn Met Val Glu Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Gly Met Arg Asn Asp Thr Asn Asp Asn Val Thr Met
    130                 135                 140

Glu Glu Gly Glu Met Lys Asn Cys Ser Phe Asn Ile Thr Thr Glu Val
145                 150                 155                 160

Arg Asp Lys Lys Lys Gln Val His Ala Leu Phe Tyr Lys Leu Asp Val
                165                 170                 175

Val Pro Ile Asp Asp Asn Asn Thr Asn Asn Ser Asn Tyr Arg Leu Ile
            180                 185                 190

Asn Cys Asn Thr Ser Ala Ile Thr Gln Ala Cys Pro Lys Val Thr Phe
        195                 200                 205

Glu Pro Ile Pro Ile His Tyr Cys Ala Pro Ala Gly Phe Ala Ile Leu
    210                 215                 220

Lys Cys Lys Asp Lys Lys Phe Asn Gly Thr Gly Pro Cys Lys Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Ile Ile Ile Arg Ser
            260                 265                 270

Glu Asn Leu Thr Asn Asn Ala Lys Ile Ile Ile Val Gln Leu Asn Glu
        275                 280                 285

Ser Val Thr Ile Asn Cys Thr Arg Pro Tyr Asn Asn Thr Arg Lys Arg
    290                 295                 300

Ile Pro Ile Gly Leu Gly Gln Ala Phe Tyr Thr Thr Arg Gly Ile Ile
305                 310                 315                 320

Gly Asp Ile Arg Gln Ala His Cys Asn Ile Ser Gly Ala Glu Trp Asn
                325                 330                 335

Lys Thr Leu Gln Gln Val Ala Lys Lys Leu Gly Asp Leu Leu Asn Lys
            340                 345                 350
```

```
Thr Thr Ile Ile Phe Lys Pro Ser Ser Gly Arg Pro Arg Ile Thr
            355                 360                 365

Thr His Ser Phe Asn Cys Gly Gly Glu Phe Phe Tyr Cys Asn Thr Ser
370                 375                 380

Arg Leu Phe Asn Ser Thr Trp Ser Lys Asn Ser Thr Ser Asn Ser Thr
385                 390                 395                 400

Lys Glu Asn Asn Thr Ile Thr Leu Pro Cys Arg Ile Lys Gln Ile Ile
                405                 410                 415

Asn Met Trp Gln Gly Val Gly Lys Ala Met Tyr Ala Pro Pro Ile Glu
            420                 425                 430

Gly Leu Ile Lys Cys Ser Ser Asn Ile Thr Gly Leu Leu Leu Thr Arg
            435                 440                 445

Asp Gly Gly Ala Asn Asn Ser His Asn Glu Thr Phe Arg Pro Gly Gly
            450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Glu Arg Glu Lys Arg Ala Ile Gly Leu Gly Ala Met Phe Leu
            500                 505                 510

Gly Phe Leu Gly Ala Ala Gly Ser Thr Met Gly Ala Ala Ser Leu Thr
            515                 520                 525

Leu Thr Val Gln Ala Arg Gln Leu Leu Ser Gly Ile Val Gln Gln Gln
            530                 535                 540

Asn Asn Leu Leu Arg Ala Ile Glu Ala Gln Gln His Leu Leu Gln Leu
545                 550                 555                 560

Thr Val Trp Gly Ile Lys Gln Leu Gln Ala Arg Ile Leu Ala Val Glu
                565                 570                 575

Arg Tyr Leu Lys Asp Gln Gln Leu Leu Gly Ile Trp Gly Cys Ser Gly
            580                 585                 590

Lys His Ile Cys Thr Thr Thr Val Pro Trp Asn Ser Ser Trp Ser Asn
            595                 600                 605

Lys Ser Leu Asp Glu Ile Trp Asn Asn Met Thr Trp Met Glu Trp Glu
            610                 615                 620

Arg Glu Ile Asp Asn Tyr Thr Gly Leu Ile Tyr Ser Leu Ile Glu Glu
625                 630                 635                 640

Ser Gln Thr Gln Gln Glu Lys Asn Glu Gln Glu Leu Leu Glu Leu Asp
                645                 650                 655

Lys Trp Ala Ser Leu Trp Asn Trp Phe Ser Ile Thr Gln Trp Leu Trp
            660                 665                 670

Tyr Ile Lys Ile Phe Ile Met Ile Val Gly Gly Leu Ile Gly Leu Arg
            675                 680                 685

Ile Val Phe Ala Val Leu Ser Leu
            690                 695

<210> SEQ ID NO 27
<211> LENGTH: 323
<212> TYPE: PRT
<213> ORGANISM: Influenza virus

<400> SEQUENCE: 27

Ser Lys Arg Ser Val Val Gly Trp Pro Thr Val Arg Glu Arg Met Arg
1               5                   10                  15

Arg Ala Glu Pro Ala Ala Asp Gly Val Gly Ala Val Ser Arg Asp Leu
            20                  25                  30
```

Glu Lys His Gly Ala Ile Thr Ser Ser Asn Thr Ala Ala Asn Asn Ala
                35                  40                  45

Asp Cys Ala Trp Leu Glu Ala Gln Glu Glu Glu Val Gly Phe Pro
    50                  55                  60

Val Arg Ala Gln Val Ala Leu Arg Ala Met Thr Tyr Lys Ala Ala Val
65                  70                  75                  80

Asp Leu Ser His Phe Leu Lys Glu Lys Gly Gly Leu Glu Gly Leu Ile
                85                  90                  95

Tyr Ser Gln Lys Arg Gln Asp Ile Leu Asp Leu Trp Val Tyr His Thr
                100                 105                 110

Gln Gly Tyr Phe Pro Asp Trp Gln Asn Tyr Thr Pro Gly Pro Gly Ile
                115                 120                 125

Arg Tyr Pro Leu Thr Phe Gly Trp Cys Phe Lys Leu Val Pro Val Glu
                130                 135                 140

Pro Glu Lys Val Glu Glu Ala Asn Glu Gly Glu Asn Asn Ser Ala Ala
145                 150                 155                 160

His Pro Met Ser Leu His Gly Met Asp Asp Pro Glu Arg Glu Val Leu
                165                 170                 175

Val Trp Lys Phe Asp Ser Arg Leu Ala Phe His His Met Ala Arg Glu
                180                 185                 190

Leu His Pro Glu Tyr Tyr Lys Asp Cys Arg Gly Arg Lys Arg Arg Ser
                195                 200                 205

Ala Gly Arg Ser Gly Asp Ser Asp Glu Glu Leu Leu Lys Thr Val Arg
                210                 215                 220

Leu Ile Lys Phe Leu Tyr Gln Ser Asn Pro Pro Ser Pro Glu Gly
225                 230                 235                 240

Thr Arg Gln Ala Arg Arg Asn Arg Arg Arg Trp Arg Glu Arg Gln
                245                 250                 255

Arg Gln Ile Arg Ser Ile Ser Glu Trp Ile Leu Ser Thr Tyr Leu Gly
                260                 265                 270

Arg Pro Ala Glu Pro Val Pro Leu Gln Leu Pro Pro Leu Glu Arg Leu
                275                 280                 285

Thr Leu Asp Cys Asn Glu Asp Cys Gly Thr Ser Thr Gln Gly Val
                290                 295                 300

Gly Ser Pro Gln Ile Leu Val Glu Ser Pro Ala Val Leu Glu Ser Gly
305                 310                 315                 320

Thr Lys Glu

<210> SEQ ID NO 28
<211> LENGTH: 506
<212> TYPE: PRT
<213> ORGANISM: Influenza virus

<400> SEQUENCE: 28

Gly Ala Arg Ala Ser Val Leu Ser Gly Gly Lys Leu Asp Ala Trp Glu
1               5                   10                  15

Lys Ile Arg Leu Arg Pro Gly Gly Lys Lys Tyr Arg Leu Lys His
                20                  25                  30

Leu Val Trp Ala Ser Arg Glu Leu Glu Arg Phe Ala Leu Asn Pro Gly
                35                  40                  45

Leu Leu Glu Thr Ser Glu Gly Cys Lys Gln Ile Ile Gly Gln Leu Gln
                50                  55                  60

Pro Ala Leu Gln Thr Gly Ser Glu Glu Leu Arg Ser Leu Tyr Asn Thr
65                  70                  75                  80

```
Val Ala Thr Leu Tyr Cys Val His Glu Lys Ile Glu Val Lys Asp Thr
                85                  90                  95
Lys Glu Ala Leu Asp Lys Ile Glu Glu Gln Asn Lys Ser Lys Gln
            100                 105                 110
Lys Ala Gln Gln Ala Ala Asp Thr Gly Asn Ser Ser Gln Val Ser
            115                 120                 125
Gln Asn Tyr Pro Ile Val Gln Asn Leu Gln Gly Gln Met Val His Gln
130                 135                 140
Ala Ile Ser Pro Arg Thr Leu Asn Ala Trp Val Lys Val Ile Glu Glu
145                 150                 155                 160
Lys Ala Phe Ser Pro Glu Val Ile Pro Met Phe Ser Ala Leu Ser Glu
                165                 170                 175
Gly Ala Thr Pro Gln Asp Leu Asn Thr Met Leu Asn Thr Val Gly Gly
            180                 185                 190
His Gln Ala Ala Met Gln Met Leu Lys Asp Thr Ile Asn Glu Glu Ala
            195                 200                 205
Ala Glu Trp Asp Arg Leu His Pro Val His Ala Gly Pro Ile Ala Pro
210                 215                 220
Gly Gln Met Arg Glu Pro Arg Gly Ser Asp Ile Ala Gly Thr Thr Ser
225                 230                 235                 240
Thr Leu Gln Glu Gln Ile Gly Trp Met Thr Ser Asn Pro Pro Ile Pro
                245                 250                 255
Val Gly Asp Ile Tyr Lys Arg Trp Ile Ile Leu Gly Leu Asn Lys Ile
                260                 265                 270
Val Arg Met Tyr Ser Pro Val Ser Ile Leu Asp Ile Arg Gln Gly Pro
                275                 280                 285
Lys Glu Pro Phe Arg Asp Tyr Val Asp Arg Phe Phe Lys Thr Leu Arg
            290                 295                 300
Ala Glu Gln Ala Ser Gln Asp Val Lys Asn Trp Met Thr Glu Thr Leu
305                 310                 315                 320
Leu Val Gln Asn Ala Asn Pro Asp Cys Lys Thr Ile Leu Arg Ala Leu
                325                 330                 335
Gly Pro Gly Ala Thr Leu Glu Glu Met Met Thr Ala Cys Gln Gly Val
                340                 345                 350
Gly Gly Pro Gly His Lys Ala Arg Val Leu Ala Glu Ala Met Ser Gln
            355                 360                 365
Ala Thr Asn Ser Asn Ile Met Met Gln Arg Gly Asn Phe Arg Gly Pro
370                 375                 380
Arg Arg Ile Val Lys Cys Phe Asn Cys Gly Lys Glu Gly His Ile Ala
385                 390                 395                 400
Arg Asn Cys Arg Ala Pro Arg Lys Lys Gly Cys Trp Lys Cys Gly Lys
                405                 410                 415
Glu Gly His Gln Met Lys Asp Cys Thr Glu Arg Gln Ala Asn Phe Leu
                420                 425                 430
Gly Lys Ile Trp Pro Ser His Lys Gly Arg Pro Gly Asn Phe Leu Gln
            435                 440                 445
Ser Arg Pro Glu Pro Thr Ala Pro Pro Ala Glu Ser Phe Gly Phe Gly
            450                 455                 460
Glu Glu Ile Thr Pro Ser Pro Lys Gln Glu Pro Lys Asp Arg Glu Leu
465                 470                 475                 480
Tyr Pro Leu Ala Ser Leu Lys Ser Leu Phe Gly Asn Asp Pro Leu Ser
                485                 490                 495
```

Gln Tyr Pro Tyr Asp Val Pro Asp Tyr Ala
        500             505

<210> SEQ ID NO 29
<211> LENGTH: 1707
<212> TYPE: DNA
<213> ORGANISM: Influenza virus

<400> SEQUENCE: 29

| | |
|---|---|
| atggaaaaga tcgtgctgct gttcgccatc gtgagcctgg tgaagagcga ccagatctgc | 60 |
| atcggctacc acgccaacaa cagcaccgag caggtggaca ccatcatgga aaaaaacgtg | 120 |
| accgtgaccc acgcccagga catcctggaa aagacccaca acggcaagct gtgcgacctg | 180 |
| gacggcgtga agcccctgat cctgcgggac tgcagcgtgg ccggctggct gctgggcaac | 240 |
| cccatgtgcg acgagttcat caacgtgccc gagtggagct acatcgtgga aaaggccaac | 300 |
| cccgtgaacg acctgtgcta ccccggcgac ttcaacgact acgaggaact gaagcacctg | 360 |
| ctgtcccgga tcaaccactt cgagaagatc cagatcatcc caagagcag ctggtccagc | 420 |
| cacgaggcca gcctgggcgt gagcagcgcc tgcccatacc agggcaagtc cagcttcttc | 480 |
| cggaacgtgg tgtggctgat caagaagaac agcacctacc ccaccatcaa gcggagctac | 540 |
| aacaacacca ccaggaaga tctgctggtc ctgtggggca tccaccaccc caacgacgcc | 600 |
| gccgagcaga ccaagctgta ccagaacccc accacctaca tcagcgtggg caccagcacc | 660 |
| ctgaaccagc ggctggtgcc ccggatcgcc acccggtcca aggtgaacgg ccagagcggc | 720 |
| cggatggaat tcttctggac catcctgaag cccaacgatg ccatcaactt cgagagcaac | 780 |
| ggcaacttca tcgccccga gtacgcctac aagatcgtga agaagggcga cagcaccatc | 840 |
| atgaagagcg agctggaata cggcaactgc aacaccaagt gccagacccc catgggcgcc | 900 |
| atcaacagca gcatgccctt ccacaacatc caccccctga ccatcggcga gtgccccaag | 960 |
| tacgtgaaga gcaacaggct ggtgctggcc accggcctgc ggaacagccc ccagcgggag | 1020 |
| cggcgggccg ccgcccgggg cctgttcggc gccatcgccg gcttcatcga gggcggctgg | 1080 |
| cagggcatgg tggacgggtg gtacggctac caccacagca atgagcaggg cagcggctac | 1140 |
| gccgccgaca agagagcac ccagaaggcc atcgacggcg tcaccaacaa ggtgaacagc | 1200 |
| atcatcgaca gatgaacac ccagttcgag gccgtgggcc gggagttcaa caacctggaa | 1260 |
| cggcggatcg agaacctgaa caagaaaatg gaagatggct cctgacgt gtggacctac | 1320 |
| aacgccgagc tgctggtgct gatggaaaac gagcggaccc tggacttcca cgacagcaac | 1380 |
| gtgaagaacc tgtacgacaa agtgcggctg cagctgcggg acaacgccaa agagctgggc | 1440 |
| aacggctgct tcgagttcta ccacaagtgc gacaacgagt gcatggaaag cgtgcggaac | 1500 |
| ggcacctacg actaccccca gtacagcgag gaagcccggc tgaagcggga ggaaatcagc | 1560 |
| ggcgtgaaac tggaaagcat cggcatctac cagatcctga gcatctacag caccgtggcc | 1620 |
| agcagcctgg ccctggccat catggtggcc ggcctgagcc tgtggatgtg cagcaacggc | 1680 |
| agcctgcagt gccggatctg catctag | 1707 |

<210> SEQ ID NO 30
<211> LENGTH: 567
<212> TYPE: PRT
<213> ORGANISM: Influenza virus

<400> SEQUENCE: 30

Glu Lys Ile Val Leu Leu Phe Ala Ile Val Ser Leu Val Lys Ser Asp
1               5                   10                  15

```
Gln Ile Cys Ile Gly Tyr His Ala Asn Asn Ser Thr Glu Gln Val Asp
             20                  25                  30

Thr Ile Met Glu Lys Asn Val Thr Val Thr His Ala Gln Asp Ile Leu
         35                  40                  45

Glu Lys Thr His Asn Gly Lys Leu Cys Asp Leu Asp Gly Val Lys Pro
 50                  55                  60

Leu Ile Leu Arg Asp Cys Ser Val Ala Gly Trp Leu Leu Gly Asn Pro
 65                  70                  75                  80

Met Cys Asp Glu Phe Ile Asn Val Pro Glu Trp Ser Tyr Ile Val Glu
                 85                  90                  95

Lys Ala Asn Pro Val Asn Asp Leu Cys Tyr Pro Gly Asp Phe Asn Asp
            100                 105                 110

Tyr Glu Glu Leu Lys His Leu Leu Ser Arg Ile Asn His Phe Glu Lys
            115                 120                 125

Ile Gln Ile Ile Pro Lys Ser Ser Trp Ser Ser His Glu Ala Ser Leu
130                 135                 140

Gly Val Ser Ser Ala Cys Pro Tyr Gln Gly Lys Ser Ser Phe Phe Arg
145                 150                 155                 160

Asn Val Val Trp Leu Ile Lys Lys Asn Ser Thr Tyr Pro Thr Ile Lys
                165                 170                 175

Arg Ser Tyr Asn Asn Thr Asn Gln Glu Asp Leu Leu Val Leu Trp Gly
            180                 185                 190

Ile His His Pro Asn Asp Ala Ala Glu Gln Thr Lys Leu Tyr Gln Asn
            195                 200                 205

Pro Thr Thr Tyr Ile Ser Val Gly Thr Ser Thr Leu Asn Gln Arg Leu
            210                 215                 220

Val Pro Arg Ile Ala Thr Arg Ser Lys Val Asn Gly Gln Ser Gly Arg
225                 230                 235                 240

Met Glu Phe Phe Trp Thr Ile Leu Lys Pro Asn Asp Ala Ile Asn Phe
                245                 250                 255

Glu Ser Asn Gly Asn Phe Ile Ala Pro Glu Tyr Ala Tyr Lys Ile Val
            260                 265                 270

Lys Lys Gly Asp Ser Thr Ile Met Lys Ser Glu Leu Glu Tyr Gly Asn
            275                 280                 285

Cys Asn Thr Lys Cys Gln Thr Pro Met Gly Ala Ile Asn Ser Ser Met
290                 295                 300

Pro Phe His Asn Ile His Pro Leu Thr Ile Gly Glu Cys Pro Lys Tyr
305                 310                 315                 320

Val Lys Ser Asn Arg Leu Val Leu Ala Thr Gly Leu Arg Asn Ser Pro
                325                 330                 335

Gln Arg Glu Arg Arg Ala Ala Arg Gly Leu Phe Gly Ala Ile Ala
            340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
            370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430
```

```
Phe Leu Asp Val Trp Thr Tyr Asn Ala Glu Leu Leu Val Leu Met Glu
                435                 440                 445
Asn Glu Arg Thr Leu Asp Phe His Asp Ser Asn Val Lys Asn Leu Tyr
            450                 455                 460
Asp Lys Val Arg Leu Gln Leu Arg Asp Asn Ala Lys Glu Leu Gly Asn
465                 470                 475                 480
Gly Cys Phe Glu Phe Tyr His Lys Cys Asp Asn Glu Cys Met Glu Ser
                485                 490                 495
Val Arg Asn Gly Thr Tyr Asp Tyr Pro Gln Tyr Ser Glu Glu Ala Arg
            500                 505                 510
Leu Lys Arg Glu Glu Ile Ser Gly Val Lys Leu Glu Ser Ile Gly Ile
            515                 520                 525
Tyr Gln Ile Leu Ser Ile Tyr Ser Thr Val Ala Ser Ser Leu Ala Leu
            530                 535                 540
Ala Ile Met Val Ala Gly Leu Ser Leu Trp Met Cys Ser Asn Gly Ser
545                 550                 555                 560
Leu Gln Cys Arg Ile Cys Ile
                565

<210> SEQ ID NO 31
<211> LENGTH: 1466
<212> TYPE: DNA
<213> ORGANISM: Influenza virus

<400> SEQUENCE: 31
ggtaccgaat cgccaccat ggactggacc tggatcctgt tcctggtggc cgctgccacc        60
cgggtgcaca gcatgaaccc caaccagaag atcatcacca tcggcagcat ctgcatggtg      120
atcggcatcg tgagcctgat gctgcagatc ggcaacatga tcagcatctg ggtgtcccac      180
agcatccaga ccggcaacca gcaccaggcc gagcccatca gcaacaccaa ctttctgacc      240
gagaaggccg tggccagcgt gaccctggcc ggcaacagca gcctgtgccc catcagcggc      300
tgggccgtgt acagcaagga caacagcatc cggatcggca agggcgga cgtgttcgtg       360 atccgggagc ccttcatcag ctgcagccac ctggaatgcc ggaccttctt cctgacccag      420
ggggccctgc tgaacgacaa gcacagcaac ggcaccgtga aggacagaag ccccaccgg       480 accctgatga gctgccccgt gggcgaggcc cccagcccct acaacagccg gttcgagagc      540
gtggcctggt ccgccagcgc ctgccacgac ggcaccagct ggctgaccat cggcatcagc      600
ggccctgaca cggcgccgt ggccgtgctg aagtacaacg gcatcatcac cgacaccatc      660
aagagctggc ggaacaacat cctgcggacc caggaaagcg agtgcgcctg cgtgaacggc      720
agctgcttca ccgtgatgac cgacggcccc agcaacggcc aggccagcta caagatcttc      780
aagatggaaa agggcaaggt ggtgaagagc gtggagctgg acgcccccaa ctaccactac      840
gaggaatgca gctgctaccc cgacgccggc gagatcacct gcgtgtgccg ggacaactgg      900
cacggcagca accggccctg ggtgtccttc aaccagaacc tggaataccag gatcggctac      960 atctgcagcg gcgtgttcgg cgacaacccc aggcccaacg atggcaccgg cagctgcggc     1020
cctgtgagcg ccaacggcgc ctacggcgtg aagggcttca gcttcaagta cggcaacggc     1080
gtgtggatcg gccggaccaa gagcaccaac agcagatccg gcttcgagat gatctgggac     1140
cccaacggct ggaccgagac cgacagcagc ttcagcgtga gcaggacat cgtggccatc     1200 accgactggt ccggctacag cggcagcttc gtgcagcacc ccgagctgac cggcctggac     1260
tgcatccggc cctgctttg gtggagctg atcagaggca ggccaaaga gagcaccatc     1320
```

```
tggaccagcg gcagcagcat cagcttttgc ggcgtgaaca gcgacaccgt gagctggtcc    1380
tggcccgacg cgccgagct gcccttcacc atcgacaagt accccctacga cgtgcccgac    1440 tacgcctgat gagcggccgc gagctc                                         1466
```

<210> SEQ ID NO 32
<211> LENGTH: 476
<212> TYPE: PRT
<213> ORGANISM: Influenza virus

<400> SEQUENCE: 32

```
Met Asp Trp Thr Trp Ile Leu Phe Leu Val Ala Ala Thr Arg Val
1               5                   10                  15

His Ser Met Asn Pro Asn Gln Lys Ile Ile Thr Ile Gly Ser Ile Cys
            20                  25                  30

Met Val Ile Gly Ile Val Ser Leu Met Leu Gln Ile Gly Asn Met Ile
        35                  40                  45

Ser Ile Trp Val Ser His Ser Ile Gln Thr Gly Asn Gln His Gln Ala
    50                  55                  60

Glu Pro Ile Ser Asn Thr Asn Phe Leu Thr Glu Lys Ala Val Ala Ser
65                  70                  75                  80

Val Thr Leu Ala Gly Asn Ser Ser Leu Cys Pro Ile Ser Gly Trp Ala
                85                  90                  95

Val Tyr Ser Lys Asp Asn Ser Ile Arg Ile Gly Ser Lys Gly Asp Val
            100                 105                 110

Phe Val Ile Arg Glu Pro Phe Ile Ser Cys Ser His Leu Glu Cys Arg
        115                 120                 125

Thr Phe Phe Leu Thr Gln Gly Ala Leu Leu Asn Asp Lys His Ser Asn
    130                 135                 140

Gly Thr Val Lys Asp Arg Ser Pro Tyr Arg Thr Leu Met Ser Cys Pro
145                 150                 155                 160

Val Gly Glu Ala Pro Ser Pro Tyr Asn Ser Arg Phe Glu Ser Val Ala
                165                 170                 175

Trp Ser Ala Ser Ala Cys His Asp Gly Thr Ser Trp Leu Thr Ile Gly
            180                 185                 190

Ile Ser Gly Pro Asp Asn Gly Ala Val Ala Val Leu Lys Tyr Asn Gly
        195                 200                 205

Ile Ile Thr Asp Thr Ile Lys Ser Trp Arg Asn Asn Ile Leu Arg Thr
    210                 215                 220

Gln Glu Ser Glu Cys Ala Cys Val Asn Gly Ser Cys Phe Thr Val Met
225                 230                 235                 240

Thr Asp Gly Pro Ser Asn Gly Gln Ala Ser Tyr Lys Ile Phe Lys Met
                245                 250                 255

Glu Lys Gly Lys Val Val Lys Ser Val Glu Leu Asp Ala Pro Asn Tyr
            260                 265                 270

His Tyr Glu Glu Cys Ser Cys Tyr Pro Asp Ala Gly Glu Ile Thr Cys
        275                 280                 285

Val Cys Arg Asp Asn Trp His Gly Ser Asn Arg Pro Trp Val Ser Phe
    290                 295                 300

Asn Gln Asn Leu Glu Tyr Gln Ile Gly Tyr Ile Cys Ser Gly Val Phe
305                 310                 315                 320

Gly Asp Asn Pro Arg Pro Asn Asp Gly Thr Gly Ser Cys Gly Pro Val
                325                 330                 335

Ser Ala Asn Gly Ala Tyr Gly Val Lys Gly Phe Ser Phe Lys Tyr Gly
            340                 345                 350
```

```
Asn Gly Val Trp Ile Gly Arg Thr Lys Ser Thr Asn Ser Arg Ser Gly
        355                 360                 365

Phe Glu Met Ile Trp Asp Pro Asn Gly Trp Thr Glu Thr Asp Ser Ser
    370                 375                 380

Phe Ser Val Lys Gln Asp Ile Val Ala Ile Thr Asp Trp Ser Gly Tyr
385                 390                 395                 400

Ser Gly Ser Phe Val Gln His Pro Glu Leu Thr Gly Leu Asp Cys Ile
            405                 410                 415

Arg Pro Cys Phe Trp Val Glu Leu Ile Arg Gly Arg Pro Lys Ser
                420                 425                 430

Thr Ile Trp Thr Ser Gly Ser Ser Ile Ser Phe Cys Gly Val Asn Ser
            435                 440                 445

Asp Thr Val Ser Trp Ser Trp Pro Asp Gly Ala Glu Leu Pro Phe Thr
        450                 455                 460

Ile Asp Lys Tyr Pro Tyr Asp Val Pro Asp Tyr Ala
465                 470                 475
```

<210> SEQ ID NO 33
<211> LENGTH: 875
<212> TYPE: DNA
<213> ORGANISM: Influenza virus

<400> SEQUENCE: 33

```
ggtaccggat ccgccaccat ggactggacc tggattctgt tcctggtggc cgctgccacc    60
cgggtgcaca gcatgagcct gctgaccgag gtggagacct acgtgctgtc catcatcccc   120
agcggccctc tgaaggccga gatcgcccag cggctggaag atgtgttcgc cggcaagaac   180
accgacctgg aagccctgat ggaatggctg aaaacccggc ccatcctgag ccccctgacc   240
aagggcatcc tgggcttcgt gttcaccctg accgtgccca gcgagcgggg cctgcagcgg   300
cggagattcg tgcagaacgc cctgaacggc aacggcgacc caacaacat ggaccgggcc   360
gtgaagctgt acaagaagct gaagcgggag atcaccttcc acgcgccaa agaggtggcc   420
ctgagctaca gcacaggcgc cctggccagc tgcatgggcc tgatctacaa ccggatgggc   480
accgtgacca ccgaggtggc cttcggcctg gtgtgcgcca cctgcgagca gatcgccgac   540
agccagcaca gatcccaccg gcagatggcc accaccacca cccctgat ccggcacgag    600
aaccggatgg tcctggcctc caccaccgcc aaggccatgg aacagatggc cggcagcagc   660
gagcaggccg ccgaagccat ggaagtggcc agccaggcca ggcagatggt gcaggccatg   720
cggaccatcg gcaccacccc cagcagcagc gccggactgc gggacgacct gctggaaaac   780
ctgcaggcct accagaaacg gatgggcgtg cagatgcagc ggttcaagta cccctacgac   840
gtgcccgact acgcctgatg agcggccgcg agctc                              875
```

<210> SEQ ID NO 34
<211> LENGTH: 279
<212> TYPE: PRT
<213> ORGANISM: Influenza virus

<400> SEQUENCE: 34

```
Met Asp Trp Thr Trp Ile Leu Phe Leu Val Ala Ala Ala Thr Arg Val
1               5                   10                  15

His Ser Met Ser Leu Leu Thr Glu Val Glu Thr Tyr Val Leu Ser Ile
            20                  25                  30

Ile Pro Ser Gly Pro Leu Lys Ala Glu Ile Ala Gln Arg Leu Glu Asp
        35                  40                  45
```

```
Val Phe Ala Gly Lys Asn Thr Asp Leu Glu Ala Leu Met Glu Trp Leu
 50                  55                  60

Lys Thr Arg Pro Ile Leu Ser Pro Leu Thr Lys Gly Ile Leu Gly Phe
 65                  70                  75                  80

Val Phe Thr Leu Thr Val Pro Ser Glu Arg Gly Leu Gln Arg Arg Arg
                 85                  90                  95

Phe Val Gln Asn Ala Leu Asn Gly Asn Gly Asp Pro Asn Asn Met Asp
            100                 105                 110

Arg Ala Val Lys Leu Tyr Lys Lys Leu Lys Arg Glu Ile Thr Phe His
        115                 120                 125

Gly Ala Lys Glu Val Ala Leu Ser Tyr Ser Thr Gly Ala Leu Ala Ser
    130                 135                 140

Cys Met Gly Leu Ile Tyr Asn Arg Met Gly Thr Val Thr Thr Glu Val
145                 150                 155                 160

Ala Phe Gly Leu Val Cys Ala Thr Cys Glu Gln Ile Ala Asp Ser Gln
                165                 170                 175

His Arg Ser His Arg Gln Met Ala Thr Thr Thr Asn Pro Leu Ile Arg
            180                 185                 190

His Glu Asn Arg Met Val Leu Ala Ser Thr Thr Ala Lys Ala Met Glu
        195                 200                 205

Gln Met Ala Gly Ser Ser Glu Gln Ala Ala Glu Ala Met Glu Val Ala
    210                 215                 220

Ser Gln Ala Arg Gln Met Val Gln Ala Met Arg Thr Ile Gly Thr His
225                 230                 235                 240

Pro Ser Ser Ser Ala Gly Leu Arg Asp Asp Leu Leu Glu Asn Leu Gln
                245                 250                 255

Ala Tyr Gln Lys Arg Met Gly Val Gln Met Gln Arg Phe Lys Tyr Pro
            260                 265                 270

Tyr Asp Val Pro Asp Tyr Ala
        275

<210> SEQ ID NO 35
<211> LENGTH: 1700
<212> TYPE: DNA
<213> ORGANISM: Influenza virus

<400> SEQUENCE: 35
ggtaccgaat cgccaccat ggactggacc tggatcctgt tcctggtcgc tgccgccacc      60
agggtgcaca gcagcctgct gaccgaggtg gagaccccca cccggaacga gtggggctgc    120
cggtgcagcg acagcagcga ccggggcagg aagcggagaa gcgccagcca gggcaccaag    180
cggagctacg agcagatgga acaggcggc gagcggcaga acgccaccga gatccgggcc     240
agcgtgggca gaatggtcgg cggcatcggc cggttctaca tccagatgtg caccgagctg    300
aagctgtccg actacgaggg ccggctgatc cagaacagca tcaccatcga gcggatggtg    360
ctgtccgcct tcgacgagcg gcggaacaga tacctggaag agcaccccag cgccggcaag    420
gaccccaaga aaaccggcgg acccatctac cggcggaggg acggcaagtg ggtgcgggag    480
ctgatcctgt acgacaaaga ggaaatccgg cggatctggc ggcaggccaa caacggcgag    540
gacgccacag ccggcctgac ccacctgatg atctggcaca gcaacctgaa cgacgccacc    600
taccagcgga caggctct ggtccggacc ggcatggacc ccggatgtg cagcctgatg       660 cagggcagca cactgcccag aagaagcgga gccgctggcg cagccgtgaa gggcgtgggc    720
accatggtga tggaactgat ccggatgatc aagcggggca tcaacgaccg gaattttttgg    780
```

-continued

```
agggcgaga acggcaggcg gacccggatc gcctacgagc ggatgtgcaa catcctgaag    840
ggcaagttcc agacagccgc ccagcgggcc atgatggacc aggtccggga gagccggaac    900
cccggcaacg ccgagatcga ggacctgatc ttcctggcca gaagcgccct gatcctgcgg    960
ggcagcgtgg cccacaagag ctgcctgccc gcctgcgtgt acggactggc cgtggccagc   1020
ggctacgact cgagcggga gggctacagc ctggtcggca tcgaccccttt ccggctgctg   1080 cagaactccc aggtgttcag cctgatccgg cccaacgaga ccccgccca caagtcccag   1140 ctggtctgga tggcctgcca gcgccgcc ttcgaggatc tgagagtgag cagcttcatc    1200
cggggcacca gagtggtgcc cagggccag ctgtccacca ggggcgtgca gatcgccagc   1260
aacgagaaca tggaagccat ggacagcaac accctggaac tgcggagccg gtactgggcc   1320
atccggacca gaagcggcgg caacaccaac cagcagcggg ccagcgccgg acagatcagc   1380
gtgcagccca ccttctccgt gcagcggaac ctgcccttcg agagggccac catcatggcc   1440
gccttcaccg gcaacaccga gggccggacc agcgacatgc ggaccgagat catcaggatg   1500
atggaaagcg ccaggcccga ggacgtgagc ttccagggca ggggcgtgtt cgagctgtcc   1560
gatgagaagg ccaccaaccc catcgtgccc agcttcgaca tgaacaacga gggcagctac   1620
ttcttcggcg acaacgccga ggaatacgac aactacccct acgacgtgcc cgactacgcc   1680
tgatgagcgg ccgcgagctc                                              1700
```

<210> SEQ ID NO 36
<211> LENGTH: 554
<212> TYPE: PRT
<213> ORGANISM: Influenza virus

<400> SEQUENCE: 36

```
Met Asp Trp Thr Trp Ile Leu Phe Leu Val Ala Ala Thr Arg Val
1               5                  10                  15

His Ser Ser Leu Leu Thr Glu Val Glu Thr Pro Thr Arg Asn Glu Trp
        20                  25                  30

Gly Cys Arg Cys Ser Asp Ser Ser Asp Arg Gly Arg Lys Arg Arg Ser
    35                  40                  45

Ala Ser Gln Gly Thr Lys Arg Ser Tyr Glu Gln Met Glu Thr Gly Gly
50                  55                  60

Glu Arg Gln Asn Ala Thr Glu Ile Arg Ala Ser Val Gly Arg Met Val
65                  70                  75                  80

Gly Gly Ile Gly Arg Phe Tyr Ile Gln Met Cys Thr Glu Leu Lys Leu
                85                  90                  95

Ser Asp Tyr Glu Gly Arg Leu Ile Gln Asn Ser Ile Thr Ile Glu Arg
            100                 105                 110

Met Val Leu Ser Ala Phe Asp Glu Arg Arg Asn Arg Tyr Leu Glu Glu
        115                 120                 125

His Pro Ser Ala Gly Lys Asp Pro Lys Lys Thr Gly Gly Pro Ile Tyr
    130                 135                 140

Arg Arg Arg Asp Gly Lys Trp Val Arg Glu Leu Ile Leu Tyr Asp Lys
145                 150                 155                 160

Glu Glu Ile Arg Arg Ile Trp Arg Gln Ala Asn Asn Gly Glu Asp Ala
                165                 170                 175

Thr Ala Gly Leu Thr His Leu Met Ile Trp His Ser Asn Leu Asn Asp
            180                 185                 190

Ala Thr Tyr Gln Arg Thr Arg Ala Leu Val Arg Thr Gly Met Asp Pro
        195                 200                 205
```

Arg Met Cys Ser Leu Met Gln Gly Ser Thr Leu Pro Arg Ser Gly
    210                 215                 220

Ala Ala Gly Ala Ala Val Lys Gly Val Gly Thr Met Val Met Glu Leu
225                 230                 235                 240

Ile Arg Met Ile Lys Arg Gly Ile Asn Asp Arg Asn Phe Trp Arg Gly
            245                 250                 255

Glu Asn Gly Arg Arg Thr Arg Ile Ala Tyr Glu Arg Met Cys Asn Ile
            260                 265                 270

Leu Lys Gly Lys Phe Gln Thr Ala Ala Gln Arg Ala Met Met Asp Gln
        275                 280                 285

Val Arg Glu Ser Arg Asn Pro Gly Asn Ala Glu Ile Glu Asp Leu Ile
    290                 295                 300

Phe Leu Ala Arg Ser Ala Leu Ile Leu Arg Gly Ser Val Ala His Lys
305                 310                 315                 320

Ser Cys Leu Pro Ala Cys Val Tyr Gly Leu Ala Val Ala Ser Gly Tyr
            325                 330                 335

Asp Phe Glu Arg Glu Gly Tyr Ser Leu Val Gly Ile Asp Pro Phe Arg
            340                 345                 350

Leu Leu Gln Asn Ser Gln Val Phe Ser Leu Ile Arg Pro Asn Glu Asn
        355                 360                 365

Pro Ala His Lys Ser Gln Leu Val Trp Met Ala Cys His Ser Ala Ala
    370                 375                 380

Phe Glu Asp Leu Arg Val Ser Ser Phe Ile Arg Gly Thr Arg Val Val
385                 390                 395                 400

Pro Arg Gly Gln Leu Ser Thr Arg Gly Val Gln Ile Ala Ser Asn Glu
            405                 410                 415

Asn Met Glu Ala Met Asp Ser Asn Thr Leu Glu Leu Arg Ser Arg Tyr
            420                 425                 430

Trp Ala Ile Arg Thr Arg Ser Gly Gly Asn Thr Asn Gln Gln Arg Ala
        435                 440                 445

Ser Ala Gly Gln Ile Ser Val Gln Pro Thr Phe Ser Val Gln Arg Asn
    450                 455                 460

Leu Pro Phe Glu Arg Ala Thr Ile Met Ala Ala Phe Thr Gly Asn Thr
465                 470                 475                 480

Glu Gly Arg Thr Ser Asp Met Arg Thr Glu Ile Ile Arg Met Met Glu
            485                 490                 495

Ser Ala Arg Pro Glu Asp Val Ser Phe Gln Gly Arg Gly Val Phe Glu
            500                 505                 510

Leu Ser Asp Glu Lys Ala Thr Asn Pro Ile Val Pro Ser Phe Asp Met
        515                 520                 525

Asn Asn Glu Gly Ser Tyr Phe Phe Gly Asp Asn Ala Glu Glu Tyr Asp
    530                 535                 540

Asn Tyr Pro Tyr Asp Val Pro Asp Tyr Ala
545                 550

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Asp Trp Thr Trp Ile Leu Phe Leu Val Ala Ala Ala Thr Arg Val

His Ser

<210> SEQ ID NO 38
<211> LENGTH: 818
<212> TYPE: DNA
<213> ORGANISM: Human papillomavirus

<400> SEQUENCE: 38

```
gaattcgcca ccatggactg gacctggatc ctgttcctgg tggccgccgc cacacgggtg      60
cacagcttcc aggaccccca ggagagcggc agaaagctgc ctcagctgtg taccgagctg     120
cagaccacca tccacgacat catcctggag tgtgtgtact gtaagcagca gctgctgagg     180
agagaggtgt acgaccggga cctgtgtatc gtgtacaggg acggcaatcc ctacgccgtg     240
tgtgacaagt gcctgaagtt ctacagcaag atcagcgagt accggcacta ctgctacagc     300
ctgtacggca ccaccctgga gcagcagtac aacaagcccc tgtgtgacct gctgatccgg     360
tgtatcaact gccagaagcc cctgcagaga cacctggaca gaagcagcg gttccacaac     420
atcaggggca gatggaccgg cagatgtatg agctgctgcc ggagcagcag aaccagaagg     480
gagacccagc tgagaggccg aagagaaga gccacggcg ataccccac cctgcacgag        540
tacatgctgg acctgcagcc tgagaccacc gatctgtacg ctacggcca gctgaatgac     600
agcagcgagg aggaggatga gatcgacggc cctgccggcc aggccgagcc cgacagagcc     660
cactacaaca tcgtgacctt ttgctgtaag tgtgacagca ccctgagact gtgcgtgcag     720
agcacccacg tggacatcag aaccctggag gatctgctga tgggcaccct gggcatcgtg     780
tgtcccatct gctcccagaa acctgatga gcggccgc                              818
```

<210> SEQ ID NO 39
<211> LENGTH: 264
<212> TYPE: PRT
<213> ORGANISM: Human papillomavirus

<400> SEQUENCE: 39

Met Asp Trp Thr Trp Ile Leu Phe Leu Val Ala Ala Thr Arg Val
1               5                   10                  15

His Ser Phe Gln Asp Pro Gln Glu Ser Gly Arg Lys Leu Pro Gln Leu
                20                  25                  30

Cys Thr Glu Leu Gln Thr Thr Ile His Asp Ile Ile Leu Glu Cys Val
            35                  40                  45

Tyr Cys Lys Gln Gln Leu Leu Arg Arg Glu Val Tyr Asp Arg Asp Leu
        50                  55                  60

Cys Ile Val Tyr Arg Asp Gly Asn Pro Tyr Ala Val Cys Asp Lys Cys
65                  70                  75                  80

Leu Lys Phe Tyr Ser Lys Ile Ser Glu Tyr Arg His Tyr Cys Tyr Ser
                85                  90                  95

Leu Tyr Gly Thr Thr Leu Glu Gln Gln Tyr Asn Lys Pro Leu Cys Asp
            100                 105                 110

Leu Leu Ile Arg Cys Ile Asn Cys Gln Lys Pro Leu Gln Arg His Leu
        115                 120                 125

Asp Lys Lys Gln Arg Phe His Asn Ile Arg Gly Arg Trp Thr Gly Arg
    130                 135                 140

Cys Met Ser Cys Cys Arg Ser Ser Arg Thr Arg Arg Glu Thr Gln Leu
145                 150                 155                 160

Arg Gly Arg Lys Arg Arg Ser His Gly Asp Thr Pro Thr Leu His Glu

```
                    165                 170                 175
Tyr Met Leu Asp Leu Gln Pro Glu Thr Thr Asp Leu Tyr Gly Tyr Gly
                180                 185                 190

Gln Leu Asn Asp Ser Ser Glu Glu Glu Asp Glu Ile Asp Gly Pro Ala
            195                 200                 205

Gly Gln Ala Glu Pro Asp Arg Ala His Tyr Asn Ile Val Thr Phe Cys
        210                 215                 220

Cys Lys Cys Asp Ser Thr Leu Arg Leu Cys Val Gln Ser Thr His Val
225                 230                 235                 240

Asp Ile Arg Thr Leu Glu Asp Leu Leu Met Gly Thr Leu Gly Ile Val
                245                 250                 255

Cys Pro Ile Cys Ser Gln Lys Pro
            260

<210> SEQ ID NO 40
<211> LENGTH: 15
<212> TYPE: PRT
<213> ORGANISM: Human papillomavirus

<400> SEQUENCE: 40

Leu Cys Ile Val Tyr Arg Asp Gly Asn Pro Tyr Ala Val Cys Asp
1               5                   10                  15

<210> SEQ ID NO 41
<211> LENGTH: 15
<212> TYPE: PRT
<213> ORGANISM: Human papillomavirus

<400> SEQUENCE: 41

Ala Glu Pro Asp Arg Ala His Tyr Asn Ile Val Thr Phe Cys Cys
1               5                   10                  15

<210> SEQ ID NO 42
<211> LENGTH: 142
<212> TYPE: PRT
<213> ORGANISM: Human papillomavirus

<400> SEQUENCE: 42

Phe Gln Asp Pro Gln Glu Ser Gly Arg Lys Leu Pro Gln Leu Cys Thr
1               5                   10                  15

Glu Leu Gln Thr Thr Ile His Asp Ile Ile Leu Glu Cys Val Tyr Cys
            20                  25                  30

Lys Gln Gln Leu Leu Arg Arg Glu Val Tyr Asp Arg Asp Leu Cys Ile
        35                  40                  45

Val Tyr Arg Asp Gly Asn Pro Tyr Ala Val Cys Asp Lys Cys Leu Lys
    50                  55                  60

Phe Tyr Ser Lys Ile Ser Glu Tyr Arg His Tyr Cys Tyr Ser Leu Tyr
65                  70                  75                  80

Gly Thr Thr Leu Glu Gln Gln Tyr Asn Lys Pro Leu Cys Asp Leu Leu
                85                  90                  95

Ile Arg Cys Ile Asn Cys Gln Lys Pro Leu Gln Arg His Leu Asp Lys
            100                 105                 110

Lys Gln Arg Phe His Asn Ile Arg Gly Arg Trp Thr Gly Arg Cys Met
        115                 120                 125

Ser Cys Cys Arg Ser Ser Arg Thr Arg Arg Glu Thr Gln Leu
    130                 135                 140

<210> SEQ ID NO 43
```

```
<211> LENGTH: 97
<212> TYPE: PRT
<213> ORGANISM: Human papillomavirus

<400> SEQUENCE: 43

His Gly Asp Thr Pro Thr Leu His Glu Tyr Met Leu Asp Leu Gln Pro
1               5                   10                  15

Glu Thr Thr Asp Leu Tyr Gly Tyr Gly Gln Leu Asn Asp Ser Ser Glu
            20                  25                  30

Glu Glu Asp Glu Ile Asp Gly Pro Ala Gly Gln Ala Glu Pro Asp Arg
        35                  40                  45

Ala His Tyr Asn Ile Val Thr Phe Cys Cys Lys Cys Asp Ser Thr Leu
50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Cys Pro Ile Cys Ser Gln Lys
                85                  90                  95

Pro

<210> SEQ ID NO 44
<211> LENGTH: 1766
<212> TYPE: DNA
<213> ORGANISM: Hepatitis C virus

<400> SEQUENCE: 44
gaattcgcca ccatggactg gacctggatc ctgttcctgg tggccgctgc aacacgggtg      60
cacagctacc aagtgaggaa tagcagcggc ctgtaccacg tgaccaacga ctgctccaac     120
agcagcatcg tgtacgaggc cgccgacatg atcatgcaca cccccggctg tgtgccctgt     180
gtgagagagg gcaacagctc cagatgctgg gtggccctga cccctaccgt ggccgccaga     240
gatggcagcc tgcccaccac cacccctgagg agacacgtgg acctgcttgt gggcagcgcc     300
accctgtgta cgccatgta tgtgggcgat ctgtgtggca cgtgtttcct gtgggccag      360
ctgttcacct tcagccccag aaggcactgg accgtgcagg actgtaactg ctccatctac     420
cccggccaca tcaccggcca cagaatggcc tgggacatga tgatgaactg gagccctacc     480
accgccctgg tggtgtccca gctgctgaga atccctcagg ccatcgtgga catggtggcc     540
ggagcccact ggggcgtgct ggccggcatc gcctacttca gcatggtggg caactgggcc     600
aaggtgctcg tggtgctgct gctgttcgcc ggcgtggacg cagaggcag aagagaagg     660
agcgagaccc acgtgaccgg cggcaccgcc ggcagaacca cagccggcct tgtgggcctg     720
ttcacccctg gcgccaagca gaacatccag ctgatcaaca ccaacggcag ctggcacatc     780
aacagcaccg ccctgaactg taacgacagc ctgaacaccg gctggctggc cggcctgttc     840
taccagcaca agttcaacag cagcggctgc cccgagagaa tggccagctg tagaccctg      900
gatgagttcg cccagggctg gggccccatc acctacgcca atggcagcgg ccctgaccag     960
agaccctact gctggcacta cgcccccaga ccctgtggca tcgtgcccgc caagagcgtg    1020
tgtggcccg tgtactgctt caccccctagc cccgtggttg tgggcaccac cgacagaagc    1080
ggagcccca cctacagctg gggcgagaac gagaccgacg tgctggtgct gaacaacacc    1140
agaccccccc tgggcaattg gttcggctgt acctggatga cagcaccgg cttcaccaaa    1200
gtgtgtggcg cccctccctg tgtgatcggc ggagtgggca acaacaccct gacctgcccc    1260
accgactgct cagaaagca ccccgaggcc acctactcca gatgtggcag cggaccttgg    1320
ctgacccca gatgtatggt ggactacccc tacaggctgt ggcactaccc ctgtaccgtg    1380
```

```
aacttcacca tcttcaaagt gaggatgtat gtggggggcg tggagcacag actggaggcc    1440
gcctgtaatt ggaccagggg cgagagatgt gacctggagg accgggatag aagcgagctg    1500
tcccctctgc tgctgtccac caccgagtgg caggtgctgc cttgtagctt caccaccctg    1560
cccgccctga gcaccggcct gatccacctg caccagaaca tcgtggacgt gcagtacctg    1620
tacggagtgg gctctagcat cgtgtcctgg gccatcaagt gggagtacgt ggtgctgctg    1680
ttcctgctgc tggccgacgc cagagtgtgt agctgcctgt ggatgatgct gctgatcagc    1740
caggccgagg cctgatgagc ggccgc                                         1766
```

<210> SEQ ID NO 45
<211> LENGTH: 580
<212> TYPE: PRT
<213> ORGANISM: Hepatitis C virus

<400> SEQUENCE: 45

Met Asp Trp Thr Trp Ile Leu Phe Leu Val Ala Ala Thr Arg Val
1               5                   10                  15

His Ser Tyr Gln Val Arg Asn Ser Ser Gly Leu Tyr His Val Thr Asn
            20                  25                  30

Asp Cys Ser Asn Ser Ser Ile Val Tyr Glu Ala Ala Asp Met Ile Met
            35                  40                  45

His Thr Pro Gly Cys Val Pro Cys Val Arg Glu Gly Asn Ser Ser Arg
    50                  55                  60

Cys Trp Val Ala Leu Thr Pro Thr Val Ala Arg Asp Gly Ser Leu
65                  70                  75                  80

Pro Thr Thr Thr Leu Arg Arg His Val Asp Leu Leu Val Gly Ser Ala
                85                  90                  95

Thr Leu Cys Ser Ala Met Tyr Val Gly Asp Leu Cys Gly Ser Val Phe
            100                 105                 110

Leu Val Gly Gln Leu Phe Thr Phe Ser Pro Arg Arg His Trp Thr Val
            115                 120                 125

Gln Asp Cys Asn Cys Ser Ile Tyr Pro Gly His Ile Thr Gly His Arg
    130                 135                 140

Met Ala Trp Asp Met Met Met Asn Trp Ser Pro Thr Thr Ala Leu Val
145                 150                 155                 160

Val Ser Gln Leu Leu Arg Ile Pro Gln Ala Ile Val Asp Met Val Ala
                165                 170                 175

Gly Ala His Trp Gly Val Leu Ala Gly Ile Ala Tyr Phe Ser Met Val
            180                 185                 190

Gly Asn Trp Ala Lys Val Leu Val Val Leu Leu Phe Ala Gly Val
            195                 200                 205

Asp Gly Arg Gly Arg Lys Arg Ser Glu Thr His Val Thr Gly Gly
    210                 215                 220

Thr Ala Gly Arg Thr Thr Ala Gly Leu Val Gly Leu Phe Thr Pro Gly
225                 230                 235                 240

Ala Lys Gln Asn Ile Gln Leu Ile Asn Thr Asn Gly Ser Trp His Ile
                245                 250                 255

Asn Ser Thr Ala Leu Asn Cys Asn Asp Ser Leu Asn Thr Gly Trp Leu
            260                 265                 270

Ala Gly Leu Phe Tyr Gln His Lys Phe Asn Ser Ser Gly Cys Pro Glu
            275                 280                 285

Arg Met Ala Ser Cys Arg Pro Leu Asp Glu Phe Ala Gln Gly Trp Gly
            290                 295                 300

```
Pro Ile Thr Tyr Ala Asn Gly Ser Gly Pro Asp Gln Arg Pro Tyr Cys
305                 310                 315                 320

Trp His Tyr Ala Pro Arg Pro Cys Gly Ile Val Pro Ala Lys Ser Val
                325                 330                 335

Cys Gly Pro Val Tyr Cys Phe Thr Pro Ser Pro Val Val Val Gly Thr
            340                 345                 350

Thr Asp Arg Ser Gly Ala Pro Thr Tyr Ser Trp Gly Glu Asn Glu Thr
        355                 360                 365

Asp Val Leu Val Leu Asn Asn Thr Arg Pro Pro Leu Gly Asn Trp Phe
    370                 375                 380

Gly Cys Thr Trp Met Asn Ser Thr Gly Phe Thr Lys Val Cys Gly Ala
385                 390                 395                 400

Pro Pro Cys Val Ile Gly Gly Val Gly Asn Asn Thr Leu Thr Cys Pro
                405                 410                 415

Thr Asp Cys Phe Arg Lys His Pro Glu Ala Thr Tyr Ser Arg Cys Gly
            420                 425                 430

Ser Gly Pro Trp Leu Thr Pro Arg Cys Met Val Asp Tyr Pro Tyr Arg
        435                 440                 445

Leu Trp His Tyr Pro Cys Thr Val Asn Phe Thr Ile Phe Lys Val Arg
    450                 455                 460

Met Tyr Val Gly Gly Val Glu His Arg Leu Glu Ala Ala Cys Asn Trp
465                 470                 475                 480

Thr Arg Gly Glu Arg Cys Asp Leu Glu Asp Arg Asp Arg Ser Glu Leu
                485                 490                 495

Ser Pro Leu Leu Leu Ser Thr Thr Glu Trp Gln Val Leu Pro Cys Ser
            500                 505                 510

Phe Thr Thr Leu Pro Ala Leu Ser Thr Gly Leu Ile His Leu His Gln
        515                 520                 525

Asn Ile Val Asp Val Gln Tyr Leu Tyr Gly Val Gly Ser Ser Ile Val
    530                 535                 540

Ser Trp Ala Ile Lys Trp Glu Tyr Val Val Leu Leu Phe Leu Leu Leu
545                 550                 555                 560

Ala Asp Ala Arg Val Cys Ser Cys Leu Trp Met Met Leu Leu Ile Ser
                565                 570                 575

Gln Ala Glu Ala
            580

<210> SEQ ID NO 46
<211> LENGTH: 192
<212> TYPE: PRT
<213> ORGANISM: Hepatitis C virus

<400> SEQUENCE: 46

Tyr Gln Val Arg Asn Ser Ser Gly Leu Tyr His Val Thr Asn Asp Cys
1               5                   10                  15

Ser Asn Ser Ser Ile Val Tyr Glu Ala Ala Asp Met Ile Met His Thr
                20                  25                  30

Pro Gly Cys Val Pro Cys Val Arg Glu Gly Asn Ser Ser Arg Cys Trp
            35                  40                  45

Val Ala Leu Thr Pro Thr Val Ala Ala Arg Asp Gly Ser Leu Pro Thr
        50                  55                  60

Thr Thr Leu Arg Arg His Val Asp Leu Leu Val Gly Ser Ala Thr Leu
65                  70                  75                  80

Cys Ser Ala Met Tyr Val Gly Asp Leu Cys Gly Ser Val Phe Leu Val
```

```
                    85                  90                  95
Gly Gln Leu Phe Thr Phe Ser Pro Arg Arg His Trp Thr Val Gln Asp
                100                 105                 110
Cys Asn Cys Ser Ile Tyr Pro Gly His Ile Thr Gly His Arg Met Ala
                115                 120                 125
Trp Asp Met Met Met Asn Trp Ser Pro Thr Thr Ala Leu Val Val Ser
130                 135                 140
Gln Leu Leu Arg Ile Pro Gln Ala Ile Val Asp Met Val Ala Gly Ala
145                 150                 155                 160
His Trp Gly Val Leu Ala Gly Ile Ala Tyr Phe Ser Met Val Gly Asn
                165                 170                 175
Trp Ala Lys Val Leu Val Val Leu Leu Leu Phe Ala Gly Val Asp Gly
                180                 185                 190
```

<210> SEQ ID NO 47
<211> LENGTH: 362
<212> TYPE: PRT
<213> ORGANISM: Hepatitis C virus

<400> SEQUENCE: 47

```
Glu Thr His Val Thr Gly Gly Thr Ala Gly Arg Thr Ala Gly Val
1               5                   10                  15
Gly Leu Phe Thr Pro Gly Ala Lys Gln Asn Ile Gln Leu Ile Asn Thr
                20                  25                  30
Asn Gly Ser Trp His Ile Asn Ser Thr Ala Leu Asn Cys Asn Asp Ser
                35                  40                  45
Leu Asn Thr Gly Trp Leu Ala Gly Leu Phe Tyr Gln His Lys Phe Asn
50                  55                  60
Ser Ser Gly Cys Pro Glu Arg Met Ala Ser Cys Arg Pro Leu Asp Glu
65                  70                  75                  80
Phe Ala Gln Gly Trp Gly Pro Ile Thr Tyr Ala Asn Gly Ser Gly Pro
                85                  90                  95
Asp Gln Arg Pro Tyr Cys Trp His Tyr Ala Pro Arg Pro Cys Gly Ile
                100                 105                 110
Val Pro Ala Lys Ser Val Cys Gly Pro Val Tyr Cys Phe Thr Pro Ser
                115                 120                 125
Pro Val Val Val Gly Thr Thr Asp Arg Ser Gly Ala Pro Thr Tyr Ser
130                 135                 140
Trp Gly Glu Asn Glu Thr Asp Val Leu Val Leu Asn Asn Thr Arg Pro
145                 150                 155                 160
Pro Leu Gly Asn Trp Phe Gly Cys Thr Trp Met Asn Ser Thr Gly Phe
                165                 170                 175
Thr Lys Val Cys Gly Ala Pro Pro Cys Val Ile Gly Gly Val Gly Asn
                180                 185                 190
Asn Thr Leu Thr Cys Pro Thr Asp Cys Phe Arg Lys His Pro Glu Ala
                195                 200                 205
Thr Tyr Ser Arg Cys Gly Ser Gly Pro Trp Leu Thr Pro Arg Cys Met
                210                 215                 220
Val Asp Tyr Pro Tyr Arg Leu Trp His Tyr Pro Cys Thr Val Asn Phe
225                 230                 235                 240
Thr Ile Phe Lys Val Arg Met Tyr Val Gly Gly Val Glu His Arg Leu
                245                 250                 255
Glu Ala Ala Cys Asn Trp Thr Arg Gly Glu Arg Cys Asp Leu Glu Asp
                260                 265                 270
```

```
Arg Asp Arg Ser Glu Leu Ser Pro Leu Leu Leu Ser Thr Thr Glu Trp
            275                 280                 285
Gln Val Leu Pro Cys Ser Phe Thr Thr Leu Pro Ala Leu Ser Thr Gly
        290                 295                 300
Leu Ile His Leu His Gln Asn Ile Val Asp Val Gln Tyr Leu Tyr Gly
305                 310                 315                 320
Val Gly Ser Ser Ile Val Ser Trp Ala Ile Lys Trp Glu Tyr Val Val
                325                 330                 335
Leu Leu Phe Leu Leu Ala Asp Ala Arg Val Cys Ser Cys Leu Trp
                340                 345                 350
Met Met Leu Leu Ile Ser Gln Ala Glu Ala
                355                 360

<210> SEQ ID NO 48
<211> LENGTH: 3512
<212> TYPE: DNA
<213> ORGANISM: Homo sapiens

<400> SEQUENCE: 48
```

| | | | | |
|---|---|---|---|---|
| ggtaccgaat | tcgccaccat | ggactggacc | tggatcctgt | tcctggtggc cgctgccaca | 60 |
| agagtgcaca | gccccagggc | cccaggtgc | agagccgtgc | ggagcctgct gcggagccac | 120 |
| taccgggagg | tgctgcccct | ggccaccttc | gtgcggaggc | tgggccctca ggggtggcgg | 180 |
| ctggtgcaga | gaggcgaccc | tgccgccttc | agagccctgg | tgcccagtg cctggtgtgc | 240 |
| gtgccctggg | acgccagacc | tcccctgcc | gcccctagct | tccggcaggt gtcctgcctg | 300 |
| aaagaactgg | tggcccgggt | gctgcagcgg | ctgtgcgaga | ggggcgccaa gaacgtgctg | 360 |
| gccttcggct | tcgccctgct | ggacggcgcc | agaggcggcc | ctcccgaggc cttcaccacc | 420 |
| tccgtgagaa | gctacctgcc | caacaccgtg | accgacgccc | tgagaggcag cggcgcttgg | 480 |
| ggcctgctgc | tgcgcagagt | gggcgacgac | gtgctggtgc | acctgctggc cagatgcgcc | 540 |
| ctgttcgtgt | tggtcgcccc | cagctgcgcc | taccaggtgt | gcggccccac cctgtaccag | 600 |
| ctgggagccg | ccacccaggc | cagaccccct | cctcacgcct | ccggcccag cggagactg | 660 |
| ggctgcgagc | gggcctggaa | ccacagcgtg | cggaggccg | cgtgcccct gggcctgcca | 720 |
| gcccctggcg | ccagaagaag | gggcggcagc | gccagcagaa | gcctgcccct gcccaagcgg | 780 |
| cccagacgcg | gagccgcccc | tgagcccgag | agaaccccg | tgggccaggg ctcttgggcc | 840 |
| caccctggcc | ggaccagagg | ccccagcgac | cggggcttct | gcgtggtgtc cccgccaga | 900 |
| cccgccgagg | aagccacctc | cctggaaggc | gccctgagcg | gcaccaggca cagccacccc | 960 |
| agcgtgggcc | gccagcacca | cgccggaccc | cccagcacct | ccaggccccc caggccctgg | 1020 |
| gacaccccttt | gccccctgt | gtacgccgag | accaagcact | tcctgtacag cagcggcgac | 1080 |
| aaagagcagc | tgcggcccag | cttcctgctg | tccagcctga | ggcctccct gaccggcgct | 1140 |
| aggcgcctgg | tggagaccat | cttctctggc | agccggccct | ggatgcccgg cacccccagg | 1200 |
| cggctgccca | ggctgcccca | gcggtactgg | cagatgagcc | tctgttcct ggaactgctg | 1260 |
| ggcaaccacg | cccagtgccc | ctacggcgtg | ctgctgaaaa | cccactgccc cctgagagcc | 1320 |
| gccgtgaccc | cagccgccgg | agtgtgcgcc | agagagaagc | tcagggcag cgtgccgct | 1380 |
| cccgaggaag | aggacaccga | ccccagacgc | ctggtgcagc | tgctgcggca gcacagcagc | 1440 |
| ccttggcagg | tgtacggctt | cgtgcgggcc | tgcctgagaa | ggctggtgcc cctggcctg | 1500 |
| tgggggcagca | ggcacaacga | gcggcggttt | ctgcggaaca | ccaagaagtt catcagcctg | 1560 |
| gggaagcacg | ccaagctgtc | cctgcaggaa | ctgacctgga | agatgagcgt gcggggctgc | 1620 |

```
gcctggctga aagatccccc tggcgtgggc tgcgtgcctg ccgccgagca ccggctgcgg    1680
gaggaaatcc tggccaagtt cctgcactgg ctgatgagcg tgtacgtggt ggagctgctg    1740
agatccttct tctacgtgac cgagaccacc ttccagaaga actacctgtt cttctaccgg    1800
aagagcgtgt ggagcaagct gcagagcatc ggcatccggc agcacctgaa gcgggtgcag    1860
ctgagagagc tgtccgaggc cgaagtgagg cagcaccggg aggccagacc tgccctgctg    1920
accagccggc tgcggttcat ccccaagccc gacggcctgc ggcccatcgt gaacatggac    1980
tacgtggtgg gcgccaggac cttccggcgg gagaagcggg ccgagcggct gacctcgagg    2040
gtgaaggccc tgttcagcgt gctgaactac gagcgggcca ggcggccagg cctgctgggc    2100
gccagcgtgc tgggcctgga cgacatccac cgggcctggc ggaccttcgt gctgagagtg    2160
cgggcccagg accccctcc cgagctgtac ttcgtgaagg tggacgtgac aggcgcctac    2220
gacaccatcc cccaggaccg gctgaccgag gtgatcgcca gcatcatcaa gccccagaac    2280
acctactgcg tgcggagata cgccgtggtg cagaaggccg cccacggcca cgtgcggaag    2340
gccttcaaga gccacgtgag caccctgacc gacctgcagc cctacatgcg gcagttcgtg    2400
gcccacctgc aggaaaccag ccccctgcgg gatgccgtgg tgatcgagca gagcagcagc    2460
ctgaacgagg ccagcagcgg cctgttcgac gtgttcctga gattcatgtg ccaccacgcc    2520
gtgcggatcc ggggcaagag ctacgtgcag tgccagggca tcccacaggg cagcatcctg    2580
tccaccctgc tgtgctccct gtgctacggc gacatggaaa acaagctgtt cgccggcatc    2640
aggcgggacg gactgctgct gagactggtg gacgacttcc tgctggtgac cccccacctg    2700
acccacgcca agacctttct gcggaccctg gtgcgcggcg tgcccgagta cggctgcgtg    2760
gtgaacctga aaagaccgt ggtgaacttc cccgtggagg acgaggccct gggcggcaca    2820
gccttcgtgc agatgcctgc ccatggactg ttcccttggt gcgggctgct gctggacacc    2880
cggaccctgg aagtgcagag cgactacagc agctacgccc ggaccagcat ccgggcctcc    2940
ctgaccttca caggggctt caaggccggc aggaacatgc ggcggaagct gtttggcgtg    3000
ctgcggctga agtgccacag cctgtttctg tacctgcagg tgaacagcct gcagaccgtg    3060
tgcaccaaca tctacaagat cctgctgctg caggcctacc ggttccacgc ctgcgtgctg    3120
cagctgccct tcaccagca ggtgtggaag aaccctacct tcttcctgcg ggtgatcagc    3180
gacaccgcca gcctgtgcta cagcatcctg aaggccaaga cgccggcat gagcctgggc    3240 gccaagggag ccgccggacc tctgcccagc gaggccgtgc agtggctgtg ccaccaggcc    3300
tttctgctga agctgacccg gcaccgggtg acctacgtgc cctgctggg cagcctgcgg    3360 accgcccaga cccagctgtc ccggaagctg cctggcacca ccctgacagc cctggaagcc    3420
gccgccaacc ccgccctgcc ctccgacttc aagaccatcc tggactaccc ctacgacgtg    3480
cccgactacg cctgatgagc ggccgcgagc tc                                  3512
```

<210> SEQ ID NO 49
<211> LENGTH: 1158
<212> TYPE: PRT
<213> ORGANISM: Homo sapiens

<400> SEQUENCE: 49

Met Asp Trp Thr Trp Ile Leu Phe Leu Val Ala Ala Thr Arg Val
1               5                   10                  15

His Ser Pro Arg Ala Pro Arg Cys Arg Ala Val Arg Ser Leu Leu Arg
            20                  25                  30

-continued

```
Ser His Tyr Arg Glu Val Leu Pro Leu Ala Thr Phe Val Arg Arg Leu
         35                  40                  45

Gly Pro Gln Gly Trp Arg Leu Val Gln Arg Gly Asp Pro Ala Ala Phe
 50                  55                  60

Arg Ala Leu Val Ala Gln Cys Leu Val Cys Val Pro Trp Asp Ala Arg
 65                  70                  75                  80

Pro Pro Pro Ala Ala Pro Ser Phe Arg Gln Val Ser Cys Leu Lys Glu
                 85                  90                  95

Leu Val Ala Arg Val Leu Gln Arg Leu Cys Glu Arg Gly Ala Lys Asn
                100                 105                 110

Val Leu Ala Phe Gly Phe Ala Leu Leu Asp Gly Ala Arg Gly Gly Pro
             115                 120                 125

Pro Glu Ala Phe Thr Thr Ser Val Arg Ser Tyr Leu Pro Asn Thr Val
         130                 135                 140

Thr Asp Ala Leu Arg Gly Ser Gly Ala Trp Gly Leu Leu Arg Arg
145                 150                 155                 160

Val Gly Asp Asp Val Leu Val His Leu Leu Ala Arg Cys Ala Leu Phe
                165                 170                 175

Val Leu Val Ala Pro Ser Cys Ala Tyr Gln Val Cys Gly Pro Pro Leu
            180                 185                 190

Tyr Gln Leu Gly Ala Ala Thr Gln Ala Arg Pro Pro His Ala Ser
        195                 200                 205

Gly Pro Arg Arg Leu Gly Cys Glu Arg Ala Trp Asn His Ser Val
    210                 215                 220

Arg Glu Ala Gly Val Pro Leu Gly Leu Pro Ala Pro Gly Ala Arg Arg
225                 230                 235                 240

Arg Gly Gly Ser Ala Ser Arg Ser Leu Pro Leu Pro Lys Arg Pro Arg
                245                 250                 255

Arg Gly Ala Ala Pro Glu Pro Glu Arg Thr Pro Val Gly Gln Gly Ser
            260                 265                 270

Trp Ala His Pro Gly Arg Thr Arg Gly Pro Ser Asp Arg Gly Phe Cys
        275                 280                 285

Val Val Ser Pro Ala Arg Pro Ala Glu Glu Ala Thr Ser Leu Glu Gly
    290                 295                 300

Ala Leu Ser Gly Thr Arg His Ser His Pro Ser Val Gly Arg Gln His
305                 310                 315                 320

His Ala Gly Pro Pro Ser Thr Ser Arg Pro Pro Arg Pro Trp Asp Thr
                325                 330                 335

Pro Cys Pro Pro Val Tyr Ala Glu Thr Lys His Phe Leu Tyr Ser Ser
            340                 345                 350

Gly Asp Lys Glu Gln Leu Arg Pro Ser Phe Leu Leu Ser Ser Leu Arg
        355                 360                 365

Pro Ser Leu Thr Gly Ala Arg Arg Leu Val Glu Thr Ile Phe Leu Gly
370                 375                 380

Ser Arg Pro Trp Met Pro Gly Thr Pro Arg Arg Leu Pro Arg Leu Pro
385                 390                 395                 400

Gln Arg Tyr Trp Gln Met Arg Pro Leu Phe Leu Glu Leu Leu Gly Asn
                405                 410                 415

His Ala Gln Cys Pro Tyr Gly Val Leu Leu Lys Thr His Cys Pro Leu
            420                 425                 430

Arg Ala Ala Val Thr Pro Ala Ala Gly Val Cys Ala Arg Glu Lys Pro
        435                 440                 445

Gln Gly Ser Val Ala Ala Pro Glu Glu Glu Asp Thr Asp Pro Arg Arg
```

```
              450                 455                 460
Leu Val Gln Leu Leu Arg Gln His Ser Ser Pro Trp Gln Val Tyr Gly
465                 470                 475                 480

Phe Val Arg Ala Cys Leu Arg Arg Leu Val Pro Pro Gly Leu Trp Gly
                485                 490                 495

Ser Arg His Asn Glu Arg Arg Phe Leu Arg Asn Thr Lys Lys Phe Ile
                500                 505                 510

Ser Leu Gly Lys His Ala Lys Leu Ser Leu Gln Glu Leu Thr Trp Lys
                515                 520                 525

Met Ser Val Arg Gly Cys Ala Trp Leu Arg Arg Ser Pro Gly Val Gly
530                 535                 540

Cys Val Pro Ala Ala Glu His Arg Leu Arg Glu Glu Ile Leu Ala Lys
545                 550                 555                 560

Phe Leu His Trp Leu Met Ser Val Tyr Val Glu Leu Leu Arg Ser
                565                 570                 575

Phe Phe Tyr Val Thr Glu Thr Thr Phe Gln Lys Asn Tyr Leu Phe Phe
                580                 585                 590

Tyr Arg Lys Ser Val Trp Ser Lys Leu Gln Ser Ile Gly Ile Arg Gln
                595                 600                 605

His Leu Lys Arg Val Gln Leu Arg Glu Leu Ser Glu Ala Glu Val Arg
                610                 615                 620

Gln His Arg Glu Ala Arg Pro Ala Leu Leu Thr Ser Arg Leu Arg Phe
625                 630                 635                 640

Ile Pro Lys Pro Asp Gly Leu Arg Pro Ile Val Asn Met Asp Tyr Val
                645                 650                 655

Val Gly Ala Arg Thr Phe Arg Arg Glu Lys Arg Ala Glu Arg Leu Thr
                660                 665                 670

Ser Arg Val Lys Ala Leu Phe Ser Val Leu Asn Tyr Glu Arg Ala Arg
                675                 680                 685

Arg Pro Gly Leu Leu Gly Ala Ser Val Leu Gly Leu Asp Asp Ile His
                690                 695                 700

Arg Ala Trp Arg Thr Phe Val Leu Arg Val Arg Ala Gln Asp Pro Pro
705                 710                 715                 720

Pro Glu Leu Tyr Phe Val Lys Val Asp Val Thr Gly Ala Tyr Asp Thr
                725                 730                 735

Ile Pro Gln Asp Arg Leu Thr Glu Val Ile Ala Ser Ile Ile Lys Pro
                740                 745                 750

Gln Asn Thr Tyr Cys Val Arg Arg Tyr Ala Val Val Gln Lys Ala Ala
                755                 760                 765

His Gly His Val Arg Lys Ala Phe Lys Ser His Val Ser Thr Leu Thr
                770                 775                 780

Asp Leu Gln Pro Tyr Met Arg Gln Phe Val Ala His Leu Gln Glu Thr
785                 790                 795                 800

Ser Pro Leu Arg Asp Ala Val Val Ile Glu Gln Ser Ser Ser Leu Asn
                805                 810                 815

Glu Ala Ser Ser Gly Leu Phe Asp Val Phe Leu Arg Phe Met Cys His
                820                 825                 830

His Ala Val Arg Ile Arg Gly Lys Ser Tyr Val Gln Cys Gln Gly Ile
                835                 840                 845

Pro Gln Gly Ser Ile Leu Ser Thr Leu Leu Cys Ser Leu Cys Tyr Gly
                850                 855                 860

Asp Met Glu Asn Lys Leu Phe Ala Gly Ile Arg Arg Asp Gly Leu Leu
865                 870                 875                 880
```

```
Leu Arg Leu Val Asp Asp Phe Leu Leu Val Thr Pro His Leu Thr His
                885                 890                 895
Ala Lys Thr Phe Leu Arg Thr Leu Val Arg Gly Val Pro Glu Tyr Gly
            900                 905                 910
Cys Val Val Asn Leu Arg Lys Thr Val Val Asn Phe Pro Val Glu Asp
        915                 920                 925
Glu Ala Leu Gly Gly Thr Ala Phe Val Gln Met Pro Ala His Gly Leu
    930                 935                 940
Phe Pro Trp Cys Gly Leu Leu Leu Asp Thr Arg Thr Leu Glu Val Gln
945                 950                 955                 960
Ser Asp Tyr Ser Ser Tyr Ala Arg Thr Ser Ile Arg Ala Ser Leu Thr
                965                 970                 975
Phe Asn Arg Gly Phe Lys Ala Gly Arg Asn Met Arg Arg Lys Leu Phe
            980                 985                 990
Gly Val Leu Arg Leu Lys Cys His Ser Leu Phe Leu Tyr Leu Gln Val
        995                 1000                1005
Asn Ser Leu Gln Thr Val Cys Thr Asn Ile Tyr Lys Ile Leu Leu
    1010                1015                1020
Leu Gln Ala Tyr Arg Phe His Ala Cys Val Leu Gln Leu Pro Phe
    1025                1030                1035
His Gln Gln Val Trp Lys Asn Pro Thr Phe Phe Leu Arg Val Ile
    1040                1045                1050
Ser Asp Thr Ala Ser Leu Cys Tyr Ser Ile Leu Lys Ala Lys Asn
    1055                1060                1065
Ala Gly Met Ser Leu Gly Ala Lys Gly Ala Ala Gly Pro Leu Pro
    1070                1075                1080
Ser Glu Ala Val Gln Trp Leu Cys His Gln Ala Phe Leu Leu Lys
    1085                1090                1095
Leu Thr Arg His Arg Val Thr Tyr Val Pro Leu Leu Gly Ser Leu
    1100                1105                1110
Arg Thr Ala Gln Thr Gln Leu Ser Arg Lys Leu Pro Gly Thr Thr
    1115                1120                1125
Leu Thr Ala Leu Glu Ala Ala Ala Asn Pro Ala Leu Pro Ser Asp
    1130                1135                1140
Phe Lys Thr Ile Leu Asp Tyr Pro Tyr Asp Val Pro Asp Tyr Ala
    1145                1150                1155

<210> SEQ ID NO 50
<211> LENGTH: 789
<212> TYPE: DNA
<213> ORGANISM: Homo sapiens

<400> SEQUENCE: 50
atgtgggtcc tggtggtgtt cctgactctg agcgtcacat ggatcggcgc cgctccactg    60
attctgagcc gcctggtggg cgggtgggag tgcgaaaagc actcccagcc atggcaggtg   120
ctggtcgctt ctaggggccg agcagtgtgc ggaggcgtgc tggtccaccc tcagtgggtc   180
ctgaccgcag cccattgtat ccgacagaag agcgtgattc tgctggggcg acaccagcca   240
ttctaccccg aggacacagg acaggtgttc caggtctctc acagttttcc ccatcctctg   300
tacaacatga gcctgctgaa aaacagatat ctgggacctg cgacgatag ctcccatgat   360 ctgatgctgc tgaggctgtc cgagccagcc gaactgactg acgctgtgca ggtcctggat   420
ctgcccaccc aggagcctgc cctgggaacc acatgttatg cttcaggctg ggggagcatc   480
```

```
gaaccagagg aacatctgac tcccaagaaa ctgcagtgcg tggacctgca cctgattagt      540
aacgatgtgt gtgcacaggt ccattcacag aaggtgacaa agttcatgct gtgcgccggc      600
tcttggatgg gcggcaagtc aacttgcagc ggggactccg gcgggccact ggtgtgtgat      660
ggagtcctgc agggcatcac ctcttggggc agtcagcctt gtgccctgcc tcggagacca      720
agtctgtaca ctaaggtggt ccggtatagg aaatggattc aggacactat tgccgctaac      780
ccctgataa                                                              789
```

```
<210> SEQ ID NO 51
<211> LENGTH: 261
<212> TYPE: PRT
<213> ORGANISM: Homo sapiens

<400> SEQUENCE: 51

Met Trp Val Leu Val Phe Leu Thr Leu Ser Val Thr Trp Ile Gly
1               5                   10                  15

Ala Ala Pro Leu Ile Leu Ser Arg Leu Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Gln Lys Ser Val Ile Leu Leu Gly Arg His Gln Pro
65                  70                  75                  80

Phe Tyr Pro Glu Asp Thr Gly Gln Val Phe Gln Val Ser His Ser Phe
                85                  90                  95

Pro His Pro Leu Tyr Asn Met Ser Leu Leu Lys Asn Arg Tyr Leu Gly
            100                 105                 110

Pro Gly Asp Asp Ser Ser His Asp Leu Met Leu Leu Arg Leu Ser Glu
        115                 120                 125

Pro Ala Glu Leu Thr Asp Ala Val Gln Val Leu Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
                165                 170                 175

His Leu Ile Ser Asn Asp Val Cys Ala Gln Val His Ser Gln Lys Val
            180                 185                 190

Thr Lys Phe Met Leu Cys Ala Gly Ser Trp Met Gly Gly Lys Ser Thr
        195                 200                 205

Cys Ser Gly Asp Ser Gly Gly Pro Leu Val Cys Asp Gly Val Leu Gln
    210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
                245                 250                 255

Ile Ala Ala Asn Pro
            260
```

```
<210> SEQ ID NO 52
<211> LENGTH: 840
<212> TYPE: DNA
<213> ORGANISM: Homo sapiens

<400> SEQUENCE: 52
```

-continued

```
atggactgga catggattct gttcctggtc gccgccgcaa ctcgcgtgca ttcctgggtc    60
ctggtggtgt tcctgactct gagcgtcaca tggatcggcg ccgctccact gattctgagc   120
cgcctggtgg gcgggtggga gtgcgaaaag cactcccagc catggcaggt gctggtcgct   180
tctaggggcc gagcagtgtg cggaggcgtg ctggtccacc ctcagtgggt cctgaccgca   240
gcccattgta tccgacagaa gagcgtgatt ctgctggggc gacaccagcc attctacccc   300
gaggacacag acaggtgtt ccaggtctct cacagttttc cccatcctct gtacaacatg   360
agcctgctga aaaacagata tctgggacct ggcgacgata gctcccatga tctgatgctg   420
ctgaggctgt ccgagccagc cgaactgact gacgctgtgc aggtcctgga tctgcccacc   480
caggagcctg ccctgggaac acatgttat gcttcaggct gggggagcat cgaaccagag   540
gaacatctga ctcccaagaa actgcagtgc gtggacctgc acctgattag taacgatgtg   600
tgtgcacagg tccattcaca aaggtgaca aagttcatgc tgtgcgccgg ctcttggatg   660
ggcggcaagt caacttgcag cggggactcc ggcgggccac tggtgtgtga tggagtcctg   720
cagggcatca cctcttgggg cagtcagcct tgtgccctgc ctcggagacc aagtctgtac   780
actaaggtgg tccggtatag gaaatggatt caggacacta ttgccgctaa ccctgataa    840
```

<210> SEQ ID NO 53
<211> LENGTH: 278
<212> TYPE: PRT
<213> ORGANISM: Homo sapiens

<400> SEQUENCE: 53

```
Met Asp Trp Thr Trp Ile Leu Phe Leu Val Ala Ala Thr Arg Val
1               5                   10                  15

His Ser Trp Val Leu Val Val Phe Leu Thr Leu Ser Val Thr Trp Ile
            20                  25                  30

Gly Ala Ala Pro Leu Ile Leu Ser Arg Leu Val Gly Gly Trp Glu Cys
        35                  40                  45

Glu Lys His Ser Gln Pro Trp Gln Val Leu Val Ala Ser Arg Gly Arg
    50                  55                  60

Ala Val Cys Gly Gly Val Leu Val His Pro Gln Trp Val Leu Thr Ala
65                  70                  75                  80

Ala His Cys Ile Arg Gln Lys Ser Val Ile Leu Leu Gly Arg His Gln
                85                  90                  95

Pro Phe Tyr Pro Glu Asp Thr Gly Gln Val Phe Gln Val Ser His Ser
            100                 105                 110

Phe Pro His Pro Leu Tyr Asn Met Ser Leu Leu Lys Asn Arg Tyr Leu
        115                 120                 125

Gly Pro Gly Asp Asp Ser Ser His Asp Leu Met Leu Leu Arg Leu Ser
    130                 135                 140

Glu Pro Ala Glu Leu Thr Asp Ala Val Gln Val Leu Asp Leu Pro Thr
145                 150                 155                 160

Gln Glu Pro Ala Leu Gly Thr Thr Cys Tyr Ala Ser Gly Trp Gly Ser
                165                 170                 175

Ile Glu Pro Glu Glu His Leu Thr Pro Lys Lys Leu Gln Cys Val Asp
            180                 185                 190

Leu His Leu Ile Ser Asn Asp Val Cys Ala Gln Val His Ser Gln Lys
        195                 200                 205

Val Thr Lys Phe Met Leu Cys Ala Gly Ser Trp Met Gly Gly Lys Ser
    210                 215                 220

Thr Cys Ser Gly Asp Ser Gly Gly Pro Leu Val Cys Asp Gly Val Leu
```

```
                225                 230                 235                 240
Gln Gly Ile Thr Ser Trp Gly Ser Gln Pro Cys Ala Leu Pro Arg Arg
                    245                 250                 255

Pro Ser Leu Tyr Thr Lys Val Val Arg Tyr Arg Lys Trp Ile Gln Asp
                260                 265                 270

Thr Ile Ala Ala Asn Pro
            275

<210> SEQ ID NO 54
<211> LENGTH: 2283
<212> TYPE: DNA
<213> ORGANISM: Homo sapiens

<400> SEQUENCE: 54
atgtggaacg cactgcatga gactgattct gctgtcgcac tgggacggag accccggtgg      60
ctgtgcgctg gagcactggt gctggccggc ggggattcc  tgctgggatt cctgtttggc     120
tggtttatca aaagctccag cgaggctacc aatattaccc ctaagcacaa taagaaagca     180
ttcctggatg aactgaaagc cgagaacatc aagaaattcc tgtacaactt cacaagaatt     240
ccacatctgg ctggcactga gcagaacttc agctggcaa  acagatcca  gagtcagtgg     300 aaggaatttg ggctggactc agtggagctg acccactacg atgtcctgct gtcctatcca     360
aataagactc atcccaacta catctctatc attaacgaag acggaaatga gatttttcaac    420 acctctctgt tgaacccccc tccacccggc tatgagaatg tcagtgacgt ggtccctcca     480
ttctcagcct tcagccccca ggggatgcct gagggagatc tggtgtacgt caattatgct     540
agaacagaag acttctttaa gctggagagg gatatgaaaa tcaactgttc cggcaagatc     600
gtgattgccc ggtacgggaa ggtgttcaga ggaaataagg tcaaaaacgc tcagctggcc     660
ggagctaccg gcgtgatcct gtacagcgac cccgctgatt attttgcacc tggcgtgaag     720
tcctatccag acggatggaa tctgcccggc ggggagtgc  agaggggaaa catcctgaac     780
ctgaatggag ccggcgatcc tctgactcca ggatacccg  ccaacgaata cgcttatcgc     840
cggggaattg cagaggccgt gggcctgcct agcatcccag tccatcccat tggctattac     900
gatgcccaga agctgctgga aaaatgggc  gggagcgctc cccctgactc tagttggaag     960
ggctccctga agtgccttta caatgtcggg ccaggattca ctgggaactt ttctacccag    1020
aaggtgaaaa tgcacatcca tagtaccagc gaggtgacac gaatctacaa cgtcattggc    1080
accctgagag cgccgtggga gcctgatcgc tatgtcattc tgggaggcca cagagactca    1140
tgggtgttcg ggggaatcga tccacagagc ggagcagctg tggtccatga aattgtgcgc    1200
agctttggga ccctgaagaa gagggatgg  cgacccaggc gcacaatcct gttcgcatcc    1260
tgggacgccg aggaatttgg gctgctgggc agcacagaat gggccgagga aaattctcgc    1320
ctgctgcagg agcgagggt  ggcttacatc aatgcagact caagcattga aggaaactat    1380
accctgcggt ggattgcac  cccctgatg  tacagtctgg tctataacct gacaaaggag    1440
ctgaaatcac ctgacgaggg cttcgaaggg aaaagcctgt acgaatcctg gactgagaag    1500
agcccatccc ccgaattcag cggcatgcct aggatctcta agctgggcag tgggaacgat    1560
tttgaggtgt tctttcagcg cctgggaatt gcctctggcc gagctcggta cacaaaaaat    1620
tgggagacta acaagttctc ctcttaccca ctgtatcaca gcgtgtacga gacttatgaa    1680
ctggtcgaga aattctacga ccccacttt  aagtatcatc tgaccgtggc acaggtcagg    1740
ggcgggatgg tgttcgaact ggccaatagc atcgtcctgc catttgactg tcgagattac    1800
```

```
gctgtggtcc tgcggaagta cgcagacaag atctataaca tctccatgaa gcaccccag    1860 gagatgaagg cctattctgt gagtttcgat tccctgtttt ctgccgtcaa aaatttcacc    1920
gaaatcgcta gtaagttttc agagcgcctg caggacctgg ataagtccaa tcccatcctg    1980
ctgcggatta tgaacgatca gctgatgttc ctggaaagag cctttatcga ccctctgggc    2040
ctgcctgata gaccattcta caggcacgtg atctacgcac ctagttcaca taacaagtac    2100
gccggcgagt cttttcccagg gatctatgac gctctgtttg atattgaatc aaaggtggac    2160
cccagcaaag catggggcga ggtcaagaga cagatcagca ttgcagcctt tacagtgcag    2220
gccgccgccg aaaccctgtc cgaagtcgct tacccatacg atgtccccga ttacgcatga    2280
taa                                                                  2283
```

<210> SEQ ID NO 55
<211> LENGTH: 750
<212> TYPE: PRT
<213> ORGANISM: Homo sapiens

<400> SEQUENCE: 55

```
Met Trp Asn Ala Leu His Glu Thr Asp Ser Ala Val Ala Leu Gly Arg
1               5                   10                  15

Arg Pro Arg Trp Leu Cys Ala Gly Ala Leu Val Leu Ala Gly Gly Gly
                20                  25                  30

Phe Leu Leu Gly Phe Leu Phe Gly Trp Phe Ile Lys Ser Ser Ser Glu
            35                  40                  45

Ala Thr Asn Ile Thr Pro Lys His Asn Lys Lys Ala Phe Leu Asp Glu
        50                  55                  60

Leu Lys Ala Glu Asn Ile Lys Lys Phe Leu Tyr Asn Phe Thr Arg Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Val Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Thr Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285
```

```
Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Lys
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Ser Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val Tyr Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Glu Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Ser Tyr Pro Leu Tyr His Ser Val Tyr Glu Thr Tyr Glu
545                 550                 555                 560

Leu Val Glu Lys Phe Tyr Asp Pro Thr Phe Lys Tyr His Leu Thr Val
            565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Ala
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Leu Asp Lys Ser
            645                 650                 655

Asn Pro Ile Leu Leu Arg Ile Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700
```

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Ser Ile Ala Ala
            725                 730                 735

Phe Thr Val Gln Ala Ala Ala Glu Thr Leu Ser Glu Val Ala
            740                 745                 750

<210> SEQ ID NO 56
<211> LENGTH: 2334
<212> TYPE: DNA
<213> ORGANISM: Homo sapiens

<400> SEQUENCE: 56

| | |
|---|---|
| atggactgga catggattct gttcctggtc gccgccgcaa ctcgcgtgca ttcctggaac | 60 |
| gcactgcatg agactgattc tgctgtcgca ctgggacgga gaccccggtg gctgtgcgct | 120 |
| ggagcactgg tgctggccgg cggggggattc ctgctgggat tcctgtttgg ctggtttatc | 180 |
| aaaagctcca gcgaggctac caatattacc cctaagcaca ataagaaagc attcctggat | 240 |
| gaactgaaag ccgagaacat caagaaattc ctgtacaact tcacaagaat tccacatctg | 300 |
| gctggcactg agcagaactt ccagctggca aaacagatcc agagtcagtg aaggaatttt | 360 |
| gggctggact cagtggagct gacccactac gatgtcctgc tgtcctatcc aaataagact | 420 |
| catcccaact acatctctat cattaacgaa acggaaatg agattttcaa cacctctctg | 480 |
| tttgaacccc ctccacccgg ctatgagaat gtcagtgacg tggtccctcc attctcagcc | 540 |
| ttcagccccc aggggatgcc tgagggagat ctggtgtacg tcaattatgc tagaacagaa | 600 |
| gacttcttta agctggagag ggatatgaaa atcaactgtt ccggcaagat cgtgattgcc | 660 |
| cggtacggga aggtgttcag aggaaataag gtcaaaaacg ctcagctggc cggagctacc | 720 |
| ggcgtgatcc tgtacagcga ccccgctgat tattttgcac ctggcgtgaa gtcctatcca | 780 |
| gacggatgga tctgcccggg cggggggagtg cagaggggaa acatcctgaa cctgaatgga | 840 |
| gccggcgatc ctctgactcc aggataccccc gccaacgaat acgcttatcg ccggggaatt | 900 |
| gcagaggccg tgggcctgcc tagcatccca gtccatccca ttggctatta cgatgcccag | 960 |
| aagctgctgg agaaaatggg cgggagcgct ccccctgact cagttggaa gggctccctg | 1020 |
| aaagtgcctt acaatgtcgg gccaggattc actgggaact tttctaccca gaaggtgaaa | 1080 |
| atgcacatcc atagtaccag cgaggtgaca cgaatctaca cgtcattgg caccctgaga | 1140 |
| ggcgccgtgg agcctgatcg ctatgtcatt ctgggaggcc acagagactc atgggtgttc | 1200 |
| ggggggaatcg atccacagag cggagcagct gtggtccatg aaattgtgcg cagctttggg | 1260 |
| accctgaaga agagggatg gcgacccagg cgcacaatcc tgttcgcatc ctgggacgcc | 1320 |
| gaggaatttg gctgctggg cagcacagaa tgggccgagg aaaattctcg cctgctgcag | 1380 |
| gagcgagggg tggcttacat caatgcagac tcaagcattg aaggaaacta ccctgcgg | 1440 |
| gtggattgca cacccctgat gtacagtctg gtctataacc tgacaaagga gctgaaatca | 1500 |
| cctgacgagg gcttcgaagg gaaaagcctg tacgaatcct ggactgagaa gagcccatcc | 1560 |
| cccgaattca gcggcatgcc taggatctct aagctgggca gtgggaacga ttttgaggtg | 1620 |
| ttctttcagc gcctgggaat tgcctctggc cgagctcggt acacaaaaaa ttgggagact | 1680 |
| aacaagttct cctcttaccc actgtatcac agcgtgtacg agacttatga actggtcgag | 1740 |
| aaattctacg accccacttt taagtatcat ctgaccgtgg cacaggtcag ggggcgggatg | 1800 |
| gtgttcgaac tggccaatag catcgtcctg ccatttgact gtcgagatta cgctgtggtc | 1860 |

-continued

```
ctgcggaagt acgcagacaa gatctataac atctccatga agcaccccca ggagatgaag   1920
gcctattctg tgagtttcga ttccctgttt tctgccgtca aaatttcac cgaaatcgct    1980 agtaagtttt cagagcgcct gcaggacctg gataagtcca atcccatcct gctgcggatt   2040
atgaacgatc agctgatgtt cctggaaaga gcctttatcg accctctggg cctgcctgat   2100
agaccattct acaggcacgt gatctacgca cctagttcac ataacaagta cgccggcgag   2160
tctttcccag ggatctatga cgctctgttt gatattgaat caaaggtgga ccccagcaaa   2220
gcatggggcg aggtcaagag acagatcagc attgcagcct ttacagtgca ggccgccgcc   2280
gaaaccctgt ccgaagtcgc ttacccatac gatgtccccg attacgcatg ataa          2334
```

<210> SEQ ID NO 57
<211> LENGTH: 766
<212> TYPE: PRT
<213> ORGANISM: Homo sapiens

<400> SEQUENCE: 57

```
Met Trp Thr Trp Ile Leu Phe Leu Val Ala Ala Thr Arg Val His
1               5                   10                  15

Ser Trp Asn Ala Leu His Glu Thr Asp Ser Ala Val Ala Leu Gly Arg
            20                  25                  30

Arg Pro Arg Trp Leu Cys Ala Gly Ala Leu Val Leu Ala Gly Gly Gly
        35                  40                  45

Phe Leu Leu Gly Phe Leu Phe Gly Trp Phe Ile Lys Ser Ser Ser Glu
    50                  55                  60

Ala Thr Asn Ile Thr Pro Lys His Asn Lys Lys Ala Phe Leu Asp Glu
65                  70                  75                  80

Leu Lys Ala Glu Asn Ile Lys Lys Phe Leu Tyr Asn Phe Thr Arg Ile
                85                  90                  95

Pro His Leu Ala Gly Thr Glu Gln Asn Phe Gln Leu Ala Lys Gln Ile
            100                 105                 110

Gln Ser Gln Trp Lys Glu Phe Gly Leu Asp Ser Val Glu Leu Thr His
        115                 120                 125

Tyr Asp Val Leu Leu Ser Tyr Pro Asn Lys Thr His Pro Asn Tyr Ile
    130                 135                 140

Ser Ile Ile Asn Glu Asp Gly Asn Glu Ile Phe Asn Thr Ser Leu Phe
145                 150                 155                 160

Glu Pro Pro Pro Pro Gly Tyr Glu Asn Val Ser Asp Val Val Pro Pro
                165                 170                 175

Phe Ser Ala Phe Ser Pro Gln Gly Met Pro Glu Gly Asp Leu Val Tyr
            180                 185                 190

Val Asn Tyr Ala Arg Thr Glu Asp Phe Phe Lys Leu Glu Arg Asp Met
        195                 200                 205

Lys Ile Asn Cys Ser Gly Lys Ile Val Ile Ala Arg Tyr Gly Lys Val
    210                 215                 220

Phe Arg Gly Asn Lys Val Lys Asn Ala Gln Leu Ala Gly Ala Thr Gly
225                 230                 235                 240

Val Ile Leu Tyr Ser Asp Pro Ala Asp Tyr Phe Ala Pro Gly Val Lys
                245                 250                 255

Ser Tyr Pro Asp Gly Trp Asn Leu Pro Gly Gly Val Gln Arg Gly
            260                 265                 270

Asn Ile Leu Asn Leu Asn Gly Ala Gly Asp Pro Leu Thr Pro Gly Tyr
        275                 280                 285

Pro Ala Asn Glu Tyr Ala Tyr Arg Arg Gly Ile Ala Glu Ala Val Gly
```

```
                290                 295                 300
Leu Pro Ser Ile Pro Val His Pro Ile Gly Tyr Tyr Asp Ala Gln Lys
305                 310                 315                 320

Leu Leu Glu Lys Met Gly Gly Ser Ala Pro Asp Ser Ser Trp Lys
                325                 330                 335

Gly Ser Leu Lys Val Pro Tyr Asn Val Gly Pro Gly Phe Thr Gly Asn
                340                 345                 350

Phe Ser Thr Gln Lys Val Lys Met His Ile His Ser Thr Ser Glu Val
                355                 360                 365

Thr Arg Ile Tyr Asn Val Ile Gly Thr Leu Arg Gly Ala Val Glu Pro
        370                 375                 380

Asp Arg Tyr Val Ile Leu Gly Gly His Arg Asp Ser Trp Val Phe Gly
385                 390                 395                 400

Gly Ile Asp Pro Gln Ser Gly Ala Ala Val Val His Glu Ile Val Arg
                405                 410                 415

Ser Phe Gly Thr Leu Lys Lys Glu Gly Trp Arg Pro Arg Arg Thr Ile
                420                 425                 430

Leu Phe Ala Ser Trp Asp Ala Glu Glu Phe Gly Leu Leu Gly Ser Thr
            435                 440                 445

Glu Trp Ala Glu Glu Asn Ser Arg Leu Leu Gln Glu Arg Gly Val Ala
        450                 455                 460

Tyr Ile Asn Ala Asp Ser Ser Ile Glu Gly Asn Tyr Thr Leu Arg Val
465                 470                 475                 480

Asp Cys Thr Pro Leu Met Tyr Ser Leu Val Tyr Asn Leu Thr Lys Glu
                485                 490                 495

Leu Lys Ser Pro Asp Glu Gly Phe Glu Gly Lys Ser Leu Tyr Glu Ser
                500                 505                 510

Trp Thr Glu Lys Ser Pro Ser Pro Glu Phe Ser Gly Met Pro Arg Ile
                515                 520                 525

Ser Lys Leu Gly Ser Gly Asn Asp Phe Glu Val Phe Phe Gln Arg Leu
        530                 535                 540

Gly Ile Ala Ser Gly Arg Ala Arg Tyr Thr Lys Asn Trp Glu Thr Asn
545                 550                 555                 560

Lys Phe Ser Ser Tyr Pro Leu Tyr His Ser Val Tyr Glu Thr Tyr Glu
                565                 570                 575

Leu Val Glu Lys Phe Tyr Asp Pro Thr Phe Lys Tyr His Leu Thr Val
                580                 585                 590

Ala Gln Val Arg Gly Gly Met Val Phe Glu Leu Ala Asn Ser Ile Val
        595                 600                 605

Leu Pro Phe Asp Cys Arg Asp Tyr Ala Val Val Leu Arg Lys Tyr Ala
610                 615                 620

Asp Lys Ile Tyr Asn Ile Ser Met Lys His Pro Gln Glu Met Lys Ala
625                 630                 635                 640

Tyr Ser Val Ser Phe Asp Ser Leu Phe Ser Ala Val Lys Asn Phe Thr
                645                 650                 655

Glu Ile Ala Ser Lys Phe Ser Glu Arg Leu Gln Asp Leu Asp Lys Ser
                660                 665                 670

Asn Pro Ile Leu Leu Arg Ile Met Asn Asp Gln Leu Met Phe Leu Glu
                675                 680                 685

Arg Ala Phe Ile Asp Pro Leu Gly Leu Pro Asp Arg Pro Phe Tyr Arg
        690                 695                 700

His Val Ile Tyr Ala Pro Ser Ser His Asn Lys Tyr Ala Gly Glu Ser
705                 710                 715                 720
```

```
Phe Pro Gly Ile Tyr Asp Ala Leu Phe Asp Ile Glu Ser Lys Val Asp
                725                 730                 735

Pro Ser Lys Ala Trp Gly Glu Val Lys Arg Gln Ile Ser Ile Ala Ala
            740                 745                 750

Phe Thr Val Gln Ala Ala Glu Thr Leu Ser Glu Val Ala
        755                 760                 765

<210> SEQ ID NO 58
<211> LENGTH: 1023
<212> TYPE: DNA
<213> ORGANISM: Homo sapiens

<400> SEQUENCE: 58
atggagagcc gcaaggacat cacaaatcag gaagagctgt ggaagatgaa accacggaga       60
aacctggagg aagacgatta cctgcacaag gacaccggcg aaacaagtat gctgaaaaga     120
ccagtgctgc tgcacctgca tcagactgct catgcagacg agtttgattg cccctctgaa     180
ctgcagcaca cccaggagct gttcccacag tggcatctgc ccatcaagat tgccgctatc     240
attgcttcac tgacatttct gtatactctg ctgagagaag tgatccaccc tctggccacc     300
agccatcagc agtacttcta aagatccct attctggtca tcaacaaggt cctgccaatg     360
gtgagcatca cactgctggc cctggtctac ctgcctggcg tgatcgcagc cattgtccag     420
ctgcacaacg aacaaagta caagaagttc ccacattggc tggataagtg gatgctgact     480
aggaaacagt tcgggctgct gtccttcttt ttcgccgtgc tgcacgctat ctacagcctg     540
tcctatccca tgaggcgctc ttaccgatat aagctgctga actgggctta ccagcaggtg     600
cagcagaaca aggaggacgc atggattgaa cacgatgtgt ggcggatgga aatctatgtg     660
tctctgggca ttgtcgggct ggccatcctg gctctgctgg cagtgaccag tatcccttct     720
gtcagtgact cactgacatg gcgcgagttt cactacattc agagcaagct gggaatcgtg     780
tccctgctgc tgggcaccat ccatgcactg attttttgcct ggaataagtg gatcgatatc     840
aagcagttcg tgtggtatac tccccctacc tttatgattg ccgtcttcct gcccatcgtg     900
gtcctgattt taagtccat cctgttcctg ccttgtctgc gaaagaaaat cctgaaaatc     960
cgacatgggt gggaagacgt gacaaaaatc aataagaccg aaatctcaag ccagctgtga    1020
taa                                                                 1023

<210> SEQ ID NO 59
<211> LENGTH: 339
<212> TYPE: PRT
<213> ORGANISM: Homo sapiens

<400> SEQUENCE: 59

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95
```

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
            210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
                260                 265                 270

Ala Trp Asn Lys Trp Ile Asp Ile Lys Gln Phe Val Trp Tyr Thr Pro
            275                 280                 285

Pro Thr Phe Met Ile Ala Val Phe Leu Pro Ile Val Val Leu Ile Phe
            290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Ser
                325                 330                 335

Ser Gln Leu

<210> SEQ ID NO 60
<211> LENGTH: 1074
<212> TYPE: DNA
<213> ORGANISM: Homo sapiens

<400> SEQUENCE: 60
atggactgga catggattct gtttctggtc gctgccgcaa cccgcgtgca ttcagagagc    60
cgcaaggaca tcacaaatca ggaagagctg tggaagatga accacggag aaacctggag   120
gaagacgatt acctgcacaa ggacaccggc gaaacaagta tgctgaaaag accagtgctg   180
ctgcacctgc atcagactgc tcatgcagac gagtttgatt gccctctga actgcagcac   240
acccaggagc tgttcccaca gtggcatctg cccatcaaga ttgccgctat cattgcttca   300
ctgacatttc tgtatactct gctgagagaa gtgatccacc tctggccac cagccatcag   360
cagtacttct ataagatccc tattctggtc atcaacaagg tcctgccaat ggtgagcatc   420
acactgctgg ccctggtcta cctgcctggc gtgatcgcag ccattgtcca gctgcacaac   480
ggaacaaagt acaagaagtt cccacattgg ctggataagt ggatgctgac taggaaacag   540
ttcgggctgc tgtccttctt tttcgccgtg ctgcacgcta tctacagcct gtcctatccc   600
atgaggcgct cttaccgata taagctgctg aactgggctt accagcaggt gcagcagaac   660
aaggaggacg catggattga acacgatgtg tggcggatgg aaatctatgt gtctctgggc   720

-continued

```
attgtcgggc tggccatcct ggctctgctg gcagtgacca gtatcccttc tgtcagtgac      780
tcactgacat ggcgcgagtt tcactacatt cagagcaagc tgggaatcgt gtccctgctg      840
ctgggcacca tccatgcact gattttcgcc tggaataagt ggatcgatat caagcagttc      900
```
(Note: line 900 as printed: `ctgggcacca tccatgcact gattttgcc tggaataagt ggatcgatat caagcagttc`)

```
gtgtggtata ctcccctac ctttatgatt gccgtcttcc tgcccatcgt ggtcctgatt       960
tttaagtcca tcctgttcct gccttgtctg cgaagaaaa tcctgaaaat ccgacatggg      1020
tgggaagacg tgacaaaaat caataagacc gaaatctcaa gccagctgtg ataa           1074
```

<210> SEQ ID NO 61
<211> LENGTH: 356
<212> TYPE: PRT
<213> ORGANISM: Homo sapiens

<400> SEQUENCE: 61

```
Met Asp Trp Thr Trp Ile Leu Phe Leu Val Ala Ala Thr Arg Val
1               5                   10                  15

His Ser Glu Ser Arg Lys Asp Ile Thr Asn Gln Glu Glu Leu Trp Lys
            20                  25                  30

Met Lys Pro Arg Arg Asn Leu Glu Glu Asp Asp Tyr Leu His Lys Asp
        35                  40                  45

Thr Gly Glu Thr Ser Met Leu Lys Arg Pro Val Leu Leu His Leu His
    50                  55                  60

Gln Thr Ala His Ala Asp Glu Phe Asp Cys Pro Ser Glu Leu Gln His
65                  70                  75                  80

Thr Gln Glu Leu Phe Pro Gln Trp His Leu Pro Ile Lys Ile Ala Ala
                85                  90                  95

Ile Ile Ala Ser Leu Thr Phe Leu Tyr Thr Leu Leu Arg Glu Val Ile
            100                 105                 110

His Pro Leu Ala Thr Ser His Gln Gln Tyr Phe Tyr Lys Ile Pro Ile
        115                 120                 125

Leu Val Ile Asn Lys Val Leu Pro Met Val Ser Ile Thr Leu Leu Ala
    130                 135                 140

Leu Val Tyr Leu Pro Gly Val Ile Ala Ala Ile Val Gln Leu His Asn
145                 150                 155                 160

Gly Thr Lys Tyr Lys Lys Phe Pro His Trp Leu Asp Lys Trp Met Leu
                165                 170                 175

Thr Arg Lys Gln Phe Gly Leu Leu Ser Phe Phe Ala Val Leu His
            180                 185                 190

Ala Ile Tyr Ser Leu Ser Tyr Pro Met Arg Arg Ser Tyr Arg Tyr Lys
        195                 200                 205

Leu Leu Asn Trp Ala Tyr Gln Gln Val Gln Gln Asn Lys Glu Asp Ala
    210                 215                 220

Trp Ile Glu His Asp Val Trp Arg Met Glu Ile Tyr Val Ser Leu Gly
225                 230                 235                 240

Ile Val Gly Leu Ala Ile Leu Ala Leu Leu Ala Val Thr Ser Ile Pro
                245                 250                 255

Ser Val Ser Asp Ser Leu Thr Trp Arg Glu Phe His Tyr Ile Gln Ser
            260                 265                 270

Lys Leu Gly Ile Val Ser Leu Leu Gly Thr Ile His Ala Leu Ile
        275                 280                 285

Phe Ala Trp Asn Lys Trp Ile Asp Ile Lys Gln Phe Val Trp Tyr Thr
    290                 295                 300

Pro Pro Thr Phe Met Ile Ala Val Phe Leu Pro Ile Val Val Leu Ile
```

```
                305                 310                 315                 320
Phe Lys Ser Ile Leu Phe Leu Pro Cys Leu Arg Lys Lys Ile Leu Lys
                    325                 330                 335
Ile Arg His Gly Trp Glu Asp Val Thr Lys Ile Asn Lys Thr Glu Ile
                    340                 345                 350
Ser Ser Gln Leu
            355

<210> SEQ ID NO 62
<211> LENGTH: 399
<212> TYPE: DNA
<213> ORGANISM: Homo sapiens

<400> SEQUENCE: 62
atggactgga catggattct gtttctggtc gccgccgcaa cccgcgtgca ttctgctggc      60
ctggcactgc agcctggaac cgccctgctg tgctactctt gtaaggccca ggtgagtaac     120
gaggactgcc tgcaggtcga aaattgtact cagctgggag agcagtgctg gaccgcacgg     180
atcagagcag tgggactgct gacagtcatt agcaaagggt gctccctgaa ctgtgtggac     240
gatagccagg attactatgt cggaaagaaa aacatcacct gctgtgacac agatctgtgt     300
aatgcttctg gcgcccacgc tctgcagccc gcagccgcta ttctggctct gctgcccgct     360
ctgggactgc tgctgtgggg acccggacag ctgtgataa                            399

<210> SEQ ID NO 63
<211> LENGTH: 131
<212> TYPE: PRT
<213> ORGANISM: Homo sapiens

<400> SEQUENCE: 63

Met Asp Trp Thr Trp Ile Leu Phe Leu Val Ala Ala Ala Thr Arg Val
1               5                   10                  15

His Ser Ala Gly Leu Ala Leu Gln Pro Gly Thr Ala Leu Leu Cys Tyr
                20                  25                  30

Ser Cys Lys Ala Gln Val Ser Asn Glu Asp Cys Leu Gln Val Glu Asn
            35                  40                  45

Cys Thr Gln Leu Gly Glu Gln Cys Trp Thr Ala Arg Ile Arg Ala Val
        50                  55                  60

Gly Leu Leu Thr Val Ile Ser Lys Gly Cys Ser Leu Asn Cys Val Asp
65                  70                  75                  80

Asp Ser Gln Asp Tyr Tyr Val Gly Lys Lys Asn Ile Thr Cys Cys Asp
                85                  90                  95

Thr Asp Leu Cys Asn Ala Ser Gly Ala His Ala Leu Gln Pro Ala Ala
            100                 105                 110

Ala Ile Leu Ala Leu Leu Pro Ala Leu Gly Leu Leu Trp Gly Pro
        115                 120                 125

Gly Gln Leu
    130

<210> SEQ ID NO 64
<211> LENGTH: 2916
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 64
```

| | |
|---|---|
| atgctgaacg gcgactggaa ggccaaggtg cagcgcaagc tgaagggcgc cggccagagc | 60 |
| agccccgcca ccggcagcca gaaccagagc ggcaacaccg gcagcatcat caacaactac | 120 |
| tacatgcagc agtaccagaa cagcatggac acccagctgg gcgacaacgc catcagcggc | 180 |
| ggcagcaacg agggcagcac cgacaccacc agcacccaca ccaccaacac ccagaacaac | 240 |
| gactggttca gcaagctggc cagcagcgcc ttcaccggcc tgttcggcgc cctgctggcc | 300 |
| gacaagaaga ccgaggagac caccctgctg gaggaccgca tcctgaccac ccgcaacggc | 360 |
| cacaccacca gcaccaccca gagcagcgtg ggcgtgacct acggctacag caccaccgag | 420 |
| gaccacgtgg ccggccccaa caccagcggc ctggagaccc gcgtggtgca ggccgagcgc | 480 |
| ttcttcaaga agttcctgtt cgactggacc accgacaagc ccttcggcca cctgcacaag | 540 |
| ctggagctgc ccaccgacca ccacggcgtg ttcggccacc tggtggacag ctacgcctac | 600 |
| atgcgcaacg gctgggacgt ggaggtgagc gccgtgggca accagttcaa cggcggctgc | 660 |
| ctgctggtgg ccatggtgcc cgagtggaag gagttcgaca cccgcgagaa gtaccagctg | 720 |
| accctgttcc ccaccagtt catcagcccc cgcaccaaca tgaccgccca catcaccgtg | 780 |
| ccctacctgg gcgtgaaccg ctacgaccag tacaagaagc acaagccctg gaccctggtg | 840 |
| gtgatggtgg tgagccccct gaccgtgaac accgccgccc agatcaaggt gtacgccaac | 900 |
| atcgccccca cctacgtgca cgtggccggc gagctgccca gcaaggaggg catcttcccc | 960 |
| gtggcctgcg ccgacggcta cggcggcctg gtgaccaccg accccaagac cgccgacccc | 1020 |
| gcctacggca aggtgtacaa ccccccccgc accaactacc ccggccgctt caccaacctg | 1080 |
| ctggacgtgg ccgaggcctg ccccaccttc ctgtgcttcg acgacggcaa gccctacgtg | 1140 |
| accacccgca ccgacgagac ccgcctgctg gccaagttcg acgtgagcct ggccgccaag | 1200 |
| cacatgagca cacctacct gagcggcatc gcccagtact acacccagta cagcggcacc | 1260 |
| atcaacctgc acttcatgtt caccggcagc accgacagca aggcccgcta catggtggcc | 1320 |
| tacatccccc ccggcgtgga accccccccc gacacccccg agcgcgccgc ccactgcatc | 1380 |
| cacgccgagt gggacaccgg cctgaacagc aagttcacct tcagcatccc ctacgtgagc | 1440 |
| gccgccgact acgcctacac cgccagcgac accgccgaga ccaccaacgt gcagggctgg | 1500 |
| gtgtgcgtgt accagatcac ccacggcaag gccgagaacg cacccctggt ggtgagcgtg | 1560 |
| agcgccggca aggacttcga gctgcgcctg cccatcgacc ccgccagca gaccaccgcc | 1620 |
| accggcgaga gcgccgaccc cgtgaccacc accgtggaga actacggcgg cgagacccag | 1680 |
| gtgcagcgcc gccaccacac cgacgtgggc ttcatcatgg accgcttcgt gaagatcaac | 1740 |
| agccccaagc ccacccacgt gatcgacctg atgcagaccc accagcacgg cctggtgggc | 1800 |
| gccctgctgc gcgccgccac ctactacttc agcgacctgg agatcgtggt gcgccacgac | 1860 |
| ggcctgacct gggtgcccaa cggcgccccc gagagcgccc tgagcaacac cagcaacccc | 1920 |
| accgcctaca caaggccccc cttcacccgc ctggccctgc cctacaccgc cccccaccgc | 1980 |
| gtgctggcca ccgtgtacaa cggcaccagc aagtacaccg tgagcggcag cagccgccgc | 2040 |
| ggcgacctgg gcagcctggc cgccgcgtg gccaagcagc tgcccgccag cttcaactac | 2100 |
| ggcgccatca aggccgacac catccacgag ctgctggtgc gcatgaagcg cgccgagctg | 2160 |
| tactgcgtga agaagcccgt ggccctgaag gtgaaggcca agaacaccct gatcgtgacc | 2220 |
| gagagcggcg cccccccccac cgacctgcag aagatggtga tgggcaacac caagcccgtg | 2280 |
| gagctgatcc tggacggcaa gaccgtggcc atctgctgcg ccaccggcgt gttcggcacc | 2340 |
| gcctacctgg tgccccgcca cctgttcgcc gagaagtacg acaagatcat gctggacggc | 2400 |

-continued

```
cgcgccatga ccgacagcga ctaccgcgtg ttcgagttcg agatcaaggt gaagggccag    2460
gacatgctga gcgacgccgc cctgatggtg ctgcaccgcg gcaaccgcgt gcgcgacatc    2520
accaagcact tccgcgacac cgcccgcatg aagaagggca ccccgtggt gggcgtgatc     2580 aacaacgccg acgtgggccg cctgatcttc agcggcgagg ccctgaccta caaggacatc    2640
gtggtgtgca tggacggcga caccatgccc ggcctgttcg cctacaaggc cgccaccaag    2700
gccggctact gcggcggcgc cgtgctggcc aaggacggcg ccgacacctt catcgtgggc    2760
acccacagcg ccggcggccg caacggcgtg ggctactgca gctgcgtgag ccgcagcatg    2820
ctgctgaaga tgaaggccca catcgacccc gagccccacc acgagggcct gatcgtggac    2880
acccgcgacg tggaggagcg cgtgcacgtg atgtga                              2916
```

<210> SEQ ID NO 65
<211> LENGTH: 971
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 65

```
Met Leu Asn Gly Asp Trp Lys Ala Lys Val Gln Arg Lys Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Thr Asn Thr Gln Asn Asn
65                  70                  75                  80

Asp Trp Phe Ser Lys Leu Ala Ser Ser Ala Phe Thr Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Tyr Gly Tyr Ser Thr Thr Glu Asp His Val Ala
    130                 135                 140

Gly Pro Asn Thr Ser Gly Leu Glu Thr Arg Val Val Gln Ala Glu Arg
145                 150                 155                 160

Phe Phe Lys Lys Phe Leu Phe Asp Trp Thr Thr Asp Lys Pro Phe Gly
                165                 170                 175

His Leu His Lys Leu Glu Leu Pro Thr Asp His His Gly Val Phe Gly
            180                 185                 190

His Leu Val Asp Ser Tyr Ala Tyr Met Arg Asn Gly Trp Asp Val Glu
        195                 200                 205

Val Ser Ala Val Gly Asn Gln Phe Asn Gly Gly Cys Leu Leu Val Ala
    210                 215                 220

Met Val Pro Glu Trp Lys Glu Phe Asp Thr Arg Glu Lys Tyr Gln Leu
225                 230                 235                 240

Thr Leu Phe Pro His Gln Phe Ile Ser Pro Arg Thr Asn Met Thr Ala
                245                 250                 255

His Ile Thr Val Pro Tyr Leu Gly Val Asn Arg Tyr Asp Gln Tyr Lys
```

-continued

```
                260                 265                 270
Lys His Lys Pro Trp Thr Leu Val Val Met Val Ser Pro Leu Thr
            275                 280                 285
Val Asn Thr Ala Ala Gln Ile Lys Val Tyr Ala Asn Ile Ala Pro Thr
            290                 295                 300
Tyr Val His Val Ala Gly Glu Leu Pro Ser Lys Glu Gly Ile Phe Pro
305                 310                 315                 320
Val Ala Cys Ala Asp Gly Tyr Gly Gly Leu Val Thr Thr Asp Pro Lys
                325                 330                 335
Thr Ala Asp Pro Ala Tyr Gly Lys Val Tyr Asn Pro Pro Arg Thr Asn
                340                 345                 350
Tyr Pro Gly Arg Phe Thr Asn Leu Leu Asp Val Ala Glu Ala Cys Pro
                355                 360                 365
Thr Phe Leu Cys Phe Asp Asp Gly Lys Pro Tyr Val Thr Thr Arg Thr
                370                 375                 380
Asp Glu Thr Arg Leu Leu Ala Lys Phe Asp Val Ser Leu Ala Ala Lys
385                 390                 395                 400
His Met Ser Asn Thr Tyr Leu Ser Gly Ile Ala Gln Tyr Tyr Thr Gln
                405                 410                 415
Tyr Ser Gly Thr Ile Asn Leu His Phe Met Phe Thr Gly Ser Thr Asp
                420                 425                 430
Ser Lys Ala Arg Tyr Met Val Ala Tyr Ile Pro Pro Gly Val Glu Thr
                435                 440                 445
Pro Pro Asp Thr Pro Glu Arg Ala Ala His Cys Ile His Ala Glu Trp
                450                 455                 460
Asp Thr Gly Leu Asn Ser Lys Phe Thr Phe Ser Ile Pro Tyr Val Ser
465                 470                 475                 480
Ala Ala Asp Tyr Ala Tyr Thr Ala Ser Asp Thr Ala Glu Thr Thr Asn
                485                 490                 495
Val Gln Gly Trp Val Cys Val Tyr Gln Ile Thr His Gly Lys Ala Glu
                500                 505                 510
Asn Asp Thr Leu Val Val Ser Val Ser Ala Gly Lys Asp Phe Glu Leu
                515                 520                 525
Arg Leu Pro Ile Asp Pro Arg Gln Gln Thr Thr Ala Thr Gly Glu Ser
                530                 535                 540
Ala Asp Pro Val Thr Thr Thr Val Glu Asn Tyr Gly Gly Glu Thr Gln
545                 550                 555                 560
Val Gln Arg Arg His His Thr Asp Val Gly Phe Ile Met Asp Arg Phe
                565                 570                 575
Val Lys Ile Asn Ser Pro Lys Pro Thr His Val Ile Asp Leu Met Gln
                580                 585                 590
Thr His Gln His Gly Leu Val Gly Ala Leu Leu Arg Ala Thr Tyr
                595                 600                 605
Tyr Phe Ser Asp Leu Glu Ile Val Val Arg His Asp Gly Leu Thr Trp
                610                 615                 620
Val Pro Asn Gly Ala Pro Glu Ser Ala Leu Ser Asn Thr Ser Asn Pro
625                 630                 635                 640
Thr Ala Tyr Asn Lys Ala Pro Phe Thr Arg Leu Ala Leu Pro Tyr Thr
                645                 650                 655
Ala Pro His Arg Val Leu Ala Thr Val Tyr Asn Gly Thr Ser Lys Tyr
                660                 665                 670
Thr Val Ser Gly Ser Ser Arg Arg Gly Asp Leu Gly Ser Leu Ala Ala
                675                 680                 685
```

Arg Val Ala Lys Gln Leu Pro Ala Ser Phe Asn Tyr Gly Ala Ile Lys
690                 695                 700

Ala Asp Thr Ile His Glu Leu Leu Val Arg Met Lys Arg Ala Glu Leu
705                 710                 715                 720

Tyr Cys Val Lys Lys Pro Val Ala Leu Lys Val Lys Ala Lys Asn Thr
                725                 730                 735

Leu Ile Val Thr Glu Ser Gly Ala Pro Pro Thr Asp Leu Gln Lys Met
                740                 745                 750

Val Met Gly Asn Thr Lys Pro Val Glu Leu Ile Leu Asp Gly Lys Thr
                755                 760                 765

Val Ala Ile Cys Cys Ala Thr Gly Val Phe Gly Thr Ala Tyr Leu Val
                770                 775                 780

Pro Arg His Leu Phe Ala Glu Lys Tyr Asp Lys Ile Met Leu Asp Gly
785                 790                 795                 800

Arg Ala Met Thr Asp Ser Asp Tyr Arg Val Phe Glu Phe Glu Ile Lys
                805                 810                 815

Val Lys Gly Gln Asp Met Leu Ser Asp Ala Ala Leu Met Val Leu His
                820                 825                 830

Arg Gly Asn Arg Val Arg Asp Ile Thr Lys His Phe Arg Asp Thr Ala
                835                 840                 845

Arg Met Lys Lys Gly Thr Pro Val Val Gly Val Ile Asn Asn Ala Asp
850                 855                 860

Val Gly Arg Leu Ile Phe Ser Gly Glu Ala Leu Thr Tyr Lys Asp Ile
865                 870                 875                 880

Val Val Cys Met Asp Gly Asp Thr Met Pro Gly Leu Phe Ala Tyr Lys
                885                 890                 895

Ala Ala Thr Lys Ala Gly Tyr Cys Gly Gly Ala Val Leu Ala Lys Asp
                900                 905                 910

Gly Ala Asp Thr Phe Ile Val Gly Thr His Ser Ala Gly Gly Arg Asn
                915                 920                 925

Gly Val Gly Tyr Cys Ser Cys Val Ser Arg Ser Met Leu Leu Lys Met
                930                 935                 940

Lys Ala His Ile Asp Pro Glu Pro His Glu Gly Leu Ile Val Asp
945                 950                 955                 960

Thr Arg Asp Val Glu Glu Arg Val His Val Met
                965                 970

<210> SEQ ID NO 66
<211> LENGTH: 2916
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 66
atgctgaacg gcgagtggaa ggccaaggtg cagaagcgcc tgaagggcgc cggccagagc    60
agccccgcca ccggcagcca gaaccagagc ggcaacaccg gcagcatcat caacaactac   120
tacatgcagc agtaccagaa cagcatggac acccagctgg cgacaacgc catcagcggc    180 ggcagcaacg agggcagcac cgacaccacc agcacccaca ccaacaacac ccagaacaac   240
gactggttca gccgcctggc cagcagcgcc ttcagcggcc tgttcggcgc cctgctggcc   300
gacaagaaga ccgaggagac caccctgctg aggaccgca tcctgaccac ccgcaacggc   360
cacaccacca gcaccaccca gagcagcgtg ggcgtgacct acggctacgc cgtggccgag   420

```
gacgccgtga gcggccccaa caccagcggc ctggagaccc gcgtgcagca ggccgagcgc      480
ttcttcaaga agcacctgtt cgactggacc cccaacctgg ccttcggcca ctgccactac      540
ctggagctgc ccaccgagca aagggcgtg tacggcagcc tgatggacag ctacgcctac       600
atgcgcaacg gctgggacat cgaggtgacc gccgtgggca accagttcaa cggcggctgc      660
ctgctggtgg ccctggtgcc cgagctgaag agcctggaca cccgccagaa gtaccagctg      720
accctgttcc cccaccagtt catcaacccc cgcaccaaca tgaccgccca catcaacgtg      780
cccttcgtgg gcgtgaaccg ctacgaccag tacgccctgc acaagccctg gaccctggtg      840
gtgatggtgg tggccccccct gaccgtgaag accggcggca gcgagcagat caaggtgtac     900
atgaacgccg ccccaccta cgtgcacgtg gccggcgagc tgcccagcaa ggagggcatc       960
gtgcccgtgg cctgcgccga cggctacggc aacatggtga ccaccgaccc caagaccgcc    1020
gaccccgtgt acggcaaggt gttcaacccc cccgcacca acctgcccgg ccgcttcacc     1080
aacttcctgg acgtggccga ggcctgcccc accttcctgc gcttcggcga ggtgcccttc    1140
gtgaagaccg tgaacagcgg cgaccgcctg ctggccaagt cgacgtgag cctggccgcc    1200 ggccacatga gcaacaccta cctggccggc ctggcccagt actacaccca gtacagcggc    1260
accatgaacg tgcacttcat gttcaccggc cccaccgacg ccaaggcccg ctacatggtg    1320
gcctacatcc cccccggcat gaccccccc accgaccccg agcgccgcgc ccactgcatc    1380
cacagcgagt gggacaccgg cctgaacagc aagttcacct tcagcatccc ctacctgagc    1440
gccgccgact acgcctacac cgccagcgac accgccgaga ccaccagcgt gcagggctgg    1500
gtgtgcatct accagatcac ccacggcaag gccgagggcg acgccctggt ggtgagcgtg    1560
agcgccggca aggacttcga gttccgcctg cccgtggacg cccgccgcca gaccaccacc    1620
accggcgaga gcgccgaccc cgtgaccacc accgtgaga actacggcgg cgagacccag    1680 accgccgcc gcctgcacac cgacgtggcc ttcgtgctgg accgcttcgt gaagctgacc    1740
gcccccaaga acacccagac cctggacctg atgcagatcc ccagccacac cctggtgggc    1800
gccctgctgc gcagcgccac ctactacttc agcgacctgg aggtggccct ggtgcacacc    1860
ggccccgtga cctgggtgcc caacggcagc cccaaggacg ccctggacaa ccagaccaac    1920
cccaccgcct accagaagca gcccatcacc cgcctggccc tgccctacac cgccccccac    1980
cgcgtgctgg ccaccgtgta caacggcaag accacctacg gcgagacccc cagccgccgc    2040
ggcgacatgg ccgccctggc ccagcgcctg agcgagcgcc tgccaccag cttcaactac    2100 ggcgccgtga aggccgagac catcaccgag ctgctgatcc gcatgaagcg cgccgagacc    2160
tactgcgtga agaagcccgt ggccctgaag gtgaaggcca agaacaccct gatcgtgacc    2220
gagagcggcg cccccccac cgacctgcag aagatggtga tgggcaacac caagcccgtg    2280
gagctgatcc tggacggcaa gaccgtggcc atctgctgcg ccaccggcgt gttcggcacc    2340
gcctacctgg tgccccgcca cctgttcgcc gagaagtacg acaagatcat gctggacggc    2400
cgcgccatga ccgacagcga ctaccgcgtg ttcgagttcg agatcaaggt gaagggccag    2460
gacatgctga gcgacgccgc cctgatggtg ctgcaccgcg gcaaccgcgt gcgcgacatc    2520
accaagcact tccgcgacac cgcccgcatg aagaagggca ccccgtggt gggcgtgatc    2580 aacaacgccg acgtgggccg cctgatcttc agcggcgagg ccctgaccta caaggacatc    2640
gtggtgtgca tggacggcga caccatgccc ggcctgttcg cctacaaggc cgccaccaag    2700
gccggctact gcggcggcgc cgtgctggcc aaggacggcg ccgacacctt catcgtgggc    2760
```

```
acccacagcg ccggcggccg caacggcgtg ggctactgca gctgcgtgag ccgcagcatg    2820
ctgctgaaga tgaaggccca catcgacccc gagccccacc acgagggcct gatcgtggac    2880
acccgcgacg tggaggagcg cgtgcacgtg atgtga                              2916
```

<210> SEQ ID NO 67
<211> LENGTH: 971
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 67

```
Met Leu Asn Gly Glu Trp Lys Ala Lys Val Gln Lys Arg Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Arg Leu Ala Ser Ser Ala Phe Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Tyr Gly Tyr Ala Val Ala Glu Asp Ala Val Ser
    130                 135                 140

Gly Pro Asn Thr Ser Gly Leu Glu Thr Arg Val Gln Gln Ala Glu Arg
145                 150                 155                 160

Phe Phe Lys Lys His Leu Phe Asp Trp Thr Pro Asn Leu Ala Phe Gly
                165                 170                 175

His Cys His Tyr Leu Glu Leu Pro Thr Glu His Lys Gly Val Tyr Gly
            180                 185                 190

Ser Leu Met Asp Ser Tyr Ala Tyr Met Arg Asn Gly Trp Asp Ile Glu
        195                 200                 205

Val Thr Ala Val Gly Asn Gln Phe Asn Gly Gly Cys Leu Leu Val Ala
    210                 215                 220

Leu Val Pro Glu Leu Lys Ser Leu Asp Thr Arg Gln Lys Tyr Gln Leu
225                 230                 235                 240

Thr Leu Phe Pro His Gln Phe Ile Asn Pro Arg Thr Asn Met Thr Ala
                245                 250                 255

His Ile Asn Val Pro Phe Val Gly Val Asn Arg Tyr Asp Gln Tyr Ala
            260                 265                 270

Leu His Lys Pro Trp Thr Leu Val Val Met Val Val Ala Pro Leu Thr
        275                 280                 285

Val Lys Thr Gly Gly Ser Glu Gln Ile Lys Val Tyr Met Asn Ala Ala
    290                 295                 300

Pro Thr Tyr Val His Val Ala Gly Glu Leu Pro Ser Lys Glu Gly Ile
305                 310                 315                 320

Val Pro Val Ala Cys Ala Asp Gly Tyr Gly Asn Met Val Thr Thr Asp
                325                 330                 335
```

```
Pro Lys Thr Ala Asp Pro Val Tyr Gly Lys Val Phe Asn Pro Pro Arg
            340                 345                 350
Thr Asn Leu Pro Gly Arg Phe Thr Asn Phe Leu Asp Val Ala Glu Ala
            355                 360                 365
Cys Pro Thr Phe Leu Arg Phe Gly Glu Val Pro Phe Val Lys Thr Val
            370                 375                 380
Asn Ser Gly Asp Arg Leu Leu Ala Lys Phe Asp Val Ser Leu Ala Ala
385                 390                 395                 400
Gly His Met Ser Asn Thr Tyr Leu Ala Gly Leu Ala Gln Tyr Tyr Thr
                405                 410                 415
Gln Tyr Ser Gly Thr Met Asn Val His Phe Met Phe Thr Gly Pro Thr
            420                 425                 430
Asp Ala Lys Ala Arg Tyr Met Val Ala Tyr Ile Pro Pro Gly Met Thr
            435                 440                 445
Pro Pro Thr Asp Pro Glu Arg Ala Ala His Cys Ile His Ser Glu Trp
            450                 455                 460
Asp Thr Gly Leu Asn Ser Lys Phe Thr Phe Ser Ile Pro Tyr Leu Ser
465                 470                 475                 480
Ala Ala Asp Tyr Ala Tyr Thr Ala Ser Asp Thr Ala Glu Thr Thr Ser
                485                 490                 495
Val Gln Gly Trp Val Cys Ile Tyr Gln Ile Thr His Gly Lys Ala Glu
            500                 505                 510
Gly Asp Ala Leu Val Val Ser Val Ser Ala Gly Lys Asp Phe Glu Phe
            515                 520                 525
Arg Leu Pro Val Asp Ala Arg Arg Gln Thr Thr Thr Thr Gly Glu Ser
            530                 535                 540
Ala Asp Pro Val Thr Thr Thr Val Glu Asn Tyr Gly Gly Glu Thr Gln
545                 550                 555                 560
Thr Ala Arg Arg Leu His Thr Asp Val Ala Phe Val Leu Asp Arg Phe
                565                 570                 575
Val Lys Leu Thr Ala Pro Lys Asn Thr Gln Thr Leu Asp Leu Met Gln
            580                 585                 590
Ile Pro Ser His Thr Leu Val Gly Ala Leu Leu Arg Ser Ala Thr Tyr
            595                 600                 605
Tyr Phe Ser Asp Leu Glu Val Ala Leu Val His Thr Gly Pro Val Thr
            610                 615                 620
Trp Val Pro Asn Gly Ser Pro Lys Asp Ala Leu Asp Asn Gln Thr Asn
625                 630                 635                 640
Pro Thr Ala Tyr Gln Lys Gln Pro Ile Thr Arg Leu Ala Leu Pro Tyr
                645                 650                 655
Thr Ala Pro His Arg Val Leu Ala Thr Val Tyr Asn Gly Lys Thr Thr
            660                 665                 670
Tyr Gly Glu Thr Pro Ser Arg Arg Gly Asp Met Ala Ala Leu Ala Gln
            675                 680                 685
Arg Leu Ser Glu Arg Leu Pro Thr Ser Phe Asn Tyr Gly Ala Val Lys
            690                 695                 700
Ala Glu Thr Ile Thr Glu Leu Leu Ile Arg Met Lys Arg Ala Glu Thr
705                 710                 715                 720
Tyr Cys Val Lys Lys Pro Val Ala Leu Lys Val Lys Ala Lys Asn Thr
                725                 730                 735
Leu Ile Val Thr Glu Ser Gly Ala Pro Pro Thr Asp Leu Gln Lys Met
            740                 745                 750
```

| | | | | | | | | | | | |
|---|---|---|---|---|---|---|---|---|---|---|---|
| Val | Met | Gly | Asn | Thr | Lys | Pro | Val | Glu | Leu | Ile | Leu | Asp | Gly | Lys | Thr |
| | | 755 | | | | 760 | | | | 765 | |

Val Ala Ile Cys Cys Ala Thr Gly Val Phe Gly Thr Ala Tyr Leu Val
     770                        775                     780

Pro Arg His Leu Phe Ala Glu Lys Tyr Asp Lys Ile Met Leu Asp Gly
785                     790                     795                   800

Arg Ala Met Thr Asp Ser Asp Tyr Arg Val Phe Glu Phe Glu Ile Lys
           805                     810                     815

Val Lys Gly Gln Asp Met Leu Ser Asp Ala Ala Leu Met Val Leu His
             820                     825                     830

Arg Gly Asn Arg Val Arg Asp Ile Thr Lys His Phe Arg Asp Thr Ala
       835                     840                     845

Arg Met Lys Lys Gly Thr Pro Val Gly Val Ile Asn Asn Ala Asp
850                     855                     860

Val Gly Arg Leu Ile Phe Ser Gly Glu Ala Leu Thr Tyr Lys Asp Ile
865                   870                     875                   880

Val Val Cys Met Asp Gly Asp Thr Met Pro Gly Leu Phe Ala Tyr Lys
             885                     890                     895

Ala Ala Thr Lys Ala Gly Tyr Cys Gly Gly Ala Val Leu Ala Lys Asp
           900                     905                     910

Gly Ala Asp Thr Phe Ile Val Gly Thr His Ser Ala Gly Gly Arg Asn
       915                     920                     925

Gly Val Gly Tyr Cys Ser Cys Val Ser Arg Ser Met Leu Leu Lys Met
930                     935                     940

Lys Ala His Ile Asp Pro Glu Pro His His Glu Gly Leu Ile Val Asp
945                     950                     955                   960

Thr Arg Asp Val Glu Glu Arg Val His Val Met
           965                     970

<210> SEQ ID NO 68
<211> LENGTH: 2913
<212> TYPE: DNA
<213> ORGANISM: Artificial Sequence
<220> FEATURE:
<223> OTHER INFORMATION: Description of Artificial Sequence: Synthetic
     consensus sequence

<400> SEQUENCE: 68

| | | |
|---|---|---|
| atgctgaacg agggctggaa ggccagcgtg cagcgcaagc tgaagggcgc cggccagagc | 60 |
| agccccgcca ccggcagcca gaaccagagc ggcaacaccg gcagcatcat caacaactac | 120 |
| tacatgcagc agtaccagaa cagcatggac acccagctgg cgacaacgc catcagcggc | 180 |
| ggcagcaacg agggcagcac cgacaccacc agcacccaca ccaccaacac cagaacaac | 240 |
| gactggttca gcaagctggc cagcagcgcc ttcagcggcc tgttcggcgc cctgctggcc | 300 |
| gacaagaaga ccgaggagac caccctgctg gaggaccgca tcctgaccac ccgcaacggc | 360 |
| cacaccacca gcaccaccca gagcagcgtg ggcgtgacct cggctacgc caccgccgag | 420 |
| gacagcacca gcggccccaa caccagcggc ctggagaccc gcgtgcacca ggccgagcgc | 480 |
| ttcttcaaga tggccctgtt cgactgggtg cccagccaga acttcggcca catgcacaag | 540 |
| gtggtgctgc ccacgagcc aagggcgtg tacggcggcc tggtgaagag ctacgcctac | 600 |
| atgcgcaacg gctgggacgt ggaggtgacc gccgtgggca accagttcaa cggcggctgc | 660 |
| ctgctggtgg ccctggtgcc cgagatgggc gacatcagcg accgcgagaa gtaccagctg | 720 |
| accctgtacc cccaccagtt catcaacccc cgcaccaaca tgaccgccca catcaccgtg | 780 |

```
cctacgtgg gcgtgaaccg ctacgaccag tacaagcagc accgcccctg gaccctggtg    840
gtgatggtgg tggcccccct gaccaccaac accgccggcg cccagcagat caaggtgtac    900
gccaacatcg cccccaccaa cgtgcacgtg gccggcgagc tgcccagcaa ggagggcatc    960
ttccccgtgg cctgcagcga cggctacggc aacatggtga ccaccgaccc caagaccgcc   1020
gaccccgtgt acggcaaggt gtacaacccc cccgcaccg ccctgccgg ccgcttcacc   1080 aactacctgg acgtggccga ggcctgcccc accttcctga tgttcgagaa cgtgccctac   1140
gtgagcaccc gcaccgacgg ccagcgcctg ctggccaagt cgacgtgag cctggccgcc   1200 aagcacatga gcaacaccta cctggccggc ctggcccagt actacaccca gtacaccggc   1260
accatcaacc tgcacttcat gttcaccggc cccaccgacg ccaaggcccg ctacatggtg   1320
gcctacgtgc cccccggcat ggacgccccc gacaaccccg aggaggccgc ccactgcatc   1380
cacgccgagt gggacaccgg cctgaacagc aagttcacct tcagcatccc ctacatcagc   1440
gccgccgact acgcctacac cgccagccac aaggccgaga ccacctgcgt gcagggctgg   1500
gtgtgcgtgt accagatcac ccacggcaag gccgacgccg acgccctggt ggtgagcgcc   1560
agcgccggca aggacttcga gctgcgcctg cccgtggacg cccgcaagca gaccaccacc   1620
accggcgaga gcgccgaccc cgtgaccacc accgtggaga actacggcgg cgagacccag   1680
gtgcagcgcc gccaccacac cgacgtggcc ttcgtgctgg accgcttcgt ggaggtgacc   1740
gtgagcggcc gcaaccagca cccctggac gtgatgcagg cccacaagga caacatcgtg   1800
ggcgccctgc tgcgcgccgc cacctactac ttcagcgacc tggagatcgc cgtgacccac   1860
accggcaagc tgacctgggt gcccaacggc gcccccgtga gcgccctgaa caacaccacc   1920
aaccccaccg cctaccacaa gggccccgtg accgcctgg ccctgcccta caccgccccc   1980
caccgcgtgc tggccaccgc ctacaccggc accaccacct acaccgccag cgcccgcggc   2040
gacctggccc acctgaccac caccacgcc cgccacctgc ccaccagctt caacttcggc   2100
gccgtgaagg ccgagaccat caccgagctg ctggtgcgca tgaagcgcgc cgagctgtac   2160
tgcgtgaaga agcccgtggc cctgaaggtg aaggccaaga caccctgat cgtgaccgag   2220 agcggcgccc cccccaccga cctgcagaag atggtgatgg caacaccaa gcccgtggag   2280 ctgatcctgg acggcaagac cgtggccatc tgctgcgcca ccggcgtgtt cggcaccgcc   2340
tacctggtgc cccgccacct gttcgccgag aagtacgaca agatcatgct ggacggccgc   2400
gccatgaccg acagcgacta ccgcgtgttc gagttcgaga tcaaggtgaa gggccaggac   2460
atgctgagcg acgccgccct gatggtgctg caccgcggca accgcgtgcg cgacatcacc   2520
aagcacttcc gcgacaccgc ccgcatgaag aagggcaccc ccgtggtggg cgtgatcaac   2580
aacgccgacg tggccgcct gatcttcagc ggcgaggccc tgacctacaa ggacatcgtg   2640
gtgtgcatgg acggcgacac catgcccggc ctgttcgcct acaaggccgc caccaaggcc   2700
ggctactgcg gcggcgccgt gctggccaag gacggcgccg acaccttcat cgtgggcacc   2760
cacagcgccg gcggccgcaa cggcgtgggc tactgcagct gcgtgagccg cagcatgctg   2820
ctgaagatga aggcccacat cgaccccgag ccccaccacg agggcctgat cgtggacacc   2880
cgcgacgtgg aggagcgcgt gcacgtgatg tga                                2913
```

<210> SEQ ID NO 69
<211> LENGTH: 971
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 69

Met Leu Asn Gly Glu Trp Lys Ala Lys Val Gln Lys Arg Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
50                  55                  60

Gly Ser Thr Asp Thr Thr Ser Thr His Thr Asn Asn Thr Gln Asn Asn
65                  70                  75                  80

Asp Trp Phe Ser Arg Leu Ala Ser Ser Ala Phe Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Tyr Gly Tyr Ala Val Ala Glu Asp Ala Val Ser
130                 135                 140

Gly Pro Asn Thr Ser Gly Leu Glu Thr Arg Val Gln Gln Ala Glu Arg
145                 150                 155                 160

Phe Phe Lys Lys His Leu Phe Asp Trp Thr Pro Asn Leu Ala Phe Gly
                165                 170                 175

His Cys His Tyr Leu Glu Leu Pro Thr Glu His Lys Gly Val Tyr Gly
            180                 185                 190

Ser Leu Met Asp Ser Tyr Ala Tyr Met Arg Asn Gly Trp Asp Ile Glu
        195                 200                 205

Val Thr Ala Val Gly Asn Gln Phe Asn Gly Gly Cys Leu Leu Val Ala
210                 215                 220

Leu Val Pro Glu Leu Lys Ser Leu Asp Thr Arg Gln Lys Tyr Gln Leu
225                 230                 235                 240

Thr Leu Phe Pro His Gln Phe Ile Asn Pro Arg Thr Asn Met Thr Ala
                245                 250                 255

His Ile Asn Val Pro Phe Val Gly Val Asn Arg Tyr Asp Gln Tyr Ala
            260                 265                 270

Leu His Lys Pro Trp Thr Leu Val Val Met Val Val Ala Pro Leu Thr
        275                 280                 285

Val Lys Thr Gly Gly Ser Glu Gln Ile Lys Val Tyr Met Asn Ala Ala
290                 295                 300

Pro Thr Tyr Val His Val Ala Gly Glu Leu Pro Ser Lys Glu Gly Ile
305                 310                 315                 320

Val Pro Val Ala Cys Ala Asp Gly Tyr Gly Asn Met Val Thr Thr Asp
                325                 330                 335

Pro Lys Thr Ala Asp Pro Val Tyr Gly Lys Val Phe Asn Pro Pro Arg
            340                 345                 350

Thr Asn Leu Pro Gly Arg Phe Thr Asn Phe Leu Asp Val Ala Glu Ala
        355                 360                 365

Cys Pro Thr Phe Leu Arg Phe Gly Glu Val Pro Phe Val Lys Thr Val
370                 375                 380

Asn Ser Gly Asp Arg Leu Leu Ala Lys Phe Asp Val Ser Leu Ala Ala
385                 390                 395                 400

```
Gly His Met Ser Asn Thr Tyr Leu Ala Gly Leu Ala Gln Tyr Tyr Thr
                405                 410                 415
Gln Tyr Ser Gly Thr Met Asn Val His Phe Met Phe Thr Gly Pro Thr
            420                 425                 430
Asp Ala Lys Ala Arg Tyr Met Val Ala Tyr Ile Pro Pro Gly Met Thr
            435                 440                 445
Pro Pro Thr Asp Pro Glu Arg Ala Ala His Cys Ile His Ser Glu Trp
450                 455                 460
Asp Thr Gly Leu Asn Ser Lys Phe Thr Phe Ser Ile Pro Tyr Leu Ser
465                 470                 475                 480
Ala Ala Asp Tyr Ala Tyr Thr Ala Ser Asp Thr Ala Glu Thr Thr Ser
                485                 490                 495
Val Gln Gly Trp Val Cys Ile Tyr Gln Ile Thr His Gly Lys Ala Glu
            500                 505                 510
Gly Asp Ala Leu Val Val Ser Val Ser Ala Gly Lys Asp Phe Glu Phe
            515                 520                 525
Arg Leu Pro Val Asp Ala Arg Arg Gln Thr Thr Thr Thr Gly Glu Ser
            530                 535                 540
Ala Asp Pro Val Thr Thr Thr Val Glu Asn Tyr Gly Gly Glu Thr Gln
545                 550                 555                 560
Thr Ala Arg Arg Leu His Thr Asp Val Ala Phe Val Leu Asp Arg Phe
                565                 570                 575
Val Lys Leu Thr Ala Pro Lys Asn Thr Gln Thr Leu Asp Leu Met Gln
            580                 585                 590
Ile Pro Ser His Thr Leu Val Gly Ala Leu Leu Arg Ser Ala Thr Tyr
            595                 600                 605
Tyr Phe Ser Asp Leu Glu Val Ala Leu Val His Thr Gly Pro Val Thr
610                 615                 620
Trp Val Pro Asn Gly Ser Pro Lys Asp Ala Leu Asp Asn Gln Thr Asn
625                 630                 635                 640
Pro Thr Ala Tyr Gln Lys Gln Pro Ile Thr Arg Leu Ala Leu Pro Tyr
                645                 650                 655
Thr Ala Pro His Arg Val Leu Ala Thr Val Tyr Asn Gly Lys Thr Thr
            660                 665                 670
Tyr Gly Glu Thr Pro Ser Arg Arg Gly Asp Met Ala Ala Leu Ala Gln
            675                 680                 685
Arg Leu Ser Glu Arg Leu Pro Thr Ser Phe Asn Tyr Gly Ala Val Lys
            690                 695                 700
Ala Glu Thr Ile Thr Glu Leu Leu Ile Arg Met Lys Arg Ala Glu Thr
705                 710                 715                 720
Tyr Cys Val Lys Lys Pro Val Ala Leu Lys Val Lys Ala Lys Asn Thr
                725                 730                 735
Leu Ile Val Thr Glu Ser Gly Ala Pro Pro Thr Asp Leu Gln Lys Met
            740                 745                 750
Val Met Gly Asn Thr Lys Pro Val Glu Leu Ile Leu Asp Gly Lys Thr
            755                 760                 765
Val Ala Ile Cys Cys Ala Thr Gly Val Phe Gly Thr Ala Tyr Leu Val
            770                 775                 780
Pro Arg His Leu Phe Ala Glu Lys Tyr Asp Lys Ile Met Leu Asp Gly
785                 790                 795                 800
Arg Ala Met Thr Asp Ser Asp Tyr Arg Val Phe Glu Phe Glu Ile Lys
                805                 810                 815
Val Lys Gly Gln Asp Met Leu Ser Asp Ala Ala Leu Met Val Leu His
```

```
                    820                 825                 830
Arg Gly Asn Arg Val Arg Asp Ile Thr Lys His Phe Arg Asp Thr Ala
                835                 840                 845

Arg Met Lys Lys Gly Thr Pro Val Val Gly Val Ile Asn Asn Ala Asp
            850                 855                 860

Val Gly Arg Leu Ile Phe Ser Gly Glu Ala Leu Thr Tyr Lys Asp Ile
865                 870                 875                 880

Val Val Cys Met Asp Gly Asp Thr Met Pro Gly Leu Phe Ala Tyr Lys
                885                 890                 895

Ala Ala Thr Lys Ala Gly Tyr Cys Gly Gly Ala Val Leu Ala Lys Asp
            900                 905                 910

Gly Ala Asp Thr Phe Ile Val Gly Thr His Ser Ala Gly Gly Arg Asn
                915                 920                 925

Gly Val Gly Tyr Cys Ser Cys Val Ser Arg Ser Met Leu Leu Lys Met
            930                 935                 940

Lys Ala His Ile Asp Pro Glu Pro His His Glu Gly Leu Ile Val Asp
945                 950                 955                 960

Thr Arg Asp Val Glu Glu Arg Val His Val Met
                965                 970

<210> SEQ ID NO 70
<211> LENGTH: 2925
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 70
atgctgaacg gcgagtggaa ggccaaggtg cagaagcgcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180 ggcagcaacg agggcagcac cgacaccacc agcacccaca ccaccaacac ccagaacaac     240
gactggttca gcaagctggc cagcagcgcc ttcagcggcc tgttcggcgc cctgctggcc     300
gacaagaaga ccgaggagac caccctgctg gaggaccgca tcctgaccac ccgcaacggc     360
cacaccacca gcaccaccca gagcagcgtg ggcgtgacct acggctacgc caccgccgag     420
gacttcgtga gcggccccaa caccagcggc ctggagaccc gcgtggtgca ggccgagcgc     480
ttcttcaaga cccacctgtt cgactgggtg accagcgacc ccttcggccg ctgctacctg     540
ctggagctgc ccaccgacca agggcgtg tacggcagcc tgaccgacag ctacgcctac      600
atgcgcaacg gctgggacgt ggaggtgacc gccgtgggca accagttcaa cggcggctgc    660
ctgctggtgg ccatggtgcc cgagctgtgc agcatcgaca gcgcgagct gtaccagctg      720 accctgttcc cccaccagtt catcaacccc gcaccaaca tgaccgccca catcaccgtg       780
cccttcgtgg gcgtgaaccg ctacgaccag tacaaggtgc acaagcctg accctggtg      840 gtgatggtgg tggccccct gaccgtgaac accgagggcg ccccccagat caaggtgtac     900
gccaacatcg cccccaccaa cgtgcacgtg gccggcgagt cccccagcaa ggagggcatc    960
ttccccgtgg cctgcagcga cggctacggc ggcctggtga ccaccgaccc caagaccgcc   1020
gaccccgcct acggcaaggt gttcaacccc cccgcaaca tgctgcccgg ccgcttcacc    1080
aacttcctgg acgtggccga ggcctgcccc accttcctgc acttcgaggg cggcgtgccc    1140
tacgtgacca ccaagaccga cagcgaccgc gtgctggccc agttcgacct gagcctggcc    1200
```

```
gccaagcaca tgagcaacac cttcctggcc ggcctggccc agtactacac ccagtacagc   1260
ggcaccatca acctgcactt catgttcacc ggccccaccg acgccaaggc ccgctacatg   1320
atcgcctacg ccccccccgg catggagccc cccaagaccc ccgaggccgc cgcccactgc   1380
atccacgccg agtgggacac cggcctgaac agcaagttca ccttcagcat cccctacctg   1440
agcgccgccg actacgccta caccgccagc gacgccgccg agaccaccaa cgtgcagggc   1500
tgggtgtgcc tgttccagat cacccacggc aaggccgacg cgacgccct ggtggtgctg   1560 gccagcgccg gcaaggactt cgagctgcgc ctgcccgtgg acgcccgcac ccagaccacc   1620
agcgccggcg agagcgccga ccccgtgacc gccaccgtgg agaactacgg cggcgagacc   1680
caggtgcagc gccgccagca caccgacgtg agcttcatcc tggaccgctt cgtgaaggtg   1740 accccccaagg accagatcaa cgtgctggac ctgatgcaga ccccgccca cccctggtg   1800 ggcgccctgc tgcgcaccgc cacctactac ttcgccgacc tggaggtggc cgtgaagcac   1860
gagggcaacc tgacctgggt gcccaacggc gcccccgaga ccgccctgga caacaccacc   1920
aaccccaccg cctaccacaa ggcccccctg accgcctgg ccctgcccta caccgcccc   1980 caccgcgtgc tggccaccgt gtacaacggc aactgcaagt acggcgagag ccccgtgacc   2040
aacgtgcgcg gcgacctgca ggtgctggcc cagaaggccg cccgcaccct gcccaccagc   2100
ttcaactacg cgccatcaa ggccaccgc gtgaccgagc tgctgtaccg catgaagcgc   2160
gccgagacct actgcgtgaa gaagcccgtg gccctgaagg tgaaggccaa gaacaccctg   2220
atcgtgaccg agagcggcgc cccccccacc gacctgcaga gatggtgat gggcaacacc   2280 aagcccgtgg agctgatcct ggacggcaag accgtggcca tctgctgcgc caccggcgtg   2340
ttcggcaccg cctacctggt gccccgccac ctgttcgccg agaagtacga caagatcatg   2400
ctggacggcc gcgccatgac cgacagcgac taccgcgtgt cgagttcga gatcaaggtg   2460 aagggccagg acatgctgag cgacgccgcc ctgatggtgc tgcaccgcgg caaccgcgtg   2520
cgcgacatca ccaagcactt ccgcgacacc gcccgcatga agaagggcac ccccgtggtg   2580
ggcgtgatca acaacgccga cgtgggccgc ctgatcttca gcggcgaggc cctgacctac   2640
aaggacatcg tggtgtgcat ggacggcgac accatgcccg cctgttcgc ctacaaggcc   2700 gccaccaagg ccggctactg cggcggcgcc gtgctggcca aggacggcgc cgacaccttc   2760
atcgtgggca cccacagcgc cggcggccgc aacggcgtgg gctactgcag ctgcgtgagc   2820
cgcagcatgc tgctgaagat gaaggcccac atcgaccccg agccccacca cgagggcctg   2880
atcgtggaca cccgcgacgt ggaggagcgc gtgcacgtga tgtga              2925
```

<210> SEQ ID NO 71  
<211> LENGTH: 974  
<212> TYPE: PRT  
<213> ORGANISM: Artificial Sequence  
<220> FEATURE:  
<223> OTHER INFORMATION: Description of Artificial Sequence: Synthetic consensus sequence

<400> SEQUENCE: 71

Met Leu Asn Gly Glu Trp Lys Ala Lys Val Gln Lys Arg Leu Arg Gly  
1               5                   10                  15

Ala Gly Gln Ser Ser Pro Ala Thr Gly Ser Gln Asn Gln Ser Gly Asn  
            20                  25                  30

Thr Gly Ser Ile Ile Asn Asn Tyr Tyr Met Gln Tyr Gln Asn Ser  
        35                  40                  45

-continued

```
Met Asp Thr Gln Leu Gly Asp Asn Ala Ile Ser Gly Gly Ser Asn Glu
     50                  55                  60
Gly Ser Thr Asp Thr Thr Ser Thr His Thr Thr Asn Thr Gln Asn Asn
 65                  70                  75                  80
Asp Trp Phe Ser Lys Leu Ala Ser Ser Ala Phe Ser Gly Leu Phe Gly
                 85                  90                  95
Ala Leu Leu Ala Asp Lys Lys Thr Glu Glu Thr Thr Leu Leu Glu Asp
            100                 105                 110
Arg Ile Leu Thr Thr Arg Asn Gly His Thr Thr Ser Thr Thr Gln Ser
        115                 120                 125
Ser Val Gly Val Thr Tyr Gly Tyr Ala Thr Ala Glu Asp Phe Val Ser
130                 135                 140
Gly Pro Asn Thr Ser Gly Leu Glu Thr Arg Val Val Gln Ala Glu Arg
145                 150                 155                 160
Phe Phe Lys Thr His Leu Phe Asp Trp Val Thr Ser Asp Pro Phe Gly
                165                 170                 175
Arg Cys Tyr Leu Leu Glu Leu Pro Thr Asp His Lys Gly Val Tyr Gly
            180                 185                 190
Ser Leu Thr Asp Ser Tyr Ala Tyr Met Arg Asn Gly Trp Asp Val Glu
        195                 200                 205
Val Thr Ala Val Gly Asn Gln Phe Asn Gly Gly Cys Leu Leu Val Ala
210                 215                 220
Met Val Pro Glu Leu Cys Ser Ile Asp Lys Arg Glu Leu Tyr Gln Leu
225                 230                 235                 240
Thr Leu Phe Pro His Gln Phe Ile Asn Pro Arg Thr Asn Met Thr Ala
                245                 250                 255
His Ile Thr Val Pro Phe Val Gly Val Asn Arg Tyr Asp Gln Tyr Lys
            260                 265                 270
Val His Lys Pro Trp Thr Leu Val Met Val Val Ala Pro Leu Thr
        275                 280                 285
Val Asn Thr Glu Gly Ala Pro Gln Ile Lys Val Tyr Ala Asn Ile Ala
290                 295                 300
Pro Thr Asn Val His Val Ala Gly Glu Phe Pro Ser Lys Glu Gly Ile
305                 310                 315                 320
Phe Pro Val Ala Cys Ser Asp Gly Tyr Gly Gly Leu Val Thr Thr Asp
                325                 330                 335
Pro Lys Thr Ala Asp Pro Ala Tyr Gly Lys Val Phe Asn Pro Pro Arg
            340                 345                 350
Asn Met Leu Pro Gly Arg Phe Thr Asn Phe Leu Asp Val Ala Glu Ala
        355                 360                 365
Cys Pro Thr Phe Leu His Phe Glu Gly Gly Val Pro Tyr Val Thr Thr
370                 375                 380
Lys Thr Asp Ser Asp Arg Val Leu Ala Gln Phe Asp Leu Ser Leu Ala
385                 390                 395                 400
Ala Lys His Met Ser Asn Thr Phe Leu Ala Gly Leu Ala Gln Tyr Tyr
                405                 410                 415
Thr Gln Tyr Ser Gly Thr Ile Asn Leu His Phe Met Phe Thr Gly Pro
            420                 425                 430
Thr Asp Ala Lys Ala Arg Tyr Met Ile Ala Tyr Ala Pro Pro Gly Met
        435                 440                 445
Glu Pro Pro Lys Thr Pro Glu Ala Ala Ala His Cys Ile His Ala Glu
450                 455                 460
Trp Asp Thr Gly Leu Asn Ser Lys Phe Thr Phe Ser Ile Pro Tyr Leu
```

```
              465                 470                 475                 480
        Ser Ala Ala Asp Tyr Ala Tyr Thr Ala Ser Asp Ala Ala Glu Thr Thr
                            485                 490                 495

Asn Val Gln Gly Trp Val Cys Leu Phe Gln Ile Thr His Gly Lys Ala
                        500                 505                 510

Asp Gly Asp Ala Leu Val Val Leu Ala Ser Ala Gly Lys Asp Phe Glu
                    515                 520                 525

Leu Arg Leu Pro Val Asp Ala Arg Thr Gln Thr Thr Ser Ala Gly Glu
                530                 535                 540

Ser Ala Asp Pro Val Thr Ala Thr Val Glu Asn Tyr Gly Gly Glu Thr
        545                 550                 555                 560

Gln Val Gln Arg Arg Gln His Thr Asp Val Ser Phe Ile Leu Asp Arg
                            565                 570                 575

Phe Val Lys Val Thr Pro Lys Asp Gln Ile Asn Val Leu Asp Leu Met
                        580                 585                 590

Gln Thr Pro Ala His Thr Leu Val Gly Ala Leu Leu Arg Thr Ala Thr
                    595                 600                 605

Tyr Tyr Phe Ala Asp Leu Glu Val Ala Val Lys His Glu Gly Asn Leu
                610                 615                 620

Thr Trp Val Pro Asn Gly Ala Pro Glu Thr Ala Leu Asp Asn Thr Thr
        625                 630                 635                 640

Asn Pro Thr Ala Tyr His Lys Ala Pro Leu Thr Arg Leu Ala Leu Pro
                            645                 650                 655

Tyr Thr Ala Pro His Arg Val Leu Ala Thr Val Tyr Asn Gly Asn Cys
                        660                 665                 670

Lys Tyr Gly Glu Ser Pro Val Thr Asn Val Arg Gly Asp Leu Gln Val
                    675                 680                 685

Leu Ala Gln Lys Ala Ala Arg Thr Leu Pro Thr Ser Phe Asn Tyr Gly
                690                 695                 700

Ala Ile Lys Ala Thr Arg Val Thr Glu Leu Leu Tyr Arg Met Lys Arg
        705                 710                 715                 720

Ala Glu Thr Tyr Cys Val Lys Lys Pro Val Ala Leu Lys Val Lys Ala
                            725                 730                 735

Lys Asn Thr Leu Ile Val Thr Glu Ser Gly Ala Pro Pro Thr Asp Leu
                        740                 745                 750

Gln Lys Met Val Met Gly Asn Thr Lys Pro Val Glu Leu Ile Leu Asp
                    755                 760                 765

Gly Lys Thr Val Ala Ile Cys Cys Ala Thr Gly Val Phe Gly Thr Ala
                770                 775                 780

Tyr Leu Val Pro Arg His Leu Phe Ala Glu Lys Tyr Asp Lys Ile Met
        785                 790                 795                 800

Leu Asp Gly Arg Ala Met Thr Asp Ser Asp Tyr Arg Val Phe Glu Phe
                            805                 810                 815

Glu Ile Lys Val Lys Gly Gln Asp Met Leu Ser Asp Ala Ala Leu Met
                        820                 825                 830

Val Leu His Arg Gly Asn Arg Val Arg Asp Ile Thr Lys His Phe Arg
                    835                 840                 845

Asp Thr Ala Arg Met Lys Lys Gly Thr Pro Val Gly Val Ile Asn
                850                 855                 860

Asn Ala Asp Val Gly Arg Leu Ile Phe Ser Gly Glu Ala Leu Thr Tyr
        865                 870                 875                 880

Lys Asp Ile Val Val Cys Met Asp Gly Asp Thr Met Pro Gly Leu Phe
                            885                 890                 895
```

```
Ala Tyr Lys Ala Ala Thr Lys Ala Gly Tyr Cys Gly Ala Val Leu
            900                 905                 910

Ala Lys Asp Gly Ala Asp Thr Phe Ile Val Gly Thr His Ser Ala Gly
        915                 920                 925

Gly Arg Asn Gly Val Gly Tyr Cys Ser Cys Val Ser Arg Ser Met Leu
    930                 935                 940

Leu Lys Met Lys Ala His Ile Asp Pro Glu Pro His His Glu Gly Leu
945                 950                 955                 960

Ile Val Asp Thr Arg Asp Val Glu Glu Arg Val His Val Met
                965                 970

<210> SEQ ID NO 72
<211> LENGTH: 2952
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 72
atgctggacg tggactggca ggaccgcgcc ggcctgttcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180
ggcagcaacg agggcagcac cgacaccacc agcacccaca ccaacaacac ccagaacaac     240
gactggttca gcaagctggc ccagagcgcc ttcagcggcc tggtgggcgc cctgctggcc     300
gacaagaaga ccgaggagac caccctgctg gaggaccgca tcatgaccac cagccacggc     360
accaccacca gcaccaccca gagcagcgtg ggcgtgacct acggctacgc cctggccgac     420
aagttcctgc ccgccccaa caccaacggc ctggagaccc gcgtggagca ggccgagcgc     480
ttcttcaagc acaagctgtt cgactggacc accgaccagc agttcggcac acccacgtg     540
ctggagctgc ccaccgacca aagggcatc tacggccagc tggtggacag ccacgcctac     600
atccgcaacg gctgggacgt gcaggtgagc gccaccgcca cccagttcaa cggcggctgc     660
ctgctggtgg ccatggtgcc cgagctgtgc aagctggacg accgcgagaa gtaccagctg     720
accctgttcc ccaccagtt cctgaacccc cgcaccaaca ccaccgccca catccaggtg     780
ccctacctgg gcgtggaccg ccacgaccag ggcacccgcc acaaggcctg gaccctggtg     840
gtgatggtgg tggcccccta caccaacgac cagaccatcg gcagcaccaa ggccgaggtg     900
tacgtgaaca tcgcccccac caacgtgtac gtggccggcg agaagcccgc caagcagggc     960
atcctgcccg tggccgtgag cgacggctac ggcggcttcc agaacaccga ccccaagacc    1020
agcgaccccca tctacggcca cgtgtacaac cccgccgca ccctgtaccc cggccgcttc    1080
accaacctgc tggacgtggc cgaggcctgc ccaccctgc tggacttcaa cggcgtgccc    1140
tacgtgcaga cccagaacaa cagcggcagc aaggtgctgg cccgcttcga cctggccttc    1200
ggccacaaga acatgaagaa cacctacatg agcggcctgg cccagtactt cgcccagtac    1260
agcggcaccc tgaacctgca cttcatgtac accggcccca ccaacaacaa ggccaagtac    1320
atggtggcct acatccccc cggcacccac cccctgcccg agacccccga gatgcccagc    1380
cactgctacc acgccgagtg ggacaccggc ctgaacagca ccttcacctt caccgtgccc    1440
tacatcagcg ccgccgacta cgcctacacc tacgccgacg agcccgagca ggccagcgtg    1500
cagggctggg tgggcgtgta ccagatcacc gacacccacg agaaggacgg cgccgtgatc    1560
```

```
gtgaccgtga gcgccggccc cgacttcgag ttccgcatgc ccatcagccc cagccgccag   1620
accaccagcg ccggcgaggg cgccgacccc gtgaccaccg acgtgagcga gcacggcggc   1680
gacagccgca ccgcccgccg cgcccacacc gacgtggcct tcctgctgga ccgcttcacc   1740
ctggtgggca agacccagga caacaagctg gtgctggacc tgctgaccac caaggagaag   1800
agcctggtgg gcgccctgct gcgcgccgcc acctactact tcagcgacct ggaggtggcc   1860
tgcgtgggca ccaacaagtg gtgggctgg acccccaacg cagcccgt gaagctgagc      1920 gaggtgggcg acaaccccgt ggtgttcagc cacaacggca ccaccgcttc gccctgccc     1980 tacaccgccc ccaccgcgt gctggccacc gtgtacaacg cgactgcaa gtacaagccc     2040 accggcaccc cccccgcga gaacatccgc ggcgacctgg ccaccctggc cgcccgcatc   2100
gccagcgaga cccacatccc caccaccttc aactacggca tgatctacac cgaggccgag   2160
gtggacgtgt acctgcgcat gaagcgcgcc gagctgtact gcgtgaagaa gcccgtggcc   2220
ctgaaggtga aggccaagaa caccctgatc gtgaccgaga gcggcgcccc ccccaccgac   2280
ctgcagaaga tggtgatggg caacaccaag cccgtggagc tgatcctgga cggcaagacc   2340
gtggccatct gctgcgccac cggcgtgttc ggcaccgcct acctggtgcc ccgccacctg   2400
ttcgccgaga agtacgacaa gatcatgctg acggccgcg ccatgaccga cagcgactac     2460
cgcgtgttcg agttcgagat caaggtgaag ggccaggaca tgctgagcga cgccgccctg   2520
atggtgctgc accgcggcaa ccgcgtgcgc gacatcacca gcacttccg cgacaccgcc     2580 cgcatgaaga agggcacccc cgtggtgggc gtgatcaaca cgccgacgt gggccgcctg    2640 atcttcagcg gcgaggccct gacctacaag gacatcgtgg tgtgcatgga cggcgacacc   2700
atgcccggcc tgttcgccta caaggccgcc accaaggccg gctactgcgg cggcgccgtg   2760
ctggccaagg acgcgccga caccttcatc gtgggcaccc acagcgccgg cggccgcaac    2820
ggcgtgggct actgcagctg cgtgagccgc agcatgctgc tgaagatgaa ggcccacatc   2880
gaccccgagc cccaccacga gggcctgatc gtggacaccc gcgacgtgga ggagcgcgtg   2940
cacgtgatgt ga                                                          2952
```

<210> SEQ ID NO 73
<211> LENGTH: 983
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 73

Met Leu Asp Val Asp Trp Gln Asp Arg Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Phe Ser Gly Leu Val Gly
                85                  90                  95

Ala Leu Leu Ala Asp Lys Lys Thr Glu Glu Thr Thr Leu Leu Glu Asp
            100                 105                 110

```
Arg Ile Met Thr Thr Ser His Gly Thr Thr Ser Thr Thr Gln Ser
            115                 120                 125

Ser Val Gly Val Thr Tyr Gly Tyr Ala Leu Ala Asp Lys Phe Leu Pro
145 130             135                 140

Gly Pro Asn Thr Asn Gly Leu Glu Thr Arg Val Glu Gln Ala Glu Arg
145                 150                 155                 160

Phe Phe Lys His Lys Leu Phe Asp Trp Thr Thr Asp Gln Gln Phe Gly
                165                 170                 175

Thr Thr His Val Leu Glu Leu Pro Thr Asp His Lys Gly Ile Tyr Gly
            180                 185                 190

Gln Leu Val Asp Ser His Ala Tyr Ile Arg Asn Gly Trp Asp Val Gln
            195                 200                 205

Val Ser Ala Thr Ala Thr Gln Phe Asn Gly Gly Cys Leu Leu Val Ala
210                 215                 220

Met Val Pro Glu Leu Cys Lys Leu Asp Asp Arg Glu Lys Tyr Gln Leu
225                 230                 235                 240

Thr Leu Phe Pro His Gln Phe Leu Asn Pro Arg Thr Asn Thr Thr Ala
                245                 250                 255

His Ile Gln Val Pro Tyr Leu Gly Val Asp Arg His Asp Gln Gly Thr
            260                 265                 270

Arg His Lys Ala Trp Thr Leu Val Val Met Val Val Ala Pro Tyr Thr
            275                 280                 285

Asn Asp Gln Thr Ile Gly Ser Thr Lys Ala Glu Val Tyr Val Asn Ile
290                 295                 300

Ala Pro Thr Asn Val Tyr Val Ala Gly Glu Lys Pro Ala Lys Gln Gly
305                 310                 315                 320

Ile Leu Pro Val Ala Val Ser Asp Gly Tyr Gly Gly Phe Gln Asn Thr
                325                 330                 335

Asp Pro Lys Thr Ser Asp Pro Ile Tyr Gly His Val Tyr Asn Pro Ala
            340                 345                 350

Arg Thr Leu Tyr Pro Gly Arg Phe Thr Asn Leu Leu Asp Val Ala Glu
            355                 360                 365

Ala Cys Pro Thr Leu Leu Asp Phe Asn Gly Val Pro Tyr Val Gln Thr
370                 375                 380

Gln Asn Asn Ser Gly Ser Lys Val Leu Ala Arg Phe Asp Leu Ala Phe
385                 390                 395                 400

Gly His Lys Asn Met Lys Asn Thr Tyr Met Ser Gly Leu Ala Gln Tyr
                405                 410                 415

Phe Ala Gln Tyr Ser Gly Thr Leu Asn Leu His Phe Met Tyr Thr Gly
            420                 425                 430

Pro Thr Asn Asn Lys Ala Lys Tyr Met Val Ala Tyr Ile Pro Pro Gly
            435                 440                 445

Thr His Pro Leu Pro Glu Thr Pro Glu Met Ala Ser His Cys Tyr His
450                 455                 460

Ala Glu Trp Asp Thr Gly Leu Asn Ser Thr Phe Thr Phe Thr Val Pro
465                 470                 475                 480

Tyr Ile Ser Ala Ala Asp Tyr Ala Tyr Thr Tyr Ala Asp Glu Pro Glu
                485                 490                 495

Gln Ala Ser Val Gln Gly Trp Val Gly Val Tyr Gln Ile Thr Asp Thr
            500                 505                 510

His Glu Lys Asp Gly Ala Val Ile Val Thr Val Ser Ala Gly Pro Asp
            515                 520                 525
```

```
Phe Glu Phe Arg Met Pro Ile Ser Pro Ser Arg Gln Thr Thr Ser Ala
            530                 535                 540

Gly Glu Gly Ala Asp Pro Val Thr Thr Asp Val Ser Glu His Gly Gly
545                 550                 555                 560

Asp Ser Arg Thr Ala Arg Arg Ala His Thr Asp Val Ala Phe Leu Leu
                565                 570                 575

Asp Arg Phe Thr Leu Val Gly Lys Thr Gln Asp Asn Lys Leu Val Leu
            580                 585                 590

Asp Leu Leu Thr Thr Lys Glu Lys Ser Leu Val Gly Ala Leu Leu Arg
            595                 600                 605

Ala Ala Thr Tyr Tyr Phe Ser Asp Leu Glu Val Ala Cys Val Gly Thr
        610                 615                 620

Asn Lys Trp Val Gly Trp Thr Pro Asn Gly Ser Pro Val Lys Leu Ser
625                 630                 635                 640

Glu Val Gly Asp Asn Pro Val Val Phe Ser His Asn Gly Thr Thr Arg
                645                 650                 655

Phe Ala Leu Pro Tyr Thr Ala Pro His Arg Val Leu Ala Thr Val Tyr
            660                 665                 670

Asn Gly Asp Cys Lys Tyr Lys Pro Thr Gly Thr Pro Pro Arg Glu Asn
            675                 680                 685

Ile Arg Gly Asp Leu Ala Thr Leu Ala Ala Arg Ile Ala Ser Glu Thr
        690                 695                 700

His Ile Pro Thr Thr Phe Asn Tyr Gly Met Ile Tyr Thr Glu Ala Glu
705                 710                 715                 720

Val Asp Val Tyr Leu Arg Met Lys Arg Ala Glu Leu Tyr Cys Val Lys
                725                 730                 735

Lys Pro Val Ala Leu Lys Val Lys Ala Lys Asn Thr Leu Ile Val Thr
            740                 745                 750

Glu Ser Gly Ala Pro Pro Thr Asp Leu Gln Lys Met Val Met Gly Asn
        755                 760                 765

Thr Lys Pro Val Glu Leu Ile Leu Asp Gly Lys Thr Val Ala Ile Cys
770                 775                 780

Cys Ala Thr Gly Val Phe Gly Thr Ala Tyr Leu Val Pro Arg His Leu
785                 790                 795                 800

Phe Ala Glu Lys Tyr Asp Lys Ile Met Leu Asp Gly Arg Ala Met Thr
            805                 810                 815

Asp Ser Asp Tyr Arg Val Phe Glu Phe Glu Ile Lys Val Lys Gly Gln
            820                 825                 830

Asp Met Leu Ser Asp Ala Ala Leu Met Val Leu His Arg Gly Asn Arg
        835                 840                 845

Val Arg Asp Ile Thr Lys His Phe Arg Asp Thr Ala Arg Met Lys Lys
        850                 855                 860

Gly Thr Pro Val Val Gly Val Ile Asn Asn Ala Asp Val Gly Arg Leu
865                 870                 875                 880

Ile Phe Ser Gly Glu Ala Leu Thr Tyr Lys Asp Ile Val Val Cys Met
                885                 890                 895

Asp Gly Asp Thr Met Pro Gly Leu Phe Ala Tyr Lys Ala Ala Thr Lys
            900                 905                 910

Ala Gly Tyr Cys Gly Gly Ala Val Leu Ala Lys Asp Gly Ala Asp Thr
            915                 920                 925

Phe Ile Val Gly Thr His Ser Ala Gly Gly Arg Asn Gly Val Gly Tyr
        930                 935                 940

Cys Ser Cys Val Ser Arg Ser Met Leu Leu Lys Met Lys Ala His Ile
```

```
                945                 950                 955                 960
           Asp Pro Glu Pro His His Glu Gly Leu Ile Val Asp Thr Arg Asp Val
                           965                 970                 975
           Glu Glu Arg Val His Val Met
                           980

<210> SEQ ID NO 74
<211> LENGTH: 2940
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 74
atgctggacg tggactggca ggacaaggcc ggcctgttcc tgcgcggcgc cggccagagc        60
agccccgcca ccggcagcca gaaccagagc ggcaacaccg gcagcatcat caacaactac       120
tacatgcagc agtaccagaa cagcatggac acccagctgg cgacaacgc catcagcggc        180 ggcagcaacg agggcagcac cgacaccacc agcacccaca ccaacaacac cagaacaac        240 gactggttca gcaagctggc ccagagcgcc atcagcggcc tgttcggcgc cctgctggcc       300
gacaagaaga ccgaggagac caccctgctg gaggaccgca tcctgaccac ccgccacggc       360
accaccacca gcaccaccca gagcagcgtg ggcatcacct acggctacgc cgacgccgac       420
agcttccgcc ccggccccaa caccagcggc ctggagaccc gcgtggagca ggccgagcgc       480
ttcttcaagg agaagctgtt cgactggacc agcgacaagc ccttcggcac cctgtacgtg       540
ctggagctgc ccaaggacca aagggcatc tacggcagcc tgaccgacgc ctacacctac        600
atgcgcaacg gctgggacgt gcaggtgagc gccaccagca cccagttcaa cggcggcagc       660
ctgctggtgg ccatggtgcc cgagctgtgc agcctgaagg accgcgagga gttccagctg       720
accctgtacc ccaccagtt catcaacccc gcaccaaca ccaccgccca catccaggtg         780
ccctacctgg gcgtgaaccg ccacgaccag ggcaagcgcc accaggcctg gagcctggtg       840
gtgatggtgc tgaccccct gaccaccgag gcccagatga cagcggcac cgtggaggtg        900 tacgccaaca tcgcccccac caacgtgttc gtggccggcg agaagcccgc caagcagggc       960
atcatccccg tggcctgcgc cgacggctac ggcggcttcc agaacaccga ccccaagacc      1020
gccgacccca tctacggcta cgtgtacaac ccagccgca acgactgcca cggccgctac       1080
agcaacctgc tggacgtggc cgaggcctgc cccaccctgc tgaacttcga cggcaagccc       1140
tacgtggtga ccaagaacaa cggcgacaag gtgatggccg ccttcgacgt ggccttcacc       1200
cacaaggtgc acaagaacac cttcctggcc ggcctggccg actactacac ccagtaccag       1260
ggcagcctga actaccactt catgtacacc ggccccaccc accacaaggc caagttcatg       1320
gtggcctaca tcccccccgg catcgagacc gacaagctgc ccaagacccc cgaggacgcc       1380
gcccactgct accacagcga gtgggacacc ggcctgaaca ccagttcac cttcgccgtg       1440 ccctacgtga gcgccagcga cttcagctac acccacaccg acaccccgc catggccacc       1500 accaacggct gggtggccgt gttccaggtg accgacaccc acagcgccga ggccgccgtg      1560
gtggtgagcg tgagcgccgg ccccgacctg gagttccgct cccccatcga ccccgtgcgc       1620
cagaccacca cgccggcga gggcgccgag gtggtgacca ccgaccccag caccacggc       1680 ggcaaggtga ccgagaagcg ccgcgtgcac accgacgtgg ccttcgtgct ggaccgcttc       1740
acccacgtgc acaccaacaa gaccaccttc gccgtggacc tgatggacac caaggagaag       1800
```

```
acccctggtgg gcgccctgct gcgcgccgcc acctactact tctgcgacct ggagatcgcc   1860
tgcgtgggcg agcacaagcg cgtgttctgg cagcccaacg gcgcccccg caccacccag     1920 ctgggcgaca accccatggt gttcagccac aacaaggtga cccgcttcgc catcccctac   1980 accgccccc accgcctgct gagcaccgtg tacaacggcg agtgcgagta caccaagacc    2040
gtgaccgcca tccgcggcga ccgcgaggtg ctggccgcca agtacagcag cgccaagcac   2100
accctgccca gcaccttcaa cttcggcttc gtgaccgccg acgagcccgt ggacgtgtac   2160
taccgcatga agcgcgccga gctgtactgc gtgaagaagc ccgtggccct gaaggtgaag   2220
gccaagaaca ccctgatcgt gaccgagagc ggcgccccc ccaccgacct gcagaagatg    2280
gtgatgggca acaccaagcc cgtggagctg atcctggacg caagaccgt ggccatctgc    2340 tgcgccaccg gcgtgttcgg caccgcctac ctggtgcccc gccacctgtt cgccgagaag   2400
tacgacaaga tcatgctgga cggccgcgcc atgaccgaca cgactaccg cgtgttcgag    2460 ttcgagatca aggtgaaggg ccaggacatg ctgagcgacg ccgccctgat ggtgctgcac   2520
cgcggcaacc gcgtgcgcga catcaccaag cacttccgcg acaccgcccg catgaagaag   2580 ggcaccccg tggtgggcgt gatcaacaac gccgacgtgg gccgcctgat cttcagcggc    2640
gaggccctga cctacaagga catcgtggtg tgcatggacg cgacaccat gcccggcctg    2700 ttcgcctaca aggccgccac caaggccggc tactgcggcg cgccgtgct ggccaaggac    2760 ggcgccgaca ccttcatcgt gggcacccac agcgccggcg ccgcaacgg cgtgggctac   2820 tgcagctgcg tgagccgcag catgctgctg aagatgaagg cccacatcga ccccgagccc   2880
caccacgagg gcctgatcgt ggacacccgc gacgtggagg agcgcgtgca cgtgatgtga   2940
```

<210> SEQ ID NO 75
<211> LENGTH: 979
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 75

```
Met Leu Asp Val Asp Trp Gln Asp Lys Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Ile Ser Gly Leu Phe Gly
                85                  90                  95

Ala Leu Leu Ala Asp Lys Lys Thr Glu Thr Thr Leu Leu Glu Asp
            100                 105                 110

Arg Ile Leu Thr Thr Arg His Gly Thr Thr Ser Thr Thr Gln Ser
        115                 120                 125

Ser Val Gly Ile Thr Tyr Gly Tyr Ala Asp Ala Asp Ser Phe Arg Pro
    130                 135                 140

Gly Pro Asn Thr Ser Gly Leu Glu Thr Arg Val Glu Gln Ala Glu Arg
145                 150                 155                 160
```

```
Phe Phe Lys Glu Lys Leu Phe Asp Trp Thr Ser Asp Lys Pro Phe Gly
            165                 170                 175

Thr Leu Tyr Val Leu Glu Leu Pro Lys Asp His Lys Gly Ile Tyr Gly
        180                 185                 190

Ser Leu Thr Asp Ala Tyr Thr Tyr Met Arg Asn Gly Trp Asp Val Gln
        195                 200                 205

Val Ser Ala Thr Ser Thr Gln Phe Asn Gly Gly Ser Leu Leu Val Ala
    210                 215                 220

Met Val Pro Glu Leu Cys Ser Leu Lys Asp Arg Glu Glu Phe Gln Leu
225                 230                 235                 240

Thr Leu Tyr Pro His Gln Phe Ile Asn Pro Arg Thr Asn Thr Thr Ala
            245                 250                 255

His Ile Gln Val Pro Tyr Leu Gly Val Asn Arg His Asp Gln Gly Lys
            260                 265                 270

Arg His Gln Ala Trp Ser Leu Val Met Val Leu Thr Pro Leu Thr
            275                 280                 285

Thr Glu Ala Gln Met Asn Ser Gly Thr Val Glu Val Tyr Ala Asn Ile
        290                 295                 300

Ala Pro Thr Asn Val Phe Val Ala Gly Glu Lys Pro Ala Lys Gln Gly
305                 310                 315                 320

Ile Ile Pro Val Ala Cys Ala Asp Gly Tyr Gly Gly Phe Gln Asn Thr
            325                 330                 335

Asp Pro Lys Thr Ala Asp Pro Ile Tyr Gly Tyr Val Tyr Asn Pro Ser
            340                 345                 350

Arg Asn Asp Cys His Gly Arg Tyr Ser Asn Leu Leu Asp Val Ala Glu
            355                 360                 365

Ala Cys Pro Thr Leu Leu Asn Phe Asp Gly Lys Pro Tyr Val Val Thr
        370                 375                 380

Lys Asn Asn Gly Asp Lys Val Met Ala Ala Phe Asp Val Ala Phe Thr
385                 390                 395                 400

His Lys Val His Lys Asn Thr Phe Leu Ala Gly Leu Ala Asp Tyr Tyr
            405                 410                 415

Thr Gln Tyr Gln Gly Ser Leu Asn Tyr His Phe Met Tyr Thr Gly Pro
        420                 425                 430

Thr His His Lys Ala Lys Phe Met Val Ala Tyr Ile Pro Pro Gly Ile
        435                 440                 445

Glu Thr Asp Lys Leu Pro Lys Thr Pro Glu Asp Ala Ala His Cys Tyr
    450                 455                 460

His Ser Glu Trp Asp Thr Gly Leu Asn Ser Gln Phe Thr Phe Ala Val
465                 470                 475                 480

Pro Tyr Val Ser Ala Ser Asp Phe Ser Tyr Thr His Thr Asp Thr Pro
            485                 490                 495

Ala Met Ala Thr Thr Asn Gly Trp Val Ala Val Phe Gln Val Thr Asp
        500                 505                 510

Thr His Ser Ala Glu Ala Val Val Ser Val Ser Ala Gly Pro
        515                 520                 525

Asp Leu Glu Phe Arg Phe Pro Ile Asp Pro Val Arg Gln Thr Thr Ser
    530                 535                 540

Ala Gly Glu Gly Ala Glu Val Val Thr Thr Asp Pro Ser Thr His Gly
545                 550                 555                 560

Gly Lys Val Thr Glu Lys Arg Arg Val His Thr Asp Val Ala Phe Val
            565                 570                 575

Leu Asp Arg Phe Thr His Val His Thr Asn Lys Thr Thr Phe Ala Val
```

```
            580                 585                 590
Asp Leu Met Asp Thr Lys Glu Lys Thr Leu Val Gly Ala Leu Leu Arg
                595                 600                 605

Ala Ala Thr Tyr Tyr Phe Cys Asp Leu Glu Ile Ala Cys Val Gly Glu
            610                 615                 620

His Lys Arg Val Phe Trp Gln Pro Asn Gly Ala Pro Arg Thr Thr Gln
625                 630                 635                 640

Leu Gly Asp Asn Pro Met Val Phe Ser His Asn Lys Val Thr Arg Phe
                645                 650                 655

Ala Ile Pro Tyr Thr Ala Pro His Arg Leu Leu Ser Thr Val Tyr Asn
            660                 665                 670

Gly Glu Cys Glu Tyr Thr Lys Thr Val Thr Ala Ile Arg Gly Asp Arg
                675                 680                 685

Glu Val Leu Ala Ala Lys Tyr Ser Ser Ala Lys His Thr Leu Pro Ser
            690                 695                 700

Thr Phe Asn Phe Gly Phe Val Thr Ala Asp Glu Pro Val Asp Val Tyr
705                 710                 715                 720

Tyr Arg Met Lys Arg Ala Glu Leu Tyr Cys Val Lys Lys Pro Val Ala
                725                 730                 735

Leu Lys Val Lys Ala Lys Asn Thr Leu Ile Val Thr Glu Ser Gly Ala
            740                 745                 750

Pro Pro Thr Asp Leu Gln Lys Met Val Met Gly Asn Thr Lys Pro Val
            755                 760                 765

Glu Leu Ile Leu Asp Gly Lys Thr Val Ala Ile Cys Cys Ala Thr Gly
    770                 775                 780

Val Phe Gly Thr Ala Tyr Leu Val Pro Arg His Leu Phe Ala Glu Lys
785                 790                 795                 800

Tyr Asp Lys Ile Met Leu Asp Gly Arg Ala Met Thr Asp Ser Asp Tyr
                805                 810                 815

Arg Val Phe Glu Phe Glu Ile Lys Val Lys Gly Gln Asp Met Leu Ser
                820                 825                 830

Asp Ala Ala Leu Met Val Leu His Arg Gly Asn Arg Val Arg Asp Ile
            835                 840                 845

Thr Lys His Phe Arg Asp Thr Ala Arg Met Lys Lys Gly Thr Pro Val
    850                 855                 860

Val Gly Val Ile Asn Asn Ala Asp Val Gly Arg Leu Ile Phe Ser Gly
865                 870                 875                 880

Glu Ala Leu Thr Tyr Lys Asp Ile Val Val Cys Met Asp Gly Asp Thr
                885                 890                 895

Met Pro Gly Leu Phe Ala Tyr Lys Ala Ala Thr Lys Ala Gly Tyr Cys
                900                 905                 910

Gly Gly Ala Val Leu Ala Lys Asp Gly Ala Asp Thr Phe Ile Val Gly
            915                 920                 925

Thr His Ser Ala Gly Gly Arg Asn Gly Val Gly Tyr Cys Ser Cys Val
    930                 935                 940

Ser Arg Ser Met Leu Leu Lys Met Lys Ala His Ile Asp Pro Glu Pro
945                 950                 955                 960

His His Glu Gly Leu Ile Val Asp Thr Arg Asp Val Glu Glu Arg Val
                965                 970                 975

His Val Met

<210> SEQ ID NO 76
<211> LENGTH: 2937
```

<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 76

| | |
|---|---:|
| atgctggacg tggactggca ggaccgcgcc ggcctgttcc tgcgcggcgc cggccagagc | 60 |
| agccccgcca ccggcagcca gaaccagagc ggcaacaccg gcagcatcat caacaactac | 120 |
| tacatgcagc agtaccagaa cagcatggac acccagctgg gcgacaacgc catcagcggc | 180 |
| ggcagcaacg agggcagcac cgacaccacc agcacccaca ccaacaacac ccagaacaac | 240 |
| gactggttca gcaagctggc ccagagcgcc atcagcggcc tgttcggcgc cctgctggcc | 300 |
| gacaagaaga ccgaggagac cacccacctg gaggaccgca tcctgaccac ccgccacaac | 360 |
| accaccacca gcaccaccca gagcagcgtg ggcgtgacct acggctacgt gagcgccgac | 420 |
| cgcttcctgc ccggccccaa caccagcggc ctggagagcc gcgtggagca ggccgagcgc | 480 |
| ttcttcaagg agaagctgtt cacctggacc gccagccagg agtacgccca cgtgcacctg | 540 |
| ctggagctgc ccaccgacca aagggcatc tacgcgcca tggtggacag ccacgcctac | 600 |
| gtgcgcaacg gctgggacgt gcaggtgacc gccaccagca cccagttcaa cggcggcacc | 660 |
| ctgctggtgg ccatggtgcc cgagctgcac agcctggaca cccgcgacgt gagccagctg | 720 |
| accctgttcc ccaccagtt catcaacccc cgcaccaaca ccaccgccca catcgtggtg | 780 |
| ccctacgtgg gcgtgaaccg ccacgaccag gtgcagatgc acaaggcctg gaccctggtg | 840 |
| gtggccgtga tggcccccct gaccaccagc agcatgggcc aggacaacgt ggaggtgtac | 900 |
| gccaacatcg cccccaccaa cgtgtacgtg gccggcgagc gccccagcaa gagggcatc | 960 |
| atccccgtgg cctgcaacga cggctacggc ggcttccaga caccgaccc caagaccgcc | 1020 |
| gaccccatct acggctggt gagcaacccc cccgcaccg ccttcccgg ccgcttcacc | 1080 |
| aacctgctgg acgtggccga ggcctgcccc accttcctgg acttcgacgg cgtgccctac | 1140 |
| gtgaagacca cccacaacag cggcagcaag atcctgaccc acatcgacct ggccttcggc | 1200 |
| cacaagagct tcaagaacac ctacctggcc ggcctggccc agtactacgc ccagtacagc | 1260 |
| ggcagcatca acctgcactt catgtacacc ggccccaccc agagcaaggc ccgcttcatg | 1320 |
| gtggcctaca tccccccgg caccaccgtg cccaacaccc ccgagcaggc cgcccactgc | 1380 |
| taccacagcg agtgggacac cggcctgaac agcaagttca ccttcaccgt gcctacatg | 1440 |
| agcgccgccg acttcgccta cacctactgc gacgagcccg agcaggccag cgcccagggc | 1500 |
| tgggtgaccc tgtaccagat caccgacacc cacgaccccg acagcgccgt gctggtgagc | 1560 |
| gtgagcgccg cgccgactt cgagctgcgc ctgcccatca ccccgccgc ccagaccacc | 1620 |
| agcgccggcg agggcgccga cgtggtgacc accgacgtga ccacccacgg cggcgaggtg | 1680 |
| agcgtgcccc gccgcagca caccaacgtg gagttcctgc tggaccgctt cacccacatc | 1740 |
| ggcaccatca acgccaccg caccatctgc ctgatggaca ccaaggagca caccctggtg | 1800 |
| ggcgccatcc tgcgcagcgc cacctactac ttctgcgacc tggaggtggc cgtgctgggc | 1860 |
| aacgccaagt acgccgcctg ggtgcccaac ggctgccccc acaccgaccg cgtggaggac | 1920 |
| aaccccgtgg tgcacagcaa gggcagcgtg gtgcgcttcg ccctgcccta caccgccccc | 1980 |
| cacggcgtgc tggccaccgt gtacaacggc aactgcaagt acagcaccac ccagcgcgtg | 2040 |
| gcccccgcc gcgcgacct gggcgtgctg agccagcgcg tggagaacga gaccaccgc | 2100 |
| tgcatcccca ccaccttcaa cttcggccgc ctgctgtgcg agagcggcga cgtgtactac | 2160 |

```
cgcatgaagc gcaccgagct gtactgcgtg aagaagcccg tggccctgaa ggtgaaggcc      2220
aagaacaccc tgatcgtgac cgagagcggc gccccccca ccgacctgca aagatggtg       2280 atgggcaaca ccaagcccgt ggagctgatc ctggacggca agaccgtggc catctgctgc      2340
gccaccggcg tgttcggcac cgcctacctg gtgccccgcc acctgttcgc cgagaagtac      2400
gacaagatca tgctggacgg ccgcgccatg accgacagcg actaccgcgt gttcgagttc      2460
gagatcaagg tgaagggcca ggacatgctg agcgacgccg ccctgatggt gctgcaccgc      2520
ggcaaccgcg tgcgcgacat caccaagcac ttccgcgaca ccgcccgcat gaagaagggc      2580 accccgtgg tgggcgtgat caacaacgcc gacgtgggcc gcctgatctt cagcggcgag       2640
gccctgacct acaaggacat cgtggtgtgc atggacggcg acaccatgcc cggcctgttc      2700
gcctacaagg ccgccaccaa ggccggctac tgccggcggc ccgtgctggc caaggacggc      2760
gccgacacct tcatcgtggg cacccacagc gccggcggcc gcaacggcgt gggctactgc      2820
agctgcgtga ccgcagcat gctgctgaag atgaaggccc acatcgaccc cgagccccac       2880
cacgagggcc tgatcgtgga cacccgcgac gtggaggagc gcgtgcacgt gatgtga        2937
```

<210> SEQ ID NO 77
<211> LENGTH: 978
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 77

```
Met Leu Asp Val Asp Trp Gln Asp Arg Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Ile Ser Gly Leu Phe Gly
                85                  90                  95

Ala Leu Leu Ala Asp Lys Lys Thr Glu Glu Thr Thr His Leu Glu Asp
            100                 105                 110

Arg Ile Leu Thr Thr Arg His Asn Thr Thr Thr Ser Thr Thr Gln Ser
        115                 120                 125

Ser Val Gly Val Thr Tyr Gly Tyr Val Ser Ala Asp Arg Phe Leu Pro
    130                 135                 140

Gly Pro Asn Thr Ser Gly Leu Glu Ser Arg Val Glu Gln Ala Glu Arg
145                 150                 155                 160

Phe Phe Lys Glu Lys Leu Phe Thr Trp Thr Ala Ser Gln Glu Tyr Ala
                165                 170                 175

His Val His Leu Leu Glu Leu Pro Thr Asp His Lys Gly Ile Tyr Gly
            180                 185                 190

Ala Met Val Asp Ser His Ala Tyr Val Arg Asn Gly Trp Asp Val Gln
        195                 200                 205

Val Thr Ala Thr Ser Thr Gln Phe Asn Gly Gly Thr Leu Leu Val Ala
    210                 215                 220
```

```
Met Val Pro Glu Leu His Ser Leu Asp Thr Arg Asp Val Ser Gln Leu
225                 230                 235                 240

Thr Leu Phe Pro His Gln Phe Ile Asn Pro Arg Thr Asn Thr Thr Ala
            245                 250                 255

His Ile Val Val Pro Tyr Val Gly Val Asn Arg His Asp Gln Val Gln
                260                 265                 270

Met His Lys Ala Trp Thr Leu Val Ala Val Met Ala Pro Leu Thr
        275                 280                 285

Thr Ser Ser Met Gly Gln Asp Asn Val Glu Val Tyr Ala Asn Ile Ala
            290                 295                 300

Pro Thr Asn Val Tyr Val Ala Gly Glu Arg Pro Ser Lys Gln Gly Ile
305                 310                 315                 320

Ile Pro Val Ala Cys Asn Asp Gly Tyr Gly Gly Phe Gln Asn Thr Asp
                325                 330                 335

Pro Lys Thr Ala Asp Pro Ile Tyr Gly Leu Val Ser Asn Pro Pro Arg
            340                 345                 350

Thr Ala Phe Pro Gly Arg Phe Thr Asn Leu Leu Asp Val Ala Glu Ala
            355                 360                 365

Cys Pro Thr Phe Leu Asp Phe Asp Gly Val Pro Tyr Val Lys Thr Thr
370                 375                 380

His Asn Ser Gly Ser Lys Ile Leu Thr His Ile Asp Leu Ala Phe Gly
385                 390                 395                 400

His Lys Ser Phe Lys Asn Thr Tyr Leu Ala Gly Leu Ala Gln Tyr Tyr
                405                 410                 415

Ala Gln Tyr Ser Gly Ser Ile Asn Leu His Phe Met Tyr Thr Gly Pro
            420                 425                 430

Thr Gln Ser Lys Ala Arg Phe Met Val Ala Tyr Ile Pro Pro Gly Thr
            435                 440                 445

Thr Val Pro Asn Thr Pro Glu Gln Ala Ala His Cys Tyr His Ser Glu
        450                 455                 460

Trp Asp Thr Gly Leu Asn Ser Lys Phe Thr Phe Thr Val Pro Tyr Met
465                 470                 475                 480

Ser Ala Ala Asp Phe Ala Tyr Thr Tyr Cys Asp Glu Pro Glu Gln Ala
                485                 490                 495

Ser Ala Gln Gly Trp Val Thr Leu Tyr Gln Ile Thr Asp Thr His Asp
            500                 505                 510

Pro Asp Ser Ala Val Leu Val Ser Val Ser Ala Gly Ala Asp Phe Glu
        515                 520                 525

Leu Arg Leu Pro Ile Asn Pro Ala Ala Gln Thr Thr Ser Ala Gly Glu
        530                 535                 540

Gly Ala Asp Val Val Thr Thr Asp Val Thr Thr His Gly Gly Glu Val
545                 550                 555                 560

Ser Val Pro Arg Arg Gln His Thr Asn Val Glu Phe Leu Leu Asp Arg
                565                 570                 575

Phe Thr His Ile Gly Thr Ile Asn Gly His Arg Thr Ile Cys Leu Met
            580                 585                 590

Asp Thr Lys Glu His Thr Leu Val Gly Ala Ile Leu Arg Ser Ala Thr
            595                 600                 605

Tyr Tyr Phe Cys Asp Leu Glu Val Ala Val Leu Gly Asn Ala Lys Tyr
        610                 615                 620

Ala Ala Trp Val Pro Asn Gly Cys Pro His Thr Asp Arg Val Glu Asp
625                 630                 635                 640
```

Asn Pro Val Val His Ser Lys Gly Ser Val Val Arg Phe Ala Leu Pro
             645                 650                 655

Tyr Thr Ala Pro His Gly Val Leu Ala Thr Val Tyr Asn Gly Asn Cys
        660                 665                 670

Lys Tyr Ser Thr Thr Gln Arg Val Ala Pro Arg Arg Gly Asp Leu Gly
            675                 680                 685

Val Leu Ser Gln Arg Val Glu Asn Glu Thr Arg Cys Ile Pro Thr
690                 695                 700

Thr Phe Asn Phe Gly Arg Leu Leu Cys Glu Ser Gly Asp Val Tyr Tyr
705                 710                 715                 720

Arg Met Lys Arg Thr Glu Leu Tyr Cys Val Lys Lys Pro Val Ala Leu
                725                 730                 735

Lys Val Lys Ala Lys Asn Thr Leu Ile Val Thr Glu Ser Gly Ala Pro
                740                 745                 750

Pro Thr Asp Leu Gln Lys Met Val Met Gly Asn Thr Lys Pro Val Glu
            755                 760                 765

Leu Ile Leu Asp Gly Lys Thr Val Ala Ile Cys Cys Ala Thr Gly Val
770                 775                 780

Phe Gly Thr Ala Tyr Leu Val Pro Arg His Leu Phe Ala Glu Lys Tyr
785                 790                 795                 800

Asp Lys Ile Met Leu Asp Gly Arg Ala Met Thr Asp Ser Asp Tyr Arg
                805                 810                 815

Val Phe Glu Phe Glu Ile Lys Val Lys Gly Gln Asp Met Leu Ser Asp
                820                 825                 830

Ala Ala Leu Met Val Leu His Arg Gly Asn Arg Val Arg Asp Ile Thr
835                 840                 845

Lys His Phe Arg Asp Thr Ala Arg Met Lys Lys Gly Thr Pro Val Val
850                 855                 860

Gly Val Ile Asn Asn Ala Asp Val Gly Arg Leu Ile Phe Ser Gly Glu
865                 870                 875                 880

Ala Leu Thr Tyr Lys Asp Ile Val Val Cys Met Asp Gly Asp Thr Met
                885                 890                 895

Pro Gly Leu Phe Ala Tyr Lys Ala Ala Thr Lys Ala Gly Tyr Cys Gly
            900                 905                 910

Gly Ala Val Leu Ala Lys Asp Gly Ala Asp Thr Phe Ile Val Gly Thr
        915                 920                 925

His Ser Ala Gly Gly Arg Asn Gly Val Gly Tyr Cys Ser Cys Val Ser
    930                 935                 940

Arg Ser Met Leu Leu Lys Met Lys Ala His Ile Asp Pro Glu Pro His
945                 950                 955                 960

His Glu Gly Leu Ile Val Asp Thr Arg Asp Val Glu Glu Arg Val His
                965                 970                 975

Val Met

<210> SEQ ID NO 78
<211> LENGTH: 756
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 78
tactgcgtga agaagcccgt ggccctgaag gtgaaggcca agaacaccct gatcgtgacc    60
gagagcggcg ccccccccac cgacctgcag aagatggtga tgggcaacac caagcccgtg   120

```
gagctgatcc tggacggcaa gaccgtggcc atctgctgcg ccaccggcgt gttcggcacc      180
gcctacctgg tgccccgcca cctgttcgcc gagaagtacg acaagatcat gctggacggc      240
cgcgccatga ccgacagcga ctaccgcgtg ttcgagttcg agatcaaggt gaagggccag      300
gacatgctga gcgacgccgc cctgatggtg ctgcaccgcg gcaaccgcgt gcgcgacatc      360
accaagcact ccgcgacac cgcccgcatg aagaagggca ccccgtggt gggcgtgatc       420 aacaacgccg acgtgggccg cctgatcttc agcggcgagg ccctgaccta caaggacatc      480
gtggtgtgca tggacggcga caccatgccc ggcctgttcg cctacaaggc cgccaccaag      540
gccggctact gcggcggcgc cgtgctggcc aaggacggcg ccgacacctt catcgtgggc      600
acccacagcg ccggcggccg caacggcgtg ggctactgca gctgcgtgag ccgcagcatg      660
ctgctgaaga tgaaggccca catcgacccc gagccccacc acgagggcct gatcgtggac      720
acccgcgacg tggaggagcg cgtgcacgtg atgtga                              756
```

<210> SEQ ID NO 79
<211> LENGTH: 251
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 79

```
Tyr Cys Val Lys Lys Pro Val Ala Leu Lys Val Lys Ala Lys Asn Thr
1               5                   10                  15

Leu Ile Val Thr Glu Ser Gly Ala Pro Pro Thr Asp Leu Gln Lys Met
            20                  25                  30

Val Met Gly Asn Thr Lys Pro Val Glu Leu Ile Leu Asp Gly Lys Thr
        35                  40                  45

Val Ala Ile Cys Cys Ala Thr Gly Val Phe Gly Thr Ala Tyr Leu Val
    50                  55                  60

Pro Arg His Leu Phe Ala Glu Lys Tyr Asp Lys Ile Met Leu Asp Gly
65                  70                  75                  80

Arg Ala Met Thr Asp Ser Asp Tyr Arg Val Phe Glu Phe Glu Ile Lys
                85                  90                  95

Val Lys Gly Gln Asp Met Leu Ser Asp Ala Ala Leu Met Val Leu His
            100                 105                 110

Arg Gly Asn Arg Val Arg Asp Ile Thr Lys His Phe Arg Asp Thr Ala
        115                 120                 125

Arg Met Lys Lys Gly Thr Pro Val Val Gly Val Ile Asn Asn Ala Asp
    130                 135                 140

Val Gly Arg Leu Ile Phe Ser Gly Glu Ala Leu Thr Tyr Lys Asp Ile
145                 150                 155                 160

Val Val Cys Met Asp Gly Asp Thr Met Pro Gly Leu Phe Ala Tyr Lys
                165                 170                 175

Ala Ala Thr Lys Ala Gly Tyr Cys Gly Gly Ala Val Leu Ala Lys Asp
            180                 185                 190

Gly Ala Asp Thr Phe Ile Val Gly Thr His Ser Ala Gly Gly Arg Asn
        195                 200                 205

Gly Val Gly Tyr Cys Ser Cys Val Ser Arg Ser Met Leu Leu Lys Met
    210                 215                 220

Lys Ala His Ile Asp Pro Glu Pro His His Glu Gly Leu Ile Val Asp
225                 230                 235                 240
```

Thr Arg Asp Val Glu Glu Arg Val His Val Met
                245                 250

<210> SEQ ID NO 80
<211> LENGTH: 2160
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 80

| | | | | |
|---|---|---|---|---|
| atgctgaacg | gcgactggaa | ggccaaggtg | cagcgcaagc | tgaagggcgc | cggccagagc | 60 |
| agccccgcca | ccggcagcca | gaaccagagc | ggcaacaccg | gcagcatcat | caacaactac | 120 |
| tacatgcagc | agtaccagaa | cagcatggac | acccagctgg | gcgacaacgc | catcagcggc | 180 |
| ggcagcaacg | agggcagcac | cgacaccacc | agcacccaca | ccaccaacac | ccagaacaac | 240 |
| gactggttca | gcaagctggc | cagcagcgcc | ttcaccggcc | tgttcggcgc | cctgctggcc | 300 |
| gacaagaaga | ccgaggagac | caccctgctg | gaggaccgca | tcctgaccac | ccgcaacggc | 360 |
| cacaccacca | gcaccaccca | gagcagcgtg | ggcgtgacct | acggctacag | caccaccgag | 420 |
| gaccacgtgg | ccgcccccaa | caccagcggc | ctggagaccc | gcgtggtgca | ggccgagcgc | 480 |
| ttcttcaaga | agttcctgtt | cgactggacc | accgacaagc | ccttcggcca | cctgcacaag | 540 |
| ctggagctgc | ccaccgacca | ccacggcgtg | ttcggccacc | tggtggacag | ctacgcctac | 600 |
| atgcgcaacg | gctgggacgt | ggaggtgagc | gccgtgggca | accagttcaa | cggcggctgc | 660 |
| ctgctggtgg | ccatggtgcc | cgagtggaag | gagttcgaca | cccgcgagaa | gtaccagctg | 720 |
| accctgttcc | ccaccagttt | catcagcccc | cgcaccaaca | tgaccgccca | catcaccgtg | 780 |
| ccctacctgg | gcgtgaaccg | ctacgaccag | tacaagaagc | acaagccctg | gacccctggtg | 840 |
| gtgatggtgg | tgagcccccct | gaccgtgaac | accgccgccc | agatcaaggt | gtacgccaac | 900 |
| atcgccccca | cctacgtgca | cgtggccggc | gagctgccca | gcaaggaggg | catcttcccc | 960 |
| gtggcctgcg | ccgacggcta | cggcggcctg | gtgaccaccg | accccaagac | cgccgacccc | 1020 |
| gcctacggca | aggtgtacaa | ccccccccgc | accaactacc | ccggccgctt | caccaacctg | 1080 |
| ctggacgtgg | ccgaggcctg | ccccaccttc | ctgtgcttcg | acgacggcaa | gccctacgtg | 1140 |
| accacccgca | ccgacgagac | ccgcctgctg | gccaagttcg | acgtgagcct | ggccgccaag | 1200 |
| cacatgagca | acacctacct | gagcggcatc | gcccagtact | acacccagta | cagcggcacc | 1260 |
| atcaacctgc | acttcatgtt | caccggcagc | accgacagca | aggcccgcta | catggtggcc | 1320 |
| tacatccccc | ccggcgtgga | gaccccccccc | gacaccccccg | agcgcgccgc | ccactgcatc | 1380 |
| cacgccgagt | gggacaccgg | cctgaacagc | aagttcacct | tcagcatccc | ctacgtgagc | 1440 |
| gccgccgact | acgcctacac | cgccagcgac | accgccgaga | ccaccaacgt | gcagggctgg | 1500 |
| gtgtgcgtgt | accagatcac | ccacggcaag | gccgagaacg | caccctggt | ggtgagcgtg | 1560 |
| agcgccggca | aggacttcga | gctgcgcctg | cccatcgacc | ccgccagca | gaccaccgcc | 1620 |
| accggcgaga | gcgccgaccc | cgtgaccacc | accgtggaga | actacggcgg | cgagacccag | 1680 |
| gtgcagcgcc | gccaccacac | cgacgtgggc | ttcatcatgg | accgcttcgt | gaagatcaac | 1740 |
| agccccaagc | ccacccacgt | gatcgacctg | atgcagaccc | accagcacgg | cctggtgggc | 1800 |
| gccctgctgc | gcgccgccac | ctactacttc | agcgacctgg | agatcgtggt | gcgccacgac | 1860 |
| ggcctgacct | gggtgcccaa | cggcgccccc | gagagcgccc | tgagcaacac | cagcaacccc | 1920 |
| accgcctaca | acaaggcccc | cttcacccgc | ctggccctgc | cctacaccgc | ccccccaccgc | 1980 |

```
gtgctggcca ccgtgtacaa cggcaccagc aagtacaccg tgagcggcag cagccgccgc    2040
ggcgacctgg gcagcctggc cgcccgcgtg gccaagcagc tgcccgccag cttcaactac    2100
ggcgccatca aggccgacac catccacgag ctgctggtgc gcatgaagcg cgccgagctg    2160
```

<210> SEQ ID NO 81
<211> LENGTH: 720
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 81

```
Met Leu Asn Gly Asp Trp Lys Ala Lys Val Gln Arg Lys Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Thr Asn Thr Gln Asn Asn
65                  70                  75                  80

Asp Trp Phe Ser Lys Leu Ala Ser Ser Ala Phe Thr Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Tyr Gly Tyr Ser Thr Thr Glu Asp His Val Ala
    130                 135                 140

Gly Pro Asn Thr Ser Gly Leu Glu Thr Arg Val Val Gln Ala Glu Arg
145                 150                 155                 160

Phe Phe Lys Lys Phe Leu Phe Asp Trp Thr Thr Asp Lys Pro Phe Gly
                165                 170                 175

His Leu His Lys Leu Glu Leu Pro Thr Asp His His Gly Val Phe Gly
            180                 185                 190

His Leu Val Asp Ser Tyr Ala Tyr Met Arg Asn Gly Trp Asp Val Glu
        195                 200                 205

Val Ser Ala Val Gly Asn Gln Phe Asn Gly Gly Cys Leu Leu Val Ala
    210                 215                 220

Met Val Pro Glu Trp Lys Glu Phe Asp Thr Arg Glu Lys Tyr Gln Leu
225                 230                 235                 240

Thr Leu Phe Pro His Gln Phe Ile Ser Pro Arg Thr Asn Met Thr Ala
                245                 250                 255

His Ile Thr Val Pro Tyr Leu Gly Val Asn Arg Tyr Asp Gln Tyr Lys
            260                 265                 270

Lys His Lys Pro Trp Thr Leu Val Val Met Val Val Ser Pro Leu Thr
        275                 280                 285

Val Asn Thr Ala Ala Gln Ile Lys Val Tyr Ala Asn Ile Ala Pro Thr
    290                 295                 300

Tyr Val His Val Ala Gly Glu Leu Pro Ser Lys Glu Gly Ile Phe Pro
305                 310                 315                 320

Val Ala Cys Ala Asp Gly Tyr Gly Gly Leu Val Thr Thr Asp Pro Lys
```

```
                   325                 330                 335
Thr Ala Asp Pro Ala Tyr Gly Lys Val Tyr Asn Pro Pro Arg Thr Asn
                340                 345                 350
Tyr Pro Gly Arg Phe Thr Asn Leu Leu Asp Val Ala Glu Ala Cys Pro
            355                 360                 365
Thr Phe Leu Cys Phe Asp Asp Gly Lys Pro Tyr Val Thr Thr Arg Thr
        370                 375                 380
Asp Glu Thr Arg Leu Leu Ala Lys Phe Asp Val Ser Leu Ala Ala Lys
385                 390                 395                 400
His Met Ser Asn Thr Tyr Leu Ser Gly Ile Ala Gln Tyr Tyr Thr Gln
                405                 410                 415
Tyr Ser Gly Thr Ile Asn Leu His Phe Met Phe Thr Gly Ser Thr Asp
                420                 425                 430
Ser Lys Ala Arg Tyr Met Val Ala Tyr Ile Pro Pro Gly Val Glu Thr
            435                 440                 445
Pro Pro Asp Thr Pro Glu Arg Ala Ala His Cys Ile His Ala Glu Trp
        450                 455                 460
Asp Thr Gly Leu Asn Ser Lys Phe Thr Phe Ser Ile Pro Tyr Val Ser
465                 470                 475                 480
Ala Ala Asp Tyr Ala Tyr Thr Ala Ser Asp Thr Ala Glu Thr Thr Asn
                485                 490                 495
Val Gln Gly Trp Val Cys Val Tyr Gln Ile Thr His Gly Lys Ala Glu
                500                 505                 510
Asn Asp Thr Leu Val Val Ser Val Ser Ala Gly Lys Asp Phe Glu Leu
            515                 520                 525
Arg Leu Pro Ile Asp Pro Arg Gln Gln Thr Thr Ala Thr Gly Glu Ser
        530                 535                 540
Ala Asp Pro Val Thr Thr Thr Val Glu Asn Tyr Gly Gly Glu Thr Gln
545                 550                 555                 560
Val Gln Arg Arg His His Thr Asp Val Gly Phe Ile Met Asp Arg Phe
                565                 570                 575
Val Lys Ile Asn Ser Pro Lys Pro Thr His Val Ile Asp Leu Met Gln
                580                 585                 590
Thr His Gln His Gly Leu Val Gly Ala Leu Leu Arg Ala Ala Thr Tyr
            595                 600                 605
Tyr Phe Ser Asp Leu Glu Ile Val Val Arg His Asp Gly Leu Thr Trp
        610                 615                 620
Val Pro Asn Gly Ala Pro Glu Ser Ala Leu Ser Asn Thr Ser Asn Pro
625                 630                 635                 640
Thr Ala Tyr Asn Lys Ala Pro Phe Thr Arg Leu Ala Leu Pro Tyr Thr
                645                 650                 655
Ala Pro His Arg Val Leu Ala Thr Val Tyr Asn Gly Thr Ser Lys Tyr
            660                 665                 670
Thr Val Ser Gly Ser Ser Arg Arg Gly Asp Leu Gly Ser Leu Ala Ala
        675                 680                 685
Arg Val Ala Lys Gln Leu Pro Ala Ser Phe Asn Tyr Gly Ala Ile Lys
            690                 695                 700
Ala Asp Thr Ile His Glu Leu Leu Val Arg Met Lys Arg Ala Glu Leu
705                 710                 715                 720

<210> SEQ ID NO 82
<211> LENGTH: 2160
<212> TYPE: DNA
<213> ORGANISM: Artificial Sequence
```

<220> FEATURE:
<223> OTHER INFORMATION: Description of Artificial Sequence: Synthetic consensus sequence

<400> SEQUENCE: 82

```
atgctgaacg gcgagtggaa ggccaaggtg cagaagcgcc tgaagggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180
ggcagcaacg agggcagcac cgacaccacc agcacccaca ccaacaacac ccagaacaac     240
gactggttca gccgcctggc cagcagcgcc ttcagcggcc tgttcggcgc cctgctggcc     300
gacaagaaga ccgaggagac caccctgctg gaggaccgca tcctgaccac ccgcaacggc     360
cacaccacca gcaccaccca gagcagcgtg ggcgtgacct acggctacgc cgtggccgag     420
gacgccgtga gcggccccaa caccagcggc ctggagaccc gcgtgcagca ggccgagcgc     480
ttcttcaaga agcacctgtt cgactggacc cccaacctgg ccttcggcca ctgccactac     540
ctggagctgc ccaccgagca aagggcgtg tacggcagcc tgatggacag ctacgcctac     600
atgcgcaacg gctgggacat cgaggtgacc gccgtgggca accagttcaa cggcggctgc     660
ctgctggtgg ccctggtgcc cgagctgaag agcctggaca cccgccagaa gtaccagctg     720
accctgttcc ccaccagtt catcaacccc cgcaccaaca tgaccgccca catcaacgtg     780
cccttcgtgg gcgtgaaccg ctacgaccag tacgccctgc acaagcctg gaccctggtg     840
gtgatggtgg tggcccccct gaccgtgaag accggcggca gcgagcagat caaggtgtac     900
atgaacgccg cccccaccta cgtgcacgtg gccggcagc tgcccagcaa ggagggcatc     960
gtgcccgtgg cctgcgccga cggctacggc aacatggtga ccaccgaccc caagaccgcc    1020
gaccccgtgt acggcaaggt gttcaacccc ccccgcacca acctgcccgg ccgcttcacc    1080
aacttcctgg acgtggccga ggcctgcccc accttcctgc gcttcggcga ggtgcccttc    1140
gtgaagaccg tgaacagcgg cgaccgcctg ctggccaagt cgacgtgag cctggccgcc    1200
ggccacatga gcaacaccta cctggccggc ctggcccagt actacaccca gtacagcggc    1260
accatgaacg tgcacttcat gttcaccggc cccaccgacg ccaaggcccg ctacatggtg    1320
gcctacatcc cccccggcat gaccccccc accgaccccg agcgcgccgc ccactgcatc    1380
cacagcgagt gggacaccgg cctgaacagc aagttcacct tcagcatccc ctacctgagc    1440
gccgccgact acgcctacac cgccagcgac accgccgaga ccaccagcgt gcagggctgg    1500
gtgtgcatct accagatcac ccacggcaag gccgagggcg acgccctggt ggtgagcgtg    1560
agcgccggca aggacttcga gttccgcctg cccgtggacg cccgccgcca gaccaccacc    1620
accggcgaga cgccgaccc cgtgaccacc accgtggaga actacggcgg cgagacccag    1680
accgcccgcc gcctgcacac cgacgtggcc ttcgtgctgg accgcttcgt gaagctgacc    1740
gccccaaga cacccagac cctggacctg atgcagatcc ccagccacac cctggtgggc    1800
gccctgctgc gcagcgccac ctactacttc agcgacctgg aggtggccct ggtgcacacc    1860
ggccccgtga cctgggtgcc caacggcagc cccaaggacg ccctggacaa ccagaccaac    1920
cccaccgcct accagaagca gcccatcacc gcctggccc tgccctacac cgccccccac    1980
cgcgtgctgg ccaccgtgta caacggcaag accacctacg gcgagacccc cagccgccgc    2040
ggcgacatgg ccgccctggc ccagcgcctg agcgagcgcc tgcccaccag cttcaactac    2100
ggcgccgtga aggccgagac catcaccgag ctgctgatcc gcatgaagcg cgccgagacc    2160
```

-continued

```
<210> SEQ ID NO 83
<211> LENGTH: 704
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 83

Ala Gly Gln Ser Ser Pro Ala Thr Gly Ser Gln Asn Gln Ser Gly Asn
1               5                   10                  15

Thr Gly Ser Ile Ile Asn Asn Tyr Tyr Met Gln Gln Tyr Gln Asn Ser
            20                  25                  30

Met Asp Thr Gln Leu Gly Asp Asn Ala Ile Ser Gly Gly Ser Asn Glu
        35                  40                  45

Gly Ser Thr Asp Thr Thr Ser Thr His Thr Asn Asn Thr Gln Asn Asn
50                  55                  60

Asp Trp Phe Ser Arg Leu Ala Ser Ser Ala Phe Ser Gly Leu Phe Gly
65                  70                  75                  80

Ala Leu Leu Ala Asp Lys Lys Thr Glu Glu Thr Thr Leu Leu Glu Asp
                85                  90                  95

Arg Ile Leu Thr Thr Arg Asn Gly His Thr Thr Ser Thr Thr Gln Ser
            100                 105                 110

Ser Val Gly Val Thr Tyr Gly Tyr Ala Val Ala Glu Asp Ala Val Ser
        115                 120                 125

Gly Pro Asn Thr Ser Gly Leu Glu Thr Arg Val Gln Gln Ala Glu Arg
130                 135                 140

Phe Phe Lys Lys His Leu Phe Asp Trp Thr Pro Asn Leu Ala Phe Gly
145                 150                 155                 160

His Cys His Tyr Leu Glu Leu Pro Thr Glu His Lys Gly Val Tyr Gly
                165                 170                 175

Ser Leu Met Asp Ser Tyr Ala Tyr Met Arg Asn Gly Trp Asp Ile Glu
            180                 185                 190

Val Thr Ala Val Gly Asn Gln Phe Asn Gly Gly Cys Leu Leu Val Ala
        195                 200                 205

Leu Val Pro Glu Leu Lys Ser Leu Asp Thr Arg Gln Lys Tyr Gln Leu
210                 215                 220

Thr Leu Phe Pro His Gln Phe Ile Asn Pro Arg Thr Asn Met Thr Ala
225                 230                 235                 240

His Ile Asn Val Pro Phe Val Gly Val Asn Arg Tyr Asp Gln Tyr Ala
                245                 250                 255

Leu His Lys Pro Trp Thr Leu Val Val Met Val Val Ala Pro Leu Thr
            260                 265                 270

Val Lys Thr Gly Gly Ser Glu Gln Ile Lys Val Tyr Met Asn Ala Ala
        275                 280                 285

Pro Thr Tyr Val His Val Ala Gly Glu Leu Pro Ser Lys Glu Gly Ile
290                 295                 300

Val Pro Val Ala Cys Ala Asp Gly Tyr Gly Asn Met Val Thr Thr Asp
305                 310                 315                 320

Pro Lys Thr Ala Asp Pro Val Tyr Gly Lys Val Phe Asn Pro Pro Arg
                325                 330                 335

Thr Asn Leu Pro Gly Arg Phe Thr Asn Phe Leu Asp Val Ala Glu Ala
            340                 345                 350

Cys Pro Thr Phe Leu Arg Phe Gly Glu Val Pro Phe Val Lys Thr Val
        355                 360                 365
```

Asn Ser Gly Asp Arg Leu Leu Ala Lys Phe Asp Val Ser Leu Ala Ala
370                 375                 380

Gly His Met Ser Asn Thr Tyr Leu Ala Gly Leu Ala Gln Tyr Tyr Thr
385                 390                 395                 400

Gln Tyr Ser Gly Thr Met Asn Val His Phe Met Phe Thr Gly Pro Thr
            405                 410                 415

Asp Ala Lys Ala Arg Tyr Met Val Ala Tyr Ile Pro Pro Gly Met Thr
            420                 425                 430

Pro Pro Thr Asp Pro Glu Arg Ala Ala His Cys Ile His Ser Glu Trp
            435                 440                 445

Asp Thr Gly Leu Asn Ser Lys Phe Thr Phe Ser Ile Pro Tyr Leu Ser
450                 455                 460

Ala Ala Asp Tyr Ala Tyr Thr Ala Ser Asp Thr Ala Glu Thr Thr Ser
465                 470                 475                 480

Val Gln Gly Trp Val Cys Ile Tyr Gln Ile Thr His Gly Lys Ala Glu
                485                 490                 495

Gly Asp Ala Leu Val Val Ser Val Ser Ala Gly Lys Asp Phe Glu Phe
            500                 505                 510

Arg Leu Pro Val Asp Ala Arg Gln Thr Thr Thr Gly Glu Ser
            515                 520                 525

Ala Asp Pro Val Thr Thr Val Glu Asn Tyr Gly Gly Glu Thr Gln
530                 535                 540

Thr Ala Arg Arg Leu His Thr Asp Val Ala Phe Val Leu Asp Arg Phe
545                 550                 555                 560

Val Lys Leu Thr Ala Pro Lys Asn Thr Gln Thr Leu Asp Leu Met Gln
                565                 570                 575

Ile Pro Ser His Thr Leu Val Gly Ala Leu Leu Arg Ser Ala Thr Tyr
            580                 585                 590

Tyr Phe Ser Asp Leu Glu Val Ala Leu Val His Thr Gly Pro Val Thr
            595                 600                 605

Trp Val Pro Asn Gly Ser Pro Lys Asp Ala Leu Asp Asn Gln Thr Asn
610                 615                 620

Pro Thr Ala Tyr Gln Lys Gln Pro Ile Thr Arg Leu Ala Leu Pro Tyr
625                 630                 635                 640

Thr Ala Pro His Arg Val Leu Ala Thr Val Tyr Asn Gly Lys Thr Thr
            645                 650                 655

Tyr Gly Glu Thr Pro Ser Arg Arg Gly Asp Met Ala Ala Leu Ala Gln
            660                 665                 670

Arg Leu Ser Glu Arg Leu Pro Thr Ser Phe Asn Tyr Gly Ala Val Lys
            675                 680                 685

Ala Glu Thr Ile Thr Glu Leu Leu Ile Arg Met Lys Arg Ala Glu Thr
690                 695                 700

<210> SEQ ID NO 84
<211> LENGTH: 2157
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 84
atgctgaacg agggctggaa ggccagcgtg cagcgcaagc tgaagggcgc cggccagagc      60
agccccgcca ccggcagcca gaaccagagc ggcaacaccg gcagcatcat caacaactac     120
tacatgcagc agtaccagaa cagcatggac acccagctgg gcgacaacgc catcagcggc     180

```
ggcagcaacg agggcagcac cgacaccacc agcacccaca ccaccaacac ccagaacaac    240
gactggttca gcaagctggc cagcagcgcc ttcagcggcc tgttcggcgc cctgctggcc    300
gacaagaaga ccgaggagac caccctgctg gaggaccgca tcctgaccac ccgcaacggc    360
cacaccacca gcaccaccca gagcagcgtg ggcgtgacct tcggctacgc caccgccgag    420
gacagcacca gcggccccaa caccagcggc ctggagaccc gcgtgcacca ggccgagcgc    480
ttcttcaaga tggcccctgt tcgactgggtg cccagccaga acttcggcca catgcacaag    540
gtggtgctgc ccacgagcc aagggcgtg tacggcggcc tggtgaagag ctacgcctac    600
atgcgcaacg ctgggacgt ggaggtgacc gccgtgggca ccagttcaa cggcggctgc    660
ctgctggtgg ccctggtgcc cgagatgggc gacatcagcg accgcgagaa gtaccagctg    720
accctgtacc cccaccagtt catcaaccccc gcaccaaca tgaccgccca catcaccgtg    780
ccctacgtgg gcgtgaaccg ctacgaccag tacaagcagc accgcccctg accctggtg    840
gtgatggtgg tggcccccct gaccaccaac accgccggcg cccagcagat caaggtgtac    900
gccaacatcg cccccaccaa cgtgcacgtg gccggcgagc tgcccagcaa ggagggcatc    960
ttccccgtgg cctgcagcga cggctacggc aacatggtga ccaccgaccc caagaccgcc   1020
gaccccgtgt acggcaaggt gtacaacccc cccgcaccg ccctgccgg ccgcttcacc   1080
aactacctgg acgtggccga ggcctgcccc accttcctga tgttcgagaa cgtgccctac   1140
gtgagcaccc gcaccgacgg ccagcgcctg ctggccaagt cgacgtgag cctggccgcc   1200
aagcacatga gcaacaccta cctggccggc ctggcccagt actacaccca gtacaccggc   1260
accatcaacc tgcacttcat gttcaccggc cccaccgacg ccaaggcccg ctacatggtg   1320
gcctacgtgc cccccggcat ggacgccccc gacaaccccg aggaggccgc ccactgcatc   1380
cacgccgagt gggacaccgg cctgaacagc aagttcacct tcagcatccc ctacatcagc   1440
gccgccgact acgcctacac cgccagccac aaggccgaga ccacctgcgt gcagggctgg   1500
gtgtgcgtgt accagatcac ccacggcaag gccgacgccg acgccctggt ggtgagcgcc   1560
agcgccggca aggacttcga gctgcgcctg cccgtggacg cccgcaagca gaccaccacc   1620
accggcgaga gcgccgaccc cgtgaccacc accgtggaga actacggcgg cgagacccag   1680
gtgcagcgcc gccaccacac cgacgtggcc ttcgtgctgg accgcttcgt ggaggtgacc   1740
gtgagcggcc gcaaccagca caccctggac gtgatgcagg cccacaagga caacatcgtg   1800
ggcgccctgc tgcgcgccgc cacctactac ttcagcgacc tggagatcgc cgtgacccac   1860
accggcaagc tgacctgggt gcccaacggc gcccccgtga gcgccctgaa caccaccacc   1920
aaccccaccg cctaccacaa gggccccgtg accgcctgg ccctgcccta caccgccccc   1980
caccgcgtgc tggccaccgc ctacaccggc accaccacct acaccgccag cgcccgcggc   2040
gacctggccc acctgaccac cacccacgcc cgccacctgc caccagctt caacttcggc   2100
gccgtgaagg ccgagaccat caccgagctg ctggtgcgca tgaagcgcgc cgagctg      2157
```

<210> SEQ ID NO 85
<211> LENGTH: 719
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 85

Met Leu Asn Glu Gly Trp Lys Ala Ser Val Gln Arg Lys Leu Lys Gly

```
1               5                   10                  15
Ala Gly Gln Ser Ser Pro Ala Thr Gly Ser Gln Asn Gln Ser Gly Asn
                20                  25                  30

Thr Gly Ser Ile Ile Asn Asn Tyr Tyr Met Gln Gln Tyr Gln Asn Ser
                35                  40                  45

Met Asp Thr Gln Leu Gly Asp Asn Ala Ile Ser Gly Ser Asn Glu
    50                  55                  60

Gly Ser Thr Asp Thr Thr Ser Thr His Thr Thr Asn Thr Gln Asn Asn
65                  70                  75                  80

Asp Trp Phe Ser Lys Leu Ala Ser Ser Ala Phe Ser Gly Leu Phe Gly
                85                  90                  95

Ala Leu Leu Ala Asp Lys Lys Thr Glu Glu Thr Thr Leu Leu Glu Asp
                100                 105                 110

Arg Ile Leu Thr Thr Arg Asn Gly His Thr Thr Ser Thr Thr Gln Ser
                115                 120                 125

Ser Val Gly Val Thr Phe Gly Tyr Ala Thr Ala Glu Asp Ser Thr Ser
    130                 135                 140

Gly Pro Asn Thr Ser Gly Leu Glu Thr Arg Val His Gln Ala Glu Arg
145                 150                 155                 160

Phe Phe Lys Met Ala Leu Phe Asp Trp Val Pro Ser Gln Asn Phe Gly
                165                 170                 175

His Met His Lys Val Val Leu Pro His Glu Pro Lys Gly Val Tyr Gly
                180                 185                 190

Gly Leu Val Lys Ser Tyr Ala Tyr Met Arg Asn Gly Trp Asp Val Glu
                195                 200                 205

Val Thr Ala Val Gly Asn Gln Phe Asn Gly Gly Cys Leu Leu Val Ala
    210                 215                 220

Leu Val Pro Glu Met Gly Asp Ile Ser Asp Arg Glu Lys Tyr Gln Leu
225                 230                 235                 240

Thr Leu Tyr Pro His Gln Phe Ile Asn Pro Arg Thr Asn Met Thr Ala
                245                 250                 255

His Ile Thr Val Pro Tyr Val Gly Val Asn Arg Tyr Asp Gln Tyr Lys
                260                 265                 270

Gln His Arg Pro Trp Thr Leu Val Val Met Val Val Ala Pro Leu Thr
                275                 280                 285

Thr Asn Thr Ala Gly Ala Gln Gln Ile Lys Val Tyr Ala Asn Ile Ala
    290                 295                 300

Pro Thr Asn Val His Val Ala Gly Glu Leu Pro Ser Lys Glu Gly Ile
305                 310                 315                 320

Phe Pro Val Ala Cys Ser Asp Gly Tyr Gly Asn Met Val Thr Thr Asp
                325                 330                 335

Pro Lys Thr Ala Asp Pro Val Tyr Gly Lys Val Tyr Asn Pro Pro Arg
                340                 345                 350

Thr Ala Leu Pro Gly Arg Phe Thr Asn Tyr Leu Asp Val Ala Glu Ala
                355                 360                 365

Cys Pro Thr Phe Leu Met Phe Glu Asn Val Pro Tyr Val Ser Thr Arg
    370                 375                 380

Thr Asp Gly Gln Arg Leu Leu Ala Lys Phe Asp Val Ser Leu Ala Ala
385                 390                 395                 400

Lys His Met Ser Asn Thr Tyr Leu Ala Gly Leu Ala Gln Tyr Tyr Thr
                405                 410                 415

Gln Tyr Thr Gly Thr Ile Asn Leu His Phe Met Phe Thr Gly Pro Thr
                420                 425                 430
```

Asp Ala Lys Ala Arg Tyr Met Val Ala Tyr Val Pro Pro Gly Met Asp
        435                 440                 445

Ala Pro Asp Asn Pro Glu Glu Ala Ala His Cys Ile His Ala Glu Trp
    450                 455                 460

Asp Thr Gly Leu Asn Ser Lys Phe Thr Phe Ser Ile Pro Tyr Ile Ser
465                 470                 475                 480

Ala Ala Asp Tyr Ala Tyr Thr Ala Ser His Lys Ala Glu Thr Thr Cys
                485                 490                 495

Val Gln Gly Trp Val Cys Val Tyr Gln Ile Thr His Gly Lys Ala Asp
            500                 505                 510

Ala Asp Ala Leu Val Val Ser Ala Ser Ala Gly Lys Asp Phe Glu Leu
        515                 520                 525

Arg Leu Pro Val Asp Ala Arg Lys Gln Thr Thr Thr Thr Gly Glu Ser
    530                 535                 540

Ala Asp Pro Val Thr Thr Thr Val Glu Asn Tyr Gly Gly Glu Thr Gln
545                 550                 555                 560

Val Gln Arg Arg His His Thr Asp Val Ala Phe Val Leu Asp Arg Phe
                565                 570                 575

Val Glu Val Thr Val Ser Gly Arg Asn Gln His Thr Leu Asp Val Met
            580                 585                 590

Gln Ala His Lys Asp Asn Ile Val Gly Ala Leu Leu Arg Ala Ala Thr
        595                 600                 605

Tyr Tyr Phe Ser Asp Leu Glu Ile Ala Val Thr His Thr Gly Lys Leu
    610                 615                 620

Thr Trp Val Pro Asn Gly Ala Pro Val Ser Ala Leu Asn Asn Thr Thr
625                 630                 635                 640

Asn Pro Thr Ala Tyr His Lys Gly Pro Val Thr Arg Leu Ala Leu Pro
                645                 650                 655

Tyr Thr Ala Pro His Arg Val Leu Ala Thr Ala Tyr Thr Gly Thr Thr
            660                 665                 670

Thr Tyr Thr Ala Ser Ala Arg Gly Asp Leu Ala His Leu Thr Thr Thr
        675                 680                 685

His Ala Arg His Leu Pro Thr Ser Phe Asn Phe Gly Ala Val Lys Ala
    690                 695                 700

Glu Thr Ile Thr Glu Leu Leu Val Arg Met Lys Arg Ala Glu Leu
705                 710                 715

<210> SEQ ID NO 86
<211> LENGTH: 2169
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 86
atgctgaacg gcgagtggaa ggccaaggtg cagaagcgcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180 ggcagcaacg agggcagcac cgacaccacc agcacccaca ccaccaacac ccagaacaac     240
gactggttca gcaagctggc cagcagcgcc ttcagcggcc tgttcggcgc cctgctggcc     300
gacaagaaga ccgaggagac caccctgctg gaggaccgca tcctgaccac ccgcaacggc     360
cacaccacca gcaccaccca gagcagcgtg ggcgtgacct acggctacgc caccgccgag     420

-continued

```
gacttcgtga gcggccccaa caccagcggc ctggagaccc gcgtggtgca ggccgagcgc    480
ttcttcaaga cccacctgtt cgactgggtg accagcgacc ccttcggccg ctgctacctg    540
ctggagctgc ccaccgacca agggcgtgta cggcagcc tgaccgacag ctacgcctac     600
atgcgcaacg gctgggacgt ggaggtgacc gccgtgggca accagttcaa cggcggctgc    660
ctgctggtgg ccatggtgcc cgagctgtgc agcatcgaca agcgcgagct gtaccagctg    720
accctgttcc cccaccagtt catcaacccc gcaccaaca tgaccgccca catcaccgtg    780
cccttcgtgg gcgtgaaccg ctacgaccag tacaaggtgc acaagccctg accctggtg    840
gtgatggtgg tggcccccct gaccgtgaac accgagggcg cccccagat caaggtgtac    900
gccaacatcg cccccaccaa cgtgcacgtg gccggcgagt tccccagcaa ggagggcatc    960
ttccccgtgg cctgcagcga cggctacggc ggcctggtga ccaccgaccc caagaccgcc    1020
gaccccgcct acggcaaggt gttcaacccc cccgcaaca tgctgcccgg ccgcttcacc    1080
aacttcctgg acgtggccga ggcctgcccc accttcctgc acttcgaggg cggcgtgccc    1140
tacgtgacca ccaagaccga cagcgaccgc gtgctggccc agttcgacct gagcctggcc    1200
gccaagcaca tgagcaacac cttcctggcc ggcctggccc agtactacac ccagtacagc    1260
ggcaccatca acctgcactt catgttcacc ggccccaccg acgccaaggc ccgctacatg    1320
atcgcctacg ccccccccgg catggagccc ccaagaccc ccgaggccgc cgcccactgc    1380
atccacgccg agtgggacac cggcctgaac agcaagttca ccttcagcat ccctacctg    1440
agcgccgccg actacgccta caccgccagc gacgccgccg agaccaccaa cgtgcagggc    1500
tgggtgtgcc tgttccagat cacccacggc aaggccgacg gcgacgccct ggtggtgctg    1560
gccagcgccg gcaaggactt cgagctgcgc ctgcccgtgg acgcccgcac ccagaccacc    1620
agcgccggcg agagcgccga ccccgtgacc gccaccgtgg agaactacgg cggcgagacc    1680
caggtgcagc gccgccagca caccgacgtg agcttcatcc tggaccgctt cgtgaaggtg    1740
acccccaagg accagatcaa cgtgctggac ctgatgcaga cccccgccca caccctggtg    1800
ggcgccctgc tgcgcaccgc cacctactac ttcgccgacc tggaggtggc cgtgaagcac    1860
gagggcaacc tgacctgggt gcccaacggc gcccccgaga ccgccctgga caacaccacc    1920
aaccccaccg cctaccacaa ggcccccctg accgcctggc ccctgcccta caccgccccc    1980
caccgcgtgc tggccaccgt gtacaacggc aactgcaagt acggcgagag ccccgtgacc    2040
aacgtgcgcg gcgacctgca ggtgctggcc cagaaggccg cccgcaccct gccaccagc    2100
ttcaactacg gcgccatcaa ggccaccgc gtgaccgagc tgctgtaccg catgaagcgc    2160
gccgagacc                                                           2169
```

<210> SEQ ID NO 87
<211> LENGTH: 723
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 87

```
Met Leu Asn Gly Glu Trp Lys Ala Lys Val Gln Lys Arg Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
```

```
            35                  40                  45
Met Asp Thr Gln Leu Gly Asp Asn Ala Ile Ser Gly Gly Ser Asn Glu
 50                  55                  60

Gly Ser Thr Asp Thr Thr Ser Thr His Thr Thr Asn Thr Gln Asn Asn
 65                  70                  75                  80

Asp Trp Phe Ser Lys Leu Ala Ser Ser Ala Phe Ser Gly Leu Phe Gly
                 85                  90                  95

Ala Leu Leu Ala Asp Lys Lys Thr Glu Glu Thr Thr Leu Leu Glu Asp
                100                 105                 110

Arg Ile Leu Thr Thr Arg Asn Gly His Thr Thr Ser Thr Thr Gln Ser
            115                 120                 125

Ser Val Gly Val Thr Tyr Gly Tyr Ala Thr Ala Glu Asp Phe Val Ser
        130                 135                 140

Gly Pro Asn Thr Ser Gly Leu Glu Thr Arg Val Val Gln Ala Glu Arg
145                 150                 155                 160

Phe Phe Lys Thr His Leu Phe Asp Trp Val Thr Ser Asp Pro Phe Gly
                165                 170                 175

Arg Cys Tyr Leu Leu Glu Leu Pro Thr Asp His Lys Gly Val Tyr Gly
                180                 185                 190

Ser Leu Thr Asp Ser Tyr Ala Tyr Met Arg Asn Gly Trp Asp Val Glu
            195                 200                 205

Val Thr Ala Val Gly Asn Gln Phe Asn Gly Gly Cys Leu Leu Val Ala
        210                 215                 220

Met Val Pro Glu Leu Cys Ser Ile Asp Lys Arg Glu Leu Tyr Gln Leu
225                 230                 235                 240

Thr Leu Phe Pro His Gln Phe Ile Asn Pro Arg Thr Asn Met Thr Ala
                245                 250                 255

His Ile Thr Val Pro Phe Val Gly Val Asn Arg Tyr Asp Gln Tyr Lys
                260                 265                 270

Val His Lys Pro Trp Thr Leu Val Val Met Val Val Ala Pro Leu Thr
            275                 280                 285

Val Asn Thr Glu Gly Ala Pro Gln Ile Lys Val Tyr Ala Asn Ile Ala
        290                 295                 300

Pro Thr Asn Val His Val Ala Gly Glu Phe Pro Ser Lys Glu Gly Ile
305                 310                 315                 320

Phe Pro Val Ala Cys Ser Asp Gly Tyr Gly Gly Leu Val Thr Thr Asp
                325                 330                 335

Pro Lys Thr Ala Asp Pro Ala Tyr Gly Lys Val Phe Asn Pro Pro Arg
                340                 345                 350

Asn Met Leu Pro Gly Arg Phe Thr Asn Phe Leu Asp Val Ala Glu Ala
            355                 360                 365

Cys Pro Thr Phe Leu His Phe Glu Gly Gly Val Pro Tyr Val Thr Thr
        370                 375                 380

Lys Thr Asp Ser Asp Arg Val Leu Ala Gln Phe Asp Leu Ser Leu Ala
385                 390                 395                 400

Ala Lys His Met Ser Asn Thr Phe Leu Ala Gly Leu Ala Gln Tyr Tyr
                405                 410                 415

Thr Gln Tyr Ser Gly Thr Ile Asn Leu His Phe Met Phe Thr Gly Pro
                420                 425                 430

Thr Asp Ala Lys Ala Arg Tyr Met Ile Ala Tyr Ala Pro Pro Gly Met
            435                 440                 445

Glu Pro Pro Lys Thr Pro Glu Ala Ala Ala His Cys Ile His Ala Glu
        450                 455                 460
```

Trp Asp Thr Gly Leu Asn Ser Lys Phe Thr Phe Ser Ile Pro Tyr Leu
465                 470                 475                 480

Ser Ala Ala Asp Tyr Ala Tyr Thr Ala Ser Asp Ala Ala Glu Thr Thr
                485                 490                 495

Asn Val Gln Gly Trp Val Cys Leu Phe Gln Ile Thr His Gly Lys Ala
            500                 505                 510

Asp Gly Asp Ala Leu Val Val Leu Ala Ser Ala Gly Lys Asp Phe Glu
        515                 520                 525

Leu Arg Leu Pro Val Asp Ala Arg Thr Gln Thr Thr Ser Ala Gly Glu
    530                 535                 540

Ser Ala Asp Pro Val Thr Ala Thr Val Glu Asn Tyr Gly Gly Glu Thr
545                 550                 555                 560

Gln Val Gln Arg Arg Gln His Thr Asp Val Ser Phe Ile Leu Asp Arg
                565                 570                 575

Phe Val Lys Val Thr Pro Lys Asp Gln Ile Asn Val Leu Asp Leu Met
            580                 585                 590

Gln Thr Pro Ala His Thr Leu Val Gly Ala Leu Leu Arg Thr Ala Thr
        595                 600                 605

Tyr Tyr Phe Ala Asp Leu Glu Val Ala Val Lys His Glu Gly Asn Leu
    610                 615                 620

Thr Trp Val Pro Asn Gly Ala Pro Glu Thr Ala Leu Asp Asn Thr Thr
625                 630                 635                 640

Asn Pro Thr Ala Tyr His Lys Ala Pro Leu Thr Arg Leu Ala Leu Pro
                645                 650                 655

Tyr Thr Ala Pro His Arg Val Leu Ala Thr Val Tyr Asn Gly Asn Cys
            660                 665                 670

Lys Tyr Gly Glu Ser Pro Val Thr Asn Val Arg Gly Asp Leu Gln Val
        675                 680                 685

Leu Ala Gln Lys Ala Ala Arg Thr Leu Pro Thr Ser Phe Asn Tyr Gly
    690                 695                 700

Ala Ile Lys Ala Thr Arg Val Thr Glu Leu Leu Tyr Arg Met Lys Arg
705                 710                 715                 720

Ala Glu Thr

<210> SEQ ID NO 88
<211> LENGTH: 2196
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 88
atgctggacg tggactggca ggaccgcgcc ggcctgttcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180 ggcagcaacg agggcagcac cgacaccacc agcacccaca ccaacaacac ccagaacaac     240
gactggttca gcaagctggc ccagagcgcc ttcagcggcc tggtgggcgc cctgctggcc     300
gacaagaaga ccgaggagac caccctgctg gaggaccgca tcatgaccac cagccacggc     360
accaccacca gcaccaccca gagcagcgtg ggcgtgacct acggctacgc cctggccgac     420
aagttcctgc ccgccccaa caccaacggc ctggagaccc gcgtggagca ggccgagcgc     480
ttcttcaagc acaagctgtt cgactggacc accgaccagc agttcggcac cacccacgtg     540

```
ctggagctgc caccgacca agggcatc tacggccagc tggtggacag ccacgcctac    600
atccgcaacg gctgggacgt gcaggtgagc gccaccgcca cccagttcaa cggcggctgc    660
ctgctggtgg ccatggtgcc cgagctgtgc aagctggacg accgcgagaa gtaccagctg    720
accctgttcc cccaccagtt cctgaacccc cgcaccaaca ccaccgccca catccaggtg    780
ccctacctgg gcgtggaccg ccacgaccag ggcacccgcc acaaggcctg accctggtg    840
gtgatggtgg tggcccccta caccaacgac cagaccatcg gcagcaccaa ggccgaggtg    900
tacgtgaaca tcgcccccac caacgtgtac gtggccggcg agaagcccgc caagcagggc    960
atcctgcccg tggccgtgag cgacggctac ggcggcttcc agaacaccga ccccaagacc   1020
agcgacccca tctacggcca cgtgtacaac cccgcccgca cctgtaccc cggccgcttc   1080
accaacctgc tggacgtggc cgaggcctgc ccaccctgc tggacttcaa cggcgtgccc   1140
tacgtgcaga cccagaacaa cagcggcagc aaggtgctgg cccgcttcga cctggccttc   1200
ggccacaaga acatgaagaa cacctacatg agcggcctgg cccagtactt cgcccagtac   1260
agcggcaccc tgaacctgca cttcatgtac accggcccca ccaacaacaa ggccaagtac   1320
atggtggcct acatcccccc cggcacccac cccctgcccg agaccccga gatggccagc   1380
cactgctacc acgccgagtg ggacaccggc ctgaacagca ccttcacctt caccgtgccc   1440
tacatcagcg ccgccgacta cgcctacacc tacgccgacg agcccgagca ggccagcgtg   1500
cagggctggg tgggcgtgta ccagatcacc gacacccacg agaaggacgg cgccgtgatc   1560
gtgaccgtga cgccggccc cgacttcgag ttccgcatgc ccatcagccc cagccgccag   1620
accaccagcg ccggcgaggg cgccgacccc gtgaccaccg acgtgagcga gcacggcggc   1680
gacagccgca ccgcccgccg cgcccacacc gacgtggcct tcctgctgga ccgcttcacc   1740
ctggtgggca gacccagga caacaagctg gtgctggacc tgctgaccac caaggagaag   1800
agcctggtgg gcgccctgct gcgcgccgcc acctactact tcagcgacct ggaggtggcc   1860
tgcgtgggca ccaacaagtg ggtgggctgg accccaacg gcagcccgt gaagctgagc   1920
gaggtgggcg acaaccccgt ggtgttcagc cacaacggca ccaccgcttc gccctgccc   1980
tacaccgccc ccaccgcgt gctggccacc gtgtacaacg gcgactgcaa gtacaagccc   2040
accggcaccc cccccgcga aacatccgc ggcgacctgg ccaccctggc cgcccgcatc   2100
gccagcgaga cccacatccc caccaccttc aactacggca tgatctacac cgaggccgag   2160
gtggacgtgt acctgcgcat gaagcgcgcc gagctg                            2196
```

<210> SEQ ID NO 89
<211> LENGTH: 732
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 89

Met Leu Asp Val Asp Trp Gln Asp Arg Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

-continued

```
Gly Ser Thr Asp Thr Thr Ser Thr His Thr Asn Asn Thr Gln Asn Asn
 65                  70                  75                  80

Asp Trp Phe Ser Lys Leu Ala Gln Ser Ala Phe Ser Gly Leu Val Gly
                 85                  90                  95

Ala Leu Leu Ala Asp Lys Lys Thr Glu Glu Thr Thr Leu Leu Glu Asp
            100                 105                 110

Arg Ile Met Thr Thr Ser His Gly Thr Thr Ser Thr Thr Gln Ser
            115                 120                 125

Ser Val Gly Val Thr Tyr Gly Tyr Ala Leu Ala Asp Lys Phe Leu Pro
        130                 135                 140

Gly Pro Asn Thr Asn Gly Leu Glu Thr Arg Val Glu Gln Ala Glu Arg
145                 150                 155                 160

Phe Phe Lys His Lys Leu Phe Asp Trp Thr Thr Asp Gln Gln Phe Gly
                165                 170                 175

Thr Thr His Val Leu Glu Leu Pro Thr Asp His Lys Gly Ile Tyr Gly
            180                 185                 190

Gln Leu Val Asp Ser His Ala Tyr Ile Arg Asn Gly Trp Asp Val Gln
        195                 200                 205

Val Ser Ala Thr Ala Thr Gln Phe Asn Gly Gly Cys Leu Leu Val Ala
210                 215                 220

Met Val Pro Glu Leu Cys Lys Leu Asp Asp Arg Glu Lys Tyr Gln Leu
225                 230                 235                 240

Thr Leu Phe Pro His Gln Phe Leu Asn Pro Arg Thr Asn Thr Thr Ala
                245                 250                 255

His Ile Gln Val Pro Tyr Leu Gly Val Asp Arg His Asp Gln Gly Thr
            260                 265                 270

Arg His Lys Ala Trp Thr Leu Val Val Met Val Val Ala Pro Tyr Thr
        275                 280                 285

Asn Asp Gln Thr Ile Gly Ser Thr Lys Ala Glu Val Tyr Val Asn Ile
290                 295                 300

Ala Pro Thr Asn Val Tyr Val Ala Gly Glu Lys Pro Ala Lys Gln Gly
305                 310                 315                 320

Ile Leu Pro Val Ala Val Ser Asp Gly Tyr Gly Gly Phe Gln Asn Thr
                325                 330                 335

Asp Pro Lys Thr Ser Asp Pro Ile Tyr Gly His Val Tyr Asn Pro Ala
            340                 345                 350

Arg Thr Leu Tyr Pro Gly Arg Phe Thr Asn Leu Leu Asp Val Ala Glu
        355                 360                 365

Ala Cys Pro Thr Leu Leu Asp Phe Asn Gly Val Pro Tyr Val Gln Thr
370                 375                 380

Gln Asn Asn Ser Gly Ser Lys Val Leu Ala Arg Phe Asp Leu Ala Phe
385                 390                 395                 400

Gly His Lys Asn Met Lys Asn Thr Tyr Met Ser Gly Leu Ala Gln Tyr
                405                 410                 415

Phe Ala Gln Tyr Ser Gly Thr Leu Asn Leu His Phe Met Tyr Thr Gly
            420                 425                 430

Pro Thr Asn Asn Lys Ala Lys Tyr Met Val Ala Tyr Ile Pro Pro Gly
        435                 440                 445

Thr His Pro Leu Pro Glu Thr Pro Glu Met Ala Ser His Cys Tyr His
    450                 455                 460

Ala Glu Trp Asp Thr Gly Leu Asn Ser Thr Phe Thr Phe Thr Val Pro
465                 470                 475                 480
```

```
Tyr Ile Ser Ala Ala Asp Tyr Ala Tyr Thr Tyr Ala Asp Glu Pro Glu
                485                 490                 495

Gln Ala Ser Val Gln Gly Trp Val Gly Val Tyr Gln Ile Thr Asp Thr
            500                 505                 510

His Glu Lys Asp Gly Ala Val Ile Val Thr Val Ser Ala Gly Pro Asp
        515                 520                 525

Phe Glu Phe Arg Met Pro Ile Ser Pro Ser Arg Gln Thr Thr Ser Ala
    530                 535                 540

Gly Glu Gly Ala Asp Pro Val Thr Thr Asp Val Ser Glu His Gly Gly
545                 550                 555                 560

Asp Ser Arg Thr Ala Arg Arg Ala His Thr Asp Val Ala Phe Leu Leu
                565                 570                 575

Asp Arg Phe Thr Leu Val Gly Lys Thr Gln Asp Asn Lys Leu Val Leu
            580                 585                 590

Asp Leu Leu Thr Thr Lys Glu Lys Ser Leu Val Gly Ala Leu Leu Arg
        595                 600                 605

Ala Ala Thr Tyr Tyr Phe Ser Asp Leu Glu Val Ala Cys Val Gly Thr
    610                 615                 620

Asn Lys Trp Val Gly Trp Thr Pro Asn Gly Ser Pro Val Lys Leu Ser
625                 630                 635                 640

Glu Val Gly Asp Asn Pro Val Val Phe Ser His Asn Gly Thr Thr Arg
                645                 650                 655

Phe Ala Leu Pro Tyr Thr Ala Pro His Arg Val Leu Ala Thr Val Tyr
            660                 665                 670

Asn Gly Asp Cys Lys Tyr Lys Pro Thr Gly Thr Pro Pro Arg Glu Asn
        675                 680                 685

Ile Arg Gly Asp Leu Ala Thr Leu Ala Ala Arg Ile Ala Ser Glu Thr
    690                 695                 700

His Ile Pro Thr Thr Phe Asn Tyr Gly Met Ile Tyr Thr Glu Ala Glu
705                 710                 715                 720

Val Asp Val Tyr Leu Arg Met Lys Arg Ala Glu Leu
                725                 730

<210> SEQ ID NO 90
<211> LENGTH: 2184
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 90
atgctggacg tggactggca ggacaaggcc ggcctgttcc tgcgcggcgc cggccagagc     60
agccccgcca ccggcagcca gaaccagagc ggcaacaccg gcagcatcat caacaactac    120
tacatgcagc agtaccagaa cagcatggac acccagctgg gcgacaacgc catcagcggc    180
ggcagcaacg agggcagcac cgacaccacc agcacccaca ccaacaacac ccagaacaac    240
gactggttca gcaagctggc ccagagcgcc atcagcggcc tgttcggcgc cctgctggcc    300
gacaagaaga ccgaggagac caccctgctg gaggaccgca tcctgaccac ccgccacggc    360
accaccacca gcaccaccca gagcagcgtg ggcatcacct acggctacgc cgacgccgac    420
agcttccgcc ccggccccaa caccagcggc ctggagaccc gcgtggagca ggccgagcgc    480
ttcttcaagg agaagctgtt cgactggacc agcgacaagc ccttcggcac cctgtacgtg    540
ctggagctgc ccaaggacca aagggcatc tacggcagcc tgaccgacgc ctacacctac    600
```

-continued

| | |
|---|---|
| atgcgcaacg gctgggacgt gcaggtgagc gccaccagca cccagttcaa cggcggcagc | 660 |
| ctgctggtgg ccatggtgcc cgagctgtgc agcctgaagg accgcgagga gttccagctg | 720 |
| accctgtacc cccaccagtt catcaacccc cgcaccaaca ccaccgccca catccaggtg | 780 |
| ccctacctgg gcgtgaaccg ccacgaccag ggcaagcgcc accaggcctg gagcctggtg | 840 |
| gtgatggtgc tgaccccccct gaccaccgag gcccagatga acagcggcac cgtggaggtg | 900 |
| tacgccaaca tcgcccccac caacgtgttc gtggccggcg agaagcccgc caagcagggc | 960 |
| atcatccccg tggcctgcgc cgacggctac ggcggcttcc agaacaccga ccccaagacc | 1020 |
| gccgacccca tctacggcta cgtgtacaac cccagccgca acgactgcca cggccgctac | 1080 |
| agcaacctgc tggacgtggc cgaggcctgc cccacctgc tgaacttcga cggcaagccc | 1140 |
| tacgtggtga ccaagaacaa cggcgacaag gtgatggccg ccttcgacgt ggccttcacc | 1200 |
| cacaaggtgc acaagaacac cttcctggcc ggcctggccg actactacac ccagtaccag | 1260 |
| ggcagcctga actaccactt catgtacacc ggccccaccc accacaaggc caagttcatg | 1320 |
| gtggcctaca tcccccccgg catcgagacc gacaagctgc ccaagacccc cgaggacgcc | 1380 |
| gcccactgct accacagcga gtgggacacc ggcctgaaca gccagttcac cttcgccgtg | 1440 |
| ccctacgtga gcgccagcga cttcagctac cccacaccg acacccccgc catggccacc | 1500 |
| accaacggct gggtggccgt gttccaggtg accgacaccc acagcgccga ggccgccgtg | 1560 |
| gtggtgagcg tgagcgccgg ccccgacctg gagttccgct tccccatcga ccccgtgcgc | 1620 |
| cagaccacca gcgccggcga gggcgccgag gtggtgacca ccgacccag cacccacggc | 1680 |
| ggcaaggtga ccgagaagcg ccgcgtgcac accgacgtgg ccttcgtgct ggaccgcttc | 1740 |
| acccacgtgc acaccaacaa gaccaccttc gccgtggacc tgatggacac caaggagaag | 1800 |
| accctggtgg gcgccctgct gcgcgccgcc acctactact tctgcgacct ggagatcgcc | 1860 |
| tgcgtgggcg agcacaagcg cgtgttctgg cagcccaacg gcgcccccg caccacccag | 1920 |
| ctgggcgaca ccccatggt gttcagccac aacaaggtga cccgcttcgc catcccctac | 1980 |
| accgcccccc accgcctgct gagcaccgtg tacaacggcg agtgcgagta caccaagacc | 2040 |
| gtgaccgcca tccgcggcga ccgcgaggtg ctggccgcca gtacagcag cgccaagcac | 2100 |
| accctgccca gcaccttcaa cttcggcttc gtgaccgccg acgagcccgt ggacgtgtac | 2160 |
| taccgcatga agcgcgccga gctg | 2184 |

<210> SEQ ID NO 91
<211> LENGTH: 728
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 91

Met Leu Asp Val Asp Trp Gln Asp Lys Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

```
Asp Trp Phe Ser Lys Leu Ala Gln Ser Ala Ile Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg His Gly Thr Thr Ser Thr Thr Gln Ser
            115                 120                 125

Ser Val Gly Ile Thr Tyr Gly Tyr Ala Asp Ala Asp Ser Phe Arg Pro
        130                 135                 140

Gly Pro Asn Thr Ser Gly Leu Glu Thr Arg Val Glu Gln Ala Glu Arg
145                 150                 155                 160

Phe Phe Lys Glu Lys Leu Phe Asp Trp Thr Ser Asp Lys Pro Phe Gly
                165                 170                 175

Thr Leu Tyr Val Leu Glu Leu Pro Lys Asp His Lys Gly Ile Tyr Gly
                180                 185                 190

Ser Leu Thr Asp Ala Tyr Thr Tyr Met Arg Asn Gly Trp Asp Val Gln
            195                 200                 205

Val Ser Ala Thr Ser Thr Gln Phe Asn Gly Gly Ser Leu Leu Val Ala
        210                 215                 220

Met Val Pro Glu Leu Cys Ser Leu Lys Asp Arg Glu Glu Phe Gln Leu
225                 230                 235                 240

Thr Leu Tyr Pro His Gln Phe Ile Asn Pro Arg Thr Asn Thr Thr Ala
                245                 250                 255

His Ile Gln Val Pro Tyr Leu Gly Val Asn Arg His Asp Gln Gly Lys
            260                 265                 270

Arg His Gln Ala Trp Ser Leu Val Met Val Leu Thr Pro Leu Thr
                275                 280                 285

Thr Glu Ala Gln Met Asn Ser Gly Thr Val Glu Val Tyr Ala Asn Ile
            290                 295                 300

Ala Pro Thr Asn Val Phe Val Ala Gly Glu Lys Pro Ala Lys Gln Gly
305                 310                 315                 320

Ile Ile Pro Val Ala Cys Ala Asp Gly Tyr Gly Gly Phe Gln Asn Thr
                325                 330                 335

Asp Pro Lys Thr Ala Asp Pro Ile Tyr Gly Tyr Val Tyr Asn Pro Ser
            340                 345                 350

Arg Asn Asp Cys His Gly Arg Tyr Ser Asn Leu Leu Asp Val Ala Glu
        355                 360                 365

Ala Cys Pro Thr Leu Leu Asn Phe Asp Gly Lys Pro Tyr Val Val Thr
    370                 375                 380

Lys Asn Asn Gly Asp Lys Val Met Ala Ala Phe Asp Val Ala Phe Thr
385                 390                 395                 400

His Lys Val His Lys Asn Thr Phe Leu Ala Gly Leu Ala Asp Tyr Tyr
                405                 410                 415

Thr Gln Tyr Gln Gly Ser Leu Asn Tyr His Phe Met Tyr Thr Gly Pro
                420                 425                 430

Thr His His Lys Ala Lys Phe Met Val Ala Tyr Ile Pro Pro Gly Ile
            435                 440                 445

Glu Thr Asp Lys Leu Pro Lys Thr Pro Glu Asp Ala Ala His Cys Tyr
        450                 455                 460

His Ser Glu Trp Asp Thr Gly Leu Asn Ser Gln Phe Thr Phe Ala Val
465                 470                 475                 480

Pro Tyr Val Ser Ala Ser Asp Phe Ser Tyr Thr His Thr Asp Thr Pro
                485                 490                 495
```

```
Ala Met Ala Thr Thr Asn Gly Trp Val Ala Val Phe Gln Val Thr Asp
            500                 505                 510

Thr His Ser Ala Glu Ala Val Val Val Ser Val Ser Ala Gly Pro
        515                 520                 525

Asp Leu Glu Phe Arg Phe Pro Ile Asp Pro Val Arg Gln Thr Thr Ser
    530                 535                 540

Ala Gly Glu Gly Ala Glu Val Val Thr Thr Asp Pro Ser Thr His Gly
545                 550                 555                 560

Gly Lys Val Thr Glu Lys Arg Arg Val His Thr Asp Val Ala Phe Val
                565                 570                 575

Leu Asp Arg Phe Thr His Val His Thr Asn Lys Thr Thr Phe Ala Val
            580                 585                 590

Asp Leu Met Asp Thr Lys Glu Lys Thr Leu Val Gly Ala Leu Leu Arg
        595                 600                 605

Ala Ala Thr Tyr Tyr Phe Cys Asp Leu Glu Ile Ala Cys Val Gly Glu
    610                 615                 620

His Lys Arg Val Phe Trp Gln Pro Asn Gly Ala Pro Arg Thr Thr Gln
625                 630                 635                 640

Leu Gly Asp Asn Pro Met Val Phe Ser His Asn Lys Val Thr Arg Phe
                645                 650                 655

Ala Ile Pro Tyr Thr Ala Pro His Arg Leu Leu Ser Thr Val Tyr Asn
            660                 665                 670

Gly Glu Cys Glu Tyr Thr Lys Thr Val Thr Ala Ile Arg Gly Asp Arg
        675                 680                 685

Glu Val Leu Ala Ala Lys Tyr Ser Ser Ala Lys His Thr Leu Pro Ser
    690                 695                 700

Thr Phe Asn Phe Gly Phe Val Thr Ala Asp Glu Pro Val Asp Val Tyr
705                 710                 715                 720

Tyr Arg Met Lys Arg Ala Glu Leu
                725
```

<210> SEQ ID NO 92
<211> LENGTH: 2181
<212> TYPE: DNA
<213> ORGANISM: Artificial Sequence
<220> FEATURE:
<223> OTHER INFORMATION: Description of Artificial Sequence: Synthetic consensus sequence

<400> SEQUENCE: 92

```
atgctggacg tggactggca ggaccgcgcc ggcctgttcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180
ggcagcaacg agggcagcac cgacaccacc agcacccaca ccaacaacac ccagaacaac     240
gactggttca gcaagctggc ccagagcgcc atcagcggcc tgttcggcgc cctgctggcc     300
gacaagaaga ccgaggagac cacccacctg gaggaccgca tcctgaccac ccgccacaac     360
accaccacca gcaccaccca gagcagcgtg ggcgtgacct acggctacgt gagcgccgac     420
cgcttcctgc ccgcccccaa caccagcggc ctggagagcc gcgtggagca ggccgagcgc     480
ttcttcaagg agaagctgtt cacctggacc gccagccagg agtacgccca cgtgcacctg     540
ctggagctgc ccaccgacca aagggcatc tacggcgcca tggtggacag ccacgcctac     600
gtgcgcaacg gctgggacgt gcaggtgacc gccaccagca cccagttcaa cggcggcacc     660
ctgctggtgg ccatggtgcc cgagctgcac agcctggaca cccgcgacgt gagccagctg     720
```

-continued

```
accctgttcc cccaccagtt catcaacccc cgcaccaaca ccaccgccca catcgtggtg    780
ccctacgtgg gcgtgaaccg ccacgaccag gtgcagatgc acaaggcctg gaccctggtg    840
gtggccgtga tggcccccct gaccaccagc agcatgggcc aggacaacgt ggaggtgtac    900
gccaacatcg cccccaccaa cgtgtacgtg gccggcgagc gccccagcaa gagggcatc     960
atccccgtgg cctgcaacga cggctacggc ggcttccaga caccgaccc caagaccgcc    1020
gaccccatct acggcctggt gagcaacccc cccgcaccg ccttcccgg ccgcttcacc     1080
aacctgctgg acgtggccga ggcctgcccc accttcctgg acttcgacgg cgtgccctac    1140
gtgaagacca cccacaacag cggcagcaag atcctgaccc acatcgacct ggccttcggc    1200
cacaagagct tcaagaacac ctacctggcc ggcctggccc agtactacgc ccagtacagc    1260
ggcagcatca acctgcactt catgtacacc ggccccaccc agagcaaggc ccgcttcatg    1320
gtggcctaca tcccccccgg caccaccgtg cccaacaccc ccgagcaggc cgcccactgc    1380
taccacagcg agtgggacac cggcctgaac agcaagttca ccttcaccgt gccctacatg    1440
agcgccgccg acttcgccta cacctactgc gacgagcccg agcaggccag cgcccagggc    1500
tgggtgaccc tgtaccagat caccgacacc cacgaccccg acagcgccgt gctggtgagc    1560
gtgagcgccg cgccgactt cgagctgcgc ctgcccatca ccccgccgc ccagaccacc    1620
agcgccggcg agggcgccga cgtggtgacc accgacgtga ccaccacgg cggcgaggtg    1680
agcgtgcccc gccgccagca caccaacgtg gagttcctgc tggaccgctt cacccacatc    1740
ggcaccatca acgccaccg caccatctgc ctgatggaca ccaaggagca cccctggtg    1800
ggcgccatcc tgcgcagcgc cacctactac ttctgcgacc tggaggtggc cgtgctgggc    1860
aacgccaagt acgccgcctg ggtgcccaac ggctgcccc acaccgaccg cgtggaggac    1920
aaccccgtgg tgcacagcaa gggcagcgtg gtgcgcttcg ccctgcccta caccgccccc    1980
cacggcgtgc tggccaccgt gtacaacggc aactgcaagt acagcaccac ccagcgcgtg    2040
gcccccgcc gcggcgacct gggcgtgctg agccagcgcg tggagaacga gaccacccgc    2100
tgcatccca ccaccttcaa cttcggccgc ctgctgtgcg agagcggcga cgtgtactac    2160
cgcatgaagc gcaccgagct g                                              2181
```

<210> SEQ ID NO 93
<211> LENGTH: 727
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 93

```
Met Leu Asp Val Asp Trp Gln Asp Arg Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Ile Ser Gly Leu Phe Gly
                85                  90                  95
```

```
Ala Leu Leu Ala Asp Lys Lys Thr Glu Glu Thr Thr His Leu Glu Asp
            100                 105                 110

Arg Ile Leu Thr Thr Arg His Asn Thr Thr Thr Ser Thr Thr Gln Ser
            115                 120                 125

Ser Val Gly Val Thr Tyr Gly Tyr Val Ser Ala Asp Arg Phe Leu Pro
    130                 135                 140

Gly Pro Asn Thr Ser Gly Leu Glu Ser Arg Val Glu Gln Ala Glu Arg
145                 150                 155                 160

Phe Phe Lys Glu Lys Leu Phe Thr Trp Thr Ala Ser Gln Glu Tyr Ala
                165                 170                 175

His Val His Leu Leu Glu Leu Pro Thr Asp His Lys Gly Ile Tyr Gly
            180                 185                 190

Ala Met Val Asp Ser His Ala Tyr Val Arg Asn Gly Trp Asp Val Gln
        195                 200                 205

Val Thr Ala Thr Ser Thr Gln Phe Asn Gly Gly Thr Leu Leu Val Ala
    210                 215                 220

Met Val Pro Glu Leu His Ser Leu Asp Thr Arg Asp Val Ser Gln Leu
225                 230                 235                 240

Thr Leu Phe Pro His Gln Phe Ile Asn Pro Arg Thr Asn Thr Thr Ala
                245                 250                 255

His Ile Val Val Pro Tyr Val Gly Val Asn Arg His Asp Gln Val Gln
            260                 265                 270

Met His Lys Ala Trp Thr Leu Val Val Ala Val Met Ala Pro Leu Thr
        275                 280                 285

Thr Ser Ser Met Gly Gln Asp Asn Val Glu Val Tyr Ala Asn Ile Ala
    290                 295                 300

Pro Thr Asn Val Tyr Val Ala Gly Glu Arg Pro Ser Lys Gln Gly Ile
305                 310                 315                 320

Ile Pro Val Ala Cys Asn Asp Gly Tyr Gly Gly Phe Gln Asn Thr Asp
                325                 330                 335

Pro Lys Thr Ala Asp Pro Ile Tyr Gly Leu Val Ser Asn Pro Pro Arg
            340                 345                 350

Thr Ala Phe Pro Gly Arg Phe Thr Asn Leu Leu Asp Val Ala Glu Ala
        355                 360                 365

Cys Pro Thr Phe Leu Asp Phe Asp Gly Val Pro Tyr Val Lys Thr Thr
    370                 375                 380

His Asn Ser Gly Ser Lys Ile Leu Thr His Ile Asp Leu Ala Phe Gly
385                 390                 395                 400

His Lys Ser Phe Lys Asn Thr Tyr Leu Ala Gly Leu Ala Gln Tyr Tyr
                405                 410                 415

Ala Gln Tyr Ser Gly Ser Ile Asn Leu His Phe Met Tyr Thr Gly Pro
            420                 425                 430

Thr Gln Ser Lys Ala Arg Phe Met Val Ala Tyr Ile Pro Pro Gly Thr
        435                 440                 445

Thr Val Pro Asn Thr Pro Glu Gln Ala Ala His Cys Tyr His Ser Glu
    450                 455                 460

Trp Asp Thr Gly Leu Asn Ser Lys Phe Thr Phe Thr Val Pro Tyr Met
465                 470                 475                 480

Ser Ala Ala Asp Phe Ala Tyr Thr Tyr Cys Asp Glu Pro Glu Gln Ala
                485                 490                 495

Ser Ala Gln Gly Trp Val Thr Leu Tyr Gln Ile Thr Asp Thr His Asp
            500                 505                 510
```

| | | | | | | | | | | | |
|---|---|---|---|---|---|---|---|---|---|---|---|
| Pro | Asp | Ser | Ala | Val | Leu | Val | Ser | Val | Ser | Ala | Gly | Ala | Asp | Phe | Glu |
| | | 515 | | | | 520 | | | | 525 | |

Pro Asp Ser Ala Val Leu Val Ser Val Ser Ala Gly Ala Asp Phe Glu
            515                 520                 525

Leu Arg Leu Pro Ile Asn Pro Ala Ala Gln Thr Thr Ser Ala Gly Glu
    530                 535                 540

Gly Ala Asp Val Val Thr Thr Asp Val Thr Thr His Gly Gly Glu Val
545                 550                 555                 560

Ser Val Pro Arg Arg Gln His Thr Asn Val Glu Phe Leu Leu Asp Arg
                565                 570                 575

Phe Thr His Ile Gly Thr Ile Asn Gly His Arg Thr Ile Cys Leu Met
            580                 585                 590

Asp Thr Lys Glu His Thr Leu Val Gly Ala Ile Leu Arg Ser Ala Thr
        595                 600                 605

Tyr Tyr Phe Cys Asp Leu Glu Val Ala Val Leu Gly Asn Ala Lys Tyr
    610                 615                 620

Ala Ala Trp Val Pro Asn Gly Cys Pro His Thr Asp Arg Val Glu Asp
625                 630                 635                 640

Asn Pro Val Val His Ser Lys Gly Ser Val Arg Phe Ala Leu Pro
                645                 650                 655

Tyr Thr Ala Pro His Gly Val Leu Ala Thr Val Tyr Asn Gly Asn Cys
            660                 665                 670

Lys Tyr Ser Thr Thr Gln Arg Val Ala Pro Arg Gly Asp Leu Gly
            675                 680                 685

Val Leu Ser Gln Arg Val Glu Asn Glu Thr Thr Arg Cys Ile Pro Thr
    690                 695                 700

Thr Phe Asn Phe Gly Arg Leu Leu Cys Glu Ser Gly Asp Val Tyr Tyr
705                 710                 715                 720

Arg Met Lys Arg Thr Glu Leu
                725

<210> SEQ ID NO 94
<211> LENGTH: 678
<212> TYPE: DNA
<213> ORGANISM: Influenza virus

<400> SEQUENCE: 94
atggactgga cctggatcct gttcctggtc gccgctgcca ctagggtgca cagcaccacc      60
accaccggcg agagcgccga ccccgtgacc accaccgtgg agaactacgg cggcgagaca     120
cagaccgcca ggcgcctcca caccgacgtg gccttcgtgc tggacagatt cgtgaagctg     180
acccagccca agagcaccca gaccctggac ctgatgcaga tccccagcca caccctcgtg     240
ggcgccctgc tgagaagcgc cacctactac ttcagcgacc tggaagtggc cctggtgcac     300
accgccctg tgacctgggt gcccaacggc gctcccaaga ccgccctgaa caaccacacc     360
aaccccaccg cctaccagaa gcagcccatc accaggctgg ccctgcccta caccgcccct     420
cacagggtgc tgtccaccgt gtacaacggc aagaccacct acggcgagga aagcagcaga     480
agggggcgatc tggccgctct cgccaggcgc gtgaacaaca ggctgcccac ctccttcaac     540
tatggcgccg tcaaggccga caccatcacc gagctgctga tcaggatgaa gagggccgag     600
acatactgcc ccaggcccct gctggccctg gacaccaccc aggacaggcg caagcaggaa     660
atcattgccc ccgagaag                                                   678

<210> SEQ ID NO 95
<211> LENGTH: 229
<212> TYPE: PRT
<213> ORGANISM: Influenza virus

<400> SEQUENCE: 95

Met Asp Trp Thr Trp Ile Leu Phe Leu Val Ala Ala Thr Arg Val
1               5                   10                  15

His Ser Thr Thr Thr Thr Gly Glu Ser Ala Asp Pro Val Thr Thr Thr
            20                  25                  30

Val Glu Asn Tyr Gly Gly Glu Thr Gln Thr Ala Arg Arg Leu His Thr
        35                  40                  45

Asp Val Ala Phe Val Leu Asp Arg Phe Val Lys Leu Thr Gln Pro Lys
    50                  55                  60

Ser Thr Gln Thr Leu Asp Leu Met Gln Ile Pro Ser His Thr Leu Val
65                  70                  75                  80

Gly Ala Leu Leu Arg Ser Ala Thr Tyr Tyr Phe Ser Asp Leu Glu Val
                85                  90                  95

Ala Leu Val His Thr Gly Pro Val Thr Trp Val Pro Asn Gly Ala Pro
                100                 105                 110

Lys Thr Ala Leu Asn Asn His Thr Asn Pro Thr Ala Tyr Gln Lys Gln
            115                 120                 125

Pro Ile Thr Arg Leu Ala Leu Pro Tyr Thr Ala Pro His Arg Val Leu
    130                 135                 140

Ser Thr Val Tyr Asn Gly Lys Thr Thr Tyr Gly Glu Ser Ser Arg
145                 150                 155                 160

Arg Gly Asp Leu Ala Ala Leu Ala Arg Val Asn Asn Arg Leu Pro
                165                 170                 175

Thr Ser Phe Asn Tyr Gly Ala Val Lys Ala Asp Thr Ile Thr Glu Leu
            180                 185                 190

Leu Ile Arg Met Lys Arg Ala Glu Thr Tyr Cys Pro Arg Pro Leu Leu
    195                 200                 205

Ala Leu Asp Thr Thr Gln Asp Arg Arg Lys Gln Glu Ile Ile Ala Pro
    210                 215                 220

Glu Lys Gln Thr Leu
225

<210> SEQ ID NO 96
<211> LENGTH: 742
<212> TYPE: DNA
<213> ORGANISM: Influenza virus

<400> SEQUENCE: 96
atggactgga cctggatcct gttcctggtc gccgctgcca ctagggtgca cagcaccacc    60
tctaccgggg agtccgccga tcctgtgaca gccacagtgg aaaattacgg cggggaaacc   120
caggtgcaga ggcggcagca caccgatgtg tctttcatcc tggaccgctt cgtgaaagtg   180 accccccaagg ccgaccagat caacgtgctg gatctcatgc agattccgc ccatacactc   240 gtcgggctc tgctgcgcac cgccacatac tatttcgccg atctcgaggt ggccgtgaag   300
cacgagggca acctgacatg ggtgccaaat ggcgcccctg aggccgctct ggacaacacc   360
accaatccta cagcctacca caaggccccc ctgaccagac tggctctgcc ttatacagcc   420
ccccaccgcg tgctggccac agtgtataat ggcaactgca gtacggcga gtggccgtc    480 accaacgtgc gcggcgacct ccaggtgctg gcccagaagg ccgccaggac cctgcctacc   540
agctttaact acggggccat caaggccacc agagtgaccg aactgctgta cagaatgaag   600
cgcgccgaaa cctactgccc tagacctctg ctcgccatcc accccagcga ggccaggcac   660
aagcagaaaa ttgtggcccc tgtgaagcag ctgctgtgat gactgcagat atccagcaca   720

```
gtggcggccg ctcgagtcta ga                                              742
```

<210> SEQ ID NO 97
<211> LENGTH: 201
<212> TYPE: PRT
<213> ORGANISM: Influenza virus

<400> SEQUENCE: 97

```
Met Asp Trp Thr Trp Ile Leu Phe Leu Val Ala Ala Thr Arg Val
1               5                   10                  15

His Ser Thr Thr Ser Thr Gly Glu Ser Ala Asp Pro Val Thr Ala Thr
                20                  25                  30

Val Glu Asn Tyr Gly Gly Glu Thr Gln Val Gln Arg Arg Gln His Thr
            35                  40                  45

Asp Val Ser Phe Ile Leu Asp Arg Phe Val Lys Val Thr Pro Lys Ala
        50                  55                  60

Asp Gln Ile Asn Val Leu Asp Leu Met Gln Ile Pro Ala His Thr Leu
65                  70                  75                  80

Val Gly Ala Leu Leu Arg Thr Ala Thr Tyr Tyr Phe Ala Asp Leu Glu
                85                  90                  95

Val Ala Val Lys His Glu Gly Asn Leu Thr Trp Val Pro Asn Gly Ala
            100                 105                 110

Pro Glu Ala Ala Leu Asp Asn Thr Thr Asn Pro Thr Ala Tyr His Lys
        115                 120                 125

Ala Pro Leu Thr Arg Leu Ala Leu Pro Tyr Thr Ala Pro His Arg Val
        130                 135                 140

Leu Ala Thr Val Tyr Asn Gly Asn Cys Lys Tyr Gly Glu Val Ala Val
145                 150                 155                 160

Thr Asn Val Arg Gly Asp Leu Gln Val Leu Ala Gln Lys Ala Ala Arg
                165                 170                 175

Thr Leu Pro Thr Ser Phe Asn Tyr Gly Ala Ile Lys Thr Arg Val
            180                 185                 190

Thr Glu Leu Leu Tyr Arg Met Lys Arg
        195                 200
```

<210> SEQ ID NO 98
<211> LENGTH: 771
<212> TYPE: DNA
<213> ORGANISM: Influenza virus

<400> SEQUENCE: 98

```
atggactgga cctggattct gtttctggtg gccgctgcca caagagtgca ctccaccacc    60
tctgccggcg agtccgccga cccagtgacc accaccgtgg agaactacgg cggcgagaca   120
caggtgcagc gcaggcacca caccgacgtg ggcttcatca tggaccgctt cgtgaagatc   180
ggcaacacct cccccaccca cgtgatcgac ctgatgcaga cccaccagca cggactggtg   240
ggagccctgc tgagagccgc cacctactac ttctccgacc tggaaatcgt ggtgcgccac   300
gacggaaacc tgacatgggt gcccaatggc gcccagagg ccgccctgtc caacaccggc   360
aaccccaccg cctacaacaa ggccccctcc accagactgg ccctgccata ccgcccct    420
cacagggtgc tggccaccgt gtacaacggc accaacaagt actccgccgc ctccggaaga   480
acaagaggcg acctgggcac cgtggccgcc agaatcgccg cccagctgcc cgcctccttc   540
aacttcggcg ccatcaaggc cgacgccatc acgaactgc tggtgcgcat gaagcgcgcc   600
gagctgtact gcccaagacc cctgctggcc gtggaggtgt cctcccagga ccgccacaag   660
```

```
cagaagatca tcgccccagc caagcagctg ctgtacccct acgacgtgcc cgactacgcc      720
tccctgggcg gaccatgatg actcgagtct agagggcccg tttaaacccg c              771
```

<210> SEQ ID NO 99
<211> LENGTH: 231
<212> TYPE: PRT
<213> ORGANISM: Influenza virus

<400> SEQUENCE: 99

```
Met Asp Trp Thr Trp Ile Leu Phe Leu Val Ala Ala Thr Arg Val
1               5                   10                  15

His Ser Thr Thr Ser Ala Gly Glu Ser Ala Asp Pro Val Thr Thr Thr
            20                  25                  30

Val Glu Asn Tyr Gly Gly Glu Thr Gln Val Gln Arg Arg His His Thr
        35                  40                  45

Asp Val Gly Phe Ile Met Asp Arg Phe Val Lys Ile Gly Asn Thr Ser
    50                  55                  60

Pro Thr His Val Ile Asp Leu Met Gln Thr His Gln His Gly Leu Val
65                  70                  75                  80

Gly Ala Leu Leu Arg Ala Ala Thr Tyr Tyr Phe Ser Asp Leu Glu Ile
                85                  90                  95

Val Val Arg His Asp Gly Asn Leu Thr Trp Val Pro Asn Gly Ala Pro
            100                 105                 110

Glu Ala Ala Leu Ser Asn Thr Gly Asn Pro Thr Ala Tyr Asn Lys Ala
        115                 120                 125

Pro Phe Thr Arg Leu Ala Leu Pro Tyr Thr Ala Pro His Arg Val Leu
    130                 135                 140

Ala Thr Val Tyr Asn Gly Thr Asn Lys Tyr Ser Ala Ala Ser Gly Arg
145                 150                 155                 160

Thr Arg Gly Asp Leu Gly Thr Val Ala Ala Arg Ile Ala Ala Gln Leu
                165                 170                 175

Pro Ala Ser Phe Asn Phe Gly Ala Ile Lys Ala Asp Ala Ile His Glu
            180                 185                 190

Leu Leu Val Arg Met Lys Arg Ala Glu Leu Tyr Cys Pro Arg Pro Leu
        195                 200                 205

Leu Ala Val Glu Val Ser Ser Gln Asp Arg His Lys Gln Lys Ile Ile
    210                 215                 220

Ala Pro Ala Lys Gln Leu Leu
225                 230
```

<210> SEQ ID NO 100
<211> LENGTH: 732
<212> TYPE: DNA
<213> ORGANISM: Influenza virus

<400> SEQUENCE: 100

```
atggactgga cctggattct gtttctcgtg gccgctgcca caagagtgca cagcaccacc      60
accaccggcg agtccgccga cccagtgacc accaccgtgg agaactacgg cggcgagaca     120
cagacccagc gcaggcacca cagacgtg gccttcgtgc tggaccgctt cgtgaaggtg       180
caggtgtccg gcaaccagca caccctggac gtgatgcagg tgcacaagga ctccatcgtg     240
ggcgccctgc tgagagccgc cacctactac ttctccgacc tggaaatcgc cgtgacccac     300
accggaaagc tgacctgggt gcccaatggc gcccagtgt ccgccctgga caacaccacc      360 aacccccaccg cctaccacaa gggcccactg accagactgg ccctgccata caccgcccct    420
```

```
cacagagtgc tggccacagc ctacaccggc acaaccgcct actccgcctc cgccagaaga    480
ggcgatctgg cccacctcgc cgctgcccac gccagacacc tgcccaccag cttcaacttc    540
ggcgccgtga aggccgagac aatcaccgag ctgctggtgc gcatgaagcg cgccgagctg    600
tactgcccca gacccgtgct gccagtgcag ccatccggcg acagacacaa gcagcccctg    660
atcgccccag ccaagcagct gctgtacccc tacgacgtgc ccgactacgc ctccctgggc    720
ggaccatgat ga                                                        732
```

```
<210> SEQ ID NO 101
<211> LENGTH: 228
<212> TYPE: PRT
<213> ORGANISM: Influenza virus

<400> SEQUENCE: 101
```

Met Asp Trp Thr Trp Ile Leu Phe Leu Val Ala Ala Thr Arg Val
1               5                   10                  15

His Ser Thr Thr Thr Thr Gly Glu Ser Ala Asp Pro Val Thr Thr Thr
            20                  25                  30

Val Glu Asn Tyr Gly Gly Glu Thr Gln Thr Gln Arg Arg His His Thr
        35                  40                  45

Asp Val Ala Phe Val Leu Asp Arg Phe Val Lys Val Gln Val Ser Gly
    50                  55                  60

Asn Gln His Thr Leu Asp Val Met Gln Val His Lys Asp Ser Ile Val
65                  70                  75                  80

Gly Ala Leu Leu Arg Ala Ala Thr Tyr Tyr Phe Ser Asp Leu Glu Ile
                85                  90                  95

Ala Val Thr His Thr Gly Lys Leu Thr Trp Val Pro Asn Gly Ala Pro
            100                 105                 110

Val Ser Ala Leu Asp Asn Thr Thr Asn Pro Thr Ala Tyr His Lys Gly
        115                 120                 125

Pro Leu Thr Arg Leu Ala Leu Pro Tyr Thr Ala Pro His Arg Val Leu
    130                 135                 140

Ala Thr Ala Tyr Thr Gly Thr Thr Ala Tyr Ser Ala Ser Ala Arg Arg
145                 150                 155                 160

Gly Asp Leu Ala His Leu Ala Ala Ala His Ala Arg His Leu Pro Thr
                165                 170                 175

Ser Phe Asn Phe Gly Ala Val Lys Ala Glu Thr Ile Thr Glu Leu Leu
            180                 185                 190

Val Arg Met Lys Arg Ala Glu Leu Tyr Cys Pro Arg Pro Val Leu Pro
        195                 200                 205

Val Gln Pro Ser Gly Asp Arg His Lys Gln Pro Leu Ile Ala Pro Ala
    210                 215                 220

Lys Gln Leu Leu
225

```
<210> SEQ ID NO 102
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atggactgga cctggattct gtttctcgtg gccgctgcta caagagtgca ctccaccacc    60
tctgccggcg agtccgccga cccagtgacc accaccgtgg agaactacgg cggcgagaca    120
```

```
caggtgcagc gcaggcacca caccgacgtg ggcttcatca tggaccgctt cgtgaagatc      180
ggcaacacct cccccaccca cgtgatcgac ctgatgcaga cccaccagca cggactggtg      240
ggagccctgc tgagagccgc cacctactac ttctccgacc tggaaatcgt ggtgcgccac      300
gacggaaacc tgacctgggt gcccaatggc gctccagagg ccgccctgtc aacaccggc       360 aaccccaccg cctacaacaa ggccccctc accagactgg ccctgccata caccgcccct      420
cacagggtgc tggccaccgt gtacaacggc caacaagt actccgccgc ctccggaaga        480
acaagaggcg acctgggcac cgtggccgcc agaatcgccg cccagctgcc cgcctccttc      540
aacttcggcg ccatcaaggc cgacgccatc cacgaactgc tggtgcgcat gaagcgcgcc      600
gagctgtact gcccaagacc cctgctggcc gtggaggtgt cctcccagga ccgccacaag      660
cagaagatca tcgccccagc caagcagctg ctgcgcggca ggaagagaag atccaccacc      720
accacaggcg aaagcgccga tcccgtgaca caacagtgg aaaattacgg cggggaaacc       780
cagacccagc ggcgccacca cacagatgtg gccttcgtgc tggacagatt cgtgaaggtg      840
caggtgtccg gcaaccagca caccctggac gtgatgcagg tgcacaagga ctccatcgtg      900
ggcgccctgc tgagggccgc cacctactac tttagcgatc tggaaatcgc cgtgacccac      960
accggcaagc tgacatgggt gccaaatggg gcccctgtgt ctgccctgga acaccacc       1020 aacccaacag cctaccacaa agggccactg acacgcctgg ccctgcctta cacagccca      1080 caccgcgtgc tggccacagc ctacaccgga accaccgcct actccgcctc cgccagaaga     1140
ggcgatctgg cccatctggc cgctgcccac gccagacacc tgcccaccag cttcaacttt      1200
ggggccgtga agccgagac aatcaccgag ctgctggtgc ggatgaagag ggccgaactg       1260
tactgtcctc gccccgtgct gccagtgcag ccatccggcg acagacacaa gcagcccctg      1320
atcgcccctg ccaaacagct gctgtacccc tacgacgtgc ccgactacgc ctccctgggc      1380
ggaccatgat gactcgagtc taga                                             1404
```

<210> SEQ ID NO 103
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Met Asp Trp Thr Trp Ile Leu Phe Leu Val Ala Ala Thr Arg Val
1               5                   10                  15

His Ser Thr Thr Ser Ala Gly Glu Ser Ala Asp Pro Val Thr Thr
                20                  25                  30

Val Glu Asn Tyr Gly Gly Glu Thr Gln Val Gln Arg His His Thr
                35                  40                  45

Asp Val Gly Phe Ile Met Asp Arg Phe Val Lys Ile Gly Asn Thr Ser
    50                  55                  60

Pro Thr His Val Ile Asp Leu Met Gln Thr His Gln His Gly Leu Val
65                  70                  75                  80

Gly Ala Leu Leu Arg Ala Ala Thr Tyr Tyr Phe Ser Asp Leu Glu Ile
                85                  90                  95

Val Val Arg His Asp Gly Asn Leu Thr Trp Val Pro Asn Gly Ala Pro
                100                 105                 110

Glu Ala Ala Leu Ser Asn Thr Gly Asn Pro Thr Ala Tyr Asn Lys Ala
            115                 120                 125
```

```
Pro Phe Thr Arg Leu Ala Leu Pro Tyr Thr Ala Pro His Arg Val Leu
        130                 135                 140

Ala Thr Val Tyr Asn Gly Thr Asn Lys Tyr Ser Ala Ala Ser Gly Arg
145                 150                 155                 160

Thr Arg Gly Asp Leu Gly Thr Val Ala Ala Arg Ile Ala Ala Gln Leu
                165                 170                 175

Pro Ala Ser Phe Asn Phe Gly Ala Ile Lys Ala Asp Ala Ile His Glu
            180                 185                 190

Leu Leu Val Arg Met Lys Arg Ala Glu Leu Tyr Cys Pro Arg Pro Leu
        195                 200                 205

Leu Ala Val Glu Val Ser Ser Gln Asp Arg His Lys Gln Lys Ile Ile
    210                 215                 220

Ala Pro Ala Lys Gln Leu Leu Arg Gly Arg Lys Arg Arg Ser Thr Thr
225                 230                 235                 240

Ala Thr Gly Glu Ser Ala Asp Pro Val Thr Thr Val Glu Asn Tyr
                245                 250                 255

Gly Gly Glu Thr Gln Thr Gln Arg Arg His His Thr Asp Val Ala Phe
                260                 265                 270

Val Leu Asp Arg Phe Val Lys Val Gln Val Ser Gly Asn Gln His Thr
            275                 280                 285

Leu Asp Val Met Gln Val His Lys Asp Ser Ile Val Gly Ala Leu Leu
        290                 295                 300

Arg Ala Ala Thr Tyr Tyr Phe Ser Asp Leu Glu Ile Ala Val Thr His
305                 310                 315                 320

Thr Gly Lys Leu Thr Trp Val Pro Asn Gly Ala Pro Val Ser Ala Leu
                325                 330                 335

Asp Asn Thr Thr Asn Pro Thr Ala Tyr His Lys Gly Pro Leu Thr Arg
            340                 345                 350

Leu Ala Leu Pro Tyr Thr Ala Pro His Arg Val Leu Ala Thr Ala Tyr
        355                 360                 365

Thr Gly Thr Thr Ala Tyr Ser Ala Ser Ala Arg Arg Gly Asp Leu Ala
370                 375                 380

His Leu Ala Ala Ala His Ala Arg His Leu Pro Thr Ser Phe Asn Phe
385                 390                 395                 400

Gly Ala Val Lys Ala Glu Thr Ile Thr Glu Leu Leu Val Arg Met Lys
                405                 410                 415

Arg Ala Glu Leu Tyr Cys Pro Arg Pro Val Leu Pro Val Gln Pro Ser
                420                 425                 430

Gly Asp Arg His Lys Gln Pro Leu Ile Ala Pro Ala Lys Gln Leu Leu
                435                 440                 445

<210> SEQ ID NO 104
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
atggactgga cctggatcct gttcctggtc gccgctgcca ctagggtgca cagcaccacc      60
accaccggcg agagcgccga ccccgtgacc accaccgtgg agaactacgg cggcgagaca     120
cagaccgcca ggcgcctcca caccgacgtg gccttcgtgc tggacagatt cgtgaagctg     180
acccagccca agagcaccca gaccctggac ctgatgcaga tccccagcca caccctcgtg     240
```

```
ggcgccctgc tgagaagcgc cacctactac ttcagcgacc tggaagtggc cctggtgcac        300
accggccctg tgacctgggt gcccaacggc gctcccaaga ccgccctgaa caaccacacc        360
aaccccaccg cctaccagaa gcagcccatc accaggctgg ccctgcccta caccgcccct        420
cacagggtgc tgtccaccgt gtacaacggc aagaccacct acggcgagga agcagcagga        480
aggggcgatc tggccgctct cgccaggcgc gtgaacaaca ggctgcccac ctccttcaac        540 tatgcgccg tcaaggccga caccatcacc gagctgctga tcaggatgaa gagggccgag        600
acatactgcc caggcccct gctggccctg acaccaccc aggacaggcg caagcaggaa         660
atcattgccc ccgagaagca gaccctgagg ggcaggaaga ggcgctccac cacctctacc        720
ggggagtccg ccgatcctgt gacagccaca gtggaaaatt acggcgggga acccaggtg        780 cagaggcgga agcacaccga tgtgtctttc atcctggacc gcttcgtgaa agtgaccccc        840
aaggccgacc agatcaacgt gctggatctc atgcagattc ccgcccatac actcgtcggg        900
gctctgctgc gcaccgccac atactatttc gccgatctcg aggtggccgt gaagcacgag        960
ggcaacctga catgggtgcc aaatggcgcc cctgaggccg ctctggacaa caccaccaat       1020
cctacagcct accacaaggc cccctgacc agactggctc tgccttatac agccccccac        1080
cgcgtgctgg ccacagtgta atgggcaac tgcaagtacg gcgaagtggc cgtcaccaac        1140
gtgcgcggcg acctccaggt gctggcccag aaggccgcca ggaccctgcc taccagcttt       1200
aactacgggg ccatcaaggc caccagagtg accgaactgc tgtacagaat gaagcgcgcc       1260
gaaacctact gccctagacc tctgctcgcc atccacccag cgaggccagg cacaagcaga       1320
aaattgtggc ccctgtgaag cagctgctgt                                        1350
```

<210> SEQ ID NO 105
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Asp Trp Thr Trp Ile Leu Phe Leu Val Ala Ala Thr Arg Val
1               5                   10                  15

His Ser Thr Thr Thr Thr Gly Glu Ser Ala Asp Pro Val Thr Thr Thr
            20                  25                  30

Val Glu Asn Tyr Gly Gly Glu Thr Gln Thr Ala Arg Arg Leu His Thr
        35                  40                  45

Asp Val Ala Phe Val Leu Asp Arg Phe Val Lys Leu Thr Gln Pro Lys
    50                  55                  60

Ser Thr Gln Thr Leu Asp Leu Met Gln Ile Pro Ser His Thr Leu Val
65                  70                  75                  80

Gly Ala Leu Leu Arg Ser Ala Thr Tyr Tyr Phe Ser Asp Leu Glu Val
                85                  90                  95

Ala Leu Val His Thr Gly Pro Val Thr Trp Val Pro Asn Gly Ala Pro
            100                 105                 110

Lys Thr Ala Leu Asn Asn His Thr Asn Pro Thr Ala Tyr Trp Val Pro
        115                 120                 125

Asn Gly Ala Pro Lys Thr Ala Leu Asn Asn His Thr Asn Pro Thr Ala
    130                 135                 140

Tyr Gln Lys Gln Pro Ile Thr Arg Leu Ala Leu Pro Tyr Thr Ala Pro
145                 150                 155                 160

-continued

```
His Arg Val Leu Ser Thr Val Tyr Asn Gly Lys Thr Thr Tyr Gly Glu
            165                 170                 175

Glu Ser Ser Arg Arg Gly Asp Leu Ala Ala Leu Ala Arg Arg Val Asn
            180                 185                 190

Asn Arg Leu Pro Thr Ser Phe Asn Tyr Gly Ala Val Lys Ala Asp Thr
            195                 200                 205

Ile Thr Glu Leu Leu Ile Arg Met Lys Arg Ala Glu Thr Tyr Cys Pro
            210                 215                 220

Arg Pro Leu Leu Ala Leu Asp Thr Thr Gln Asp Arg Arg Lys Gln Glu
225                 230                 235                 240

Ile Ile Ala Pro Glu Lys Gln Thr Leu Arg Gly Arg Lys Arg Arg Ser
            245                 250                 255

Thr Thr Ser Thr Gly Glu Ser Ala Asp Pro Val Thr Ala Thr Val Glu
            260                 265                 270

Asn Tyr Gly Gly Glu Thr Gln Val Gln Arg Arg Gln His Thr Asp Val
            275                 280                 285

Ser Phe Ile Leu Asp Arg Phe Val Lys Val Thr Pro Lys Ala Asp Gln
            290                 295                 300

Ile Asn Val Leu Asp Leu Met Gln Ile Pro Ala His Thr Leu Val Gly
305                 310                 315                 320

Ala Leu Leu Arg Thr Ala Thr Tyr Tyr Phe Ala Asp Leu Glu Val Ala
            325                 330                 335

Val Lys His Glu Gly Asn Leu Thr Trp Val Pro Asn Gly Ala Pro Glu
            340                 345                 350

Ala Ala Leu Asp Asn Thr Thr Asn Pro Thr Ala Tyr His Lys Ala Pro
            355                 360                 365

Leu Thr Arg Leu Ala Leu Pro Tyr Thr Ala Pro His Arg Val Leu Ala
            370                 375                 380

Thr Val Tyr Asn Gly Asn Cys Lys Tyr Gly Glu Val Ala Val Thr Asn
385                 390                 395                 400

Val Arg Gly Asp Leu Gln Val Leu Ala Gln Lys Ala Ala Arg Thr Leu
            405                 410                 415

Pro Thr Ser Phe Asn Tyr Gly Ala Ile Lys Ala Thr Arg Val Thr Glu
            420                 425                 430

Leu Leu Tyr Arg Met Lys Arg Ala Glu Thr Tyr Cys Pro Arg Pro Leu
            435                 440                 445

Leu Ala Ile His Pro Ser Glu Ala Arg His Lys Gln Lys Ile Val Ala
            450                 455                 460

Pro Val Lys Gln Leu Leu
465                 470
```

FACILITATOR-DNA COMBINATION VACCINE

CROSS-REFERENCE TO RELATED APPLICATIONS

This application is a U.S. national stage entry of International Patent Application No. PCT/CN2011/001662, filed Nov. 10, 2011, the entire contents of which are fully incorporated herein by reference.

SEQUENCE LISTING

The instant application contains a Sequence Listing which has been submitted in ASCII format and is hereby incorporated by reference in its entirety. Said ASCII copy, created on Sep. 22, 2011, is named VGX0127W.txt.

FIELD OF THE INVENTION

The present invention relates to a vaccine that contains a vaccine facilitator and a DNA encoding an antigenic peptide. The vaccine may further contain the antigenic peptide.

BACKGROUND

Many vaccines rely on the 'predict and produce' approach. For example, influenza vaccines are generated based on the hemagglutinin and neuraminidase sequences of virus strains that are the most likely to spread across the globe during flu season. However, changes in a circulating virus or the emergence of a pandemic strain with major changes in its glycoproteins would render such vaccines ineffective. In addition, the current egg-based influenza vaccine manufacturing technology depends on the ability of the flu strain to replicate in eggs and takes at least six months to manufacture sufficient doses for the seasonal vaccination campaign.

The production capacity for current vaccines is estimated to be lower than what is required to vaccinate the present global population. Furthermore, vaccines, such as DNA vaccines, have long suffered from inefficient transfection of host cells via syringe-based delivery. Accordingly, drawbacks associated with a limited means for increasing vaccine dose production, as well as lack of new technologies for increasing vaccine transfection, have raised concerns among health-care professionals.

It is not known how to increase DNA vaccine transfection. Further, it is not known how to design antigenic epitopes or vaccines for antigen presentation so as to maximize the induction of an appropriate immune-response. Faster and simplified vaccine manufacturing technologies are needed for influenza and non-influenza-related vaccine strategies to be viable solutions in the event of future pandemics. Accordingly, there is a need for better methods of antigen selection and design for antigen-based vaccines, which can efficiently transfect host target cells and are effective against various diseases.

SUMMARY OF THE INVENTION

Provided herein is a vaccine comprising a vaccine facilitator and a DNA encoding an antigenic peptide. Preferably the vaccine facilitator is Na/K pump inhibitor 5-(N-ethyl-N-isopropyl_amiloride (EIPA), benzamil, or amiloride, and more preferably amiloride. The vaccine may also contain the antigenic peptide. The DNA may be a circular plasmid or vector, or it may be a linear expression cassette (LEC). The LEC may not have a phosphate backbone. The vaccine may be electroporated into a subject in need thereof. The antigen may be M2, LACK, HBV, HIV, Tumor Associated Antigen (TAA), neuraminidase, hemagglutinin, or a variant thereof or a consensus thereof, for example. The DNA may comprise a promoter such as a CMV promoter, SV40 early promoter, SV40 later promoter, metallothionein promoter, murine mammary tumor virus promoter, Rous sarcoma virus promoter, or polyhedrin promoter. The LEC may be pcrNP or perM2.

Also provided herein is a vaccination kit comprising the vaccine. The kit may further comprise an electroporation device. The electroporation device may be a minimally-invasive electroporation device.

Also provided herein is a method of vaccination. The method may comprise administering the provided vaccines to a subject in need thereof. The vaccine may be administered via electroporation. The route of electroporation may be intradermal or intramuscular. A minimally invasive electroporation device may be used to electroporate the vaccine.

µg/ml S208-215 for 12 h(A-C) or 10 µg/ml sAg for 24 h(D), then was performed with multi-color intracellular stain. PMA & Ionmycin was added as positive control. A, either IFN-γ, perforin, or granzymeB positive cells in CD8 T cell, were calculated as responsive cells. B, Cytokine expression pattern in responsive CD8 T cells, between +/− amiloride. C, amiloride's dose on IFN-γ+perforin+granzymeB+ cells' proportion. D, IFN-γ+perforin+granzymeB+cells' proportion in response to sAg restimulation. E & F, IFN-γ+ perforin+granzymeB+ in CD8 T cells, cocultured with peritoneal macrophage(E) or spleno-DC(F), then restimulated by S208-215, and stained. n>3.

Figure 7:
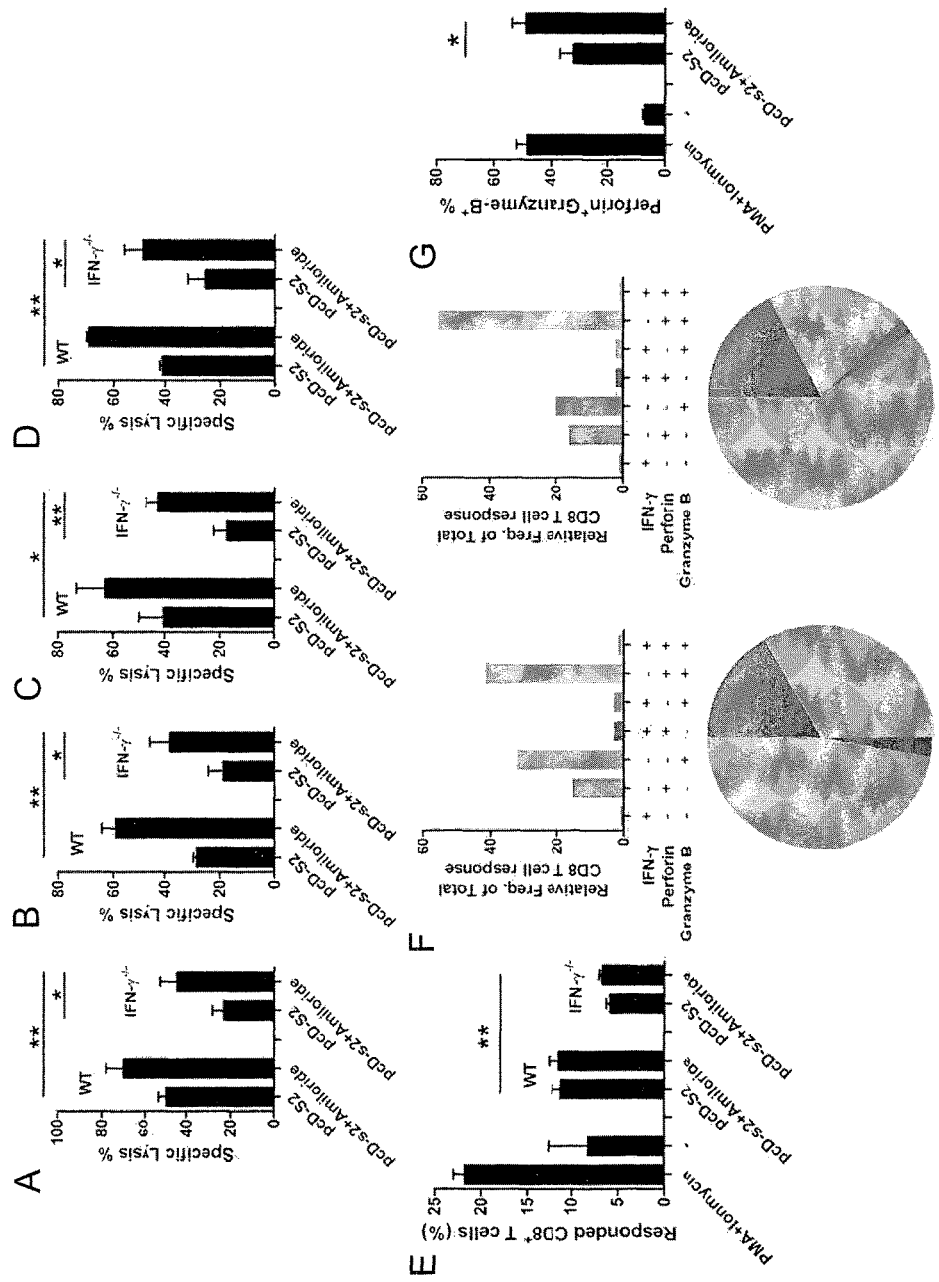

FIG. 7. IFN-γ−/− impaired CTL, but amiloride still increases double positive cells and CTL. Specific lysis was calculated as S208-215 coated naïve spelnocyte (target cell) versus naïve splenocyte (control cell) in vitro(A) and in vivo(B), or Alb1 liver cell (target ell) versus naïve C57 liver cell (control cell) in vitro(C) and in vivo(D), with WT or IFN-γ−/− mice immunized with pcD-S2 +/− amiloride as effecter CTL. Difference was calculated among all groups or between +/− amiloride. n=3. E, Responsive CD8 T cells proportion between WT and IFN-γ−/−. F, Cytokine pattern of IFN-γ−/− mice after S208-215 restimulation. G, Perforin+ granzymeB+ double positive cells proportion after HBsAg restimulation. n=3.

Figure 8:
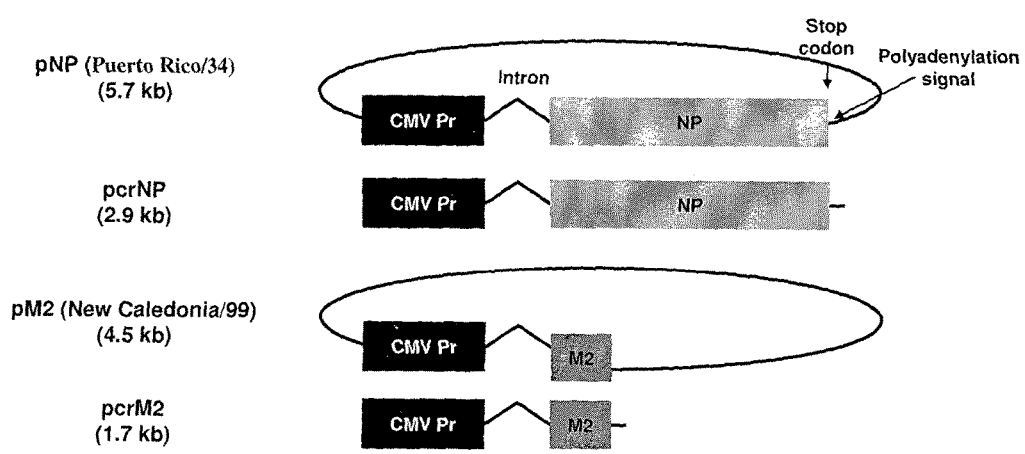

FIG. 8 shows maps of plasmid expression vectors encoding influenza nucleoprotein ("NP") and M2 antigens and the corresponding linear expression cassettes. The linear expression cassette pcrNP or perM2 contain CMV promoter, intron for splicing, full length gene of NP or M2 with stop codon and polyadenylation signal.

DETAILED DESCRIPTION

The inventors have made the surprising discovery that facilitator-based DNA vaccines can efficiently deliver antigen to a subject in need thereof for immune stimulation. A subject's immune system may be efficiently induced against specific antigens by administering a combination of a vaccine facilitator and a DNA that encodes the antigen. Preferably the vaccine facilitator is Na/K pump inhibitor 5-(N-ethyl-N-isopropyl_amiloride (EIPA), benzamil, or amiloride, and more preferably amiloride. The DNA vaccine, which may contain an antigen-encoding circular plasmid or a linear nucleic acid, can elicit antigen-specific antibody responses, which are sustainable for longer periods of time as compared to plasmid-based vaccines, when efficiently delivered to a subject. The vaccine may further contain the antigen, which may be a peptide.

The herein described vaccines may be administered to a subject so as to provide a longer lasting antigen-specific immune response that is well tolerated by the subject population. The present invention is also directed to a number of antigens that can be expressed from the DNA.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

a. Consensus or Consensus Sequence

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes or sertypes of a particular antigen. Synthetic antigens, such as fusion proteins, may be manipulated to consensus sequences (or consensus antigens).

b. Variant

"Variant" as used herein may mean a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Vaccine

Provided herein are vaccines comprised of a vaccine facilitator and a DNA encoding an antigen. Preferably the vaccine facilitator is Na/K pump inhibitor 5-(N-ethyl-N-isopropyl_amiloride (EIPA), benzamil, or amiloride, and more preferably amiloride. Target cells are efficiently transduced by the DNA whereby the vaccine induces antigen-specific immune responses. The vaccine may further comprise the antigen in the form of a peptide.

a. Sodium (Na)/Potassium (K) Pump Inhibitors—

Provided herein is a compound that facilitates DNA entry into cells in vitro and in vivo. The compound may be a sodium (Na)/potassium (K) pump inhibitor. The Na/K pump inhibitor compound may be 3,4 dichlorobenzamil hydrochloride, 3,4,5,6-tetrahydroxxanthone, bafilomycin, bumetanide, concanamycin A, dihydroouabain, esomeprazole, furosemide, lansoprazole, omeprazole, ouabain octahydrate, pantoprazole sodium, prilocaine hydrochloride, sanguinarine chloride, stevioside hydrate, torsemide, 5-(N-ethyl-N-isopropyl_amiloride (EIPA), benzamil, or amiloride. Preferably the vaccine facilitator is 5-(N-ethyl-N-isopropyl_amiloride (EIPA), benzamil, or amiloride, and more preferably amiloride. The compound can be amiloride, which is often used in the management of hypertension and congestive heart failure. Amiloride has the following structure:

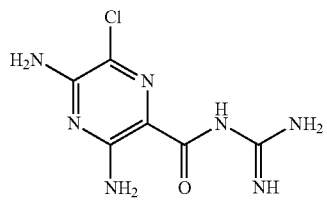 [SMILES: N=C(N)NC(=O)c1nc(Cl)c(N)nc1N]

Sodium/potassium pumps regulate the concentrations of potassium and sodium ions in cells. The sodium-potassium pump moves these two ions in opposite directions across the plasma membrane. This mechanism was investigated by observing the passage of radioactively labeled ions across the plasma membrane of certain cells. The data suggested that the same carrier transports both ions. The carrier is an ATP-ase, which pumps three sodium ions out of the cell for every two potassium ions pumped into the cell. DNA is more efficiently taken up by the cell using Na/K pump inhibitors.

The amiloride has several functional derivatives that are useful for transfecting cells with DNA antigens. The functional derivatives may be formed by modifying the amino moieties either on the pyrimidine ring (at the 3-position) or the tri-amine. The functional derivatives of amiloride may be benzamil or 5-(N-ethyl-N-isopropyl) amiloride (EIPA).

The amiloride may be present in an amount that is capable of facilitating DNA uptake into a cell. Suitably effective increases in DNA uptake by a cell include by more than 5%, preferably by more than 25%, and in particular by more than 50%, as compared to the same vaccine composition without any amiloride.

The antigen can affect a mammal, which can be a human, chimpanzee, dog, cat, horse, cow, mouse, or rat. The antigen can be contained in a protein from a mammal, which can be a human, chimpanzee, dog, cat, horse, cow, pig, sheep, mouse, or rat.

b. Antigen

Provided herein is an antigen, which may be encoded by any DNA and/or RNA sequence. The antigen may be a peptide or protein that causes an immune response. The antigen may trigger the production of an antibody by the immune system. The antibody may then kill or neutralize the antigen that is recognized as a foreign and potentially harmful invader. The antigen may be any molecule or molecular fragment that can be bound by a major histocompatibility complex (MHC) and presented to a T-cell receptor. The antigen may be an immunogen, which may be a molecule that is able to provoke an adaptive immune response if injected on its own.

The antigen may be associated with influenza, human papillomavirus, hepatitis C virus, visceral leishmaniasis, myocarditis, rheumatoid arthritis, thyroiditis, or myasthenia gravis. The antigen may be human telomerase reverse transcriptase antigen (hTERT), prostate specific antigen (PSA), prostate specific membrane antigen (PSMA), six transmembrane epithelial antigen of the prostate (STEAP), prostate stem cell antigen (PSCA), foot and mouth disease antigen, M2, LACK, HBV, neuraminidase, hemagglutinin, or consensus thereof, a fragment thereof, or a variant thereof, for example.

The antigen may affect a mammal, which may be a human, chimpanzee, dog, cat, horse, cow, mouse, or rat. The antigen may be contained in a protein from a mammal, which may be a human, chimpanzee, dog, cat, horse, cow, pig, sheep, mouse, or rat.

Also provided herein is a DNA that encodes the antigen. The DNA may include an encoding sequence that encodes the antigen. The DNA may also include additional sequences that encode linker or tag sequences that are linked to the antigen by a peptide bond.

(a) Influenza

Provided herein are antigens capable of eliciting an immune response in a mammal against one or more influenza serotypes. The antigen may be capable of eliciting an immune response in a mammal against one or more influenza serotypes, including against one or more pandemic strains, such as 209 H1N1 swine originated influenza. The antigen may be capable of eliciting an immune response in a mammal against one or more influenza serotype, including against one or more strains of swine derived human influenza. The antigen can comprise epitopes that make it particularly effective as immunogens against which anti-influenza immune response can be induced.

The antigen may be a peptide, or variant or fragment or consensus thereof, encoded by the influenza virus. The antigen may be a recombinant antigen. The antigen may be M2, neuraminidase, hemagglutinin, or a variant or consensus or fragment thereof. The neuraminidase antigen may be NP 147, which has the amino acid sequence: TYQRTRALV (SEQ ID NO:1). The neuraminidase antigen may be PR/8 IIMR-274), which is a recombinant sequence and may be purchased from Imgenex (San Diego, Calif., USA). M2 antigen may be M2e, which has the amino acid sequence: SLLTEVETPIRNEWGCRCNDSSD (SEQ ID NO:2). The influenza antigen may be from the following table.

| Antigenic Influenza Sequence | SEQ ID NO. |
|---|---|
| DNA H1 | 3 |
| Protein H1 | 4 |
| DNA H2 | 5 |
| Protein H2 | 6 |
| DNA H1 hybrid U2 | 7 |
| Protein H1 hybrid U2 | 8 |
| DNA type B hemagluttinin | 9 |
| Protein type B hemagluttinin | 10 |
| Subtype A consensus Envelope DNA | 11 |
| Subtype A consensus Envelope Protein | 12 |
| Subtype B consensus Envelope DNA | 13 |
| Subtype B consensus Envelope protein | 14 |
| Subtype C consensus Envelope DNA | 15 |
| Subtype C consensus Envelope protein | 16 |
| Subtype D consensus Envelope DNA | 17 |
| Subtype D consensus Envelope protein | 18 |
| Subtype B consensus Nef-Rev DNA | 19 |
| Subtype B consensus Nef-Rev protein | 20 |

| Antigenic Influenza Sequence | SEQ ID NO. |
| --- | --- |
| Gag consensus DNA sequence of subtype A, B, C and D construct | 21 |
| Gag consensus protein sequence of subtype A, B, C and D construct | 22 |
| Subtype A consensus Envelope protein sequence | 23 |
| Subtype B consensus Envelope protein sequence | 24 |
| Subtype C consensus Envelope protein sequence | 25 |
| Subtype D consensus Envelope protein sequence | 26 |
| Subtype B consensus Nef-Rev protein sequence | 27 |
| Gag consensus protein sequence of subtype A, B, C and D | 28 |
| Influenza H5N1 HA consensus DNA sequence | 29 |
| Influenza H5N1 HA consensus protein sequence | 30 |
| Influenza H1N1&H5N1 NA consensus DNA Sequence | 31 |
| Influenza H1N1&H5N1 NA consensus protein Sequence | 32 |
| Influenza H1N1&H5N1 M1 consensus DNA sequence | 33 |
| Influenza H1N1&H5N1 M1 consensus protein sequence | 34 |
| Influenza H5N1 M2E-NP consensus DNA sequence | 35 |
| Influenza H5N1 M2E-NP consensus protein sequence | 36 |

Any of SEQ ID NOs:3-36 may comprise the IgE leader sequence: Met Asp Trp Thr Trp Ile Leu Phe Leu Val Ala Ala Ala Thr Arg Val His Ser (SEQ ID NO:37).

(b) Human Papillomavirus (HPV)

The antigen may be encoded by a human papillomavirus (HPV) sequence. The nucleic acid and/or peptide/protein sequence may be an isolated or consensus sequence. The HPV antigenic sequence may be from the following table.

| Antigenic HPV Sequence | SEQ ID NO |
|---|---|
| HPV genotype 16 E6-E7 DNA sequence | 38 |
| HPV genotype 16 E6-E7 protein sequence | 39 |
| HPV E6 immunodominant epitope protein sequence | 40 |
| HPV E7 immunodominant epitope protein sequence | 41 |
| HPV E6 consensus protein sequence | 42 |
| HPV E7 consensus protein sequence | 43 |

(c) Hepatitis C Virus

The antigen may be encoded by a hepatitis C virus (HCV) sequence. The nucleic acid and/or peptide/protein sequence may be an isolated or consensus sequence. The HCV antigenic sequence may be from the following table.

| Antigenic HCV Sequence | SEQ ID NO. |
|---|---|
| HCV genotype 1a and 1b consensus E1-E2 DNA sequence | 44 |
| HCV genotype 1a and 1b consensus E1-E2 protein sequence | 45 |
| HCV E1 consensus protein sequence | 46 |
| HCV E2 consensus protein sequence | 47 |

(d) Other Antigens

The antigen may also be an antigen as disclosed in U.S. Patent Application Publication No. 20100143401, the contents of which are incorporated herein by reference. Other antigens may include the LACK antigen (Leishmania analogue of the receptors of activated C kinase) (36 kDa), which is highly conserved among Leishmania species and expressed by both the promastigote and amastigote forms of the parasite. Still other antigens may include human telomerase reverse transcriptase antigen (hTERT), Prostate specific antigen (PSA), prostate specific membrane antigen (PSMA), Six Transmembrane Epithelial Antigen of the Prostate (STEAP), prostate stem cell antigen (PSCA), and/or foot and mouth disease antigen.

| Antigenic Sequence | SEQ ID NO. |
|---|---|
| hTERT nucleic acid | 48 |
| hTERT amino acid sequence | 49 |
| PSA antigen 1 nucleic acid | 50 |
| PSA antigen 1 amino acid sequence | 51 |
| PSA antigen 2 nucleic acid | 52 |
| PSA antigen 2 amino acid | 53 |
| PSMA antigen 1 nucleic acid sequence | 54 |
| PSMA antigen 1 amino acid sequence | 55 |
| PSMA anitgen 2 DNA sequence | 56 |
| PSMA anitgen 2 amino acid sequence | 57 |
| STEAP antigen 1 DNA sequence | 58 |
| STEAP antigen 1 amino acid sequence | 59 |
| STEAP antigen 2 DNA sequence | 60 |
| STEAP antigen 2 amino acid sequence | 61 |
| PSCA antigen DNA sequence | 62 |
| PSCA antigen amino acid sequence | 63 |
| Consensus VP1-VP4 subtype A and consensus C3 DNA sequence | 64 |
| Consensus VP1-VP4 subtype A and consensus C3 amino acid sequence | 65 |
| consensus VP1-VP4 subtype Asia 1 and consensus C3 DNA sequence | 66 |
| consensus VP1-VP4 subtype Asia 1 and consensus C3 amino acid sequence | 67 |
| consensus VP1-VP4 subtype C and consensus C3 DNA sequence | 68 |
| consensus VP1-VP4 subtype C and consensus C3 amino acid sequence | 69 |
| consensus VP1-VP4 subtype O and consensus C3 DNA sequence | 70 |
| consensus VP1-VP4 subtype O and consensus C3 amino acid sequence | 71 |
| consensus VP1-VP4 subtype SAT1 and consensus C3 DNA sequence | 72 |
| consensus VP1-VP4 subtype SAT1 and consensus C3 amino acid sequence | 73 |
| consensus VP1-VP4 subtype SAT2 and consensus C3 DNA sequence | 74 |
| consensus VP1-VP4 subtype SAT2 and consensus C3 amino acid sequence | 75 |
| consensus VP1-VP4 subtype SAT3 and consensus C3 DNA sequence | 76 |

| Antigenic Sequence | SEQ ID NO. |
|---|---|
| consensus VP1-VP4 subtype SAT3 and consensus C3 amino acid sequence | 77 |
| consensus C3 DNA sequence | 78 |
| consensus C3 amino acid sequence | 79 |
| consensus VP1-VP4 subtype A DNA sequence | 80 |
| consensus VP1-VP4 subtype A amino acid sequence | 81 |
| consensus VP1-VP4 subtype Asia1 DNA sequence | 82 |
| consensus VP1-VP4 subtype Asia1 amino acid sequence | 83 |
| consensus VP1-VP4 subtype C DNA sequence | 84 |
| consensus VP1-VP4 subtype C amino acid sequence | 85 |
| consensus VP1-VP4 subtype O DNA sequence | 86 |
| consensus VP1-VP4 subtype O amino acid sequence | 87 |
| consensus VP1-VP4 subtype SAT1 DNA sequence | 88 |
| consensus VP1-VP4 subtype SAT1 amino acid sequence | 89 |
| consensus VP1-VP4 subtype SAT2 DNA sequence | 90 |
| consensus VP1-VP4 subtype SAT2 amino acid sequence | 91 |
| consensus VP1-VP4 subtype SAT3 DNA sequence | 92 |
| consensus VP1-VP4 subtype SAT3 amino acid sequence | 93 |
| VP1 Asia subtype DNA sequence | 94 |
| VP1 Asia subtype amino acid sequence | 95 |
| VP1 O subtype DNA sequence | 96 |
| VP1 O subtype amino acid sequence | 97 |
| VP1 A subtype DNA sequence | 98 |
| VP1 A subtype amino acid sequence | 99 |
| VP1 C subtype DNA sequence | 100 |
| VP1 C subtype amino acid sequence | 101 |
| VP1 A subtype + VP1 C subtype DNA sequence | 102 |
| VP1 A subtype + VP1 C subtype amino acid sequence | 103 |
| VP1A subtype + VP1 O subtype DNA sequence | 104 |
| VP1 A subtype + VP1 O subtype amino acid sequence | 105 |

(e) MHC Class II Binding Affinity

The antigen may have a high affinity for MHC Class II (MHC-II). The MHC-II affinity of the antigen may be an $IC_{50}$ of less than or equal to 50 nM. The affinity may also be an $IC_{50}$ of less than or equal to 100, 95, 90, 85, 80, 75, 70, 65, 60, 55, 50, 45, 40, 35, 30, 25, 20, 15, 10, 9, 8, 7, 6, 4, 3, 2, 1, 0.9, 0.8, 0.7, 0.6, 0.5, 0.4, 0.3, 0.2, or 0.1 nM.

The affinity of the antigen for MCH-II may be predicted using a computer algorithm. The algorithm may be MHCPred, as described by Guan P, Doytchinova I A, Zygouri C, Flower D R, MHCPred: bringing a quantitative dimension to the online prediction of MHC binding, Appl Bioinformatics. 2003 2:63-66; Guan P, Doytchinova I A, Zygouri C, Flower D R, MHCPred: A server for quantitative prediction of peptide-MHC binding, Nucleic Acids Res. 2003 31:3621-3624; and Hattotuwagama C K, Guan P, Doytchinova I A, Zygouri C, Flower D R, Quantitative online prediction of peptide binding to the major histocompatibility complex, J Mol Graph Model. 2004 22:195-207, the contents of which are incorporated herein by reference. The algorithm may also be NN-align or SMM-align, as described by Nielsen M and Lund O, NN-align, A neural network-based alignment algorithm for MHC class II peptide binding prediction, BMC Bioinformatics. 2009; 10:296; and Nielsen M, Lundegaard C, Lund O, Prediction of MHC class II binding affinity using SMM-align, a novel stabilization matrix alignment method, BMC Bioinformatics. 2007; 8:238, the contents of which are incorporated herein by reference.

c. Vectors

Further provided herein is a vector, which may include the DNA. The vector can be capable of expressing the antigen. The vector may be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector may be a circular plasmid or a linear nucleic acid. The circular plasmid and linear nucleic acid are capable of directing expression of a particular nucleotide sequence in an appropriate subject cell. The vector may have a promoter operably linked to the antigen-encoding nucleotide sequence, which may be operably linked to termination signals. The vector may also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

(2) Circular or Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing the DNA and enabling a cell to translate the sequence to a antigen that is recognized by the immune system. The vector can be combined with antigen at a mass ratio of between 5:1 and 1:5, or of between 1:1 and 2:1.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid may be pNP (Puerto Rico/34) or pM2 (New Caledonia/99). See FIG. 8. The plasmid may be pVAX, pcDNA3.0, or provax, or any other expression vector capable of expressing the DNA and enabling a cell to translate the sequence to a antigen that is recognized by the immune system.

The LEC may be perM2. The LEC may be pcrNP. pcrNP and pcrMR may be derived from pNP (Puerto Rico/34) and pM2 (New Caledonia/99), respectively. The LEC may be combined with antigen at a mass ratio of between 5:1 and 1:5, or of between 1:1 to 2:1.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise other components such as a transfection facilitating agent, a pharmaceutically acceptable excipient, an adjuvant. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent may be a polyanion, polycation, including poly-L-glutamate (LGS), or lipid. The transfection facilitating agent may be poly-L-glutamate. The poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions. Method of Vaccination Provided herein is a method of vaccinating a subject. The method uses electroporation as a mechanism to deliver the vaccine. The electroporation may be carried out via a minimally invasive device.

e. Minimally Invasive Electroporation Device

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (preferably automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. No. 6,520,950; U.S. Pat. No. 7,171,264; U.S. Pat. No. 6,208,893; U.S. Pat. No. 6,009,347; U.S. Pat. No. 6,120,493; U.S. Pat. No. 7,245,963; U.S. Pat. No. 7,328,064; and U.S. Pat. No. 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, preferably set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

(1) Elgen 1000 System

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (preferably automatically) inject fluid, preferably the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but will preferably be muscle tissue.

Preferably the apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus preferably includes means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. Preferably therefore, the fluid delivery means comprise piston driving means adapted to inject fluid at a controlled rate. The piston driving means could for example be activated by a servo motor. Preferably however, the piston driving means are actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it preferably further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

3. Kit

Provided herein is a kit, which may be used for vaccinating a subject. The kit may comprise a vaccine and a MID. The kit may optionally further comprise an antigenic peptide. The kit can further comprise instructions for using the kit and conducting the analysis, monitoring, or treatment.

The kit may also comprise one or more containers, such as vials or bottles, with each container containing a separate reagent. The kit may further comprise written instructions, which may describe how to perform or interpret an analysis, monitoring, treatment, or method described herein.

The present invention has multiple aspects, illustrated by the following non-limiting examples.

EXAMPLES

Example 1

Materials and Methods

The following is a description of the materials and methods used in the below-identified Examples 2-6.

With respect to animals, cell lines and reagents, adult female C57BL/6 mice (8-10 week of age) were from Beijing Vital Laboratory Animal Technology Company, Ltd. (Beijing, China) and kept in SPF condition. HBV sAg transgenic mice Alb1-HBV and IFN-γ-/- mice (B6.129S7-Ifngtm1Ts/J) were purchased from Jackson Lab (Jax, USA). All animal experiments were approved by the Committee of Experiment Animals of China Agricultural University. RAW264.7, JAWSII and DC2.4 were purchase from ATCC (VA, USA). Lipofactamine™ 2000 was purchased from Invitrogen (CA, USA). HBV sAg was purchased from NCPC Ltd. (Hebei, China). S208-215 peptide was synthesized by Scipeptide Ltd. (Shanghai, China). pcD-S2 was cloned and reserved in lab [46]. All antibodies for DC maturation (anti-CD40-PE, anti-CD80-PE, anti-CD83-PE, anti-CD86-PE, anti-MHC I-PE, anti-MHC II-PE), cell subset identification (anti-CD11c-FITC, anti-CD11b-FITC, anti-B220-PE, anti-CD3-FITC) and multi-color flow cytometry (anti-CD3-APC-Cy7, anti-CD8-FITC, anti-IFN-γ-PerCP-Cy5.5, anti-perforin-PE and anti-granzymeB-PE-Cy7) were purchased from eBioscience (CA, USA). Flexset kits for IL-6, TNF, IL-1β and IFN-γ were purchased from BD Biosciences (USA).

With respect to cell culture and inhibiter treatment, RAW264.7 and DC2.4 were cultured in DMEM/10% FCS, and JAWSII was cultured in DMEM/10% FCS with GMCSF (1000 U/ml, Peprotech, USA). Amiloride (Sigma-Aldrich, USA) was prepared as 10 mM solution and was diluted to 1 mM, 100 uM, 10 uM in DMEM medium before treatment. After culture medium was removed, cells were treated with amiloride, MβCD (5 mM, Sigma) or Fillipin (10 ng/ml, sigma) at 37° C. for 1 h. LPS (10 ng/ml, sigma) or 10 ng/ml DNA in DMEM was added at 37° C. for 0.5 h, after wash, culture medium was added and cells were cultured.

Peritoneal macrophage was prepared from peritoneal cavity with 10 ml PBS wash, routinely with ~50-70% F4/80 purity. Spleen dendritic cell was prepared from plate-adhesive cells and purified with Miltenyi DC purification kit (Miltenyi Biotec, Gladbach, Germany). Cells were treated and cultured 3 days for innate response.

With respect to plasmid preparation and fluorescence conjugation, pEGFP (Clontech, USA) and pcD-S2 plasmid were prepared from DH5a culture, purified by EndoFree Plasmid Maxi Kit (Qiagen, Germany) and endotoxin was below 10 EU/mg by LAL test. Cy5 was conjugated to plasmid with Minis Label IT Kit (Minis, USA) as manual instructed.

With respect to DNA Immunization, 20 μg Cy5-pEGFP in PBS was injected into C57/B6 mice right hind footpad +/- amiloride. 4 h later, both inguinal lymph nodes were collected. 20 ug pcD-S2 in PBS was injected into hind footpad +/- amiloride every two weeks for 4 times.

With respect to in vitro and in vivo CTL, in vitro CTL was performed as reported [47]. Briefly, CD8 T cell from immunized mice splenocyte was purified with kit (Miltenyi Biotec, Gladbach, Germany) as effecter cell. Splenocytes from naïve C57BL/6 mice pulsed with 10-6M HBsAg CTL peptide S208-215 [48] and labeled with 30 μM CFSE as target cells. Same naïve splenocytes without peptide pulse was labeled 10 μM CFSE as control. Effecter and target cell was mixed as the ratio of 10:1, 1:1 and 1:10. After 3 days of culture, target cell lysis was analyzed by FACSCalibur (BD Biosciences, USA). Specific lysis was calculated as (1-target cell/control cell)×100%.

In vivo CTL assay was performed as described previously [46] with splenocytes from naïve C57BL/6 mice with S208-215 and labeled with 30 μM CFSE as target cells. Same splenocytes without peptide was labeled 10 μM CFSE as control. The target and control cells were mixed in a 1:1 ratio and i.v. injected into immunized mice at $2\times10^7$ total cells per mouse. 12 h later, splenocyte of injected mice were collected and analyzed.

For Alb1-HBV mice, liver was collected and single cell suspension was prepare. After CFSE label as target cell, mixed 1:1 with control cell, Alb1-HBV liver cell was co-cultured with purified CD8 effecter T cell, or was i.v. transferred to immunized mice.

With respect to multi-color flow cytometry, a multi-color panel was set up with anti-CD3, anti-CD8, anti-IFN-γ, anti-perforin and anti-granzyme B. After restimulation in vitro by sAg for 24 h or S208-215 for 12 h, following monensin block for 6 h, splenocyte was fixed, penetrated and stained. Data was collected with BD Aria and analyzed with Flowjo (Tree Star, Ashland, USA).

With respect to co-cultures, pcD-S2 (10 μg/ml) with or without 100 μM amiloride treat APCs, peritoneal macrophage or spleen dendritic cell, were cultured for 2 days. At day 3, purified CD8 T cell (R&D systems, USA) was added into culture with APC:T ratio of 1:5, 1:2, 1:1. At day 8, cells were collected and restimulated with S208-215 (10 μg/ml). PMA+Ionomycin was added as positive control for restimulation.

Figure 1:
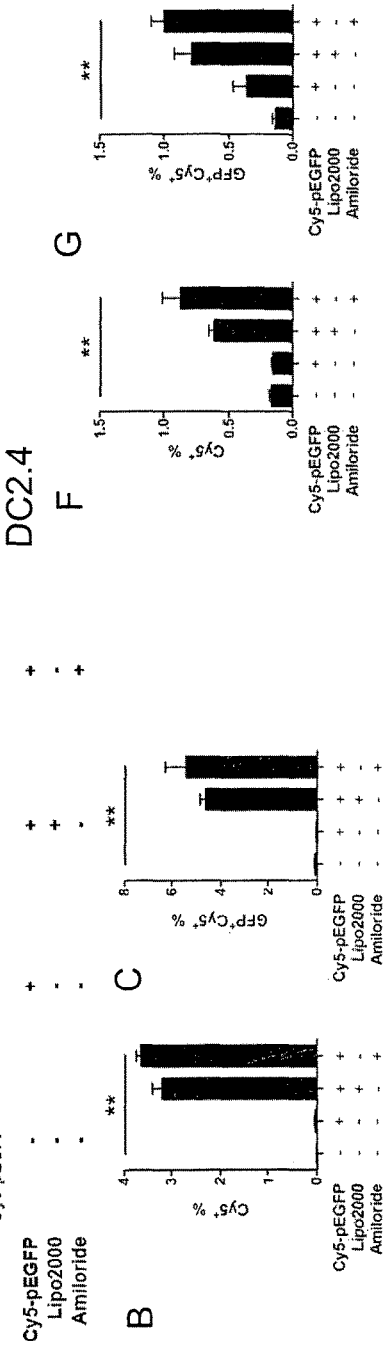
FIG. 1. Amiloride accelerates plasmid entry in vitro. Cy5-pEGFP entry into cell lines with or without 1 mM amiloride was monitored, as 2 h Cy5+% and EGFP+Cy5+% at day 3, on RAW264.7(A, B, C), JAWSII(D, E), and DC2.4(F, G). Lipofactamine™ 2000 (Lipo2000) was added as positive control. Shown is one of three independent experiments with similar results.
Figure 1:
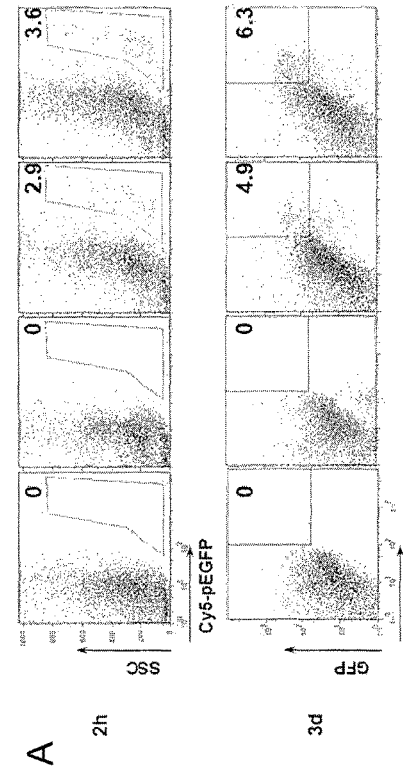
Figure 2:
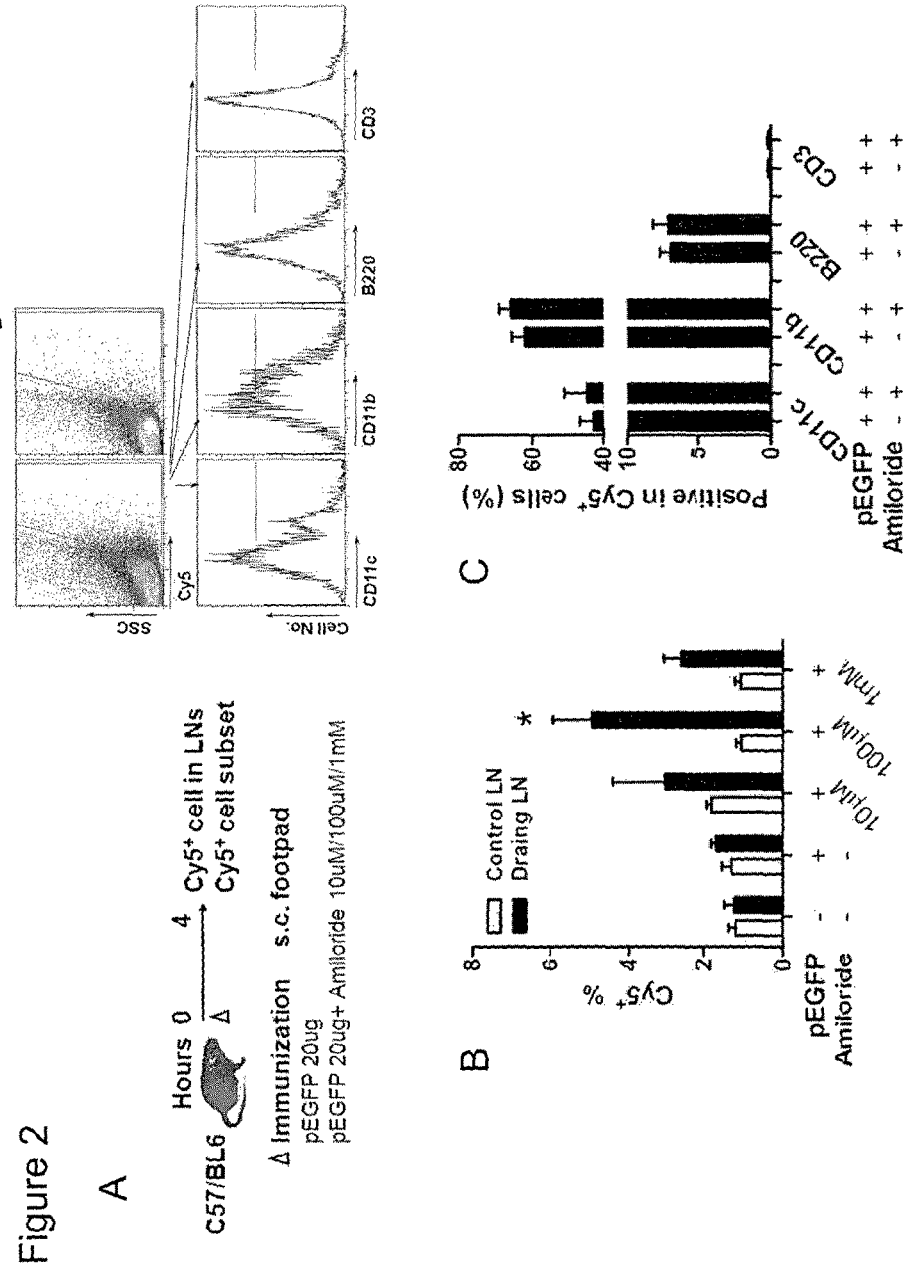
FIG. 2. Amiloride accelerates plasmid entry in vivo. Naïve C57 mice was immunized with Cy5-pEGFP s.c. in hind footpad with or without amiloride. After 4 hours, lymph nodes were collected to test Cy5+ cells' proportion (B) and subtype (C). n=3. * in B, statistical significance among all groups.
Figure 3:
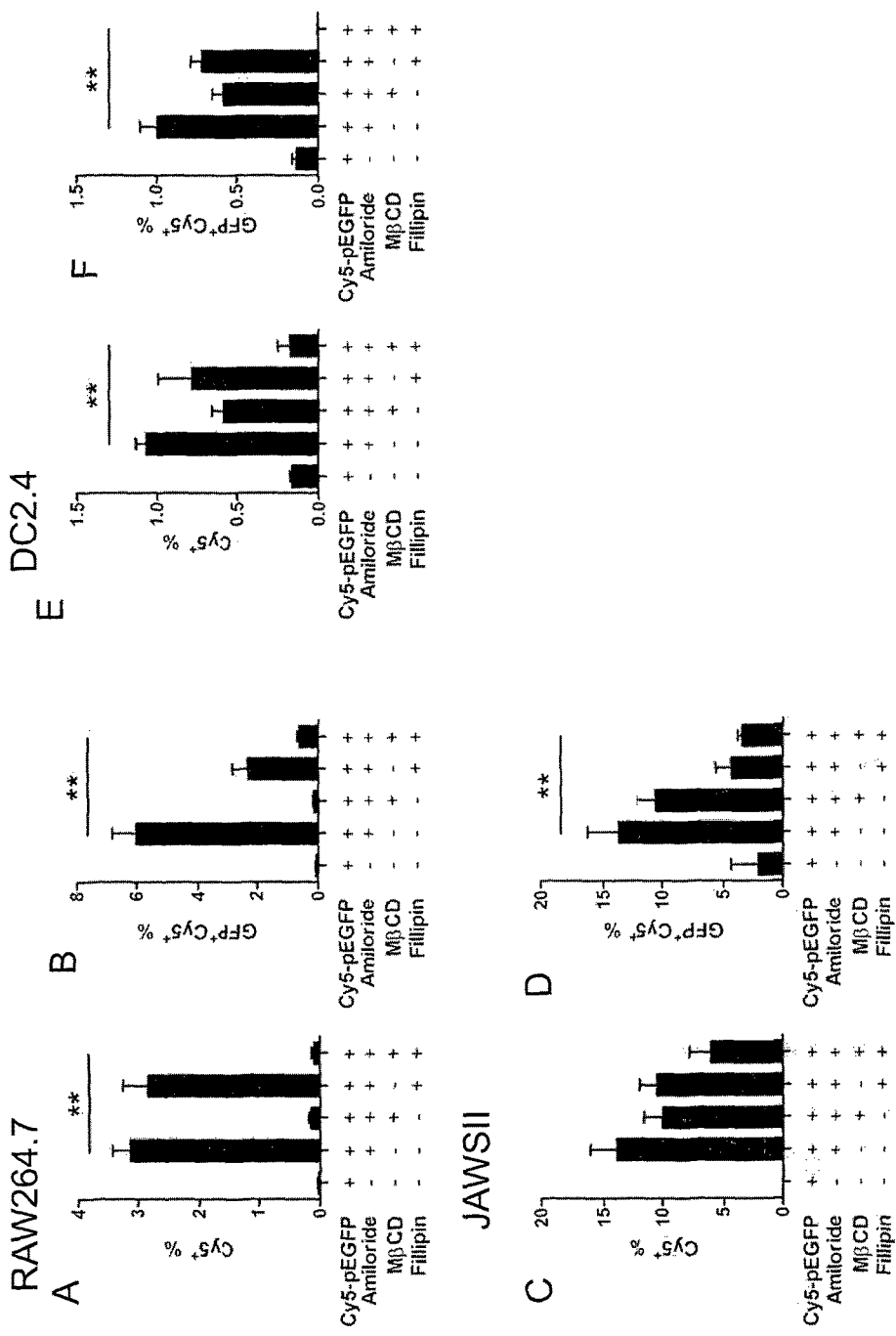
FIG. 3. Amiloride accelerates lipid-raft and caveolae-dependent plasmid entry. Lipid-raft inhibitor, MβCD, or caveolae inhibitor, fillipin was added with amiloride to block endocytosis pathways on cell lines, RAW264.7(A, B), JAWSII(C, D), and DC2.4(E, F). Then Cy5-pEGFP was added for entry in 2 h and expression in 3 days. Shown is one of three independent experiments with similar results.
Figure 4:
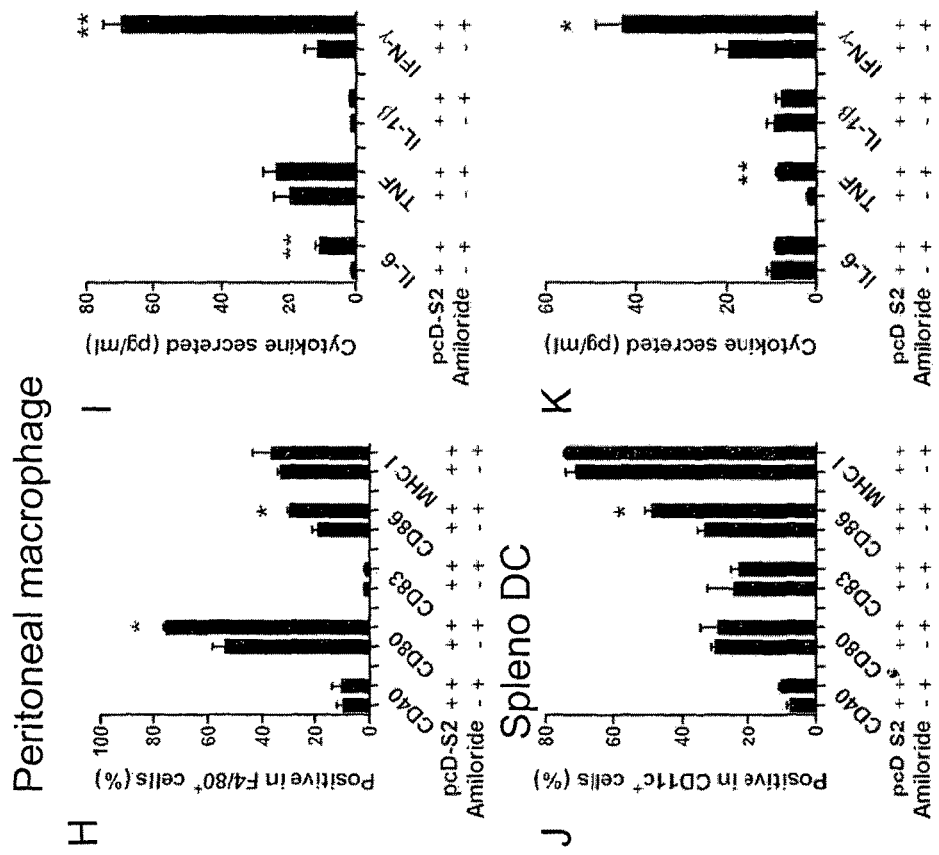
FIG. 4. Amiloride enhances APCs' maturation and innate cytokine secretion. 10 μg/ml pcD-S2 with or without 1 mM amiloride was added in cell culture for stimulation. Surface maturation marker, CD40, CD80, CD83, CD86, MHC I, MHC II and innate cytokines secreted into supernatant, IL-6, TNF-α, IL-β, IFN-γ, were tested at day 3 on RAW264.7(A, B, C), JAWSII(D, E), DC2.4(F, G), peritoneal macrophage (H, I) and spleno-DC(J, K). Shown is one of three independent experiments with similar results. For peritoneal macrophage and spleno-DC, n=3. * and **, statistical significance between +/− amiloride.
Figure 5:
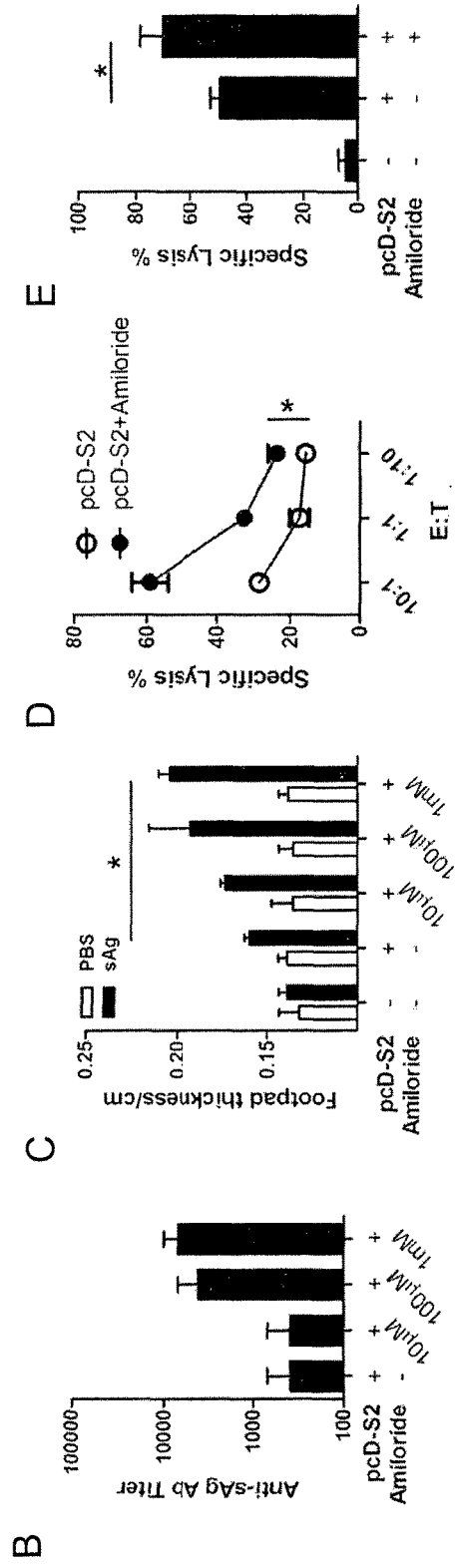
FIG. 5. Amiloride enhances adaptive immunity against HBV S2. A, Immunization routine. B, Anti-S2 IgG antibody titer. C, Delayed hypersensitivity (DTH) response after restimulated with 1 μg sAg s.c. in hind footpad for 24 h. PBS was added as negative control. *, statistical significance among all groups. D & E, HBV S208-215 specific lysis in vitro(D) and in vivo(E), *, statistical significance between +/− amiloride. F & G, HBV Alb1 trangenic mice liver lysis in vitro(F) and in vivo(G). A-G, n=3.
Figure 5:
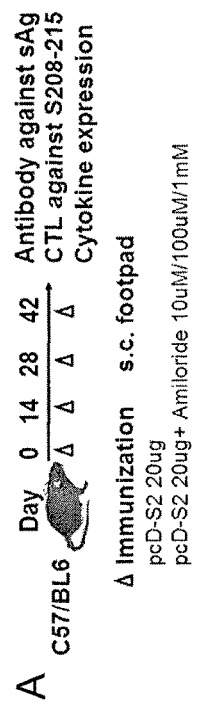
Figure 5:
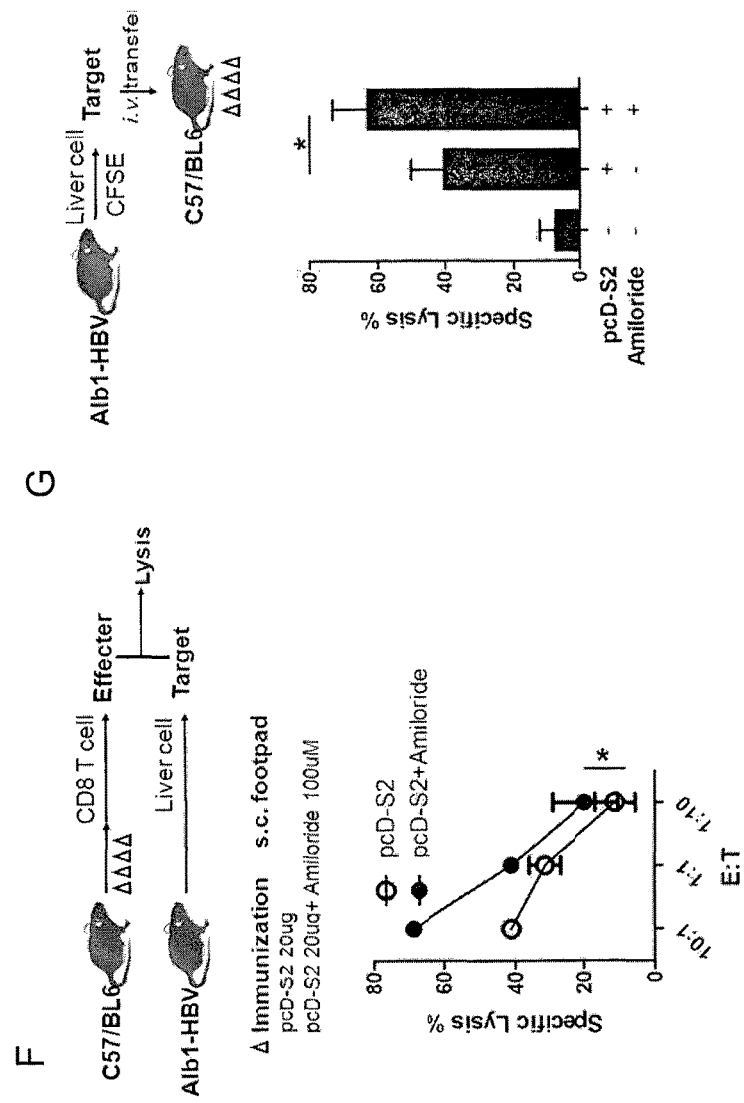
Figure 6:
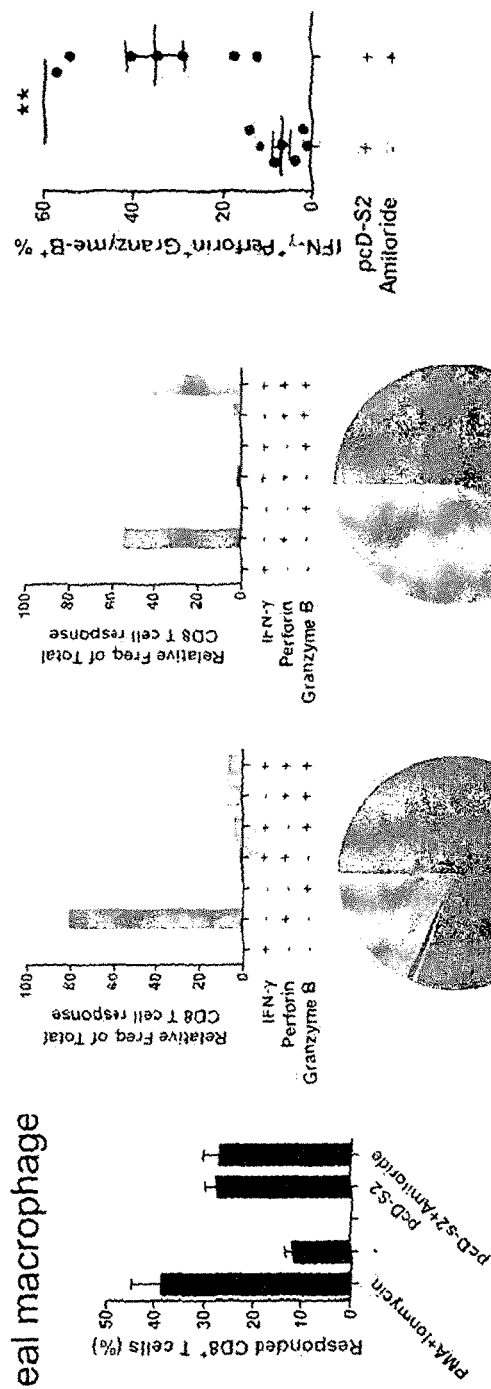
FIG. 6. Amiloride increases IFN-γ+perforin+granzymeB+ CD8 T cells' proportion. Splenocyte from pcD-S2+/− amiloride immunized mice was restimulated in vitro, by 10
Figure 6:
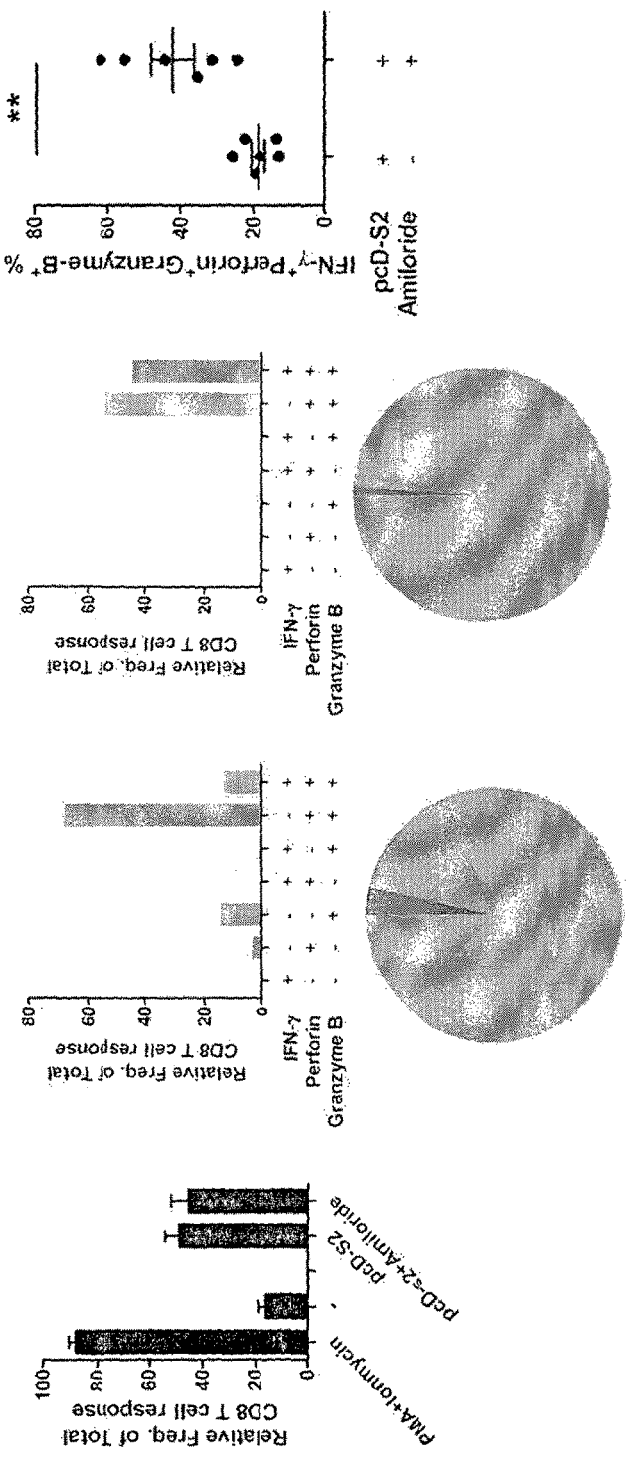

Data were analyzed using the one-tail Student's t-test (FIG. 3, 4E, 4G, 5D-F, 6A-D, 6G), one-way ANOVA for more than 2 groups (FIG. 1, 2B, 4C, 5C, 6A-D, 6E, Supplementary FIG. 1), or two-way ANOVA (FIG. 4D, 4F). Differences were considered to be statistically significant with $p<0.05$ for * and $p<0.01$ for **.

Example 2

Amiloride Accelerates DNA Entry into Antigen Presenting Cells

Amiloride enhancement of DNA entry into a JAWSII DC cell line was initially observed during an endocytosis inhibition assay (data not shown). This phenomenon was repeated on a macrophage cell line (RAW264.7) and dendritic cell lines (JAWSII and DC2.4). These cell lines were pre-treated with 1 mM amiloride for 1 h, whereafter Cy5-labeled pEGFP plasmids were significantly taken up within 2 hrs and expressed significantly higher level of GFP after 3 days culture compared with the un-treated cells. This high level of expression was comparable with that of liposome treated cells. See FIG. 1.

To explore if amiloride would overcome low transfection efficiency in vivo, Cy5-labeled pEFGP plasmid with or without amiloride was injected into hind footpads of C57B/6 mice. After 4 hrs, draining lymph nodes were collected and Cy5+ cells were analyzed by FACS analysis. See FIG. 2A. The inguinal lymph nodes from the un-injected side were also collected as negative controls. Data showed that the percentage of Cy5-plasmid+ cells in lymph nodes (LN) was increased at 10 μM and peaked at 100 μM, but decreased at 1 mM. See FIG. 2B. The majority of Cy5+ cells were CD11c+ and CD11b+, suggesting dendritic cells and macrophages. The other ~10% was B220+, a B cell marker. A few of T cells since a background signal for CD3+ cell. See FIG. 2C.

MβCD, an inhibitor of lipid-raft dependent endocytosis, or fillipin, an inhibitor of caveolae-dependent endocytosis, can affect the amiloride mediated DNA entry and gene expression. The amiloride mediated DNA entry could be completely abolished by MβCD plus fillipin in RAW264.7. See FIGS. 3A and B. Similar inhibitions were also observed in both JAWSII and DC2.4 cell lines. See FIG. 3C-F. These results suggest that amiloride mediated DNA entry is through lipid-raft or caveolae-dependent endocytosis in vivo.

Example 3

Amiloride Enhances Innate Immunity

Hepatitis B virus DNA vaccine (pcD-S2) encoding for HBV surface antigen, HBsAg, which was conjugated with Cy5, was used to test whether amiloride-facilitated DNA entry into antigen presenting cells could positively affect innate immune responses. With the amiloride treatment, pcD-S2 plasmid stimulated higher levels of expression of CD40, CD80 and CD86 on RAW264.7 in vitro, suggesting that amiloride treatment can increase the level of maturation for this macrophage cell. See FIGS. 4A and B. Consistent with macrophage maturation, higher levels of expression of TNF and IFN-γ were induced with amiloride treatment compared to the same cells without amiloride treatment. See FIG. 4C. This similar maturation status was reached in both dendritic cell lines, DC2.4 and JAWSII, although with some differences at expression levels for the pro-inflammatory cytokines. See FIG. 4D-G.

Freshly isolated antigen presenting cells, either from peritoneal macrophages or dendritic cells of the spleen were treated and cytokines were profiled. Both groups showed higher expression of maturation nmarkers and more proinflammatory cytokine secretioins in the cells treated with pcD-S2 plus amiloride than that of pcD-S2 alone. See FIG. 4H-K).

Example 4

Amiloride as CTL Adjuvant for pcD-S2 DNA Vaccine

C57B/6 mice were immunized via their footpads with pcD-S2, which expresses HBV surface antigen (HBsAg), with or without amiloride. See FIG. 5A. The results show that levels of antibody against HBsAg were increased in the amiloride group as compared to pcD-S2 alone in a dose dependent manner. See FIG. 5B. A delayed type hypersensitivity ("DTH) reaction against HBsAg was also increased in pcD-S2 plus amiloride groups compared to that of pcD-S2 alone. See FIG. 5C. Both experiments showed that 1 mM of amiloride was the most effective does for in vivo treatment.

DTH reflects the effectiveness of cell mediated immunity (CMI), of which the CD8+ cytolytic T lymphocyte (CTL) is an important factor. To explore if amiloride could also influence on CTL, CD8+ T cells from immunized mice were purified as effector cells. Naïve C57 splenocytes were treated with HBsAg peptide S208-215 and subsequently labeled with CFSE as target cells were mixed at different ratios. After 3 days in culture, 60 percent of target cells were lysed in the amiloride plus pcD-S2 group, which was significantly more than that of the approximately 30 percent from the pcD-S2 alone group. See FIG. 5D. Further, peptide treated CFSE labeled target cells were transferred into immunized synergeneic mice via i.v. to detect in vivo CTL. Stronger cytotoxicity was observed in pcD-S2 with amiloride as compared to untreated counterparts. See FIG. 5E. This antigen specific killing was further demonstrated with the use of liver cells from Alb1-HBV mice, which are liver-specific HBsAg transgenic mice. These liver cells were used in vitro and in vivo at target cells. See FIGS. 5F and G. A higher level of CTL was achieved in the amiloride plus pcD-S2 group compared to the controls.

Example 5

Amiloride Increases Triple Positive CD8 T Cells

IFN-γ, perforin and granzyme B are the essential components in CTL that contribute o viral clearance. A multifunctional panel, which included IFN-γ, perforin and granzyme B, was used to differentiate cytolytic CD8+ T effectors. Compared with pcD-S2 immunization alone, immunization of amiloride plus pcD-S2 did not increase the frequency of responsiveness to specific antigen of these CD8+ T effectors. See FIG. 6A. However, it did increase the proportion of triple positive CD8+ T effectors within the responded CD8+ population. See FIGS. 6B and C. Furthermore, the triple positive cells could also be observed in HBsAg stimulated CD8 response, suggesting amiloride generally boosts CD8 T cells cytotoxicity against HBV. See FIG. 6D. These results indicate that stronger and more efficient killing of target cells can be obtained via amiloride-enhanced proportions of triple positive CD8 T cells.

To further demonstrate the increase of triple positive CD8 T effectors was due to the subsequent effects of amiloride treated APSc, peritoneal macrophages and spleen dendritic cells were collected and treated with pcD-S2 with or without amiloride, then co-cultured for 5 days with purified CD8 T cells from HBsAg immunized mice. During the co-culture, HBsAg-derived peptide S208-215 (ILSPFLPL; H-2 Kb—restricted) was used to re-stimulate. Proportions of responsive T cells were analyzed. Amiloride significantly increased the percentage of S208-215 specific triple positive CD8 T effectors in macrophages and DCs in the co-culture system. See FIGS. 6E and F.

Example 6

Amiloride Increases Perforin and Granzyme B Proportions in CTL Impaired Background To examine the correlation between multi-functional CD8 T cells and CTL function, IFN-γ knockout mice (IFN-γ$^{-/-}$) were immunized with pcD-S2 with or without amiloride. The result showed that amiloride plus pcD-S2 provided a higher level of CTL than that of pcD-S2 alone in either wild type or the IFN-γ$^{-/-}$ knockout mice. See FIG. 7. A lower CTL response was observed in IFN-γ$^{-/-}$ knockout mice than wild type mice against S208-215 coated splenocyte in vitro or in vivo, or Alb1 liver cell in vitro or in vivo. See FIG. 7A-D. Consistent with the lower CTL response, a lower number of responsive CD8 T cells were exhibited when stimulated with S208-215 in the knockout mice that that of the wild type mice. See FIG. 7E. Notwithstanding the decrease in the level of CTL, a higher frequency of perforin+ granzyme B+ CD8 T cells were evidenced in the amiloride plus pcD-S2 treated group than that of pcD-S2 alone group, against either S208-215 or HBsAg. See FIGS. 7F and G.

We claim:

1. An immunogenic composition capable of eliciting an immune response against a desired cancer or infectious disease associated with M2, LACK, HBV, neuraminidase, hemagglutinin, comprising an immunogenic facilitator and a DNA encoding an antigenic peptide, wherein the immunogenic facilitator is a Na/K pump inhibitor selected from the group consisting of 5-(N-ethyl-N-isopropyl_amiloride (EIPA), benzamil, and amiloride, wherein the antigenic peptide is selected from the group consisting of M2, LACK, HBV, neuraminidase, hemagglutinin, a variant thereof, and a consensus thereof.

2. The composition of claim 1, wherein the immunogenic facilitator is amiloride.

3. The composition of claim 1, further comprising the antigenic peptide.

4. The composition of claim 3, wherein the DNA is a circular plasmid.

5. The composition of claim 3, wherein the DNA is a linear expression cassette.

6. The composition of claim 5, wherein the linear expression cassette is devoid of a phosphate backbone.

7. The composition of claim 4, wherein the composition is capable of being electroporated into a subject in need thereof.

8. The composition of claim 4, wherein the antigenic peptide is selected from the group consisting of M2, LACK, HBV, neuraminidase, hemagglutinin, a variant thereof, and a consensus thereof.

9. The composition of claim 4, wherein the DNA further comprises a promoter selected from the group consisting of CMV, SV40 early promoter, SV40 late promoter, metallothionein promoter, murine mammary tumor virus promoter, Rous sarcoma virus promoter, and polyhedrin promoter.

10. The composition of claim 5, wherein the linear expression cassette is selected from the group consisting of perNP and perM2.

11. A vaccination kit comprising the composition of claim 4.

12. The kit of claim 11, further comprising an electroporation device.

13. The kit of claim 12, wherein the electroporation device is a minimally-invasive electroporation device.

14. A method of vaccination comprising administering the composition of claim 4 to a subject in need thereof.

15. The method of claim 14, wherein the composition is administered via electroporation.

16. The method of claim 15, wherein the electroporation route is selected from the group consisting of intradermal and intramuscular.

17. The method of claim 16, wherein the composition is electroporated with a minimally-invasive electroporation device.

* * * * *